United States Patent
Kang et al.

(10) Patent No.: US 11,912,674 B2
(45) Date of Patent: *Feb. 27, 2024

(54) ISOXAZOLE DERIVATIVES AS NUCLEAR RECEPTOR AGONISTS AND USES THEREOF

(71) Applicant: ILDONG Pharmaceutical Co., Ltd., Seoul (KR)

(72) Inventors: Jae-Hoon Kang, Seoul (KR); Hong-Sub Lee, Youngin-si (KR); Yoon-Suk Lee, Hwaseong-si (KR); Jin-Ah Jeong, Seoul (KR); Sung-Wook Kwon, Hwaseong-si (KR); Jeong-Guen Kim, Hwaseong-si (KR); Kyung-Sun Kim, Gunpo-si (KR); Dong-Keun Song, Seoul (KR); Sun-Young Park, Hwaseong-si (KR); Kyeo-Jin Kim, Seoul (KR); Ji-Hye Choi, Hwaseong-si (KR); Hey-Min Hwang, Seoul (KR)

(73) Assignee: IL DONG PHARMACEUTICAL CO., LTD., Seoul (KR)

(*) Notice: Subject to any disclaimer, the term of this patent is extended or adjusted under 35 U.S.C. 154(b) by 189 days.

This patent is subject to a terminal disclaimer.

(21) Appl. No.: 17/191,806

(22) Filed: Mar. 4, 2021

(65) Prior Publication Data

US 2021/0188790 A1    Jun. 24, 2021

Related U.S. Application Data

(63) Continuation of application No. 16/604,180, filed as application No. PCT/KR2018/004277 on Apr. 12, 2018, now Pat. No. 10,988,449.

(30) Foreign Application Priority Data

Apr. 12, 2017  (KR) .................. 10-2017-0047393
Apr. 12, 2018  (KR) .................. 10-2018-0042545

(51) Int. Cl.
   *C07D 261/08*  (2006.01)
(52) U.S. Cl.
   CPC .................. *C07D 261/08* (2013.01)

(58) Field of Classification Search
   None
   See application file for complete search history.

(56) References Cited

FOREIGN PATENT DOCUMENTS

| JP | 2007-230909 A | 9/2007 |
| KR | 2013-0109210 A | 10/2013 |
| WO | 2009/005998 A1 | 1/2009 |
| WO | 2011/020615 A1 | 2/2011 |

OTHER PUBLICATIONS

Huang et al., "Design, Synthesis, and Biological Evaluation of Novel Nonsteroidal Farnesoid X Receptor (FXR) Antagonists: Molecular Basis of FXR Antagonism," ChemMedChem, May 15, 2015, vol. 10, 1184-1199.
Bass et al., "Substituted isoxazole analogs of farnesoid X receptor (FXR) agonist GW4064," Bioorganic & Medicinal Chemistry Letters, Jun. 1, 2009, vol. 19, 2969-2973.
Kainuma et al., "Design, synthesis, and evaluation of non-steroidal farnesoid X receptor (FXR) antagonist," Bioorganic & Medicinal Chemistry, Apr. 2007, vol. 15, 2587-2600.
Foreign Office Action in Mexican counterpart Application No. MX/a/2019/012167 dated Mar. 10, 2022.
Foreign Office Action in Vietnamese counterpart Application No. 1-2019-05615 filed on Apr. 12, 2018. (dated Jun. 24, 2022).
Sepe, V. et al. "Farnesoid X receptor modulators (2011-2014): a patent review". Expert Opin Ther Pat. 2015; 25 (8):885-96. doi: 10.1517/13543776.2015.1045413. PMID: 26183029.
Substantive Examination—Adverse Report (Section 30(1)) from the Intellectual Property Corporation of Malaysia dated Feb. 27, 2023 for Application No. PI2019006047, owner/applicant: IL Dong Pharmaceutical Co., Ltd.

*Primary Examiner* — Po-Chih Chen
(74) *Attorney, Agent, or Firm* — Sughrue Mion, PLLC

(57) ABSTRACT

The present invention provides methods for treating or ameliorating metabolic diseases, cholestatic liver diseases, or organ fibrosis, which comprises administering to a subject a therapeutically effective amount of a pharmaceutical composition comprising an isoxazole derivative, a racemate, an enantiomer, or a diastereoisomer thereof, or a pharmaceutically acceptable salt of the derivative, the racemate, the enantiomer, or the diastereoisomer.

13 Claims, No Drawings

ISOXAZOLE DERIVATIVES AS NUCLEAR RECEPTOR AGONISTS AND USES THEREOF

CROSS-REFERENCE TO RELATED APPLICATIONS

The present application is a continuation application of application Ser. No. 16/604,180 filed on Oct. 10, 2019, which is a 371 national stage entry of International Application No. PCT/KR2018/004277 filed on Apr. 12, 2018, which claims priority to Korean Application No. 10-2017-0047393 filed on Apr. 12, 2017 and Korean Patent Application No. 10-2018-0042545 filed Apr. 12, 2018, which applications are incorporated herein by reference.

TECHNICAL FIELD

The present invention relates to compounds useful as agonists for Farnesoid X receptor (FXR or NR1H4), pharmaceutical formulations comprising such compounds and its study for medicinal uses.

BACKGROUND ART

Farnesoid X receptor (FXR or NR1H4) is a member of the nuclear hormone receptor superfamily of ligand-activated transcription factors. FXR is highly expressed in the liver, intestine, kidney, adrenal glands, white adipose tissue and in induced during adipocyte differentiation in vitro (Cariu B. et al., J. Biol. Chem., 2006, 16, 11039-11049).

Not only FXR regulates various physiological processed such as modulates regulrated of bile acid (BA) regulation, lipids/glucose metabolism, inflammation/fibrosis, but recently it has also been linked to the pathology of FXR receptors.

This nuclear receptor is the intracellular bile acid "sensor" and its major physiological role is to protect liver cells from the deleterious effect of bile acids(BA) overload. Intestine is the tissue expressing the first FXR target gene identified. Indeed IBAB-P is expressed in enterocytes and binds bile acids, thus limiting the free concentration of BA intracellularly and consequently their toxicity (Makishima M, et al., Science, 1999, 284(5418), 1362-1365). FXR is highly expressed in the liver and regulates key genes involved in BA synthesis, metabolism and transport including CYP7A1, UGT2B4, BSEP, MDR3, MRP2, ASBT, NTCP, OST α and OST β in humans. One effect of FXR activation is down regulation of CYP7A1 and thus bile acid synthesis; this is accomplished through induction of small heterodimer partner (SHP) which then represses CYP7A1 transcription (Claude T, et al., Arterioscler. Thromb. Vasc. Biol., 2005, 25, 2020-2031). Altered expression or malfunction of these genes has been described in patients with cholestatic liver disease. FXR agonist 6-ethyl-chenodeoxycholic acid (6EtCDCA) was found to fully reverse the impairment of bile flow and to protect the hepatocytes against liver cell injury caused by the cytotoxic lithocholic acid (Pelliciari R, et al., J. Med. Chem., 2002, 45(17), 3569-3572).

In the intestine, FXR also induces expression of SHP which represses transcription of the apical sodium dependent bile acid transporter (ASBT or SLC10A2) gene which encodes the hight affinity apical sodium dependent bile acid transporter that mouse bile acids from the intestinal lumen into the enterocyte as part of the enterohepatic recycling of bile acids (Li H, et al., Am. J. Physiol. Gastrointest. Liver Physiol., 2005, 288, G60-G66). Ileal bile acid binding protein (IBABP) gene expression is also induced by FXR agonists in the enterocyte (Grober J, et al., J. Biol. Chem., 1999, 274(42), 29759-29754). FXR seems to be also involved in paracrine and endocrine signaling by upregulation the expression of the cytokine Fibroblast Growth Factor 15 (rodents) or 19 (monkeys, humans) (Holt J, et al., Genes Dev., 2003, 17(13), 1581-1591; Inagaki T, et al., Cell Metab., 2005, 2(4), 217-225).

FXR activation has also been described to downregulate proinflammatory enzymes iNOS and COX-2, as well as migration of vascular smooth muscle cell migration (Li YTY, et al., Arterioscler Thromb Vasc Biol., 2007, 27(12), 2606-2611). FXR is also expressed in hepatic stellate cells (HSC) which play a role in deposition of extracellular matrix during the fibrotic process. Treatment of cultured HSCs with the FXR agonist 6-ethyl-chenodeoxycholic acid (6EtCDCA) results in decreased expression of fibrotic markers such as α-smooth muscle actin and α1(I) collagen. 6EtCDCA has also been reported to present development and promote resolution of hepatic fibrosis in multiple rodent models of this disease (Fiorucci S, et al., Gastroenterology, 2004, 127(5), 1497-1512; Fiorucci S, et al., J. Pharmacol. Exp. Ther., 2005, 314(2), 584-595).

The process of enterohepatic circulation of bile acids is also a major regulator of serum cholesterol homeostasis. After biosynthesis from cholesterol in the liver, bile acid (BA) are secreted with nile into the lumen of the small intestine to aid in the digestion and absorption of fat and fat-soluble vitamins, The ratio of different BA determines the hydrophilicity of the bile acid pool and its ability to solubilize cholesterol. FXR activation increases the hydrophilicity of the pool, decreasing the intestinal solubilization of cholesterol, effectively blocking its absorption. Recent report have shown that FXR opposed this effect in part by directly repressing the expression of HMGCoA reductase via a pathway involving SHP and LRH1 (Datta S, et al., J. Biol. Chem., 2006, 281(2), 807-812).

According to subsequent studies, FXR activation affects Triglyceride (TG) metabolism via several pathways such as Sterol regulatory element-binding transcription factor 1 (SREBF1), apoC-III, apoC-II, syndecan-1 and the VLDL receptor. Recently new FXR modulator compounds show the ability to reduce both plasma triglyceride (TG) and cholesterol levels in normal and hyperlipidemic animal models (WO2007070796).

In addition, FXR agonist GW4064 or cholic acid treatment reduced plasma glucose levels and improved insulin sensitivity in three diabetic models (db/db, ob/ob and KK-A (y) mice)(Cariu B, et al., J. Biol. Chem., 2006, 281(16), 11039-11049 Zhang Y, et al., Proc. Natl. Acad. Sci., 2006, 103(4), 1006-1011; Ma K, et al., J. Clin. Invest., 2006, 116, 1102-1109). This demonstrates that FXR is involved in glucose metabolism.

Therefore, FXR activity has been implicated in variety of diseases, including, but not limited to disorder of bile acid homeostasis, inflammation/fibrosis and hight levels of plasma triglyceride (TG)/cholesterol.

Conventionally known FXR agonists INT-747(OCA) and EDP-305 are modified bile acid (BA), developed for the treatment of diseases caused by disorder of bile acid homeostasis such as nonalcoholic fatty liver disease (NASH), Alcoholic disorders, primary biliary cirrhosis (PBC), primary sclerosing cholangitis (PSC) and caused clinical side effects for the accumulation of substances in the body.

Following, small molecule compounds such as FXR agonist were derived form GW4064, PX-102(GS-9674)/PX-104 and Global Pharmaceutical Company published various patent with various derivatives (WO2000037077, WO2003015771, WO2004048349, WO2009012125, WO2009149795, WO2011020615, WO2013037482, and WO2016097933).

As FXR agonist has been progressed with respect to the prior published clinical literature, has a new mechanism of action for the treatment.

FXR agonist is development as target for variety treatment of diseases, including, but not limited to disorder of bile acid homeostasis, inflammation/fibrosis and hight levels of plasma triglyceride (TG)/cholesterol so that worldwide attention is focused.

So the present invention is expected that patients with metabolic diseases, including, but not limited to cholestatic liver diseases, organ fibrosis and liver fibrosis, will be able to open a therapeutic field of new mechanism.

SUMMARY

The present invention relates to compounds of excellent activity as FXR agonist. Particularly, the present invention relates to derivatives and processes for the preparation thereof.

In addition, the object of the present invention is to provide medical use for useful treatment of diseases, for modulating the activity as FXR receptors and for the treatment, prevention or amelioration of one or more symptoms of disease or disorder related to the activity of the receptors, including, but not limited to hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes, insulin resistance, metabolic inflexibility, nephropathy, liver diseases, atherosclerosis, cancer, inflammatory disorders, osteoporosis and skin aging.

However, the technical objects to be achieved in the present invention are not limited to those stated above and other objects may be clearly understood to those skilled in the art from the following description.

To solve the problem described above, the present invention provides a compound represented by Formula I, racemic, enantiomer, diastereoisomer thereof, or pharmaceutically acceptable salt thereof.

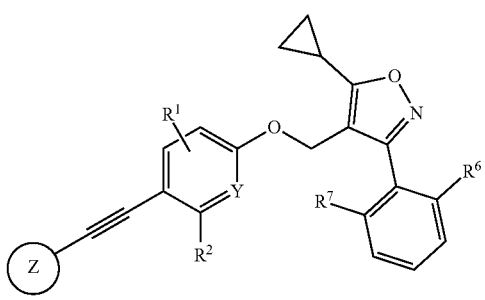

[Formula I]

In the present Formula I,

Y is carbon or nitrogen, $R^1$ and $R^2$ are each independently hydrogen, halo, or trifluoromethyl, Z is

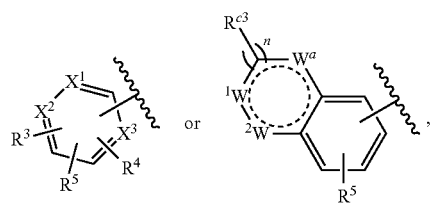

n is 0, 1 or 2, $X^1$, $X^2$ and $X^3$ are each independently carbon or nitrogen, $R^3$ and $R^4$ are each independently hydrogen, halo, cyano, $C_{1-6}$ alkyl, $C_{3-6}$ cycloalkyl, halo $C_{1-6}$ alkyl,

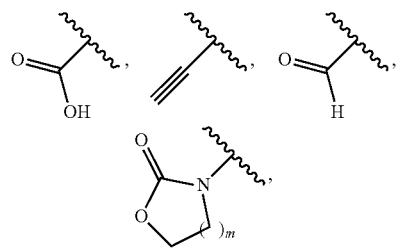

$CONR^{a1}R^{a2}$, $NR^{a1}R^{a2}$, $CH_2NR^{a1}R^{a2}$, $CH_2R^{c3}$, $COR^{a3}$, $OR^{a3}$, $NR^{a4}COR^{a3}$, $NR^{a4}CO_2R^{a3}$, $NHCONHR^{a3}$, $NHSO_2R^{a3}$, or 3- or 8-membered heterocycles containing one or two oxygen or nitrogen atom(s) therein, wherein, m is 1 or 2, $R^{a1}$ and $R^{a2}$ are each independently hydrogen, $C_{1-6}$ alkyl, $C_{3-6}$ cycloalkyl, halo $C_{1-6}$ alkyl,

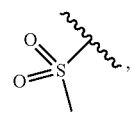

or 3- or 8-membered heterocycles containing one or two oxygen or nitrogen atom(s) therein, $R^{a3}$ is hydrogen, $C_{1-6}$ alkyl, $C_{3-6}$ cycloalkyl, halo $C_{1-6}$ alkyl,

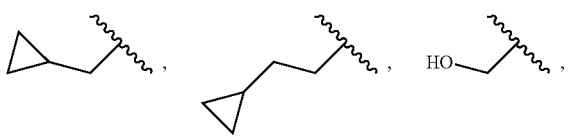

or 3- or 8-membered heterocycles containing one or two oxygen or nitrogen atom(s) therein, $R^{a4}$ is hydrogen or $C_{1-6}$ alkyl, $R^5$ is hydrogen,

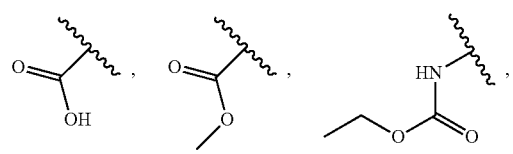

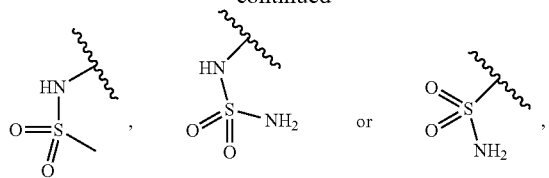

$R^6$ and $R^7$ are each independently hydrogen, halo, trifluoromethyl, or trifluoromethoxy, $R^{c3}$ is hydrogen, halo, $C_{1-6}$ alkyl, or $C_{3-6}$ cycloalkyl, $W^1$, $W^2$ and $W^3$ are each independently oxygen, nitrogen, $CHR^{w1}$, $CR^{w1}$, $NR^{w1}$ or CO, wherein, $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

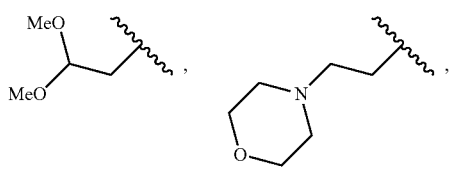 [SMILES: *CC(OC)OC ; *CCN1CCOCC1]

$(CH_2)_p$ heteroaryl, or $(CHd)_p$ aryl, wherein p is 1, 2, or 3.

The present invention provides a compound represented by Formula I, a racemate, enantiomer, or diastereoisomer of the compound, or a pharmaceutically acceptable salt of the compound, racemate, enantiomer, or diastereoisomer.

The present invention provides a pharmaceutical composition for the treatment, prevention, or amelioration of metabolic diseases, cholestatic liver diseases and organ fibrosis comprising the compound represented by Formula I, racemate, enantiomer, diastereoisomer or pharmaceutically acceptable salt.

The present invention provides a use for the treatment, prevention, or amelioration of metabolic diseases, cholestatic liver diseases and organ fibrosis comprising the compound represented by Formula I, racemate, enantiomer, diastereoisomer, or pharmaceutically acceptable salt.

The present invention provides a method for the treatment, prevention, or amelioration of metabolic diseases, cholestatic liver diseases and organ fibrosis in a subject in need thereof, comprising administering an effective amount of a pharmaceutical composition comprising the compound represented by Formula I, racemate, enantiomer, diastereoisomer thereof, or pharmaceutically acceptable salt thereof to the subject (including human).

The compounds of the present invention are highly active as FXR agonists, and pharmaceutical compositions thereof are expected to be useful for therapeutic applications which are improved by FXR agonist, such as metabolic diseases, cholestatic liver diseases and organ fibrosis.

DETAILED DESCRIPTION

Hereinafter, the present invention will be described in detail.

The present invention provides a compound represented by Formula I, racemate, enantiomer, or diastereoisomer thereof, or a pharmaceutically acceptable salt thereof:

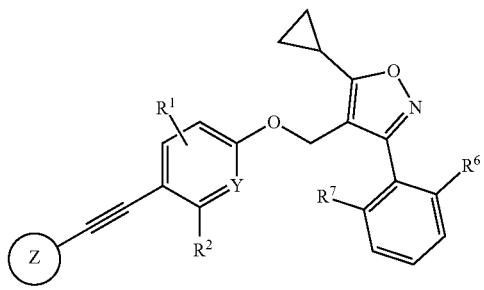

[Formula I]

In the present Formula I,
Y is carbon or nitrogen,
$R^1$ and $R^2$ are each independently hydrogen, halo, or trifluoromethyl,
Z is

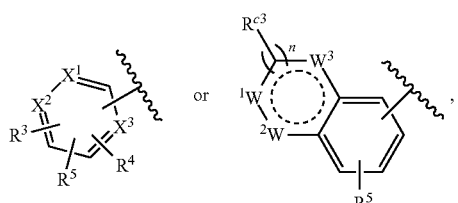

n is 0, 1, or 2,
$X^1$, $X^2$ and $X^3$ are each independently carbon or nitrogen,
$R^3$ and $R^4$ are each independently hydrogen, halo, cyano, $C_{1-6}$ alkyl, $C_{3-6}$ cycloalkyl, halo $C_{1-6}$ alkyl,

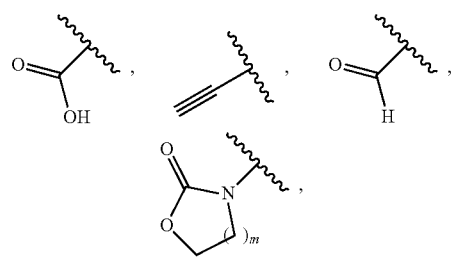

$CONR^{a1}R^{a2}$, $NR^{a1}R^{a2}$, $CH_2NR^{a1}R^{a2}$, $CH_2R^{c3}$, $COR^{a3}$, $OR^{a3}$, $NR^{a4}COR^{a3}$, $NR^{a4}CO_2R^{a3}$, $NHCONHR^{a3}$, $NHSO_2R^{a3}$, or 3- or 8-membered heterocycles containing one or two oxygen or nitrogen atom(s) therein,
wherein m is 1 or 2,
$R^{a1}$ and $R^{a2}$ are each independently hydrogen, $C_{1-6}$ alkyl, $C_{3-6}$ cycloalkyl, halo $C_{1-6}$ alkyl,

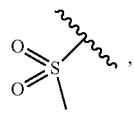

or 3- or 8-membered heterocycles containing one or two oxygen or nitrogen atom(s) therein,
$R^{a3}$ is hydrogen, $C_{1-6}$ alkyl, $C_{3-6}$ cycloalkyl, halo $C_{1-6}$ alkyl,

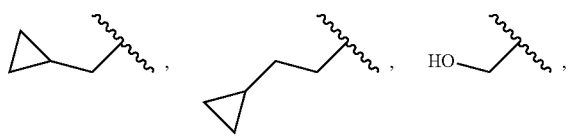

or 3- or 8-membered heterocycles containing one or two oxygen or nitrogen atom(s) therein, $R^{a4}$ is hydrogen or $C_{1-6}$ alkyl, $R^5$ is hydrogen,

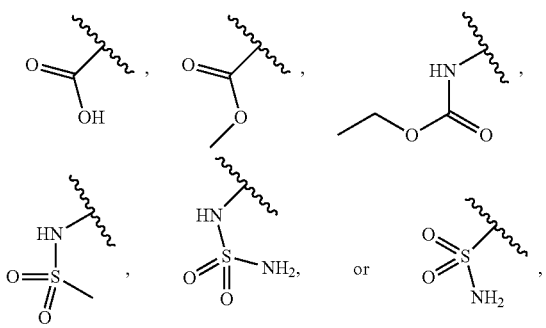

$R^6$ and $R^7$ are each independently hydrogen, halo, trifluoromethyl, or trifluoromethoxy, $R^{c3}$ is hydrogen, halo, $C_{1-6}$ alkyl, or $C_{3-6}$ cycloalkyl, and $W^1$, $W^2$ and $W^3$ are each independently oxygen, nitrogen, $CHR^{w1}$, $CR^{w1}$, $NR^{w1}$ or CO, wherein $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

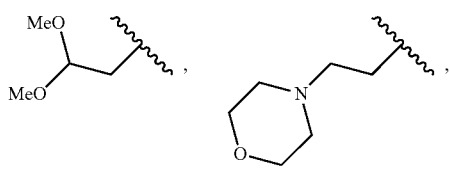 [SMILES: *CC(OC)OC ; *CCN1CCOCC1]

$(CH_2)_p$ heteroaryl, or $(CH_2)_p$ aryl, wherein p is 1, 2 or 3.

In the present invention, the compound of Formula I is preferably selected from i) through iv) disclosed below:

i) In case where Z is

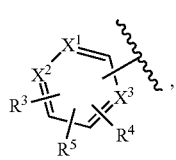

$R^3$ and $R^4$ are each independently hydrogen, halo, cyano, $C_{1-6}$ alkyl, $C_{3-6}$ cycloalkyl, trifluoromethyl,

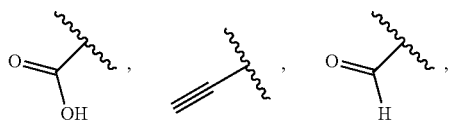

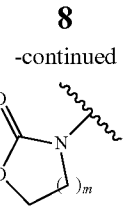

$NR^{a1}R^{a2}$, $CH_2NR^{a1}R^{a2}$, $OR^{a3}$,

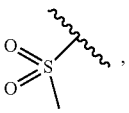

$NR^{a4}CO_2R^{a3}$,

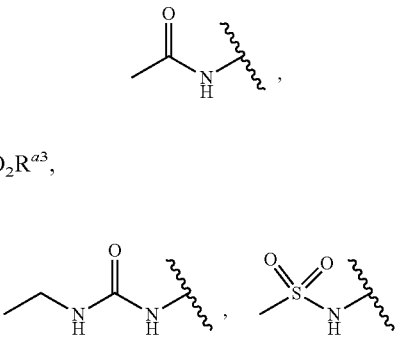

or 3- or 8-membered heterocycles containing one or two oxygen or nitrogen atom(s) therein, wherein m is 1 or 2, $R^{a1}$ and $R^{a2}$ are each independently hydrogen, methyl, ethyl, isopropyl, tert-butyl, cyclopropyl, trifluoromethyl,

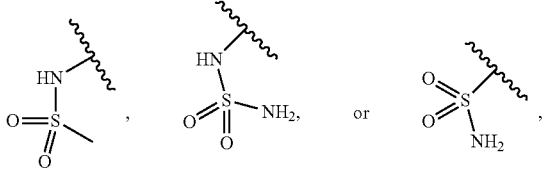

azetidine or piperidine, $R^{a3}$ is hydrogen, methyl, ethyl, propyl, tert-butyl, cyclopropyl, trifluoromethyl,

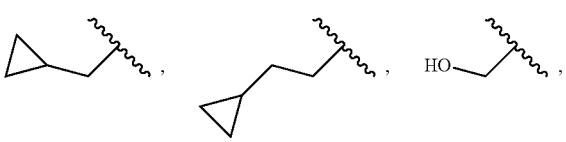

azetidine, piperidine, piperazine, or morpholine, and $R^{a4}$ is hydrogen or methyl.

ii) In case where Z is

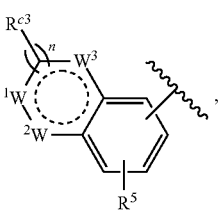

$R^{c3}$ is hydrogen or methyl, and $R^{w1}$ is hydrogen, methyl, ethyl, propyl, cyclopropyl,

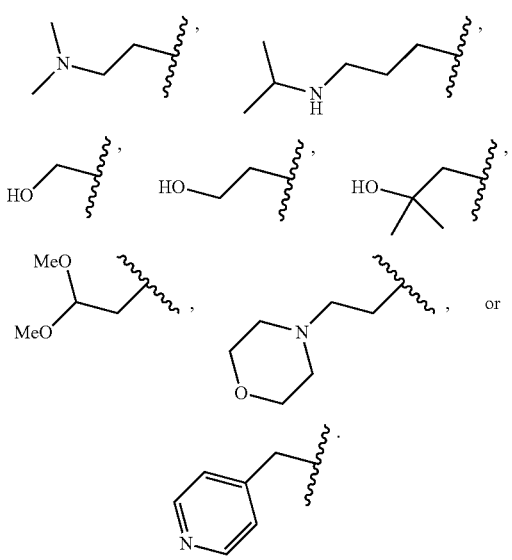

iii) In case where Z is

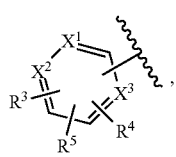

$R^1$ and $R^2$ are each independently hydrogen, chloro or trifluoromethyl, $R^3$ and $R^4$ are each independently hydrogen, chloro, fluoro, iodo, cyano, methyl, ethyl, isopropyl, cyclopropyl, trifluoromethyl,

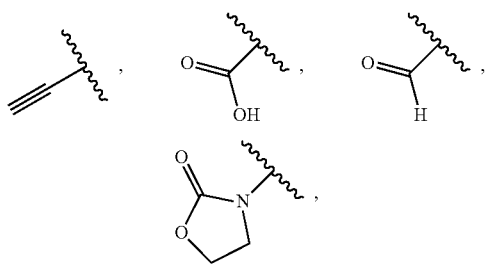

$NR^{a1}R^{a2}$, $CH_2NR^{a1}R^{a2}$, $NR^{a4}CO_2R^{a3}$, azetidine, piperazine, or pyrrolidine, wherein $R^{a1}$ and $R^{a2}$ are each independently hydrogen, methyl, ethyl, isopropyl, tert-butyl, cyclopropyl, trifluoroethyl,

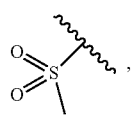

azetidine, piperidine, or oxetane, $R^{a3}$ is hydrogen, methyl, ethyl, tert-butyl, cyclopropyl, trifluoromethyl,

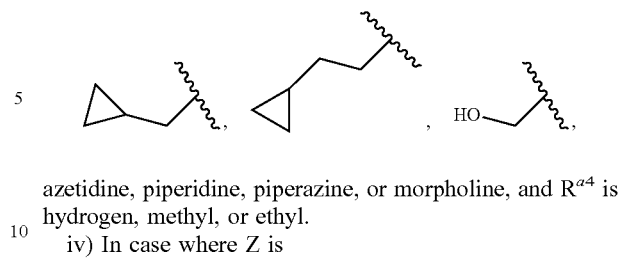

azetidine, piperidine, piperazine, or morpholine, and $R^{a4}$ is hydrogen, methyl, or ethyl.

iv) In case where Z is

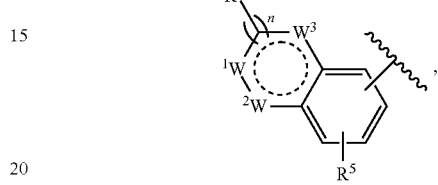

$R^1$ and $R^2$ are each independently hydrogen, chloro, or fluoro, n is 0 or 1, $R^5$ is

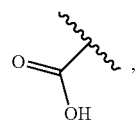

and $W^1$, $W^2$ and $W^3$ are each independently oxygen, nitrogen, $CR^{w1}$ or $NR^{w1}$, wherein, $R^{w1}$ is hydrogen, methyl, ethyl, isopropyl, cyclopropyl,

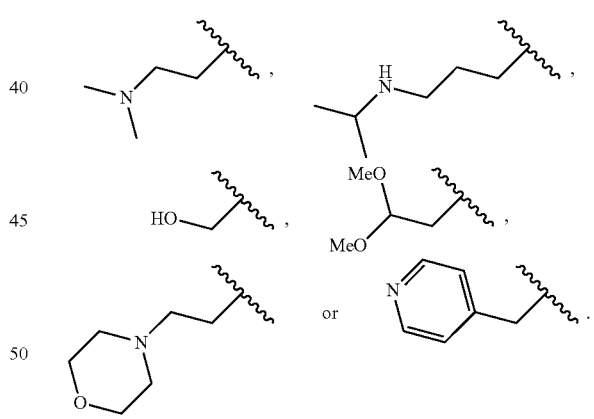

Particularly preferred examples of the compound of Formula I according to the present invention comprise the following:

4-((4-((5-cyclopropyl-3-(2,6-dichlorophenyl)isoxazol-4-yl)methoxy)phenyl)ethynyl)benzoic acid (I-1);

3-((4-((5-cyclopropyl-3-(2,6-dichlorophenyl)isoxazol-4-yl)methoxy)phenyl)ethynyl)benzoic acid (I-2);

3-((4-((5-cyclopropyl-3-(2,6-dichlorophenyl)isoxazol-4-yl)methoxy)-2-(trifluoromethyl)phenyl)ethynyl)benzoic acid (I-3);

4-((4-((5-cyclopropyl-3-(2,6-dichlorophenyl)isoxazol-4-yl)methoxy)-2-(trifluoromethyl)phenyl)ethynyl)benzoic acid (I-4);

4-((3-chloro-4-ethynylphenoxy)methyl)-5-cyclopropyl-3-(2,6-dichlorophenyl)isoxazole (I-5);

4-((3-chloro-4-(phenylethynyl)phenoxy)methyl)-5-cyclopropyl-3-(2,6-dichlorophenyl)isoxazole (I-6);

methyl 3-((2-chloro-4-((5-cyclopropyl-3-(2,6-dichlorophenyl)isoxazol-4-yl)methoxy)phenyl)ethynyl)benzoate (I-7);

methyl 3-((2-chloro-4-((5-cyclopropyl-3-(2,6-dichlorophenyl)isoxazol-4-yl)methoxy)phenyl)ethynyl)-5-((ethoxycarbonyl)amino)benzoate (I-8);

methyl 3-((tert-butoxycarbonyl)amino)-5-((2-chloro-4-((5-cyclopropyl-3-(2,6-dichlorophenyl)isoxazol-4-yl)methoxy)phenyl)ethynyl)benzoate (I-9);

methyl 3-((2-chloro-4-((5-cyclopropyl-3-(2,6-dichlorophenyl)isoxazol-4-yl)methoxy)phenyl)ethynyl)-5-((ethoxycarbonyl)(methyl)amino)benzoate (I-10);

ethyl(3-((2-chloro-4-((5-cyclopropyl-3-(2,6-dichlorophenyl)isoxazol-4-yl)methoxy)phenyl)ethynyl)phenyl)carbamate (I-11);

3-((2-chloro-4-((5-cyclopropyl-3-(2,6-dichlorophenyl)isoxazol-4-yl)methoxy)phenyl)ethynyl)benzenesulfonamide (I-12);

N-(3-((2-chloro-4-((5-cyclopropyl-3-(2,6-dichlorophenyl)isoxazol-4-yl)methoxy)phenyl)ethynyl)phenyl)methanesulfonamide (I-13);

N-(3-((2-chloro-4-((5-cyclopropyl-3-(2,6-dichlorophenyl)isoxazol-4-yl)methoxy)phenyl)ethynyl)phenyl)sulfamide (I-14);

3-((2-chloro-4-((5-cyclopropyl-3-(2,6-dichlorophenyl)isoxazol-4-yl)methoxy)phenyl)ethynyl)benzoic acid (I-15);

4-((2-chloro-4-((5-cyclopropyl-3-(2,6-dichlorophenyl)isoxazol-4-yl)methoxy)phenyl)ethynyl)benzoic acid (I-16);

6-((2-chloro-4-((5-cyclopropyl-3-(2,6-dichlorophenyl)isoxazol-4-yl)methoxy)phenyl)ethynyl)nicotinic acid (I-17);

2-((2-chloro-4-((5-cyclopropyl-3-(2,6-dichlorophenyl)isoxazol-4-yl)methoxy)phenyl)ethynyl)isonicotinic acid (I-18);

6-((2-chloro-4-((5-cyclopropyl-3-(2,6-dichlorophenyl)isoxazol-4-yl)methoxy)phenyl)ethynyl)picolinic acid (I-19);

5-((2-chloro-4-((5-cyclopropyl-3-(2,6-dichlorophenyl)isoxazol-4-yl)methoxy)phenyl)ethynyl)nicotinic acid (I-20);

3-((2-chloro-4-((5-cyclopropyl-3-(2,6-dichlorophenyl)isoxazol-4-yl)methoxy)phenyl)ethynyl)-5-(dimethylamino)benzoic acid (I-21);

4-((2-chloro-4-((5-cyclopropyl-3-(2,6-dichlorophenyl)isoxazol-4-yl)methoxy)phenyl)ethynyl)-3-(dimethylamino)benzoic acid (I-22);

4-((2-chloro-4-((5-cyclopropyl-3-(2,6-dichlorophenyl)isoxazol-4-yl)methoxy)phenyl)ethynyl)-2-(dimethylamino)benzoic acid (I-23);

3-((2-chloro-4-((5-cyclopropyl-3-(2,6-dichlorophenyl)isoxazol-4-yl)methoxy)phenyl)ethynyl)-5-(diethylamino)benzoic acid (I-24);

3-amino-5-((2-chloro-4-((5-cyclopropyl-3-(2,6-dichlorophenyl)isoxazol-4-yl)methoxy)phenyl)ethynyl)benzoic acid (I-25);

3-((2-chloro-4-((5-cyclopropyl-3-(2,6-dichlorophenyl)isoxazol-4-yl)methoxy)phenyl)ethynyl)-4-(dimethylamino)benzoic acid (I-26);

3-chloro-5-((2-chloro-4-((5-cyclopropyl-3-(2,6-dichlorophenyl)isoxazol-4-yl)methoxy)phenyl)ethynyl)benzoic acid (I-27);

4-chloro-3-((2-chloro-4-((5-cyclopropyl-3-(2,6-dichlorophenyl)isoxazol-4-yl)methoxy)phenyl)ethynyl)benzoic acid (I-28);

2-chloro-5-((2-chloro-4-((5-cyclopropyl-3-(2,6-dichlorophenyl)isoxazol-4-yl)methoxy)phenyl)ethynyl)benzoic acid (I-29);

3-((2-chloro-4-((5-cyclopropyl-3-(2,6-dichlorophenyl)isoxazol-4-yl)methoxy)phenyl)ethynyl)-5-fluorobenzoic acid (I-30);

3-((2-chloro-4-((5-cyclopropyl-3-(2,6-dichlorophenyl)isoxazol-4-yl)methoxy)phenyl)ethynyl)-5-(trifluoromethyl)benzoic acid (I-31);

3-((2-chloro-4-((5-cyclopropyl-3-(2,6-dichlorophenyl)isoxazol-4-yl)methoxy)phenyl)ethynyl)-5-ethynylbenzoic acid (I-32);

3-((2-chloro-4-((5-cyclopropyl-3-(2,6-dichlorophenyl)isoxazol-4-yl)methoxy)phenyl)ethynyl)-5-cyanobenzoic acid (I-33);

3-((2,6-dichloro-4-((5-cyclopropyl-3-(2,6-dichlorophenyl)isoxazol-4-yl)methoxy)phenyl)ethynyl)benzoic acid (I-34);

2-chloro-3-((2-chloro-4-((5-cyclopropyl-3-(2,6-dichlorophenyl)isoxazol-4-yl)methoxy)phenyl)ethynyl)benzoic acid (I-35);

3-((2-chloro-4-((5-cyclopropyl-3-(2,6-dichlorophenyl)isoxazol-4-yl)methoxy)phenyl)ethynyl)-2-fluorobenzoic acid (I-36);

5-((2-chloro-4-((5-cyclopropyl-3-(2,6-dichlorophenyl)isoxazol-4-yl)methoxy)phenyl)ethynyl)-2-fluorobenzoic acid (I-37);

3-((2-chloro-4-((5-cyclopropyl-3-(2,6-dichlorophenyl)isoxazol-4-yl)methoxy)phenyl)ethynyl)-4-fluorobenzoic acid (I-38);

3-((2-chloro-4-((5-cyclopropyl-3-(2,6-dichlorophenyl)isoxazol-4-yl)methoxy)phenyl)ethynyl)-5-(trifluoromethoxy)benzoic acid (I-39);

3-((2-chloro-4-((5-cyclopropyl-3-(2,6-dichlorophenyl)isoxazol-4-yl)methoxy)phenyl)ethynyl)-5-methoxybenzoic acid (I-40);

3-((2-chloro-4-((5-cyclopropyl-3-(2,6-dichlorophenyl)isoxazol-4-yl)methoxy)phenyl)ethynyl)-5-formylbenzoic acid (I-41);

3-((2-chloro-4-((5-cyclopropyl-3-(2,6-dichlorophenyl)isoxazol-4-yl)methoxy)phenyl)ethynyl)-5-((cyclopropylamino)methyl)benzoic acid (I-42);

3-(azetidin-1-ylmethyl)-5-((2-chloro-4-((5-cyclopropyl-3-(2,6-dichlorophenyl)isoxazol-4-yl)methoxy)phenyl)ethynyl)benzoic acid (I-43);

3-((2-chloro-4-((5-cyclopropyl-3-(2,6-dichlorophenyl)isoxazol-4-yl)methoxy)phenyl)ethynyl)-5-((methylamino)methyl)benzoic acid (I-44);

3-((2-chloro-4-((5-cyclopropyl-3-(2,6-dichlorophenyl)isoxazol-4-yl)methoxy)phenyl)ethynyl)-5-((ethylamino)methyl)benzoic acid (I-45);

3-((2-chloro-4-((5-cyclopropyl-3-(2,6-dichlorophenyl)isoxazol-4-yl)methoxy)phenyl)ethynyl)-5-(((2,2,2-trifluoroethyl)amino)methyl)benzoic acid (I-46);

3-((2-chloro-4-((5-cyclopropyl-3-(2,6-dichlorophenyl)isoxazol-4-yl)methoxy)phenyl)ethynyl)-5-((isopropylamino)methyl)benzoic acid (I-47);

3-((tert-butylamino)methyl)-5-((2-chloro-4-((5-cyclopropyl-3-(2,6-dichlorophenyl)isoxazol-4-yl)methoxy)phenyl)ethynyl)benzoic acid (I-48);

3-((2-chloro-4-((5-cyclopropyl-3-(2,6-dichlorophenyl)isoxazol-4-yl)methoxy)phenyl)ethynyl)-5-((dimethylamino)methyl)benzoic acid (I-49);

3-((2-chloro-4-((5-cyclopropyl-3-(2,6-dichlorophenyl) isoxazol-4-yl)methoxy)phenyl)ethynyl)-5-(morpholinomethyl)benzoic acid (I-50);

3-((2-chloro-4-((5-cyclopropyl-3-(2,6-dichlorophenyl) isoxazol-4-yl)methoxy)phenyl)ethynyl)-5-((oxetan-3-ylamino)methyl)benzoic acid (I-51);

3-((2-chloro-4-((5-cyclopropyl-3-(2,6-dichlorophenyl) isoxazol-4-yl)methoxy)phenyl)ethynyl)-5-(methylamino) benzoic acid (I-52);

3-((2-chloro-4-((5-cyclopropyl-3-(2,6-dichlorophenyl) isoxazol-4-yl)methoxy)phenyl)ethynyl)-5-(ethylamino) benzoic acid (I-53);

3-((2-chloro-4-((5-cyclopropyl-3-(2,6-dichlorophenyl) isoxazol-4-yl)methoxy)phenyl)ethynyl)-5-(isopropylamino)benzoic acid (I-54);

3-(azetidin-1-yl)-5-((2-chloro-4-((5-cyclopropyl-3-(2,6-dichlorophenyl)isoxazol-4-yl)methoxy)phenyl)ethynyl) benzoic acid (I-55);

3-((2-chloro-4-((5-cyclopropyl-3-(2,6-dichlorophenyl) isoxazol-4-yl)methoxy)phenyl)ethynyl)-5-(pyrrolidin-1-yl)benzoic acid (I-56);

3-(azetidin-3-ylamino)-5-((2-chloro-4-((5-cyclopropyl-3-(2,6-dichlorophenyl)isoxazol-4-yl)methoxy)phenyl)ethynyl)benzoic acid hydrochloride (I-57);

3-((2-chloro-4-((5-cyclopropyl-3-(2,6-dichlorophenyl) isoxazol-4-yl)methoxy)phenyl)ethynyl)-5-(piperidin-4-ylamino)benzoic acid hydrochloride (I-58);

3-((2-chloro-4-((5-cyclopropyl-3-(2,6-dichlorophenyl) isoxazol-4-yl)methoxy)phenyl)ethynyl)-5-(piperazin-1-yl)benzoic acid hydrochloride (I-59);

3-amino-5-((2-chloro-4-((5-cyclopropyl-3-(2,6-dichlorophenyl)isoxazol-4-yl)methoxy)phenyl)ethynyl)-4-methylbenzoic acid (I-60);

3-amino-5-((2-chloro-4-((5-cyclopropyl-3-(2,6-dichlorophenyl)isoxazol-4-yl)methoxy)phenyl)ethynyl)-4-methoxybenzoic acid (I-61);

3-amino-5-((2-chloro-4-((5-cyclopropyl-3-(2,6-dichlorophenyl)isoxazol-4-yl)methoxy)phenyl)ethynyl)-2-methoxybenzoic acid (I-62);

3-((2-chloro-4-((5-cyclopropyl-3-(2,6-dichlorophenyl) isoxazol-4-yl)methoxy)phenyl)ethynyl)-5-methylbenzoic acid (I-63);

3-((2-chloro-4-((5-cyclopropyl-3-(2,6-dichlorophenyl) isoxazol-4-yl)methoxy)phenyl)ethynyl)-5-cyclopropylbenzoic acid (I-64);

3-((2-chloro-4-((5-cyclopropyl-3-(2,6-dichlorophenyl) isoxazol-4-yl)methoxy)phenyl)ethynyl)-5-ethylbenzoic acid (I-65);

3-((2-chloro-4-((5-cyclopropyl-3-(2,6-dichlorophenyl) isoxazol-4-yl)methoxy)phenyl)ethynyl)-5-isopropylbenzoic acid (I-66);

3-((2-chloro-4-((5-cyclopropyl-3-(2,6-dichlorophenyl) isoxazol-4-yl)methoxy)phenyl)ethynyl)-5-iodobenzoic acid (I-67);

3-((2,5-dichloro-4-((5-cyclopropyl-3-(2,6-dichlorophenyl) isoxazol-4-yl)methoxy)phenyl)ethynyl)benzoic acid (I-68);

3-((2,3-dichloro-4-((5-cyclopropyl-3-(2,6-dichlorophenyl) isoxazol-4-yl)methoxy)phenyl)ethynyl)benzoic acid (I-69);

3-((2-chloro-4-((5-cyclopropyl-3-(2,6-dichlorophenyl) isoxazol-4-yl)methoxy)-6-fluorophenyl)ethynyl)benzoic acid (I-70);

3-amino-5-((2-chloro-4-((5-cyclopropyl-3-(2,6-dichlorophenyl)isoxazol-4-yl)methoxy)phenyl)ethynyl)-2-methylbenzoic acid (I-71);

3-((2-chloro-4-((5-cyclopropyl-3-(2,6-dichlorophenyl) isoxazol-4-yl)methoxy)phenyl)ethynyl)-5-(3-ethylureido)benzoic acid (I-72);

3-acetamido-5-((2-chloro-4-((5-cyclopropyl-3-(2,6-dichlorophenyl)isoxazol-4-yl)methoxy)phenyl)ethynyl)benzoic acid (I-73);

3-((2-chloro-4-((5-cyclopropyl-3-(2,6-dichlorophenyl) isoxazol-4-yl)methoxy)phenyl)ethynyl)-5-((ethoxycarbonyl)amino)benzoic acid (I-74);

3-((2-chloro-4-((5-cyclopropyl-3-(2,6-dichlorophenyl) isoxazol-4-yl)methoxy)phenyl)ethynyl)-5-((ethoxycarbonyl)(methyl)amino)benzoic acid (I-75);

3-((2-chloro-4-((5-cyclopropyl-3-(2,6-dichlorophenyl) isoxazol-4-yl)methoxy)phenyl)ethynyl)-5-((cyclopropoxycarbonyl)amino)benzoic acid (I-76);

3-((tert-butoxycarbonyl)amino)-5-((2-chloro-4-((5-cyclopropyl-3-(2,6-dichlorophenyl)isoxazol-4-yl)methoxy) phenyl)ethynyl)benzoic acid (I-77);

3-((tert-butoxycarbonyl)(methyl)amino)-5-((2-chloro-4-((5-cyclopropyl-3-(2,6-dichlorophenyl)isoxazol-4-yl) methoxy)phenyl)ethynyl)benzoic acid (I-78);

3-((2-chloro-4-((5-cyclopropyl-3-(2,6-dichlorophenyl) isoxazol-4-yl)methoxy)phenyl)ethynyl)-5-(((cyclopropylmethoxy)carbonyl)amino)benzoic acid (I-79);

3-((2-chloro-4-((5-cyclopropyl-3-(2,6-dichlorophenyl) isoxazol-4-yl)methoxy)phenyl)ethynyl)-5-(((2-cyclopropylethoxy)carbonyl)amino)benzoic acid (I-80);

3-((2-chloro-4-((5-cyclopropyl-3-(2,6-dichlorophenyl) isoxazol-4-yl)methoxy)phenyl)ethynyl)-5-(((2-hydroxyethoxy)carbonyl)amino)benzoic acid (I-81);

3-(((azetidin-3-yloxy)carbonyl)amino)-5-((2-chloro-4-((5-cyclopropyl-3-(2,6-dichlorophenyl)isoxazol-4-yl) methoxy)phenyl)ethynyl)benzoic acid (I-82);

3-((2-chloro-4-((5-cyclopropyl-3-(2,6-dichlorophenyl) isoxazol-4-yl)methoxy)phenyl)ethynyl)-5-(2-oxooxazolidin-3-yl)benzoic acid (I-83);

5-((2-chloro-4-((5-cyclopropyl-3-(2,6-dichlorophenyl) isoxazol-4-yl)methoxy)phenyl)ethynyl)isophthalic acid (I-84);

3-((2-chloro-4-((5-cyclopropyl-3-(2,6-dichlorophenyl) isoxazol-4-yl)methoxy)phenyl)ethynyl)-5-(piperazine-1-carbonyl)benzoic acid hydrochloride (I-85);

3-((2-chloro-4-((5-cyclopropyl-3-(2,6-dichlorophenyl) isoxazol-4-yl)methoxy)phenyl)ethynyl)-5-(methylsulfonamido)benzoic acid (I-86);

3-((2-chloro-4-((5-cyclopropyl-3-(2-(trifluoromethyl)phenyl)isoxazol-4-yl)methoxy)phenyl)ethynyl)benzoic acid (I-87);

3-((2-chloro-4-((5-cyclopropyl-3-(2-(trifluoromethoxy)phenyl)isoxazol-4-yl)methoxy)phenyl)ethynyl)benzoic acid (I-88);

4-((2-chloro-4-((5-cyclopropyl-3-(2,6-dichlorophenyl) isoxazol-4-yl)methoxy)phenyl)ethynyl)-1H-indazole-6-carboxylic acid (I-89);

4-((2-chloro-4-((5-cyclopropyl-3-(2,6-dichlorophenyl) isoxazol-4-yl)methoxy)phenyl)ethynyl)-1H-benzo[d]imidazole-6-carboxylic acid (I-90);

4-((2-chloro-4-((5-cyclopropyl-3-(2,6-dichlorophenyl) isoxazol-4-yl)methoxy)phenyl)ethynyl)-1H-indole-6-carboxylic acid (I-91);

4-((2-chloro-4-((5-cyclopropyl-3-(2,6-dichlorophenyl) isoxazol-4-yl)methoxy)phenyl)ethynyl)-1-(2-(dimethylamino)ethyl)-1H-indole-6-carboxylicacid (I-92);

4-((2-chloro-4-((5-cyclopropyl-3-(2,6-dichlorophenyl) isoxazol-4-yl)methoxy)phenyl)ethynyl)-1-(3-(isopropylamino)propyl)-1H-indole-6-carboxylicacid (I-93);

4-((2-chloro-4-((5-cyclopropyl-3-(2,6-dichlorophenyl)isoxazol-4-yl)methoxy)phenyl)ethynyl)-1-(pyridin-4-ylmethyl)-1H-indole-6-carboxylicacid (I-94);

4-((2-chloro-4-((5-cyclopropyl-3-(2,6-dichlorophenyl)isoxazol-4-yl)methoxy)phenyl)ethynyl)-1-(2-morpholinoethyl)-1H-indole-6-carboxylicacid hydrochloride (I-95);

4-((2-chloro-4-((5-cyclopropyl-3-(2,6-dichlorophenyl)isoxazol-4-yl)methoxy)phenyl)ethynyl)-1-(2,2-dimethoxyethyl)-1H-indole-6-carboxylic acid (I-96);

4-((2-chloro-4-((5-cyclopropyl-3-(2,6-dichlorophenyl)isoxazol-4-yl)methoxy)phenyl)ethynyl)-1-(2-hydroxyethyl)-1H-indole-6-carboxylic acid (I-97);

4-((2-chloro-4-((5-cyclopropyl-3-(2,6-dichlorophenyl)isoxazol-4-yl)methoxy)phenyl)ethynyl)-1-(2-hydroxy-2-methylpropyl)-1H-indole-6-carboxylic acid (I-98);

6-((2-chloro-4-((5-cyclopropyl-3-(2,6-dichlorophenyl)isoxazol-4-yl)methoxy)phenyl)ethynyl)-1H-indazole-4-carboxylic acid (I-99);

5-((2-chloro-4-((5-cyclopropyl-3-(2,6-dichlorophenyl)isoxazol-4-yl)methoxy)phenyl)ethynyl)-2,3-dihydrobenzofuran-7-carboxylic acid (I-100);

6-((2-chloro-4-((5-cyclopropyl-3-(2,6-dichlorophenyl)isoxazol-4-yl)methoxy)phenyl)ethynyl)-1H-indole-4-carboxylic acid (I-101);

5-((2-chloro-4-((5-cyclopropyl-3-(2,6-dichlorophenyl)isoxazol-4-yl)methoxy)phenyl)ethynyl)benzo[d]oxazole-7-carboxylic acid (I-102);

5-((2-chloro-4-((5-cyclopropyl-3-(2,6-dichlorophenyl)isoxazol-4-yl)methoxy)phenyl)ethynyl)-2-methylbenzo[d]oxazole-7-carboxylic acid (I-103);

5-((2-chloro-4-((5-cyclopropyl-3-(2,6-dichlorophenyl)isoxazol-4-yl)methoxy)phenyl)ethynyl)-2-ethylbenzo[d]oxazole-7-carboxylic acid (I-104);

5-((2-chloro-4-((5-cyclopropyl-3-(2,6-dichlorophenyl)isoxazol-4-yl)methoxy)phenyl)ethynyl)-2-propylbenzo[d]oxazole-7-carboxylic acid (I-105);

5-((2-chloro-4-((5-cyclopropyl-3-(2,6-dichlorophenyl)isoxazol-4-yl)methoxy)phenyl)ethynyl)-2-isopropylbenzo[d]oxazole-7-carboxylic acid (I-106);

5-((2-chloro-4-((5-cyclopropyl-3-(2,6-dichlorophenyl)isoxazol-4-yl)methoxy)phenyl)ethynyl)-2-(hydroxymethyl)benzo[d]oxazole-7-carboxylic acid (I-107);

7-((2-chloro-4-((5-cyclopropyl-3-(2,6-dichlorophenyl)isoxazol-4-yl)methoxy)phenyl)ethynyl)quinoxaline-5-carboxylic acid (I-108);

7-((2-chloro-4-((5-cyclopropyl-3-(2,6-dichlorophenyl)isoxazol-4-yl)methoxy)phenyl)ethynyl)-2,3-dimethylquinoxaline-5-carboxylic acid (I-109);

5-((2-chloro-4-((5-cyclopropyl-3-(2,6-dichlorophenyl)isoxazol-4-yl)methoxy)phenyl)ethynyl)-2-cyclopropylbenzo[d]oxazole-7-carboxylic acid (I-110);

2-butyl-5-((2-chloro-4-((5-cyclopropyl-3-(2,6-dichlorophenyl)isoxazol-4-yl)methoxy)phenyl)ethynyl)benzo[d]oxazole-7-carboxylic acid (I-111);

6-((2-chloro-4-((5-cyclopropyl-3-(2,6-dichlorophenyl)isoxazol-4-yl)methoxy)phenyl)ethynyl)-2-methylbenzo[d]oxazole-4-carboxylic acid (I-112);

6-((2-chloro-4-((5-cyclopropyl-3-(2,6-dichlorophenyl)isoxazol-4-yl)methoxy)phenyl)ethynyl)-2-ethylbenzo[d]oxazole-4-carboxylic acid (I-113);

6-((2-chloro-4-((5-cyclopropyl-3-(2,6-dichlorophenyl)isoxazol-4-yl)methoxy)phenyl)ethynyl)-2-propylbenzo[d]oxazole-4-carboxylic acid (I-114); and 6-((2-chloro-4-((5-cyclopropyl-3-(2,6-dichlorophenyl)isoxazol-4-yl)methoxy)phenyl)ethynyl)-2-isopropylbenzo[d]oxazole-4-carboxylic acid (I-115).

In the present invention, "$C_{1-6}$ alkyl" is a saturated hydrocarbonyl amine with linear or branched chains of 1-6 carbon atoms. Exemplary alkyl includes, but is not limited to, methyl, ethyl, propyl, butyl, pentyl, hexyl, 1-methylethyl, 1-methylpropyl, 2-methylpropyl, 1,1-dimethylethyl, 1-methylbutyl, 1,1-dimethylpropyl, 1-methylpentyl, and 1,1-dimethylbutyl.

In the present invention, "$C_{3-6}$ cycloalkyl" is intended as a saturated hydrocarbonyl ring with 3-6 carbon atoms. Exemplary cycloalkyl include, but is not limited to, cyclopropyl, cyclobutyl, cyclopentyl, and cyclohexyl.

In the present invention, "$C_{1-6}$ alkylamine" is a saturated hydrocarbonyl amine with linear or branched chains of 1-6 carbon atoms. Exemplary alkylamines include, but are not limited to, methylamine, ethylamine, propylamine, butylamine, 1-methylethylamine, diethylamine, and dimethylamine.

In the present invention, "$C_{1-6}$ alkyl alcohol" is an R—OH group with R as defined above. Exemplary alkyl alcohol with 1-6 carbon atoms includes, but is not limited to, methyl alcohol, ethyl alcohol, propyl alcohol, isopropyl alcohol, and n-butyl alcohol.

In the present invention, "halo" is intended as bromine, fluorine, or chlorine atom.

In the present invention, "halo $C_{1-6}$ alkyl" is intended as a $C_{1-6}$ alkyl radical having one or more hydrogen atoms replaced by a halogen atom as defined above. Exemplary haloalkyl includes, but is not limited to, difluoromethyl and trifluoromethyl.

In the present invention, "aryl" is intended as aromatic ring with single ring and substituted a halogen. Exemplary aryl includes, but is not limited to, phenyl and halo phenyl.

In the present invention, "heteroaryl" is intended as a monocyclic ring with at least one nitrogen, oxygen or sulfur atom. Exemplary heteroaryl includes, but is not limited to, pyridinyl, quinolyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl, and indazolyl.

In the present invention, "heterocycle" is intended as a saturated or partially unsaturated hydrocarbonyl mono-tricyclic ring with at least one nitrogen atom. Exemplary mono heterocycles with 5-6 atoms include, but are not limited to, pyrrolidinyl, piperidinyl, piperazinyl pyrollyl, pyrazolyl, imidazolyl, oxazolyl, isoxazolyl, triazolyl, thiazolyl, pyridyl, pyridazinyl, pyrimidinyl, pyrazinyl, and triazinyl. Also, exemplary bicyclic aromatic ring includes, but is not limited to, benzothiazolyl, benzoxazolyl, benzoxazinone, benzoxadiazolyl, 1,3-benzodioxolyl, benzofuryl, benzopyrazinyl, indolyl, indazolyl, benzimidazolyl, benzopyranyl, pyrolopyridanyl, furopyridinyl, and imidazothiazolyl.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio.

The term "treatment" as used herein covers any treatment of a disease in a mammal, particularly a human, and includes inhibiting the disease, i.e., arresting its development; or relieving the disease, i.e. causing regression of the disease and/or its symptoms or conditions and slowing disease progression.

The term "therapeutically effective amount" means an amount of a compound of the present invention that ameliorates, attenuates or eliminates a particular disease or condition or prevents or delays the onset of a particular disease or condition.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. A specific stereoisomer may also be referred to as an enantiomer, and a mixture of such isomers is often called an enantiomeric mixture. A 50:50 mixture of enantiomers is referred to as a racemic-mixture or a racemate.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In another aspect, the present invention provides a method of preparing the compounds represented by Formula I or pharmaceutically acceptable salts thereof.

The method for preparing the compounds of Formula A8 according to the present invention is shown in the following scheme 1.

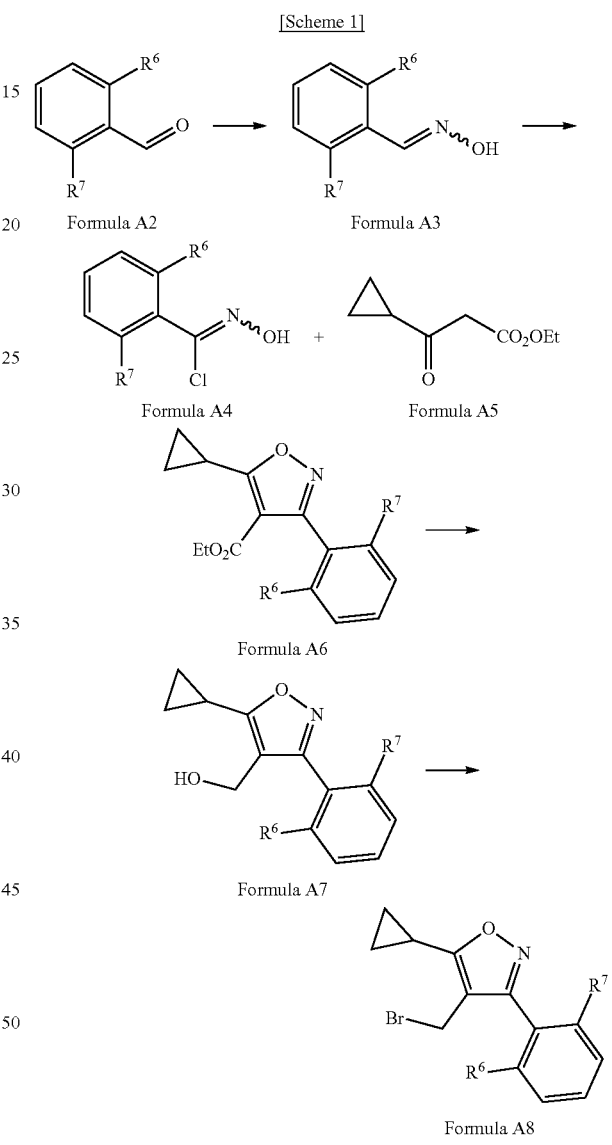

The compounds of Formula A8, which are compounds of the present invention, may be prepared by series of steps from the compounds of Formula A2 as shown in Scheme 1.

$R^6$ and $R^7$ of Formula A8, A2 and A7, illustrated in Scheme 1, are defined as below.

$R^6$ and $R^7$ are each independently hydrogen, halo, trifluoromethyl, or trifluoromethoxy.

The preparation method of the Formula A8 according to the present invention comprises:

preparing a compound of Formula A3 by reductive amination of Formula A2 (Step 1);

preparing a compound of Formula A4 by chlorination of Formula A3 (Step 2);

preparing a compound of Formula A6 by cyclization of Formula A4 with compound of Formula A5 (Step 3);

preparing a compound of Formula A7 by reduction of Formula A6 (Step 4); and preparing a compound of Formula A8 by bromination of Formula A7 (Step 5).

Each step in the above preparation method of scheme 1 is described in more detail as follows.

i) In the first step, a compound of Formula A2 may be converted to Formula A3 by reductive amination under conditions of hydroxyl amine and sodium hydroxide in ethanol and distilled water at 90° C. for 24 hours.

The example of preparing the compound of Formula A3 from the Formula A2 by reductive amination in the above Step 1 of the preparing method of the present invention is illustrated in the following reaction scheme.

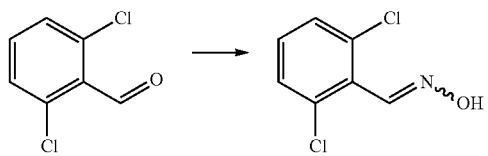 [SMILES: O=Cc1c(Cl)cccc1Cl ; ON=Cc1c(Cl)cccc1Cl]

ii) In the second step, the compound of Formula A3, prepared as described in step 1, may be converted to Formula A4 by chlorination carried out in the presence of chlorination reagents in one or more of N,N-dimethylformamide, or chloroform at room temperature for 1 hour.

An example of preparing the compound of Formula A4 from the compound of Formula A3 by chlorination in the above Step 2 of the preparing method of the present invention is illustrated in the following reaction scheme.

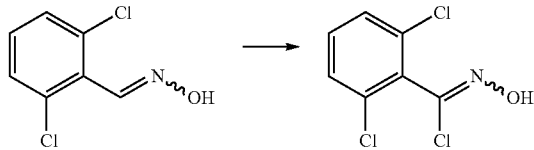 [SMILES: ON=Cc1c(Cl)cccc1Cl ; ON=C(Cl)c1c(Cl)cccc1Cl]

iii) In the third step, the compound of Formula A4, prepared as described in step 2, may be converted to Formula A6 by cyclization with Formula A5 under basic condition at room temperature for 24 hours.

An example of preparing the compound of Formula A6 from the compound of Formula A4 and A5 by cyclization in the above Step 3 of the preparing method of the present invention is illustrated in the following reaction scheme.

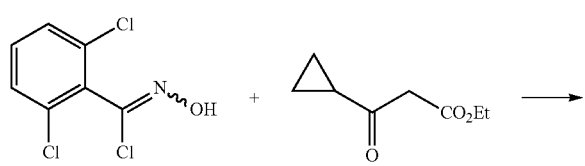

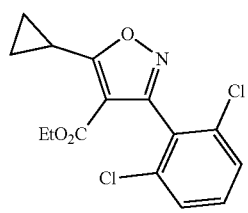

iv) In the fourth step, the compound of Formula A6, prepared as described in step 3, may be converted to Formula A7 by reduction carried out in the presence of reducing reagent in THF at room temperature for 7 hours.

An example of preparing the compound of Formula A7 from the compound of Formula A6 by reduction in the above Step 4 of the preparing method of the present invention is illustrated in the following reaction scheme.

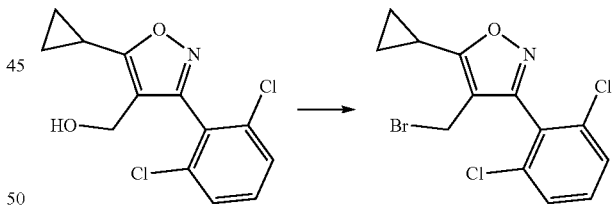

v) In the fifth step, the compound of Formula A7, prepared as described in step 4, may be converted to Formula A8 by bromination carried out in the presence of bromination reagent in dichloromethane at room temperature for 4 hours.

An example of preparing the compound of Formula A8 from the compound of Formula A7 by bromination in the above Step 5 of the preparing method of the present invention is illustrated in the following reaction scheme.

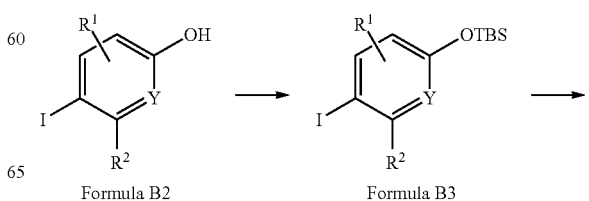

Besides, another preparation method of the compounds of Formula I according to the present invention is shown in the following reaction scheme 2.

[Scheme 2]

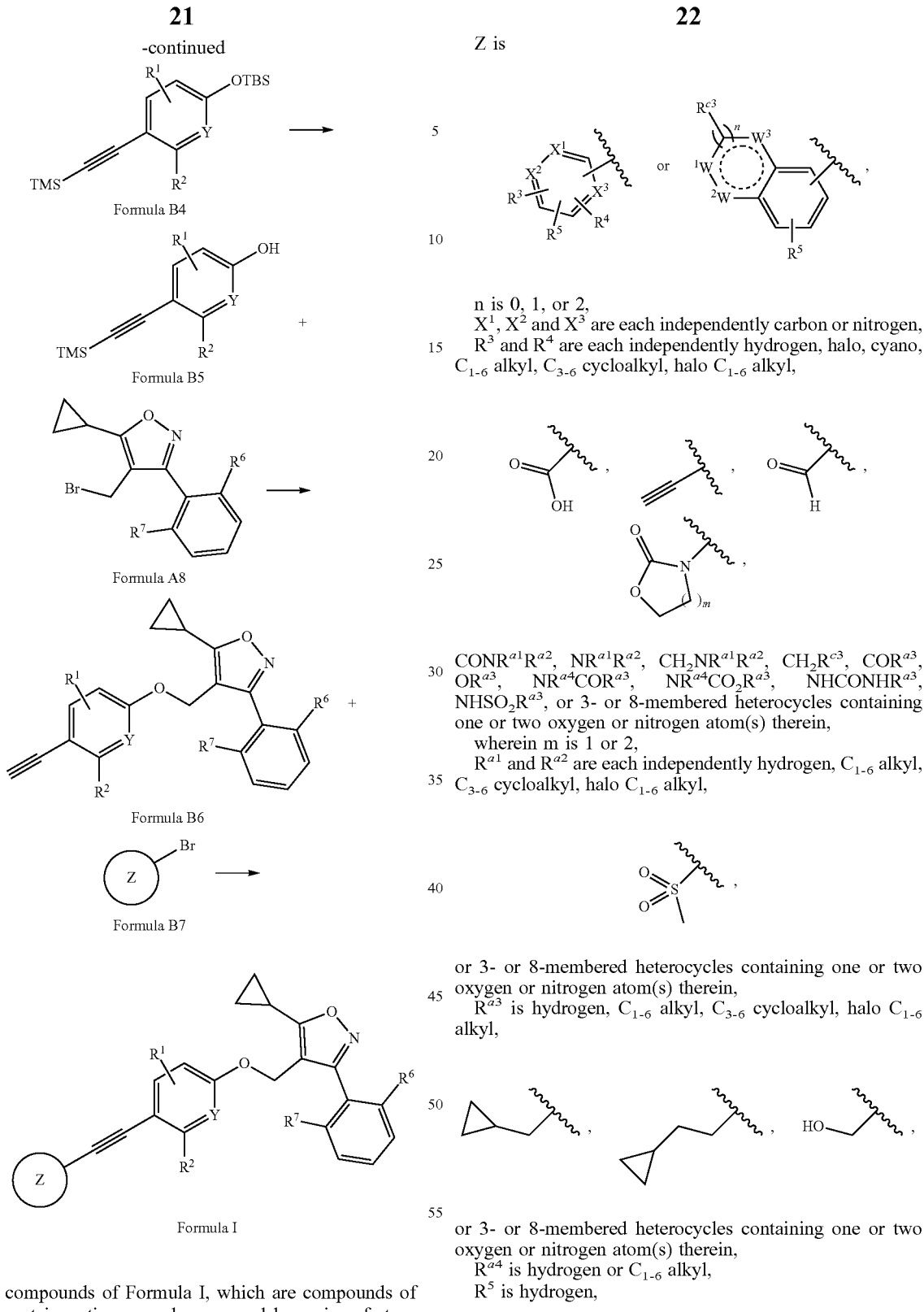

The compounds of Formula I, which are compounds of the present invention, may be prepared by series of steps from compounds of Formula B2 as shown in Scheme 2.

Y, $R^1$, $R^2$, $R^6$, $R^7$ and Z of Formula I, B2 and B7, illustrated in Scheme 2, are defined as below:

Y is carbon or nitrogen, $R^1$ and $R^2$ are each independently hydrogen, halo, or trifluoromethyl, Z is n is 0, 1, or 2, $X^1$, $X^2$ and $X^3$ are each independently carbon or nitrogen, $R^3$ and $R^4$ are each independently hydrogen, halo, cyano, $C_{1-6}$ alkyl, $C_{3-6}$ cycloalkyl, halo $C_{1-6}$ alkyl, $CONR^{a1}R^{a2}$, $NR^{a1}R^{a2}$, $CH_2NR^{a1}R^{a2}$, $CH_2R^{c3}$, $COR^{a3}$, $OR^{a3}$, $NR^{a4}COR^{a3}$, $NR^{a4}CO_2R^{a3}$, $NHCONHR^{a3}$, $NHSO_2R^{a3}$, or 3- or 8-membered heterocycles containing one or two oxygen or nitrogen atom(s) therein, wherein m is 1 or 2, $R^{a1}$ and $R^{a2}$ are each independently hydrogen, $C_{1-6}$ alkyl, $C_{3-6}$ cycloalkyl, halo $C_{1-6}$ alkyl, or 3- or 8-membered heterocycles containing one or two oxygen or nitrogen atom(s) therein, $R^{a3}$ is hydrogen, $C_{1-6}$ alkyl, $C_{3-6}$ cycloalkyl, halo $C_{1-6}$ alkyl, or 3- or 8-membered heterocycles containing one or two oxygen or nitrogen atom(s) therein, $R^{a4}$ is hydrogen or $C_{1-6}$ alkyl, $R^5$ is hydrogen,

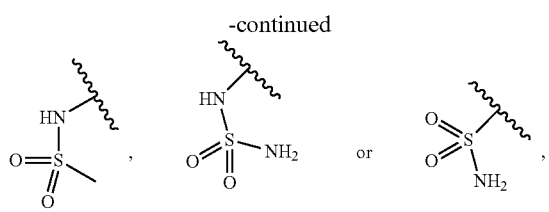

R[6] and R[7] are each independently hydrogen, halo, trifluoromethyl, or trifluoromethoxy, R[c3] is hydrogen, halo, $C_{1-6}$ alkyl, or $C_{3-6}$ cycloalkyl, and $W^1$, $W^2$ and $W^3$ are each independently oxygen, nitrogen, $CHR^{w1}$, $CR^{w1}$, $NR^{w1}$ or CO, wherein, $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

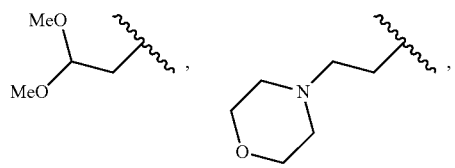 [SMILES: *CC(OC)OC ; *CCN1CCOCC1]

$(CH_2)_p$ heteroaryl, or $(CH_2)_p$ aryl, wherein p is 1, 2 or 3.

The preparation method of the Formula I according to the present invention comprises:

preparing the compound of Formula B3 by protection of hydroxyl group of Formula B2 (Step 1);

preparing the compound of Formula B4 by Sonogashira reaction of Formula B3 (Step 2);

preparing the compound of Formula B5 by deprotection of tert-butyldimethyloxy

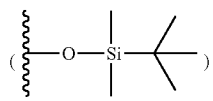

of Formula B4 (Step 3);

preparing the compound of Formula B6 by substitution of Formula B5 with A8 (Step 4); and preparing the compound of Formula I by Sonogashira reaction or hydrolysis after Sonogashira reaction of Formula B6 and B7 (Step 5).

Each step in the above preparation method of scheme 2 is described in more detail as follows.

i) In the first step, a compound of Formula B3 may be prepared by protection of hydroxyl group of Formula B2 using tert-Butyldimethylsilyl chloride (TBSCl) and imidazole in N,N-dimethylformamide at room temperature for 6-24 hours.

An example of preparing the compound of Formula B3 from the Formula B2 by protection of hydroxyl group in the above Step 1 of the preparing method of the present invention is in the following reaction scheme.

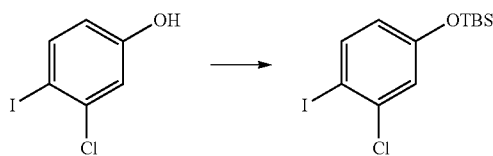 [SMILES: Oc1ccc(I)c(Cl)c1 ; CC(C)(C)[Si](C)(C)Oc1ccc(I)c(Cl)c1]

ii) In the second step, the compound of Formula B3, prepared as described in step 1, may be converted to Formula B4 by Sonogashira reaction using catalytic amount of tetrakis(triphenylphosphine)palladium(0)(Pd(PPh$_3$)$_4$) or bis(triphenylphosphine)palladium(II) dichloride (PdCl$_2$(PPh$_3$)$_2$) in one or more of N,N-dimethylformamide or methanol at 70-100° C. for 3-24 hour.

An example of preparing the compound of Formula B4 from the compound of Formula B3 by Sonogashira reaction in the above Step 2 of the preparing method of the present invention is in the following reaction scheme

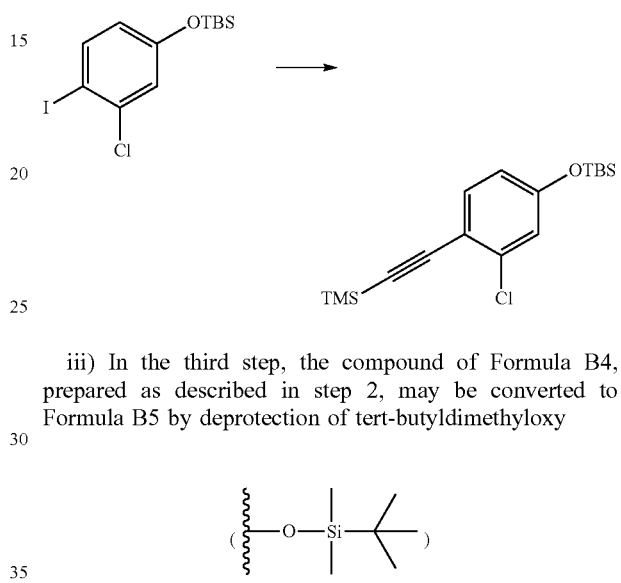

iii) In the third step, the compound of Formula B4, prepared as described in step 2, may be converted to Formula B5 by deprotection of tert-butyldimethyloxy

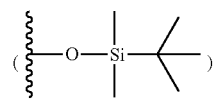

using either Potassium fluoride in one or more of tetrahydrofuran or methanol or Tetrabutylammonium fluoride solution at 0° C. to room temperature for 1-6 hours.

An example of preparing the compound of Formula B5 from the compound of Formula B4 by deprotection reaction in the above Step 3 of the preparing method of the present invention is in the following reaction scheme.

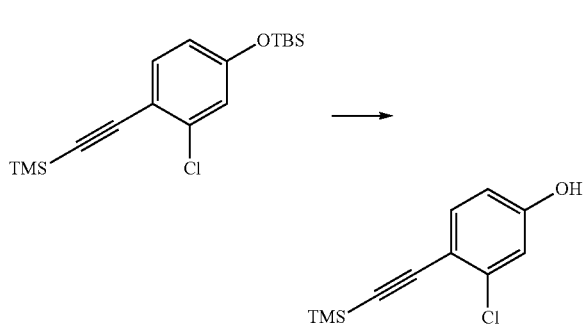

iv) In the fourth step, the compound of Formula B5, prepared as described in step 3, may be converted to Formula B6 by substitution of with A8 under basic conditions in one or more of THF or N,N-dimethylformamide at room temperature for 5-24 hours.

An example of preparing the compound of Formula B6 from the compound of Formula B5 with A8 by substitution in the above Step 4 of the preparing method of the present invention is in the following reaction scheme.

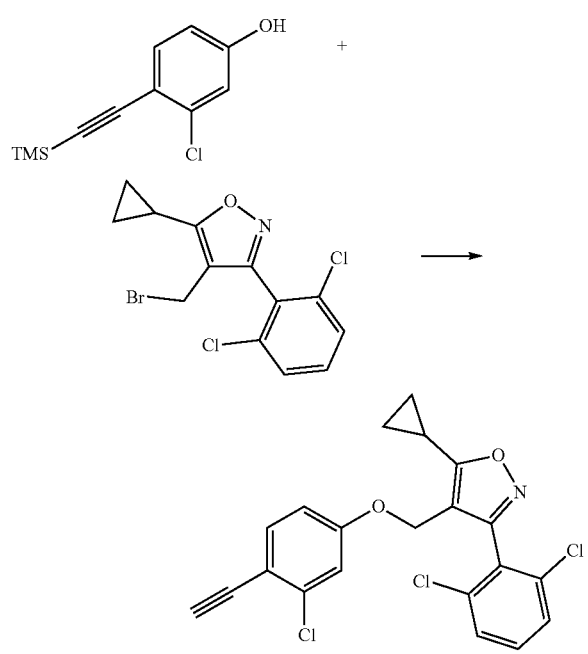

v) In the fifth step, the compound of Formula B6, prepared as described in step 4, may be converted to Formula I by Sonogashira reaction with B7 using catalytic amount of tetrakis(triphenylphosphine)palladium(0)(Pd(PPh$_3$)$_4$) or bis(triphenylphosphine)palladium(II) dichloride (PdCl$_2$(PPH$_3$)$_2$) and copper(I) iodide under basic condition in one or more of tetrahydrofuran or N,N-dimethylformamide at 70-100° C. for 3-24 hour. Besides, the compound of Formula I can be prepared from Formula B6 with B7 by Sonogashira reaction with hydrolysis using lithium hydroxide in one or more of tetrahydrofuran, 1,4-dioxane or water at 80° C. for 4-48 hours.

An example of preparing the compound of Formula I from the compound of Formula B6 with B7 by Sonogashira reaction or hydrolysis after Sonogashira reaction from in the above Step 5 of the preparing method of the present invention is illustrated below.

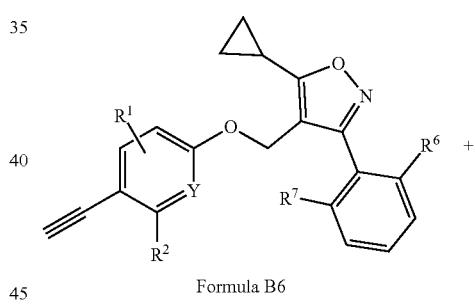

Besides, another preparation method of the compounds of Formula I according to the present invention is shown in the following reaction scheme 3.

[Scheme 3]

-continued

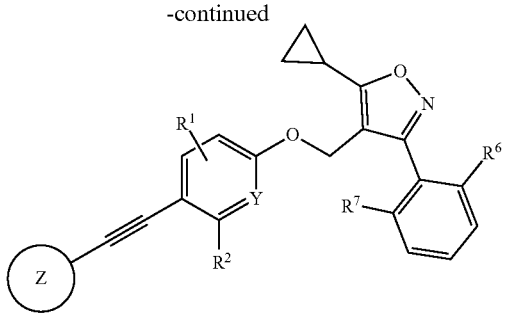

Formula I

The compounds of Formula I, which is a compound of the present invention, may be prepared by series of steps from the compound of Formula B6 as shown in Scheme 3.

$R^1$, $R^2$, $R^6$, $R^7$, $R^d$, Y and Z of Formula I, D1, B2 and B7, illustrated in Scheme 3, are defined as below.

$R^{d1}$ is bromo or iodo,

Y is carbon or nitrogen, $R^1$ and $R^2$ are each independently hydrogen, halo, or trifluoromethyl, Z is

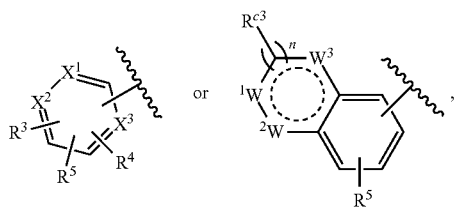

n is 0, 1, or 2, $X^1$, $X^2$ and $X^3$ are each independently carbon or nitrogen, $R^3$ and $R^4$ are each independently hydrogen, halo, cyano, $C_{1-6}$ alkyl, $C_{3-6}$ cycloalkyl, halo $C_{1-6}$ alkyl,

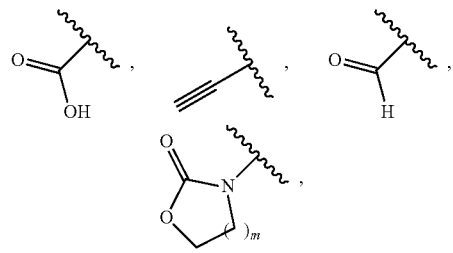

$CONR^{a1}R^{a2}$, $NR^{a1}R^{a2}$, $CH_2NR^{a1}R^{a2}$, $CH_2R^{c3}$, $COR^{a3}$, $OR^{a3}$, $NR^{a4}COR^{a3}$, $NR^{a4}CO_2R^{a3}$, $NHCONHR^{a3}$, $NHSO_2R^{a3}$, or 3- or 8-membered heterocycles containing one or two oxygen or nitrogen atom(s) therein, wherein m is 1 or 2, $R^{a1}$ and $R^{a2}$ are each independently hydrogen, $C_{1-6}$ alkyl, $C_{3-6}$ cycloalkyl, halo $C_{1-6}$ alkyl,

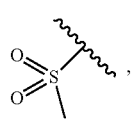

or 3- or 8-membered heterocycles containing one or two oxygen or nitrogen atom(s) therein, $R^{a3}$ is hydrogen, $C_{1-6}$ alkyl, $C_{3-6}$ cycloalkyl, halo $C_{1-6}$ alkyl,

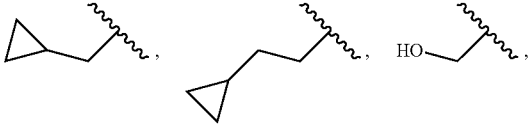

or 3- or 8-membered heterocycles containing one or two oxygen or nitrogen atom(s) therein, $R^{a4}$ is hydrogen or $C_{1-6}$ alkyl, $R^5$ is hydrogen,

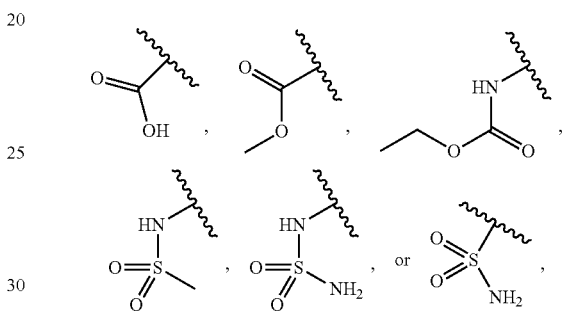

$R^6$ and $R^7$ are each independently hydrogen, halo, trifluoromethyl, or trifluoromethoxy, $R^{c3}$ is hydrogen, halo, $C_{1-6}$ alkyl, or $C_{3-6}$ cycloalkyl, and $W^1$, $W^2$ and $W^3$ are each independently oxygen, nitrogen, $CHR^{w1}$, $CR^{w1}$, $NR^{w1}$ or CO, wherein, $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

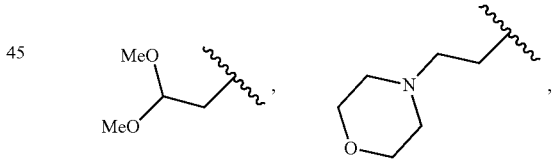

$(CH_2)_p$ heteroaryl, or $(CH_2)_p$ aryl, wherein p is 1, 2, or 3.

The preparation method of the Formula I according to the present invention comprises:

preparing the compound of Formula D2 by Sonogashira reaction of Formula B6 and D1 (Step 1); and preparing the compound of Formula I by deprotection of tert-butyloxycarbonyl

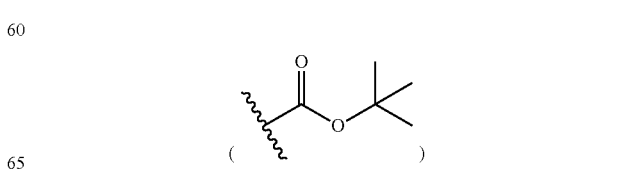

or tert-butyldimethyloxy

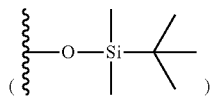

and hydrolysis of Formula D2 (Step 2);

Each step in the above preparation method of scheme 3 is described in more detail as follows.

i) In the first step, the compound of Formula B6, prepared as described in step 4 in scheme 2, may be converted to Formula D2 by Sonogashira reaction with Formula D1 using catalytic amount of tetrakis(triphenylphosphine)palladium (0)(Pd(PPh$_3$)$_4$) or bis(triphenyl phosphine)palladium(II) dichloride (PdCl$_2$(PPH$_3$)$_2$) and Copper(I)iodide under basic condition in one or more of tetrahydrofuran or N,N-dimethylformamide at 70-100° C. for 3-24 hour An example of preparing the compound of Formula D2 from the compound of Formula B6 with D1 by Sonogashira reaction in the above Step 1 of the preparing method of the present invention is illustrated in the following reaction scheme.

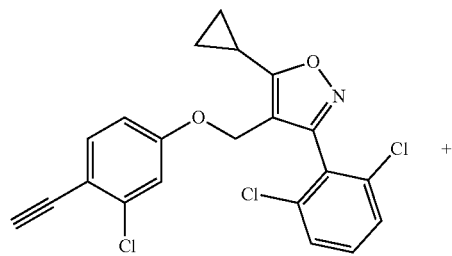 +

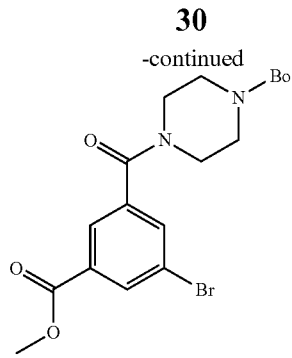

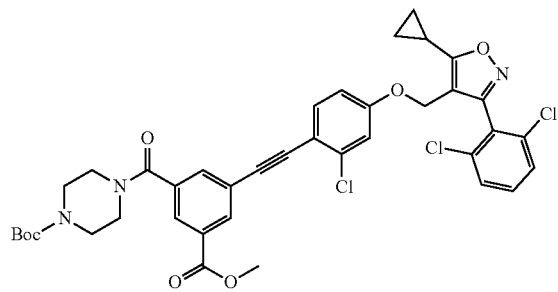

ii) In the second step, the compound of Formula D2, prepared as described in step 1, may be converted to Formula I by hydrolysis using lithium hydroxide in one or more of tetahydrofuran, 1,4-dioxane or water at rt-80° C. for 4-48 hours followed by deprotection in the presence of boron tribromide solution or hydrogen chloride solution in dichloromethane or tetahydrofuran(THF) at 0-80° C. for 2-24 hours.

An example of preparing the compound of Formula I from the compound of Formula D2 by hydrolysis and deprotection reaction in the above Step 2 of the preparing method of the present invention is illustrated in the following reaction scheme.

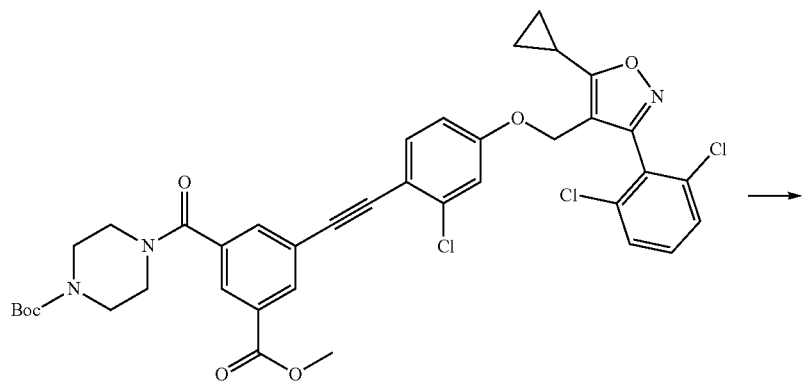

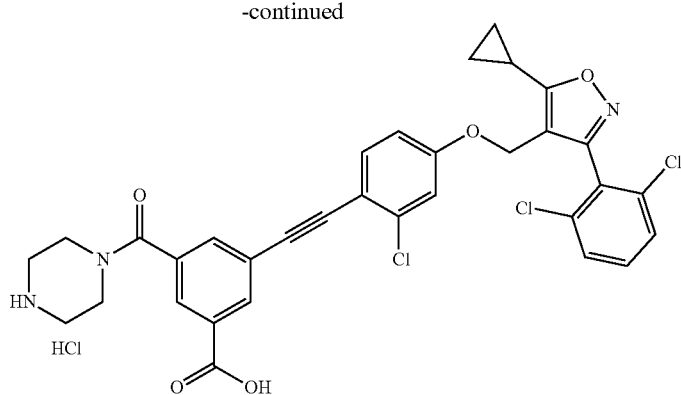

Besides, another preparation method of the compounds of Formula I according to the present invention is shown in the following reaction scheme 4.

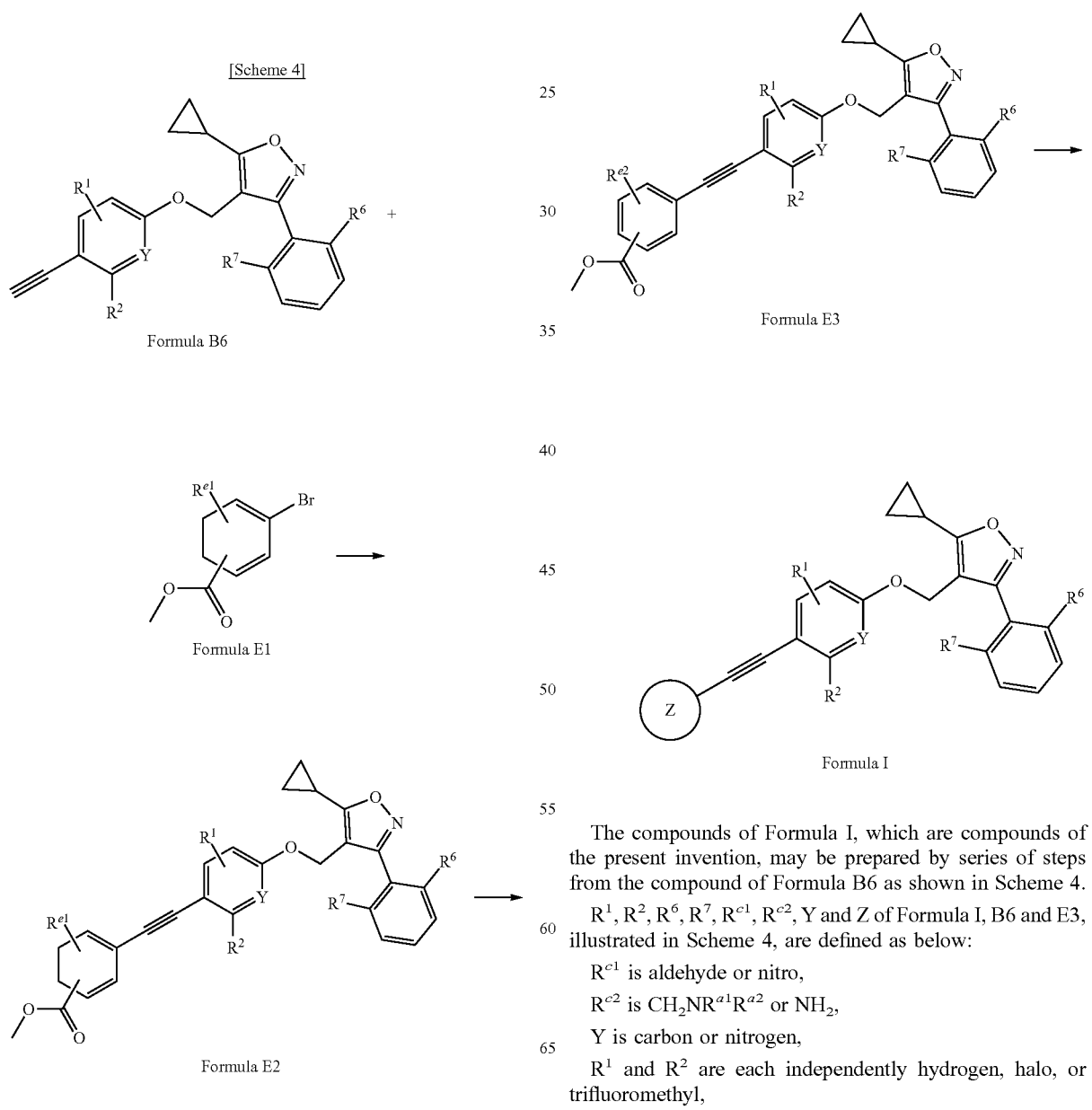

The compounds of Formula I, which are compounds of the present invention, may be prepared by series of steps from the compound of Formula B6 as shown in Scheme 4.

$R^1$, $R^2$, $R^6$, $R^7$, $R^{c1}$, $R^{c2}$, Y and Z of Formula I, B6 and E3, illustrated in Scheme 4, are defined as below:

$R^{c1}$ is aldehyde or nitro, $R^{c2}$ is $CH_2NR^{a1}R^{a2}$ or $NH_2$,

Y is carbon or nitrogen, $R^1$ and $R^2$ are each independently hydrogen, halo, or trifluoromethyl, Z is

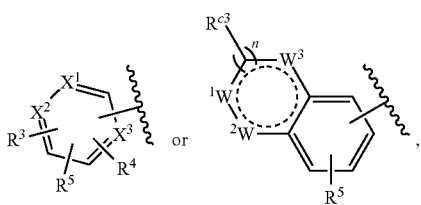

n is 0, 1 or 2,

X$^1$, X$^2$ and X$^3$ are each independently carbon or nitrogen,

R$^3$ and R$^4$ are each independently hydrogen, halo, cyano, C$_{1-6}$ alkyl, C$_{3-6}$ cycloalkyl, halo C$_{1-6}$ alkyl,

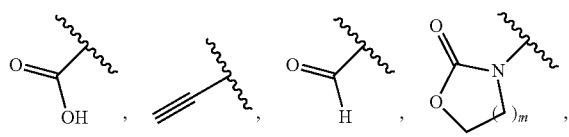

CONR$^{a1}$R$^{a2}$ NR$^{a1}$R$^{a2}$, CH$_2$NR$^{a1}$R$^{a2}$, CH$_2$R$^{c3}$, COR$^{a3}$, OR$^{a3}$, NR$^{a4}$COR$^{a3}$, NR$^{a4}$CO$_2$R$^{a3}$, NHCONHR$^{a3}$, NHSO$_2$R$^{a3}$, or 3- or 8-membered heterocycles containing one or two oxygen or nitrogen atom(s) therein, wherein m is 1 or 2, R$^{a1}$ and R$^{a2}$ are each independently hydrogen, C$_{1-6}$ alkyl, C$_{3-6}$ cycloalkyl, halo C$_{1-6}$ alkyl,

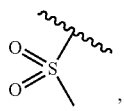

or 3- or 8-membered heterocycles containing one or two oxygen or nitrogen atom(s) therein, R$^{a3}$ is hydrogen, C$_{1-6}$ alkyl, C$_{3-6}$ cycloalkyl, halo C$_{1-6}$ alkyl,

or 3- or 8-membered heterocycles containing one or two oxygen or nitrogen atom(s) therein, R$^{a4}$ is hydrogen or C$_{1-6}$ alkyl, R$^5$ is hydrogen,

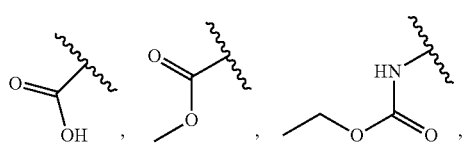

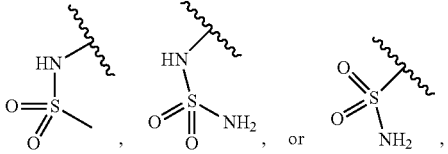

R$^6$ and R$^7$ are each independently hydrogen, halo, trifluoromethyl, or trifluoromethoxy, R$^{c3}$ is hydrogen, halo, C$_{1-6}$ alkyl, or C$_{3-6}$ cycloalkyl, and W$^1$, W$^2$ and W$^3$ are each independently oxygen, nitrogen, CHR$^{w1}$, CR$^{w1}$, NR$^{w1}$ or CO, wherein R$^{w1}$ is hydrogen, halo, C$_{1-6}$ alkyl, C$_{3-6}$ cycloalkyl, halo C$_{1-6}$ alkyl, C$_{1-6}$ alkylamine, C$_{1-6}$ alkyl alcohol, (CH$_2$)$_p$ heteroaryl, or (CH$_2$)$_p$ aryl, wherein p is 1, 2, or 3.

The preparation method of the Formula I according to the present invention comprises:

preparing the compound of Formula E2 by Sonogashira reaction of Formula B6 and E1 (Step 1);

preparing the compound of Formula E3 by reduction or reductive amination of Formula E2 (Step 2); and preparing the compound of Formula I by hydrolysis of Formula E3 (Step 3).

Each step in the above preparation method of scheme 4 is described in more detail as follows.

i) In the first step, the compound of Formula B6, prepared as described in step 4 in scheme 2, may be converted to Formula E2 by Sonogashira reaction with Formula E1 using catalytic amount of tetrakis(triphenylphosphine) palladium (0)(Pd(PPh$_3$)$_4$) or bis(triphenylphosphine)palladium(II) dichloride (PdCl$_2$(PPh$_3$)$_2$) and Copper(I) iodide under basic condition in one or more of tetrahydrofuran or N,N-dimethylformamide at 70-100° C. for 3-24 hour.

An example of preparing the compound of Formula E2 from the compound of Formula B6 with E1 by Sonogashira reaction in the above Step 1 of the preparing method of the present invention is illustrated in the following reaction scheme.

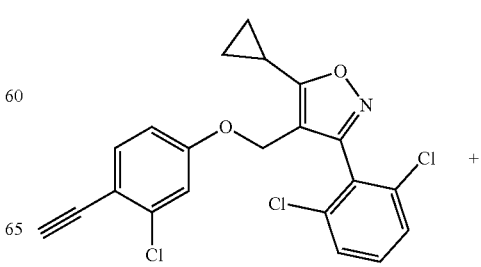

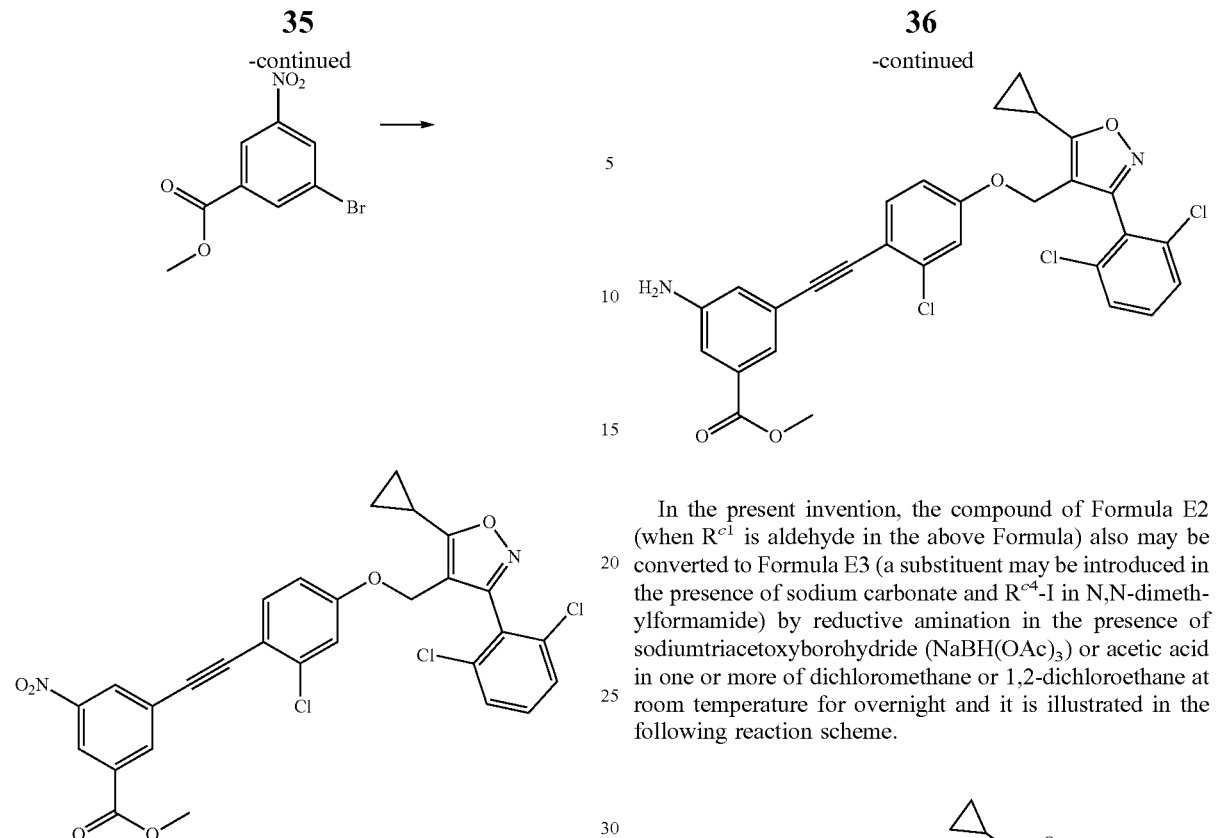

ii) In the second step, the compound of Formula E2, prepared as described in step 1, may be converted to Formula E3 by reduction or reductive amination depending on the type of the substituent $R^{c1}$.

The second step in the above preparation method of scheme 4 is described in more detail as follows.

In the second step of the preparation method, the desired compound of Formula E3 may be prepared by reduction or reductive amination.

The above reduction reaction may be carried out by Tin(II) chloride dehydrate in ethyl acetate or ethanol with the compound of Formula E2 (When $R^{c2}$ is nitro in the above Formula) at room temperature for one day and it is illustrated in the following reaction scheme.

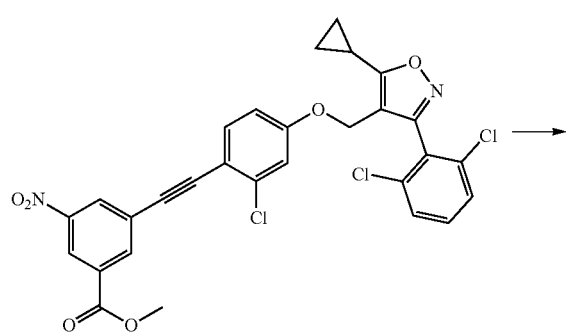

In the present invention, the compound of Formula E2 (when $R^{c1}$ is aldehyde in the above Formula) also may be converted to Formula E3 (a substituent may be introduced in the presence of sodium carbonate and $R^{c4}$-I in N,N-dimethylformamide) by reductive amination in the presence of sodiumtriacetoxyborohydride (NaBH(OAc)$_3$) or acetic acid in one or more of dichloromethane or 1,2-dichloroethane at room temperature for overnight and it is illustrated in the following reaction scheme.

iii) In the third step, the compound of Formula E3, prepared as described in step 2, may be converted to Formula I by hydrolysis using lithium hydroxide in one or more of tetrahydrofuran, 1,4-dioxane or water at rt-80° C. for 4-48 hours.

An example of preparing the compound of Formula I from the compound of Formula E3 by hydrolysis in the above Step 3 of the preparing method of the present invention is illustrated in the following reaction scheme.

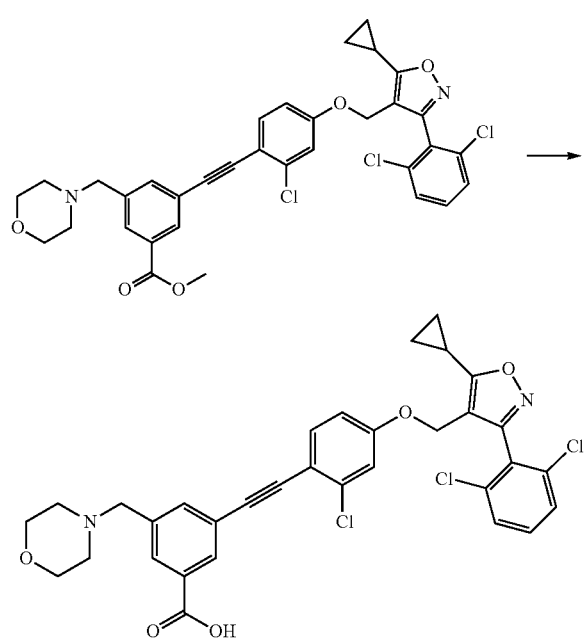

Besides, another preparation method of the compounds of Formula I according to the present invention is shown in the following reaction scheme 5.

[Scheme 5]

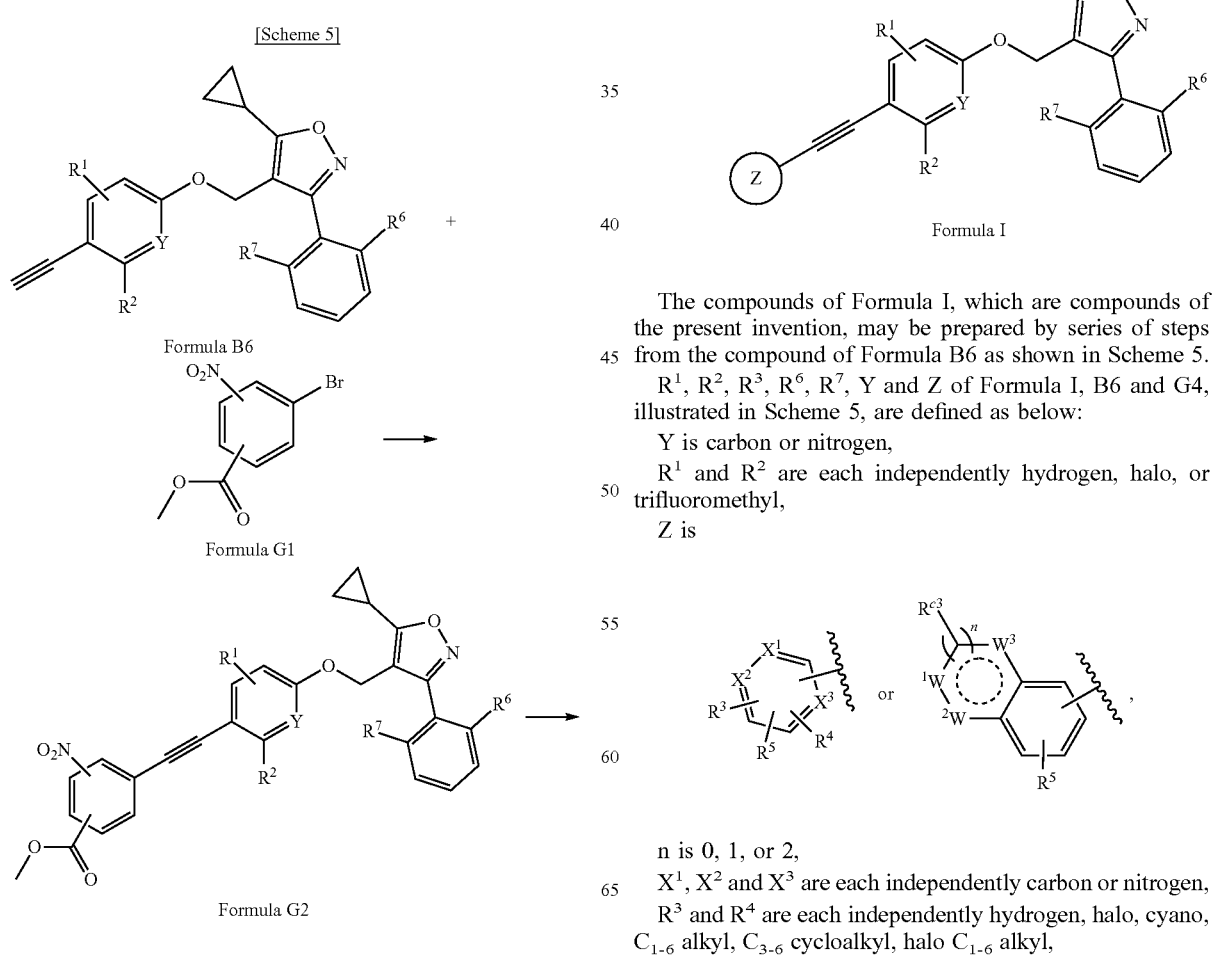

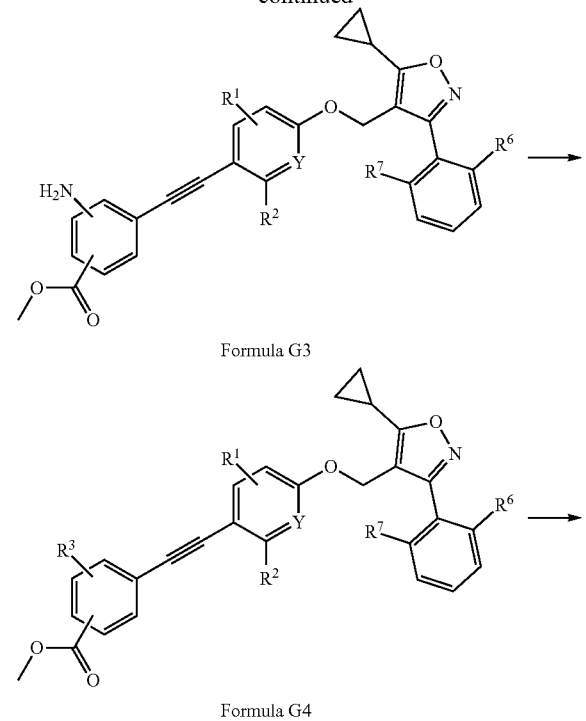

The compounds of Formula I, which are compounds of the present invention, may be prepared by series of steps from the compound of Formula B6 as shown in Scheme 5.

$R^1$, $R^2$, $R^3$, $R^6$, $R^7$, Y and Z of Formula I, B6 and G4, illustrated in Scheme 5, are defined as below:

Y is carbon or nitrogen, $R^1$ and $R^2$ are each independently hydrogen, halo, or trifluoromethyl, Z is

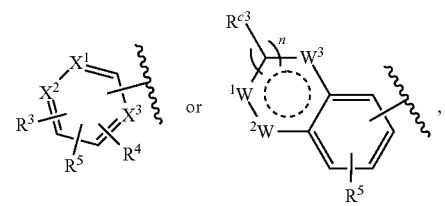

n is 0, 1, or 2, $X^1$, $X^2$ and $X^3$ are each independently carbon or nitrogen, $R^3$ and $R^4$ are each independently hydrogen, halo, cyano, $C_{1-6}$ alkyl, $C_{3-6}$ cycloalkyl, halo $C_{1-6}$ alkyl,

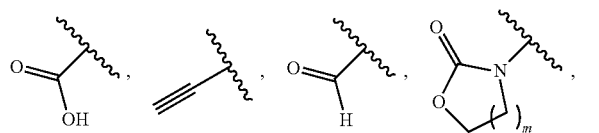 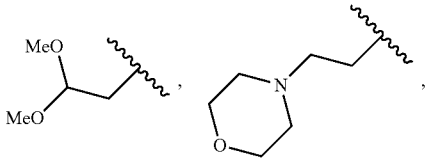

CONR$^{a1}$R$^{a2}$, NR$^{a1}$R$^{a2}$, CH$_2$NR$^{a1}$R$^{a2}$, CH$_2$R$^{c3}$, COR$^{a3}$, OR$^{a3}$, NR$^{a4}$COR$^{a3}$, NR$^{a4}$CO$_2$R$^{a3}$, NHCONHR$^{a3}$, NHSO$_2$R$^{a3}$, or 3- or 8-membered heterocycles containing one or two oxygen or nitrogen atom(s) therein, wherein m is 1 or 2, R$^{a1}$ and R$^{a2}$ are each independently hydrogen, C$_{1-6}$ alkyl, C$_{3-6}$ cycloalkyl, halo C$_{1-6}$ alkyl,

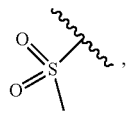

or 3- or 8-membered heterocycles containing one or two oxygen or nitrogen atom(s) therein, R$^{a3}$ is hydrogen, C$_{1-6}$ alkyl, C$_{3-6}$ cycloalkyl, halo C$_{1-6}$ alkyl,

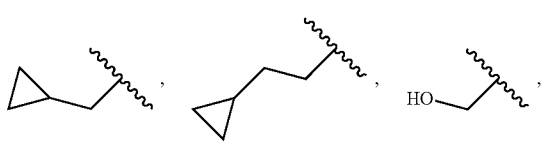

or 3- or 8-membered heterocycles containing one or two oxygen or nitrogen atom(s) therein, R$^{a4}$ is hydrogen or C$_{1-6}$ alkyl, R$^5$ is hydrogen,

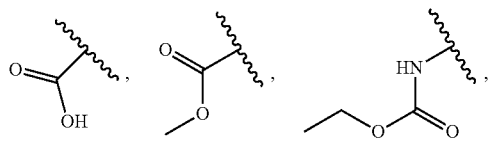

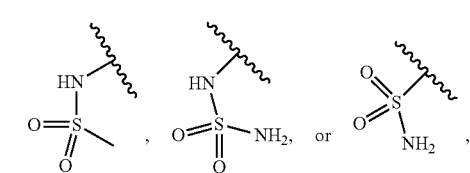

R$^6$ and R$^7$ are each independently hydrogen, halo, trifluoromethyl, or trifluoromethoxy, R$^{c3}$ is hydrogen, halo, C$_{1-6}$ alkyl, or C$_{3-6}$ cycloalkyl, and W$^1$, W$^2$ and W$^3$ are each independently oxygen, nitrogen, CHR$^{w1}$, CR$^{w1}$, NR$^{w1}$ or CO, wherein, R$^{w1}$ is hydrogen, halo, C$_{1-6}$ alkyl, C$_{3-6}$ cycloalkyl, halo C$_{1-6}$ alkyl, C$_{1-6}$ alkylamine, C$_{1-6}$ alkyl alcohol, (CH$_2$)$_p$ heteroaryl, or (CH$_2$)$_p$ aryl, wherein p is 1, 2 or 3.

The preparation method of the Formula I according to the present invention comprises:

preparing the compound of Formula G2 by Sonogashira reaction of Formula B6 and G1 (Step 1);

preparing the compound of Formula G3 by reduction of Formula G2 (Step 2);

preparing the compound of Formula G4 by substitution or addition reaction of Formula G3 (Step 3); and preparing the compound of Formula I by hydrolysis of compound of Formula G4 (Step 4).

Each step in the above preparation method of scheme 5 is described in more detail as follows.

i) In the first step, the compound of Formula B6, prepared as described in step 4 in scheme 2, may be converted to Formula G2 by Sonogashira reaction with Formula G1 using catalytic amount of tetrakis(triphenylphosphine)palladium (0)(Pd(PPh$_3$)$_4$) or bis(triphenyl phosphine)palladium(II) dichloride (PdCl$_2$(PPh$_3$)$_2$) and Copper(I) iodide under basic condition in one or more of tetrahydrofuran or N,N-dimethylformamide at 70-100° C. for 3-24 hour.

An example of preparing the compound of Formula G2 from the compound of Formula B6 with G1 by Sonogashira reaction in the above Step 1 of the preparing method of the present invention is illustrated in the following reaction scheme.

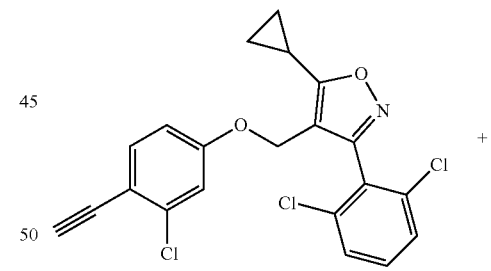

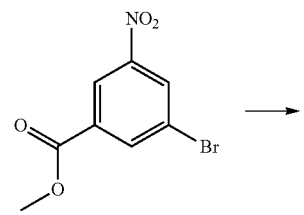

-continued

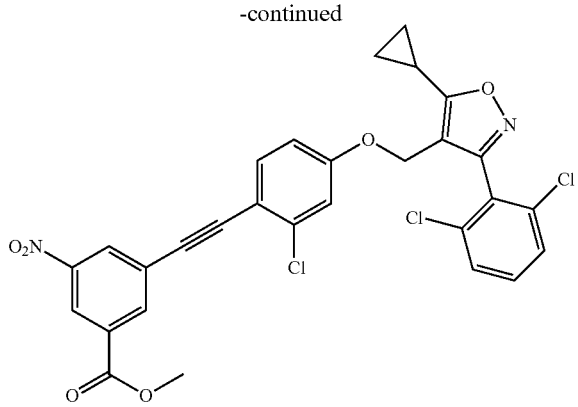

ii) In the second step, the compound of Formula G2, prepared as described in step 1, may be converted to Formula G3 using Tin(II) chloride dehydrate in ethyl acetate or ethanol at room temperature for one day and it is illustrated in the following reaction scheme.

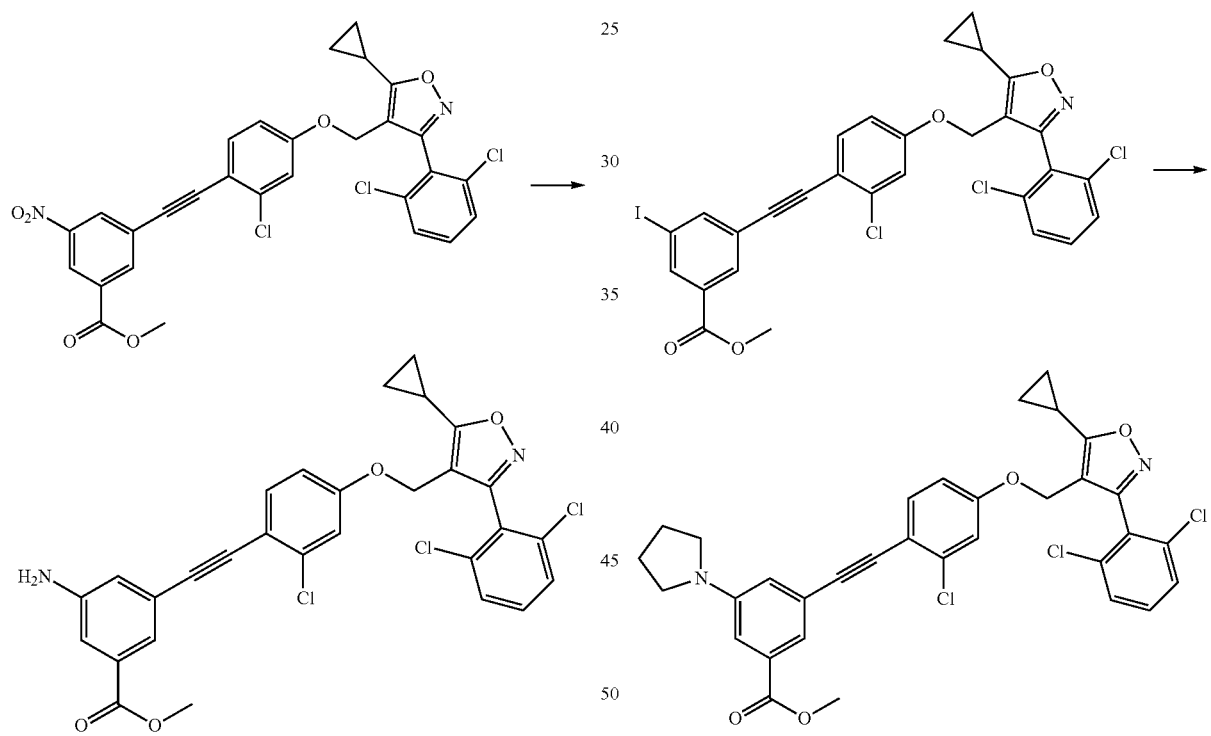

iii) In the third step, the compound of Formula G3, prepared as described in step 2, may be converted to Formula G4 by substitution or addition.

The third step in the above preparation method of scheme 5 is described in more detail as follows.

In the third step of the preparation method, the desired compound of Formula G4 may be prepared by substitution or addition.

The compound of Formula G3 may be converted to Formula G4 by the above substitution in the presence of tert-butylnitrile with iodine in toluene at room temperature for 3 hours or by iodo substitution followed by substitution with amine compound using L-proline, cesium carbonate, copper(I) iodide in dimethylsulfoxide.

An example of preparing the compound of Formula G4 from the compound of Formula G3 by substitution or iodo substitution followed by amine substitution in the above Step 3 of the preparing method of the present invention is illustrated in the following reaction scheme.

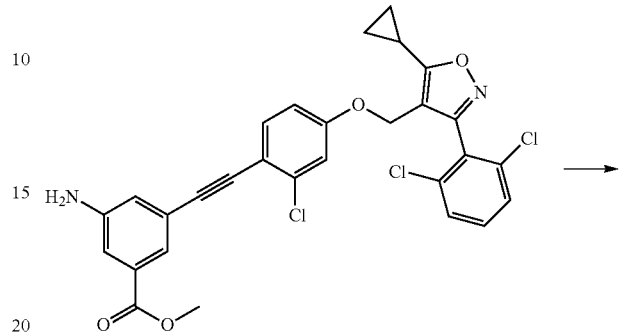

In the present invention, the compound of Formula G4 may be prepared by addition reaction which is carried out with the compound of Formula G3 and

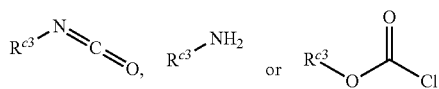

($R^{c3}$ in the Formula is same as that defined in the above Formula I) in dichloromethane or N,N-dimethylformamide at room temperature for 3-6 hours and it is illustrated in the following reaction scheme.

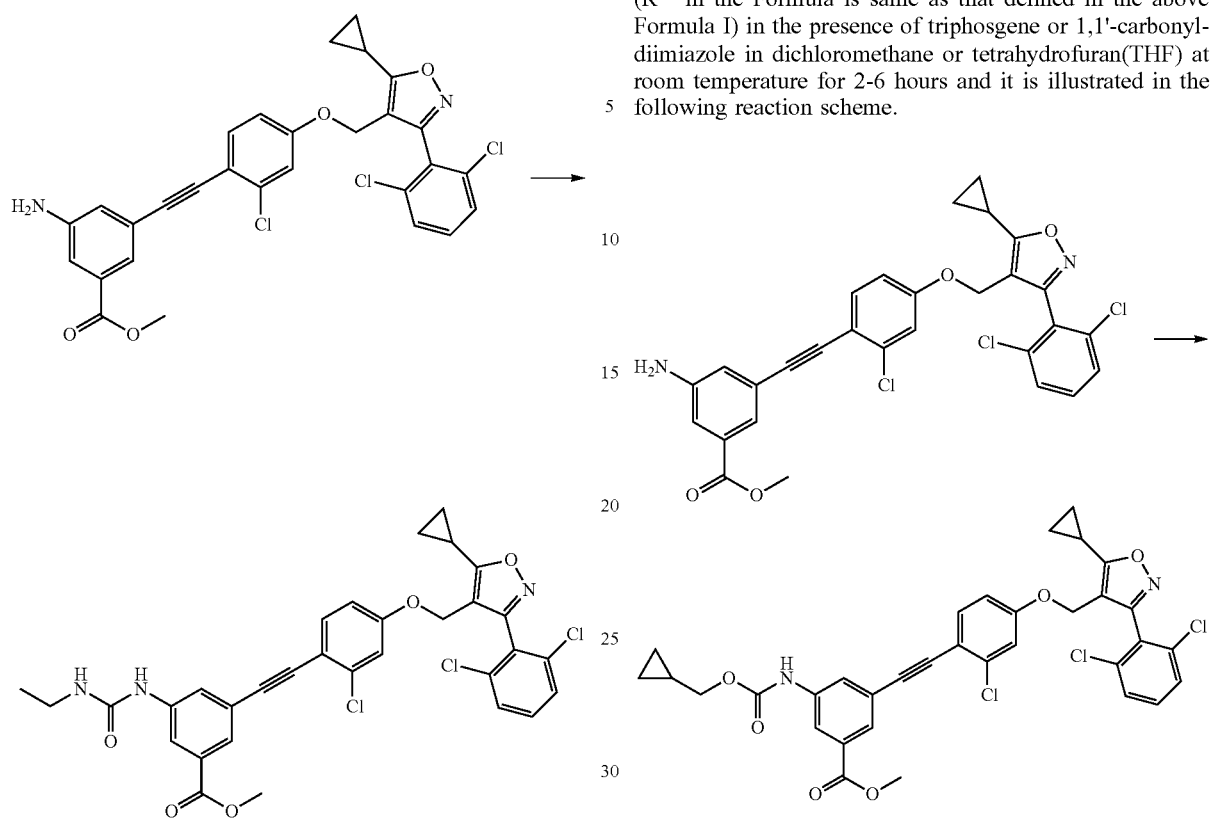

The compound of Formula G3 may be converted to Formula G4 by another method of the addition reaction which is carried out with $R^{c3}\diagup^{OH}$ ($R^{c3}$ in the Formula is same as that defined in the above Formula I) in the presence of triphosgene or 1,1'-carbonyl-diimiazole in dichloromethane or tetrahydrofuran(THF) at room temperature for 2-6 hours and it is illustrated in the following reaction scheme.

iv) In the fourth step, the compound of Formula G4, prepared as described in step 3, may be converted to Formula I by hydrolysis using lithium hydroxide in one or more of tetrahydrofuran, 1,4-dioxane or water at rt-80° C. for 4-48 hours.

An example of preparing the compound of Formula I from Formula G4 by hydrolysis in the above Step 4 of the preparing method of the present invention is illustrated in the following reaction scheme.

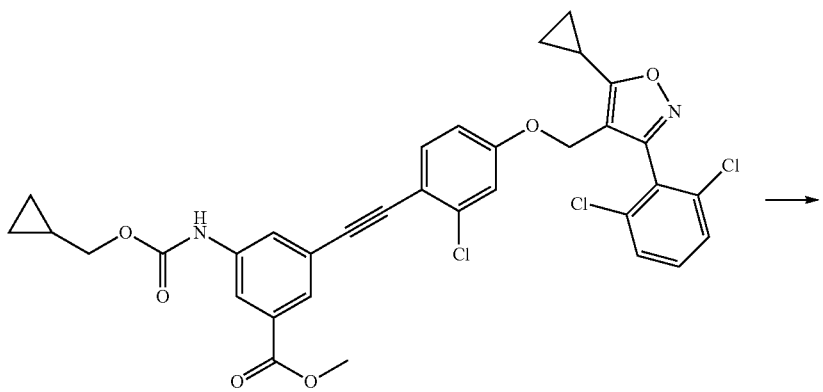

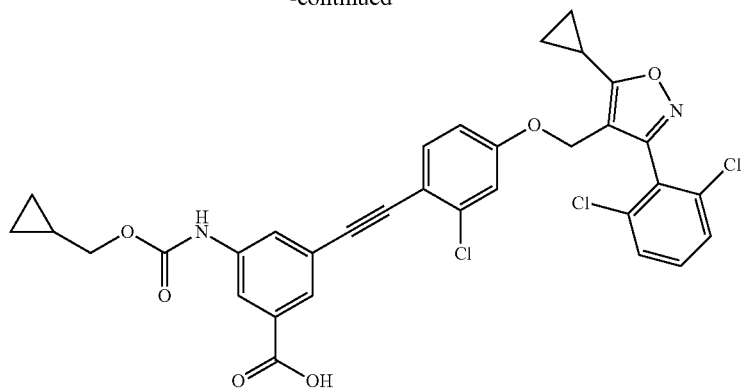

Besides, another preparation method of the compounds of Formula I according to the present invention is shown in the following reaction scheme 6.s

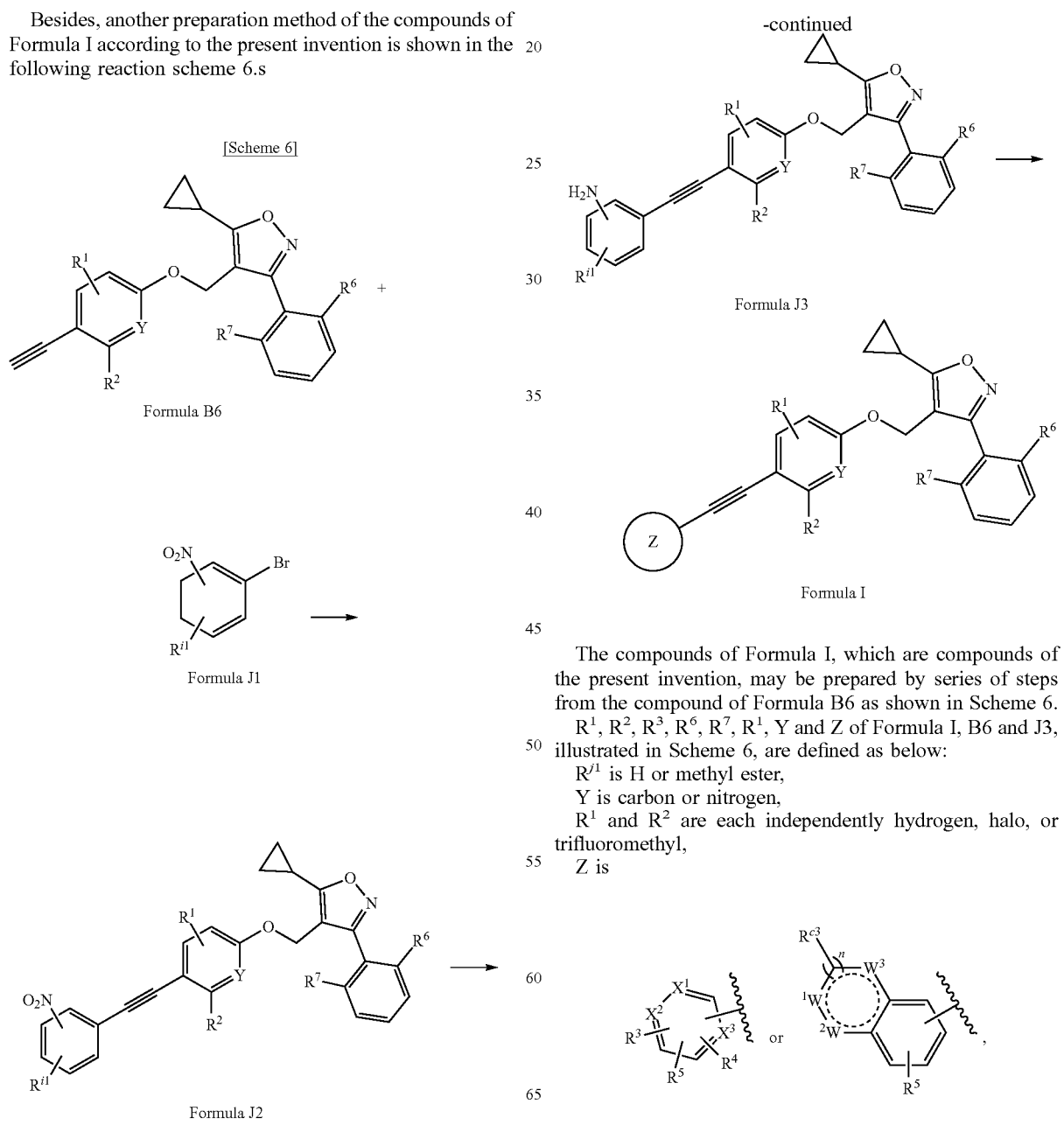

The compounds of Formula I, which are compounds of the present invention, may be prepared by series of steps from the compound of Formula B6 as shown in Scheme 6.

$R^1$, $R^2$, $R^3$, $R^6$, $R^7$, $R^1$, Y and Z of Formula I, B6 and J3, illustrated in Scheme 6, are defined as below:

$R^{j1}$ is H or methyl ester,

Y is carbon or nitrogen, $R^1$ and $R^2$ are each independently hydrogen, halo, or trifluoromethyl, Z is n is 0, 1, or 2, $X^1$, $X^2$ and $X^3$ are each independently carbon or nitrogen, $R^3$ and $R^4$ are each independently hydrogen, halo, cyano, $C_{1-6}$ alkyl, $C_{3-6}$ cycloalkyl, halo $C_{1-6}$ alkyl,

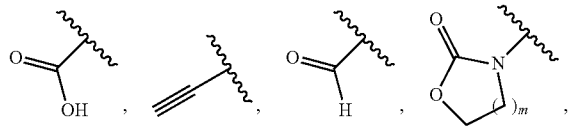

$CONR^{a1}R^{a2}$, $NR^{a1}R^{a2}$, $CH_2NR^{a1}R^{a2}$, $CH_2R^{c3}$, $COR^{a3}$, $OR^{a3}$, $NR^{a4}COR^{a3}$, $NR^{a4}CO_2Ra$, $NHCONHR^{a3}$, $NHSO_2R^{a3}$, or 3- or 8-membered heterocycles containing one or two oxygen or nitrogen atom(s) therein, wherein m is 1 or 2, $R^{a1}$ and $R^{a2}$ are each independently hydrogen, $C_{1-6}$ alkyl, $C_{3-6}$ cycloalkyl, halo $C_{1-6}$ alkyl,

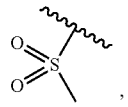

or 3- or 8-membered heterocycles containing one or two oxygen or nitrogen atom(s) therein, $R^{a3}$ is hydrogen, $C_{1-6}$ alkyl, $C_{3-6}$ cycloalkyl, halo $C_{1-6}$ alkyl,

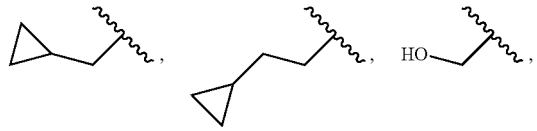

or 3- or 8-membered heterocycles containing one or two oxygen or nitrogen atom(s) therein, $R^{a4}$ is hydrogen or $C_{1-6}$ alkyl, $R^5$ is hydrogen,

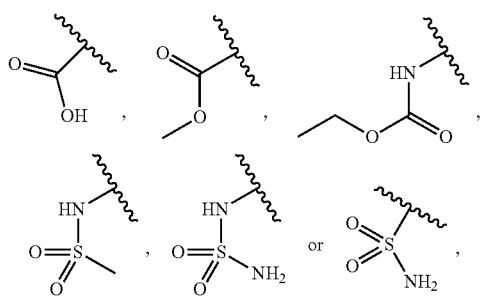

$R^6$ and $R^7$ are each independently hydrogen, halo, trifluoromethyl, or trifluoromethoxy, $R^{c3}$ is hydrogen, halo, $C_{1-6}$ alkyl, or $C_{3-6}$ cycloalkyl, and $W^1$, $W^2$ and $W^3$ are each independently oxygen, nitrogen, $CHR^{w1}$, $CR^{w1}$, $NR^{w1}$, or CO, wherein, $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

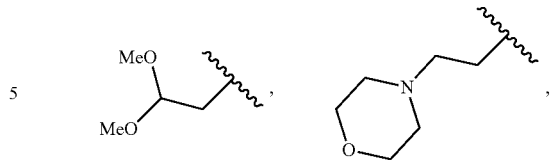

$(CH_2)_p$ heteroaryl, or $(CH_2)_p$ aryl, wherein, p is 1, 2 or 3.

The preparation method of the Formula I according to the present invention comprises:

preparing the compound of Formula J2 by Sonogashira reaction of Formula B6 and J1 (Step 1);

preparing the compound of Formula J3 by reduction of Formula J2 (Step 2); and preparing the compound of Formula I by hydrolysis or addition of compound of Formula J3 (Step 3);

Each step in the above preparation method of scheme 6 is described in more detail as follows.

i) In the first step, the compound of Formula B6, prepared as described in step 4 in scheme 2, may be converted to Formula J2 by Sonogashira reaction with Formula J1 using catalytic amount of tetrakis(triphenylphosphine) palladium (0)(Pd(PPh$_3$)$_4$) or bis(triphenyl phosphine)palladium(II)dichloride (PdCl$_2$(PPh$_3$)$_2$) and Copper(I)iodide under basic condition in one or more of tetrahydrofuran or N,N-dimethylformamide at 70-100° C. for 3-24 hour.

An example of preparing the compound of Formula J2 from the compound of Formula B6 with J1 by Sonogashira reaction in the above Step 1 of the preparing method of the present invention is illustrated in the following reaction scheme.

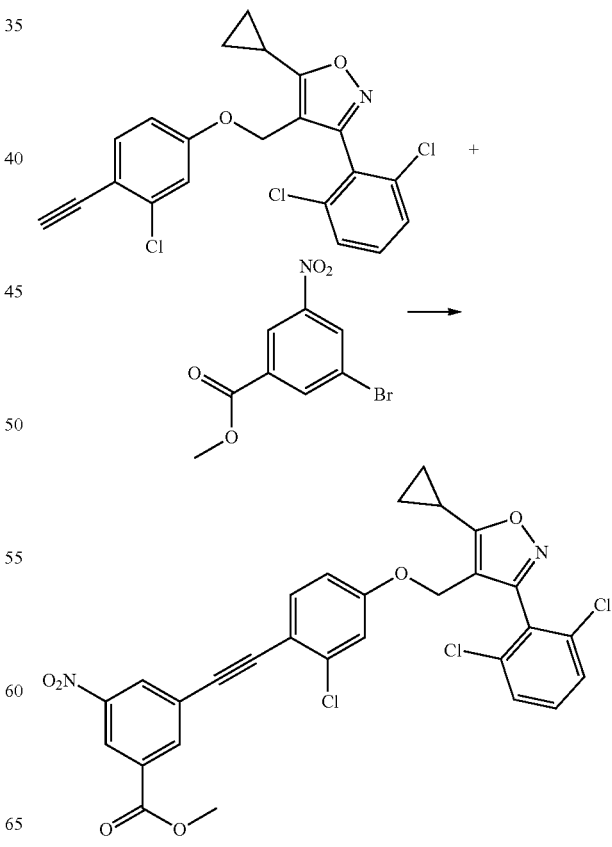

ii) In the second step, the compound of Formula J2, prepared as described in step 1, may be converted to Formula J3 by reduction reaction with Tin(II) chloride dehydrate in ethyl acetate or ethanol at room temperature for one day and it is illustrated in the following reaction scheme.

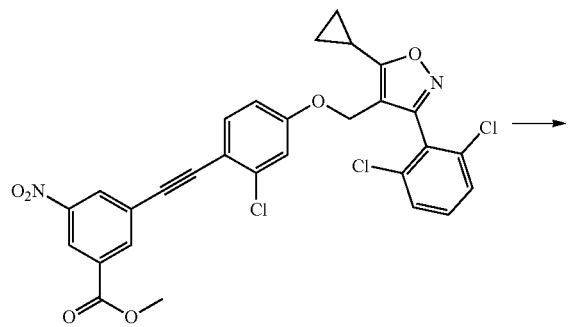

iii) In the third step, the compound of Formula J3, prepared as described in step 2, may be converted to Formula I by hydrolysis or addition reaction.

The third step in the above preparation method of scheme 6 is described in more detail as follows.

In the third step of the preparation method, the desired compound of Formula I may be prepared by hydrolysis or addition reaction.

The compound of Formula J3 may be converted to Formula I by above hydrolysis reaction under the condition of lithium hydroxide in one or more of tetrahydrofuran, 1,4-dioxane or water at rt-80° C. for 4-48 hours and it is illustrated in the following reaction scheme.

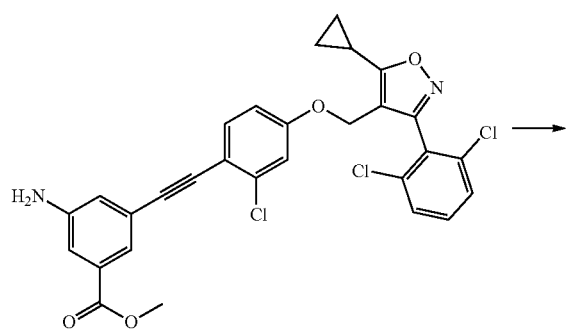

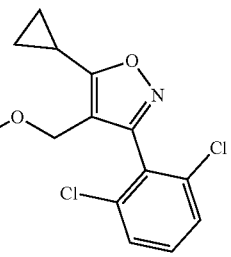

Besides, the compound of Formula I may be prepared by addition reaction with Formula J3 under basic condition in N,N-dimethylformamide or tetrahydrofuran at room temperature or heating condition for 3 or 24 hours in the present invention and it is illustrated in the following reaction scheme.

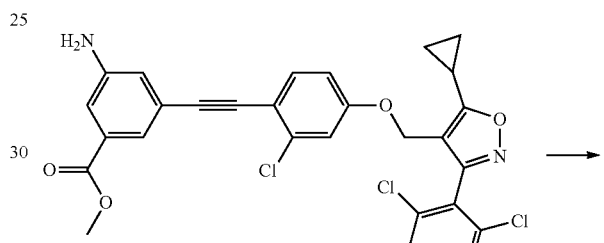

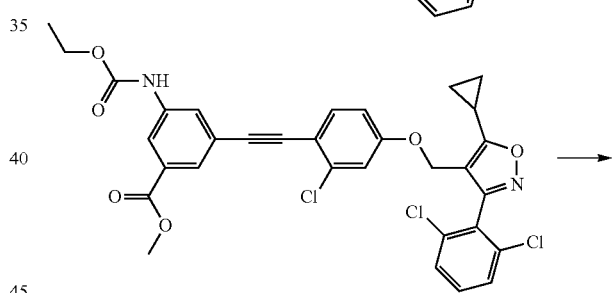

In addition, the present invention provides a pharmaceutical composition for the treatment, prevention, or amelioration of the metabolic diseases, cholestatic liver diseases and organ fibrosis comprising the compound of Formula I, racemate, enantiomer, diastereoisomer thereof, or pharmaceutically acceptable salt thereof.

The metabolic diseases, cholestatic liver diseases and organ fibrosis may be caused by FXR receptor activity. Exemplary diseases include hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes, insulin resistance, metabolic inflexibility, nephropathy, liver diseases, atherosclerosis, cancer, inflammatory disorders, osteoporosis, and skin aging.

The present invention provides a method of the treatment, prevention, or amelioration of metabolic diseases, cholestatic liver diseases and organ fibrosis in a subject in need thereof, comprising administering an effective amount of the pharmaceutical composition to the subject. The dosage of pharmaceutical composition of the present invention may vary depending on the patient's weight, age, gender, physical condition, diet, the time and mode of administration, excretion rates, and the severity of illness. Mammals (including human) are desirable for the individual without limit.

Compounds of the invention intended for pharmaceutical use may be administered as a solid or liquid, such as a tablet, capsule, solution or suspension. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 18th Edition (Mack Publishing Company, 1990.

Oral Administration

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches. Liquid (including multiple phases and dispersed systems) formulations include emulsions, suspensions, solutions, syrups and elixirs. Such formulations may be presented as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

The immediate release portion may comprise a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, powdered cellulose, loweralkyl-substituted hydroxypropyl cellulose, polacrilin potassium, starch, pregelatinized starch, sodium alginate, and mixtures thereof. Generally, the disintegrant will comprise from 1 wt % to 80 wt %, preferably from 5 wt % to 60 wt % of the layer.

Examples of matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof.

When preparing dosage forms incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol, and the like; absorbants, such as silicon dioxide; preservatives, such as methylparaben, propylparaben, and sodium benzoate; surfactants; such as sodium lauryl sulfate, polysorbate 80, and the like; flavorants; and sweeteners. If present, the surfactants would comprise of 0.2 wt % to 5 wt % and the absorbants would comprise from 0.2 wt % to 1 wt %. Other excipients include one or more of: anti-oxidants, colorant, flavouring agents, preservatives and taste-masking agents.

Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in ° Pharmaceutical Dosage Forms: Tablets, Vol. 1±, by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release Parenteral Administration The compounds of the invention may also be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular and subcutaneous.

Suitable devices for parenteral administration include needle (including micro needle) injectors, needle-free injectors, and infusion techniques. An example of a needle free injection is Powderject™

Parenteral formulations are typically aqueous solutions which may contain excipients such as salts, carbohydrates and buffering agents (preferably, to a pH of from 3 to 9), but, for some applications, they may be more suitably formulated as a sterile non aqueous solution or as a powdered, dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

A proper dosage form such as combination with solubility enhancer can increase solubility of compound of formula I used in non-oral solution.

Formulations for parenteral administration may be formulated to be immediate and/or modified/controlled release. Controlled/modified release formulations include delayed-, sustained-, pulsed-, controlled-, targeted and pro-grammed release. Thus compounds of the invention may be formulated as a solid, semi-solid, or thixotropic liquid for administration as an implanted depot providing modified release of the active compound. Examples of such formulations include drug-coated stents and PGLA microspheres.

Local Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Li-posomes may also be used.

Dose

In human patients, the precise daily dose administered depends on various factors such as the age, sex, weight and condition of the patient being treated. The amount of dose can be selected within the bounds of goal achieving treatment effect without harmful or serious adverse effect.

For instance, the dosage of the compound of invention may be administered in an effective amount raging from 0.05 to 1000 mg daily on patients. The following dosage levels and other dosage levels herein are for the average human subject having a weight range of about 65 to 70 kg. The skilled person will readily be able to determine the dosage levels required for a subject whose weight falls outside this range, such as children and the elderly.

The present invention is explained in detail through, but is not limited to, the following examples and experimental examples.

EXAMPLES

<Intermediate 1>4-(bromomethyl)-5-cyclopropyl-3-(2,6-dichlorophenyl)isoxazole

Step 1: Preparation of 2,6-dichlorobenzaldehyde oxime

Sodium hydroxide (6.3 g, 160 mmol) and 2,6-dichlorobenzaldehyde (25 g, 140 mmol) in ethanol (200 ml) was added to hydroxylamine hydrochloride (11 g, 160 mmol) in water (100 ml) and stirred for 24 hours at 90° C. The reaction mixture was evaporated in vacuum, filtered with water (200 ml, 2 times) and dried in vacuum to afford the intermediate compound 2,6-dichlorobenzaldehyde oxime (25.9 g, 96%).

$^1$H-NMR (DMSO, 400 MHz): δ 11.80 (s, 1H), 8.22 (s, 1H), 7.55 (d, 2H), 7.45-7.41 (dd, 1H).

Step 2: Preparation of 2,6-dichloro-N-hydroxybenzimidoyl chloride

N-Chlorosuccinimide (NCS, 18.4 g, 140 mmol) was added to a solution of the intermediate compound (Step 1)(25.9 g, 140 mmol) in chloroform (1000 ml) and stirred for 4 hours at room temperature. The reaction mixture was evaporated in vacuum, diluted with dicholrometane and washed with water. The combined organic layers were dried over MgSO$_4$, filtered, evaporated in vacuum and purified using silica chromatography to afford the intermediate compound 2,6-dichloro-N-hydroxybenzimidoyl chloride (29 g) without any further purification.

Step 3: Preparation of ethyl 5-cyclopropyl-3-(2,6-dichlorophenyl)isoxazole-4-carboxylate The intermediate compound (Step 2)(29 g, 129 mmol) was added to ethyl 3-cyclopropyl-3-oxopropanate (25 ml, 194 mmol) in triethylamine (150 ml) and stirred for 24 hours at room temperature. The reaction mixture was diluted with ethyl acetate and washed with water. The combined organic layers were dried over MgSO$_4$, filtered, evaporated in vacuum and purified using silica chromatography to afford the intermediate compound ethyl 5-cyclopropyl-3-(2,6-dichlorophenyl)isoxazole-4-carboxylate (22.37 g, 56%).

$^1$H-NMR (CDCl$_3$, 400 MHz): δ 7.41-7.38 (m, 2H), 7.35-7.31 (m, 4H), 3.69 (s, 3H), 2.91 (m, 1H), 1.43-1.39 (m, 2H), 1.30-1.26 (m, 2H).

Step 4: (5-cyclopropyl-3-(2,6-dichlorophenyl)isoxazol-4-yl)methanol

1M Diisobutylaluminium hydride (DIBAL-H, 144 ml, 144 mmol) was added to the intermediate compound (Step 3)(22.37 g, 71.7 mmol) in tetrahydrofuran (72 ml) at 0° C. and stirred for 7 hours at room temperature. The reaction mixture was diluted with ethyl acetate and washed with 10 w/w % citric acid solution and water. The combined organic layers were dried over MgSO$_4$, filtered, evaporated in vacuum and purified using silica chromatographyto afford the intermediate compound (5-cyclopropyl-3-(2,6-dichlorophenyl)isoxazol-4-yl)methanol (12.2 g, 60%).

$^1$H-NMR (CDCl$_3$, 400 MHz): δ 7.44-7.40 (m, 2H), 7.37-7.33 (m, 1H), 4.41 (d, 2H), 2.19 (m, 1H), 1.40 (t, 1H), 1.30-1.25 (m, 2H), 1.17-1.10 (m, 2H).

Step 5: Preparation of 4-(bromomethyl)-5-cyclopropyl-3-(2,6-dichlorophenyl) isoxazole Triphenylphosphine (TPP, 16.9 g, 64.53 mmol) and tetrabromomethane (21.4 g, 64.53 mmol) was slowly added to the intermediate compound (Step 4)(12.2 g, 43.02 mmol) in dichloromethane (158 ml) at 0° C. and stirred for 4 hours at room temperature. The reaction mixture was evaporated in vacuum and purified using silica chromatography to afford the title compound (13.44 g, 90%).

$^1$H-NMR (CDCl$_3$, 400 MHz): δ 7.46-7.45 (dd, 2H), 7.40-7.36 (dd, 1H), 4.23 (s, 2H), 2.12 (m, 1H), 1.32-1.23 (m, 2H), 1.22-1.17 (m, 2H).

<Example 1>4-((4-((5-cyclopropyl-3-(2,6-dichlorophenyl)isoxazol-4-yl) methoxy)phenyl)ethynyl)benzoic acid (I-1)

Step 1: Preparation of tert-butyl(4-iodophenoxy)dimethylsilane tert-Butyldimethylsilyl chloride (TBSCl, 2.1 g, 13.6 mmol) and imidazole (1.2 g, 18.2 mmol) were added to a solution of 4-Iodophenol (2 g, 9.1 mmol) in N,N-dimethylformamide (45 ml) and stirred for 12 hours at room temperature. The reaction mixture was diluted with ethyl acetate and washed with water. The combined organic layers were dried over MgSO$_4$, filtered, evaporated in vacuum and purified using silica chromatography to afford the intermediate compound tert-butyl(4-iodophenoxy)dimethylsilane (2.8 g, 93%).

$^1$H-NMR (CDCl$_3$, 400 MHz): δ 7.32 (m, 2H), 6.43 (m, 2H), 0.78 (t, 9H), 0.23 (t, 6H).

Step 2: Preparation of tert-butyl(4-((trimethylsilyl)ethyl)phenoxy)silane

Trimethylsilylacetylene (2.4 ml, 17 mmol), bis(triphenylphosphine)palladium(ii) dichloride (PdCl$_2$(PPh$_3$)$_2$, 0.6 g, 0.85 mmol), Copper(I) iodide (0.16 g, 0.85 mmol), and triethylamine (0.6 ml, 4.25 mmol) were added to a solution of the intermediate compound (Step 1)(2.8 g, 8.5 mmol) in N,N-dimethylformamide (50 ml) and stirred for 12 hours at 80° C. The reaction mixture was diluted with Ethyl acetate and washed with water. The combined organic layers were dried over $MgSO_4$, filtered, evaporated in vacuum and purified using silica chromatography to afford the intermediate compound tert-butyl(4-((trimethylsilyl)ethyl)phenoxy) silane (1.99 g, 77%).

$^1$H-NMR ($CDCl_3$, 400 MHz): δ 7.32 (m, 2H), 6.43 (m, 2H), 0.78 (s, 9H), 0.25 (s, 9H), 0.23 (s, 6H).

Step 3: Preparation of 4-((trimethylsilly) ethynyl)phenol

Potassium fluoride (KF, 3.8 g, 65 mmol) was added to a solution of the intermediate compound (Step 2)(1.99 g, 6.5 mmol) in methanol (65 ml) at 0° C. and stirred for 1 hour. The reaction mixture was diluted with dichloromethane and washed with water. The combined organic layers were dried over $MgSO_4$, filtered, and evaporated in vacuum. The resulting 4-((trimethylsilly)ethyl)phenol was used for next step without any further purification.

Step 4: Preparation of 5-cyclopropyl-3-(2,6-dichlorophenyl)-4-((4-ethynylphenoxy)methyl)isoxazole 4-(Bromomethyl)-5-cyclopropyl-3-(2,6-dichlorophenyl) isoxlazole (Intermediate 1)(2.25 g, 6.5 mmol) and potassium carbonate (1.34 g, 9.75 mmol) were added to a solution of the intermediate compound (Step 3)(1.25 g, 6.5 mmol) in N,N-dimethylformamide (65 ml) stirred for 12 hours at room temperature. The reaction mixture was diluted with ethyl acetate and washed with water. The combined organic layers were dried over $MgSO_4$, filtered, evaporated in vacuum and purified using silica chromatography to afford the intermediate compound 5-cyclopropyl-3-(2,6-dichlorophenyl)-4-((4-ethynylphenoxy)methyl)isoxazole (2.05 g, 82%)

$^1$H-NMR ($CDCl_3$, 400 MHz): δ 7.41-7.30 (m, 5H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 5: Preparation of methyl 4-((4-((5-cyclopropyl-3-(2,6-dichlorophenyl) isoxazol-4-yl)methoxy) phenyl)ethynyl)benzoate 4-Iodobenzoate (67 mg, 0.52 mmol), bis(triphenylphosphine)palladium(ii) dichloride ($PdCl_2(PPh_3)_2$, 42 mg, 0.06 mmol), Copper(I) iodide (11.4 mg, 0.06 mmol), and 1,8-Diazabicyclo[5.4.0]undec-7-ene (DBU, 0.4 ml, 2.6 mmol) were added to a solution of the intermediate compound (Step 4)(200 mg, 0.52 mmol) in N,N-dimethylformamide (5.2 ml) and stirred for 4 hours at 80° C. The reaction mixture was diluted with Ethyl acetate and washed with water. The combined organic layers were dried over $MgSO_4$, filtered, evaporated in vacuum and purified using silica chromatography to afford the intermediate compound methyl 4-((4-((5-cyclopropyl-3-(2,6-dichlorophenyl)isoxazol-4-yl) methoxy)phenyl)ethynyl)benzoate (175 mg, 65%).

$^1$H-NMR (MeOD, 400 MHz): δ 8.03 (d, 2H), 8.01-7.40 (m, 7H), 6.83 (d, 2H), 4.94 (s, 2H), 3.93 (s, 3H), 2.37-2.34 (m, 1H), 1.24-1.22 (m, 4H).

Step 6: Preparation of 4-((4-((5-cyclopropyl-3-(2,6-dichlorophenyl)isoxazol-4-yl)methoxy)phenyl)ethynyl)benzoic acid Lithium hydroxide (14.2 mg, 0.34 mmol) was added to a solution of the intermediate compound (Step 5)(175 mg, 0.34 mmol) in 1,4-dioxane (3 ml) and distilled water (0.4 ml) and stirred for 18 hours at room temperature. The reaction mixture was acidified to pH of 2-3 with 1N HCl and extracted with ethyl acetate. The combined organic layers were dried over $MgSO_4$, filtered, and evaporated in vacuum to afford the title compound (133 mg, 78%).

$^1$H-NMR ($CDCl_3$, 400 MHz): δ 8.01 (dd, 2H), 7.55 (dd, 2H), 7.43-7.40 (m, 4H), 7.34-7.32 (m, 1H), 6.79 (d, 2H), 4.83 (s, 2H), 2.20-2.16 (m, 1H), 1.30-1.22 (m, 2H), 1.19-1.13 (m, 2H).

<Example 2> 3-((4-((5-cyclopropyl-3-(2,6-dichlorophenyl)isoxazol-4-yl) methoxy)phenyl)ethynyl)benzoic acid (I-2)

Step 1: Preparation of methyl 3-((4-((5-cyclopropyl-3-(2,6-dichlorophenyl) isoxazol-4-yl)methoxy) phenyl)ethynyl)benzoate This compound was made using the procedure described in Example 1 (Step 5). Thus, this intermediate compound (Step 4 of Example 1)(100 mg, 0.26 mmol) was reacted with methyl 3-bromobenzoate (56 mg, 0.26 mmol), bis(triphenylphosphine) palladium(II) dichloride ($PdCl_2(PPh_3)_2$, 21 mg, 0.03 mmol), Copper(I) iodide (5.7 mg, 0.03 mmol), and 1,8-Diazabicyclo[5.4.0]undec-7-ene (DBU, 0.2 ml, 1.3 mmol) to afford the intermediate compound methyl 3-((4-((5-cyclopropyl-3-(2,6-dichlorophenyl)isoxazol-4-yl) methoxy)phenyl)ethynyl)benzoate (40 mg, 30%).

$^1$H-NMR ($CDCl_3$, 400 MHz): δ 8.17 (s, 1H), 8.17-7.96 (m, 1H), 7.68-7.65 (m, 1H), 7.42-7.40 (m, 5H), 7.34-7.30 (m, 1H), 6.80-6.77 (m, 2H), 4.82 (s, 2H), 3.93 (s, 3H), 2.19-2.15 (m, 1H), 1.31-1.27 (m, 2H), 1.17-1.13 (m, 2H).

Step 2: Preparation of 3-((4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(40 mg, 0.08 mmol) was reacted with lithium hydroxide (LiOH, 3.3 mg, 0.08 mmol) to afford the title compound (30 mg, 78%).

$^1$H-NMR ($CDCl_3$, 400 MHz): δ 8.19-8.18 (m, 1H), 8.00-7.98 (m, 1H), 7.68-7.66 (m, 1H), 7.43-7.40 (m, 5H), 7.36-7.34 (m, 1H), 6.80-6.77 (m, 2H), 4.83 (s, 2H), 2.20-2.16 (m, 1H), 1.31-1.26 (m, 2H), 1.19-1.14 (m, 2H).

<Example 3> 3-((4-((5-cyclopropyl-3-(2,6-dichlorophenyl)isoxazol-4-yl) methoxy)-2-(trifluoromethyl) phenyl)ethynyl)benzoic acid (I-3)

Step 1: Preparation of tert-butyl(4-iodo-3-(trifluoromethyl)phenoxy) dimethylsilane E This compound was made using the procedure described for Example 1 (Step 1). Thus, 4-iodo-3-(trifluoromethyl) phenol (40 mg, 0.14 mmol) was reacted with tert-Butyldimethylsilyl chloride (TBSCl, 32 mg, 0.21 mmol) and imidazole (19 mg, 0.28 mmol) to afford the intermediate compound tert-butyl(4-iodo-3-(trifluoro methyl)phenoxy) dimethylsilane (52 mg, 93%).

$^1$H-NMR (CDCl$_3$, 400 MHz): δ 7.64 (d, 1H), 6.97 (d, 1H), 6.48 (dd, 1H), 0.96 (s, 9H), 0.16 (s, 6H).

Step 2: Preparation of tert-butyldimethyl(3-(trifluoromethyl)-4-((trimethylsilyl) ethynyl)phenoxy)silane This compound was made using the procedure described in Example 1 (Step 2). Thus, this intermediate compound (Step 1)(52 mg, 0.13 mmol) was reacted with trimethylsilylacetylene (0.036 ml, 0.26 mmol), bis(triphenylphosphine) palladium(ii) dichloride (PdCl$_2$(PPh$_3$)$_2$, 9.1 mg, 0.013 mmol), Copper(I) iodide (2.4 mg, 0.013 mmol) and triethylamine (0.095 ml, 0.65 mmol) to afford the intermediate compound tert-butyldimethyl(3-(trifluoromethyl)-4-((trimethylsilyl)ethynyl) phenoxy)silane (41.1 mg, 88%).

$^1$H-NMR (CDCl$_3$, 400 MHz): δ 7.35 (d, 1H), 6.87 (d, 1H), 6.66 (dd, 1H), 0.96 (s, 9H), 0.25 (s, 9H), 0.19 (s, 6H).

Step 3: Preparation of 3-(trifluoromethyl)-4-((trimethylsilyl)ethynyl)phenol

This compound was made using the procedure described in Example 1 (Step 3). Thus, this intermediate compound (Step 2)(41.1 mg, 0.16 mmol) was reacted with Potassium fluoride (KF, 93 mg, 1.6 mmol) to afford the intermediate compound 3-(trifluoromethyl)-4-((trimethylsilyl)ethynyl) phenol. The resulting residue was used for next step without any further purification.

Step 4: Preparation of 5-cyclopropyl-3-(2,6-dichlorophenyl)-4-((4-ethynyl-3-(trifluoromethyl)phenoxy) methyl)isoxazole This compound was made using the procedure described in Example 1 (Step 4). Thus, this intermediate compound (Step 3)(0.16 mmol) was reacted with 4-(bromomethyl)-5-cyclopropyl-3-(2,6-dichlorophenyl)isoxlazole (Intermediate 1)(50 mg, 0.144 mmol), and potassium carbonate (26.6 mg, 0.192 mmol) to afford the intermediate compound 5-cyclopropyl-3-(2,6-dichlorophenyl)-4-((4-ethynyl-3-(trifluoromethyl)phenoxy)methyl)isoxazole (36 mg, 50%).

$^1$H-NMR (CDCl$_3$, 400 MHz): δ 7.50-7.48 (m, 1H), 7.40-7.30 (m, 3H), 7.08-7.04 (m, 1H), 6.90-6.86 (m, 1H), 4.86 (s, 2H), 3.25 (s, 1H), 2.17-2.11 (m, 1H), 1.35-1.22 (m, 2H), 1.18-1.14 (m, 2H).

Step 5: Preparation of methyl 3-((4-((5-cyclopropyl-3-(2,6-dichlorophenyl) isoxazol-4-yl)methoxy)-2-(trifluoromethyl)phenyl)ethynyl)benzoate This compound was made using the procedure described in Example 1 (Step 5). Thus, this intermediate compound (Step 4)(36 mg, 0.080 mmol) was reacted with methyl 3-iodobenzoate (21 mg, 0.080 mmol), bis(triphenylphosphine)palladium(II) dichloride (PdCl$_2$(PPh$_3$)$_2$, 5.6 mg, 0.008 mmol), Copper(I) iodide (1.5 mg, 0.008 mmol) and triethylamine (0.013 ml, 0.096 mmol) to afford the intermediate compound methyl 3-((4-((5-cyclopropyl-3-(2,6-dichlorophenyl)isoxazol-4-yl) methoxy)-2-(trifluoromethyl)phenyl) ethynyl)benzoate (3 mg, 75%).

$^1$H-NMR (CDCl$_3$, 400 MHz): δ 8.17-8.16 (m, 1H), 8.02-7.99 (m, 1H), 7.70-7.67 (m, 1H), 7.54-7.51 (m, 1H), 7.45-7.31 (m, 4H), 7.09-7.08 (m, 1H), 6.94-6.91 (m, 1H), 4.88 (s, 2H), 3.94 (s, 3H), 2.18-2.13 (m, 1H), 1.33-1.29 (m, 2H), 1.22-1.15 (m, 2H).

Step 6: Preparation of 3-((4-((5-cyclopropyl-3-(2,6-dichlorophenyl)isoxazol-4-yl)methoxy)-2-(trifluoromethyl)phenyl)ethynyl)benzoic acid This compound was made using the procedure described in Example 1 (Step 6). Thus, this intermediate compound (Step 5)(35 mg, 0.06 mmol) was reacted with lithium hydroxide (2.5 mg, 0.06 mmol) to afford the title compound (23 mg, 68%).

$^1$H-NMR (CDCl$_3$, 400 MHz): δ 8.23-8.21 (m, 1H), 8.06-8.05 (m, 1H), 7.71-7.66 (m, 1H), 7.55-7.31 (m, 5H), 7.09-7.08 (m, 1H), 7.00-6.91 (m, 1H), 4.88 (s, 2H), 2.17-2.12 (m, 1H), 1.33-1.28 (m, 2H), 1.20-1.15 (m, 2H).

<Example 4> 4-((4-((5-cyclopropyl-3-(2,6-dichlorophenyl)isoxazol-4-yl) methoxy)-2-(trifluoromethyl) phenyl)ethynyl)benzoic acid (I-4)

Step 1: Preparation of methyl 4-((4-((5-cyclopropyl-3-(2,6-dichlorophenyl) isoxazol-4-yl)methoxy)-2-(trifluoromethyl)phenyl)ethynyl)benzoate This compound was made using the procedure described in Example 1 (Step 5). Thus, the intermediate compound (Step 4 of Example 3) 5-cyclopropyl-3-(2,6-dichlorophenyl)-4-((4-ethynyl-3-(trifluoromethyl)phenoxy)methyl) isoxazole (45 mg, 0.1 mmol) was reacted with methyl 4-iodobenzoate (28 mg, 0.1 mmol), bis(triphenylphosphine) palladium(II) dichloride (PdCl$_2$(PPh$_3$)$_2$, 13 mg, 0.02 mmol), copper(I) iodide (1.7 mg, 0.01 mmol) and triethylamine (0.06 ml, 0.46 mmol) to afford the intermediate compound methyl 4-((4-((5-cyclopropyl-3-(2,6-dichloro phenyl)isoxazol-4-yl)methoxy)-2-(trifluoromethyl)phenyl)ethynyl)benzoate (42 mg, 71%).

$^1$H-NMR (CDCl$_3$, 400 MHz): δ 8.02 (dd, 2H), 7.57-7.52 (m, 3H), 7.41-7.39 (m, 2H), 7.35 (dd, 1H), 7.09 (d, 1H), 6.94 (dd, 1H), 4.88 (s, 2H), 3.93 (s, 3H), 2.17-2.13 (m, 1H), 1.32-1.27 (m, 2H), 1.20-1.16 (m, 2H).

Step 2: Preparation of 4-((4-((5-cyclopropyl-3-(2,6-dichlorophenyl)isoxazol-4-yl)methoxy)-2-(trifluoromethyl)phenyl)ethynyl)benzoic acid This compound was made using the procedure described in Example 1 (Step 6). Thus, the intermediate compound (Step 1)(42 mg, 0.07 mmol) was reacted with lithium hydroxide (29 mg, 0.7 mmol) to afford the title compound (40 mg, 100%).

$^1$H-NMR (DMSO, 400 MHz): δ 13.27 (s, 1H), 8.05 (d, 2H), 7.78 (d, 1H), 7.73-7.58 (m, 5H), 7.24-7.21 (m, 2H), 5.15 (s, 2H), 2.59 (m, 1H), 1.29-1.21 (m, 4H).

<Example 5> 4-((3-chloro-4-ethynylphenoxy) methyl)-5-cyclopropyl-3-(2,6-dichlorophenyl)isoxazole (I-5)

Step 1: Preparation of tert-butyl(3-chloro-4-iodophenoxy)dimethylsilane

This compound was made using the procedure described in Example 1 (Step 1). Thus, 3-chloro-4-iodophenol (10 g, 39.5 mmol) was reacted with tert-butyldimethylsilyl chloride (TBSCl, 7.5 g, 47.2 mmol) and imidazole (3 g, 59 mmol) to afford the intermediate compound tert-butyl(3-chloro-4-iodo phenoxy)dimethylsilane (9 g, 66%).

¹H-NMR (CDCl₃, 400 MHz): δ 7.64 (d, 1H), 6.97 (d, 1H), 6.48 (dd, 1H), 0.96 (s, 9H), 0.16 (s, 6H).

Step 2: Preparation of tert-butyl(3-chloro-4-((trimethylsilyl)ethynyl)phenoxy) dimethylsilane This compound was made using the procedure described in Example 1 (Step 2). Thus, the intermediate compound (Step 1)(9 g, 24.4 mmol) was reacted with trimethylsilylacetylene (6.76 ml, 48.8 mmol), bis(triphenylphosphine)palladium(II) dichloride (PdCl₂(PPh₃)₂, 0.85 g, 1.22 mmol), copper(I) iodide (0.23 g, 1.22 mmol), triethylamine (15.3 ml, 109.8 mmol) to afford the intermediate compound tert-butyl(3-chloro-4-((trimethylsilyl)ethynyl)phenoxy)dimethylsilane (7.44 g, 90%).

¹H-NMR (CDCl₃, 400 MHz): δ 7.35 (d, 1H), 6.87 (d, 1H), 6.66 (dd, 1H), 0.96 (s, 9H), 0.25 (s, 9H), 0.19 (s, 6H).

Step 3: Preparation of 3-chloro-4-((trimethylsilyl)ethynyl)phenol

This compound was made using the procedure described in Example 1 (Step 3). Thus, the intermediate compound (Step 2)(7.44 g, 21.9 mmol) was reacted with potassium fluoride (KF, 12.7 g, 219 mmol) to afford the intermediate compound 3-chloro-4-((trimethylsilyl)ethynyl)phenol and used without further purification.

Step 4: Preparation of 4-((3-chloro-4-ethyntlphenoxy)metehyl)-5-cyclopropyl-3-(2,6-dichlorophenyl)isoxazole This compound was made using the procedure described in Example 1 (Step 4). Thus, the intermediate compound (Step 3)(4.92 g, 21.9 mmol) was reacted with 4-(bromomethyl)-5-cyclopropyl-3-(2,6-dichlorophenyl)isoxazole (Example 1)(7.59 g, 21.9 mmol) and potassium carbonate (4.54 g, 32.9 mmol) to afford the title compound (7.15 g, 78%).

¹H-NMR (CDCl₃, 400 MHz): δ 7.41-7.30 (m, 4H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

<Example 6>4-((3-chloro-4-(phenylethynyl)phenoxy)methyl)-5-cyclopropyl-3-(2,6-dichlorophenyl)isoxazole (I-6)

Step 1: Preparation of 4-((3-chloro-4-(phenylethynyl)phenoxy)methyl)-5-cyclopropyl-3-(2,6-dichlorophenyl)isoxazole This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(128 mg, 0.306 mmol) was reacted with bromobenzene (48 mg, 0.306 mmol), bis(triphenylphosphine)palladium(II) dichloride (PdCl₂(PPh₃)₂, 21.5 mg, 0.031 mmol), copper(I) iodide (5.8 mg, 0.031 mmol) and triethylamine (0.052 ml, 0.367 mmol) to afford the title compound (7.15 g, 78%).

¹H-NMR (CDCl₃, 400 MHz): δ 7.54-7.52 (m, 2H), 7.42-7.31 (m, 7H), 6.87-6.86 (d, 1H), 6.69-6.66 (dd, 1H), 4.81 (s, 2H), 2.17-2.04 (m, 1H), 1.29-1.24 (m, 2H), 1.19-1.14 (m, 2H).

<Example 7> methyl 3-((2-chloro-4-((5-cyclopropyl-3-(2,6-dichlorophenyl) isoxazol-4-yl)methoxy) phenyl)ethynyl)benzoate (I-7)

Step 1: Preparation of methyl 3-((2-chloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 6)(128 mg, 0.31 mmol) was reacted with methyl 3-iodobenzoate (80 mg, 0.31 mmol), bis(triphenylphosphine)palladium(II) dichloride (PdCl₂(PPh₃)₂, 22 mg, 0.03 mmol), Copper(I) iodide (5.8 mg, 0.03 mmol) and triethylamine (0.052 ml, 0.37 mmol) to afford the title compound (107 mg, 63%).

¹H-NMR (CDCl₃, 400 MHz): δ 8.20-8.19 (m, 1H), 8.01-7.98 (m, 1H), 7.72-7.69 (m, 1H), 7.43-7.32 (m, 5H), 6.88-6.87 (m, 1H), 6.71-6.68 (m, 1H), 4.82 (s, 2H), 3.94 (s, 3H), 2.18-2.15 (m, 1H), 1.32-1.28 (m, 2H), 1.20-1.16 (m, 2H).

<Example 8> Methyl 3-((2-chloro-4-((5-cyclopropyl-3-(2,6-dichlorophenyl) isoxazol-4-yl)methoxy) phenyl)ethynyl)-5-((ethoxycarbonyl)amino)benzoate (I-8)

Step 1: Preparation of methyl 3-((2-chloro-4-((5-cyclopropyl-3-(2,6-dichlorophenyl)isoxazol-4-yl)methoxy)phenyl)ethynyl)-5-nitrobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(3.6 g, 8.59 mmol) was reacted with methyl 3-bromo-5-nitrobenzoate (2.6 g, 10.3 mmol), bis(triphenylphosphine)palladium(II) dichloride (PdCl₂(PPh₃)₂, 302 mg, 0.429 mmol), copper(I)iodide (81.8 mg, 0.429 mmol) and triethylamine (1.44 ml, 10.3 mmol) to afford the intermediate compound methyl 3-((2-chloro-4-((5-cyclopropyl-3-(2,6-dichlorophenyl)isoxazol-4-yl)methoxy)phenyl)ethynyl)-5-nitrobenzoate (3.9 g, 80%).

¹H-NMR (CDCl₃, 400 MHz): δ 8.78 (t, 1H), 8.51 (t, 1H), 8.46*t, 1H), 7.44-7.40 (m, 3H), 7.36-7.32 (m, 1H), 6.89 (d, 1H), 6.73 (dd, 1H), 4.84 (s, 2H), 4.00 (s, 3H), 2.19-2.13 (m, 1H), 1.32-1.28 (m, 2H), 1.20-1.15 (m, 2H).

Step 2: Preparation of methyl 3-amino-5-((2-chloro-4-((5-cyclopropyl-3-(2,6-dichlorophenyl)isoxazol-4-yl)methoxy)phenyl)ethynyl)benzoate The intermediate compound (Step 1) was dissolved in ethyl acetate (70 ml) and ethanol (35 ml) and tin(II) chloride dihydrate (15.5 g, 68.7 mmol) were added. The reaction was stirred at room temperature for 1 day. The reaction mixture was extracted with ethyl acetate and washed with water. The combined organic phase was dried over MgSO₄, filtered, concentrated and purified by column chromatography on silica to give methyl 3-amino-5-((2-chloro-4-((5-cyclopropyl-3-(2,6-dichlorophenyl)isoxazol-4-yl)methoxy)phenyl)ethynyl)benzoate (3.0 g, 77%).

¹H-NMR (CDCl₃, 400 MHz): δ 7.59-7.58 (m, 1H), 7.41-7.27 (m, 5H), 7.00-6.99 (m, 1H), 6.87-6.86 (m, 1H), 6.69-6.67 (m, 1H), 4.82 (s, 2H), 3.90 (s, 3H), 2.19-2.12 (m, 1H), 1.31-1.28 (m, 2H), 1.20-1.14 (m, 2H).

Step 3: Preparation of methyl 3-((2-chloro-4-((cyclopropyl-3-(2,6-dichlorophenyl)isoxazol-4-yl)methoxy)phenyl)ethynyl)-5-((ethoxycarbonyl)amino)benzoate The intermediate compound (Step 2) was dissolved in N,N-dimethylformamide (8.8 ml) and ethylchloroformate (250 ul, 2.64 mmol), triethylamine (369 ul, 2.64 mmol) and 1,8-Diazabicyclo[5.4.0]undec-7-ene (DBU, 13 ul, 0.0881 mmol) were added. The reaction was stirred at room temperature for 4 hours. The reaction mixture was extracted with ethyl acetate and washed with water. The combined organic phase was dried over MgSO$_4$, filtered, concentrated and purified by column chromatography on silica to give the title compound (254 mg, 65%).

$^1$H-NMR (CDCl$_3$, 400 MHz): δ 13.42 (br, 1H), 8.03 (d, 1H), 7.82 (t, 1H), 7.65-7.61 (m, 2H), 7.58-7.54 (m, 1H), 7.13 (d, 1H), 6.87 (dd, 1H), 5.01 (s, 2H), 1.05-1.32 (m, 5H).

<Example 9> Methyl 3-(tert-butoxycarbonyl)amino)-5-((2-chloro-4-((cyclopropyl-3-(2,6-dichlorophenyl)isoxazol-4-yl)methoxy)phenyl)ethynyl)benzoate (I-9)

Step 1: Preparation of methyl 3-(tert-butoxycarbonyl)amino)-5-((2-chloro-4-((cyclopropyl-3-(2,6-dichlorophenyl)isoxazol-4-yl)methoxy)phenyl)ethynyl)benzoate This compound was made using the procedure described in Example 8 (Step 3). Thus, methyl 3-amino-5-((2-chloro-4-((cyclopropyl-3-(2,6-dichlorophenyl) isoxazol-4-yl)methoxy)phenyl)ethynyl)benzoate (Step 2 of Example 8)(500 mg, 0.880 mmol) was reacted with di-tert-butyl decarbonate (385 mg, 1.76 mmol), 4-dimethylaminopyridine (5.4 mg, 0.044 mmol) and triethylamine (0.2 ml, 1.32 mmol) to afford the title compound (300 mg, 51%).

$^1$H-NMR (CDCl$_3$, 400 MHz): δ 8.12 (t, 1H), 7.89 (t, 1H), 7.79 (t, 1H), 7.51-7.31 (m, 5H), 6.86 (d, 1H), 6.69 (dd, 1H), 6.61 (s, 1H), 4.81 (s, 2H), 3.93 (s, 3H), 2.17 (m, 1H), 1.52 (s, 9H), 1.31-1.23 (m, 2H), 1.19-1.16 (m, 2H).

<Example 10> Methyl 3-((2-chloro-4-((cyclopropyl-3-(2,6-dichlorophenyl) isoxazol-4-yl)methoxy)phenyl)ethynyl)-5-((ethoxycarbonyl)(methyl)amino)benzoate (I-10)

Step 1: Preparation of methyl 3-((2-chloro-4-((cyclopropyl-3-(2,6-dichlorophenyl) isoxazol-4-yl)methoxy)phenyl)ethynyl)-5-((ethoxycarbonyl)(methyl)amino)benzoate The compound methyl 3-((2-chloro-4-((5-cyclopropyl-3-(2,6-dichlorophenyl) isoxazol-4-yl)methoxy)phenyl)ethynyl)-5-((ethoxycarbonyl)amino)benzoate (Example 8)(220 mg, 0.348 mmol) was dissolved in N,N-dimethylformamide (5 ml) and sodium hydride (25 mg, 1.04 mmol) and iodomethane (87 ul, 1.39 mmol) were added. The reaction was stirred at room temperature for 20 hours. The reaction mixture was extracted with ethyl acetate and washed with water. The combined organic phase was dried over MgSO$_4$, filtered, concentrated and purified by column chromatography on silica to afford the title compound (113 mg, 48%).

$^1$H-NMR (CDCl$_3$, 400 MHz): δ 8.02 (t, 1H), 7.88 (s, 1H), 7.62 (s, 1H), 7.42-7.38 (m, 1H), 7.35-7.31 (m, 1H), 6.87 (d, 1H), 6.70 (dd, 1H), 4.82 (s, 2H), 4.22 (q, 2H), 3.93 (s, 3H), 3.32 (s, 3H), 2.17-2.13 (m, 1H), 1.34 (t, 3H), 1.32-1.24 (m, 2H), 1.23-1.14 (m, 2H).

<Example 11> ethyl(3-((2-chloro-4-((5-cyclopropyl-3-(2,6-dichlorophenyl) isoxazol-4-yl)methoxy)phenyl)ethynyl)phenyl)carbamate (I-11)

Step 1: Preparation of 4-((3-chloro-4-((3-nitrophenyl)ethynyl)phenoxy)methyl)-5-cyclopropyl-3-(2,6-dichlorophenyl)isoxazole This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(300 mg, 0.72 mmol) was reacted with 1-iodo-3-nitrobenzene (178.4 mg, 0.72 mmol), tetrakis(triphenylphosphine) palladium(0) (Pd(PPh$_3$)$_4$, 81 mg, 0.07 mmol), copper(I) iodide (13.3 mg, 0.07 mmol) and N,N-diisopropylethylamine (0.15 ml, 0.86 mmol) to afford the intermediate compound 4-((3-chloro-4-((3-nitrophenyl)ethynyl)phenoxy)methyl)-5-cyclo propyl-3-(2,6-dichlorophenyl)isoxazole (368.8 mg, 95%).

$^1$H-NMR (CDCl$_3$, 400 MHz): δ 8.36 (s, 1H), 8.17 (d, 1H), 7.82 (d, 1H), 7.55-7.43 (m, 2H), 7.42-7.40 (m, 3H), 6.88 (d, 1H), 6.71 (dd, 1H), 4.83 (s, 2H), 2.18-2.13 (m, 1H), 1.31-1.30 (m, 2H), 1.19-1.17 (m, 2H).

Step 2: Preparation of 3-((2-chloro-4-((5-cyclopropyl-3-(2,6-dichlorophenyl) isoxazol-4-yl)methoxy)phenyl)ethynyl)aniline This compound was made using the procedure described in Example 8 (Step 2). Thus, this intermediate compound (Step 1)(100 mg, 0.19 mmol) was reacted with tin(I) chloride dihydrate (208.9 mg, 0.93 mmol) to afford the intermediate compound 3-((2-chloro-4-((5-cyclopropyl-3-(2,6-dichlorophenyl)isoxazol-4-yl)methoxy)phenyl)ethynyl)aniline (60 mg, 62%).

$^1$H-NMR (CDCl$_3$, 400 MHz): δ 7.70 (s, 1H), 7.68 (d, 1H), 7.55-7.33 (m, 4H), 7.15-7.12 (m, 1H), 6.99-6.93 (m, 1H), 6.88 (d, 1H), 6.66 (dd, 1H), 4.80 (s, 2H), 2.17-2.14 (m, 1H), 1.30-1.24 (m, 2H), 1.19-1.14 (m, 2H).

Step 3: Preparation of ethyl(3-((2-chloro-4-((5-cyclopropyl-3-(2,6-dichlorophenyl)isoxazol-4-yl)methoxy)phenyl)ethynyl)phenyl)carbamate Triethylamine (12.3 ul, 0.08 mmol) and ethylchloroformate (8.3 ul, 0.08 mmol) was added to a suspension of the intermediate compound (Step 2)(30 mg, 0.06 mmol) in dichloromethane and stirred for 7 hours at room temperature. Water was added to the reaction mixture and the product was extracted into dichloromethane. The combined organic layers were dried over MgSO$_4$, filtered, evaporated in vacuum and purified using silica chromatography to give the title compound (25 mg, 72%).

$^1$H-NMR (MeOD, 400 MHz): δ 7.53 (s, 1H), 7.43-7.41 (m, 2H), 7.38-7.29 (m, 3H), 7.17 (t, 1H), 7.05 (dd, 1H), 6.81 (d, 1H), 6.65 (dd, 1H), 5.90 (s, 2H), 4.08 (q, 2H), 2.28-2.21 (m, 1H), 1.19 (t, 3H), 1.14-1.08 (m, 4H).

<Example 12> 3-((2-chloro-4-((5-cyclopropyl-3-(2,6-dichlorophenyl)isoxazol-4-yl)methoxy)phenyl)ethynyl)benzenesulfonamide (I-12)

Step 1: Preparation of 3-((2-chloro-4-((5-cyclopropyl-3-(2,6-dichlorophenyl) isoxazol-4-yl)methoxy)phenyl)ethynyl)benzenesulfonamide This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(75 mg, 0.17 mmol) was reacted with 3-bromobenzenesulfonamide (200 mg, 0.85 mmol), bis(triphenylphosphine) palladium(II) dichloride ($PdCl_2(PPh_3)_2$, 13 mg, 0.02 mmol), Copper(I) iodide (3.5 mg, 0.02 mmol) and triethylamine (0.030 ml, 0.21 mmol) to afford the title compound (12 mg, 12%).

$^1$H-NMR ($CDCl_3$, 400 MHz): δ 8.08 (m, 1H), 7.86-7.89 (m, 1H), 7.70-7.64 (m, 3H), 7.57-7.44 (m, 3H), 6.88 (m, 1H), 6.71-6.68 (m, 1H), 4.83 (s, 2H), 2.17-2.14 (m, 1H), 1.33-1.28 (m, 2H), 1.20-1.15 (m, 2H).

<Example 13> N-(3-((2-chloro-4-((5-cyclopropyl-3-(2,6-dichlorophenyl) isoxazol-4-yl)methoxy)phenyl) ethynyl)phenyl)methanesulfonamide (I-13)

Step 1: Preparation of N-(3-((2-chloro-4-((5-cyclopropyl-3-(2,6-dichlorophenyl)isoxazol-4-yl) methoxy)phenyl)ethynyl)phenyl)methanesulfonamide Methanesulfonyl chloride (2 drops) was added to a solution of 3-((2-chloro-4-((5-cyclopropyl-3-(2,6-dichlorophenyl)isoxazol-4-yl)methoxy)phenyl)ethynyl)aniline (Step 2 of Example 11)(35 mg, 0.0686 mmol) in tetrahydrofuran (1 ml) and triethylamine (0.05 ml, 0.343 mmol) was added to the reaction mixture and stirred for 8 hours. The reaction mixture was concentrated in vacuum, added 1N HCl(aq) and extracted into ethyl acetate. The combined organic layers were dried over $MgSO_4$, filtered, evaporated in vacuum and purified using silica chromatography to afford the title compound (27 mg, 67%).

$^1$H-NMR ($CDCl_3$, 400 MHz): δ 7.42-7.32 (m, 7H), 7.22-7.19 (m, 1H), 6.87 (d, 1H), 6.70-6.68 (dd, 1H), 6.38 (s, 1H), 4.82 (s, 2H), 6.04 (s, 3H), 2.15-2.14 (m, 1H), 1.31-1.24 (m, 2H), 1.19-1.15 (m, 2H).

<Example 14> N-(3-((2-chloro-4-((5-cyclopropyl-3-(2,6-dichlorophenyl) isoxazol-4-yl)methoxy)phenyl) ethynyl)phenyl)sulfamide (I-14)

Step 1: Preparation of N-(3-((2-chloro-4-((5-cyclopropyl-3-(2,6-dichloro phenyl)isoxazol-4-yl) methoxy)phenyl)ethynyl)phenyl)sulfamide This compound was made using the procedure described in Example 13 (Step 1). Thus, 3-((2-chloro-4-((5-cyclopropyl-3-(2,6-dichlorophenyl)isoxazol-4-yl)methoxy)phenyl) ethynyl)aniline (Step 2 of Example 11)(34.8 mg, 0.0683 mmol) was reacted with chlorosulfonylisocyanate (2 drops) and pyridine (15 μl, 0.1366 mmol) to afford the title compound (23.9 mg, 89%).

$^1$H-NMR (DMSO, 400 MHz): δ 9.67 (s, 1H), 7.64-7.62 (m, 2H), 7.57-7.50 (m, 2H), 7.31-7.29 (d, 2H), 7.21-7.08 (m, 5H), 6.83-6.80 (dd, 1H), 4.98 (s, 2H), 1.21-1.17 (m, 2H), 1.15-1.13 (m, 2H).

<Example 15> 3-((2-chloro-4-((5-cyclopropyl-3-(2, 6-dichlorophenyl)isoxazol-4-yl)methoxy)phenyl) ethynyl)benzoic acid (I-15)

Step 1: Preparation of 3-((2-chloro-4-((5-cyclopropyl-3-(2,6-dichloropheny) isoxazol-4-yl)methoxy) phenyl)ethynyl)benzoic acid This compound was made using the procedure described in Example 1 (Step 6). Thus, methyl 3-((2-chloro-4-((5-cyclopropyl-3-(2,6-dichlorophenyl)isoxazol-4-yl)methoxy) phenyl)ethynyl)benzoate (Example 7)(105 mg, 0.190 mmol) was reacted with lithium hydroxide (8 mg, 0.19 mmol) to afford the title compound (66 mg, 65%).

$^1$H-NMR ($CDCl_3$, 400 MHz): δ 8.27-8.26 (m, 1H), 8.08-8.05 (m, 1H), 7.77-7.75 (m, 1H), 7.49-7.32 (m, 5H), 6.89-6.88 (m, 1H), 6.72-6.69 (m, 1H), 4.83 (s, 2H), 2.17-2.14 (m, 1H), 1.33-1.28 (m, 2H), 1.20-1.15 (m, 2H).

<Example 16> 4-((2-chloro-4-((5-cyclopropyl-3-(2, 6-dichlorophenyl)isoxazol-4-yl)methoxy)phenyl) ethynyl)benzoic acid (I-16)

Step 1: Preparation of methyl 4-((2-chloro-4-((5-cyclopropyl-3-(2,6-dichlorophenyl)isoxazol-4-yl) methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(175 mg, 0.42 mmol) was reacted with methyl 4-bromobenzoate (100 mg, 0.38 mmol), bis(triphenylphosphine)palladium(II) dichloride ($PdCl_2(PPh_3)_2$, 53 mg, 0.08 mmol), copper(I) iodide (7 mg, 0.04 mmol) and triethylamine (0.26 ml, 1.89 mmol) to afford the intermediate compound methyl 4-((2-chloro-4-((5-cyclopropyl-3-(2, 6-dichlorophenyl)isoxazol-4-yl)methoxy)phenyl)ethynyl) benzoate (150 mg, 71%).

$^1$H-NMR ($CDCl_3$, 400 MHz): δ 8.02 (dd, 2H), 7.59 (dd, 2H), 7.42-7.40 (m, 3H), 7.35 (dd, 1H), 6.88 (d, 1H), 6.71 (dd, 1H), 4.82 (s, 2H), 3.92 (s, 3H), 2.17-2.13 (m, 1H), 1.32-1.28 (m, 2H), 1.19-1.15 (m, 2H).

Step 2: Preparation of 4-((2-chloro-4-((5-cyclopropyl-3-(2,6-dichlorophenyl) isoxazol-4-yl)methoxy) phenyl)ethynyl)benzoic acid This compound was made using the procedure described in Example 1 (Step 6). Thus, the intermediate compound (Step 1)(150 mg, 0.27 mmol) was reacted with lithium hydroxide (114 mg, 2.7 mmol) to afford the title compound (106 mg, 73%).

$^1$H-NMR (DMSO, 400 MHz): δ 13.16 (s, 1H), 7.98 (dd, 2H), 7.65-7.62 (m, 4H), 7.57-7.53 (m, 2H), 7.11 (d, 1H), 6.85 (dd, 1H), 4.99 (s, 2H), 2.46 (m, 1H), 1.22-1.12 (m, 4H).

<Example 17> 6-((2-chloro-4-((5-cyclopropyl-3-(2, 6-dichlorophenyl)isoxazol-4-yl)methoxy)phenyl) ethynyl)nicotinic acid (I-17)

Step 1: Preparation of methyl 6-((4-((5-cyclopropyl-3-(2,6-dichlorophenyl) isoxazol-4-yl)methoxy) phenyl)ethynyl)nicotinate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 6-bromonicotinate (61.9 mg, 0.287 mmol), bis(triphenylphosphine) palladium(II) dichloride ($PdCl_2(PPh_3)_2$, 21 mg, 0.03 mmol), copper(I) iodide (5.7 mg, 0.03 mmol) and triethylamine (0.2 ml, 1.44 mmol) to afford the intermediate compound methyl 6-((4-((5-cyclopropyl-3-(2,6-dichlorophenyl)isoxazol-4-yl)methoxy)phenyl) ethynyl)nicotinate (77 mg, 68%).

$^1$H-NMR ($CDCl_3$, 400 MHz): δ 9.20 (dd, 1H), 8.28 (dd, 1H), 7.60 (dd, 1H), 7.50 (d, 1H), 7.43-7.39 (m, 2H), 7.36-

7.31 (m, 1H), 6.89 (d, 1H), 6.71 (dd, 1H), 4.83 (s, 3H), 3.97 (s, 3H), 2.20-2.10 (m, 1H), 1.34-1.29 (m, 2H), 1.21-1.15 (m, 2H).

Step 2: Preparation of 6-((2-chloro-4-((5-cyclopropyl-3-(2,6-dichlorophenyl) isoxazol-4-yl)methoxy)phenyl)ethynyl)nicotinic acid This compound was made using the procedure described in Example 1 (Step 6). Thus, this intermediate compound (Step 1)(77 mg, 0.14 mmol) was reacted with lithium hydroxide (58 mg, 1.40 mmol) to afford the title compound (23.5 mg, 27%).
$^1$H-NMR (DMSO, 400 MHz): δ 13.55 (br, 1H), 9.06 (dd, 1H), 8.29 (dd, 1H), 7.74 (dd, 1H), 7.65-7.60 (m, 3H), 7.53-7.58 (m, 1H), 7.13 (d, 1H), 6.87 (dd, 1H), 5.01 (s, 2H), 1.25-1.12 (m, 5H).

<Example 18>2-((2-chloro-4-((5-cyclopropyl-3-(2,6-dichlorophenyl)isoxazol-4-yl)methoxy)phenyl)ethynyl)isonicotinic acid (I-18)

Step 1: Preparation of methyl 2-((4-((5-cyclopropyl-3-(2,6-dichlorophenyl) isoxazol-4-yl)methoxy)phenyl)ethynyl)isonicotinate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 2-bromoisonicotinate (61.9 mg, 0.287 mmol), bis (triphenylphosphine) palladium(II) dichloride (PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate compound methyl 2-((4-((5-cyclopropyl-3-(2,6-dichlorophenyl)isoxazol-4-yl)methoxy)phenyl) ethynyl)isonicotinate (47.6 mg, 36%).
$^1$H-NMR (CDCl$_3$, 400 MHz): δ 8.77 (dd, 1H), 8.07 (dd, 1H), 7.78 (dd, 1H), 7.49 (d, 1H), 7.31-7.44 (m, 2H), 7.26 (s, 1H), 6.89 (d, 1H), 6.71 (dd, 1H), 4.83 (s, 2H), 3.98 (s, 3H), 2.18-2.13 (m, 1H), 1.35-1.21 (m, 2H), 1.21-1.11 (m, 2H).

Step 2: Preparation of 2-((2-chloro-4-((5-cyclopropyl-3-(2,6-dichlorophenyl) isoxazol-4-yl)methoxy)phenyl)ethynyl)isonicotinic acid This compound was made using the procedure described in Example 1 (Step 6). Thus, this intermediate compound (Step 1)(47.6 mg, 0.086 mmol) was reacted with lithium hydroxide (36 mg, 0.86 mmol) to afford the title compound (27 mg, 58%).
$^1$H-NMR (DMSO, 400 MHz): δ 13.73 (br, 1H), 8.03 (d, 1H), 7.82 (t, 1H), 7.60-7.65 (m, 1H), 7.58-7.53 (m, 3H), 7.13 (d, 1H), 6.87 (dd, 1H), 5.01 (s, 2H), 1.32-1.03 (m, 5H).

<Example 19>6-((2-chloro-4-((5-cyclopropyl-3-(2,6-dichlorophenyl)isoxazol-4-yl)methoxy)phenyl)ethynyl)picolinic acid (I-19)

Step 1: Preparation of methyl 6-((2-chloro-4-((5-cyclopropyl-3-(2,6-dichlorophenyl)isoxazol-4-yl)methoxy)phenyl)ethynyl)picolinate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 6-bromopicolinate (65.9 mg, 0.287 mmol), bis(triphenylphosphine) palladium(II) dichloride (PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate compound methyl 6-((2-chloro-4-((5-cyclopropyl-3-(2,6-dichlorophenyl)isoxazol-4-yl) methoxy)phenyl)ethynyl)picolinate (60.4 mg, 45%).
$^1$H-NMR (CDCl$_3$, 400 MHz): δ 8.06 (dd, 1H), 7.83 (t, 1H), 7.70 (dd 1H), 7.50 (d, 1H), 7.43-7.39 (m, 2H), 7.36-7.31 (m, 1H), 6.88 (d, 1H), 6.70 (dd, 1H), 4.83 (s, 2H), 4.49 (q, 2H), 2.18-2.12 (m, 1H), 1.45 (t, 3H), 1.30 (dd, 2H), 1.17 (dd, 2H).

Step 2: Preparation of 6-((2-chloro-4-((5-cyclopropyl-3-(2,6-dichlorophenyl) isoxazol-4-yl)methoxy)phenyl)ethynyl)picolinic acid This compound was made using the procedure described in Example 1 (Step 6). Thus, this intermediate compound (Step 1)(60.4 mg, 0.106 mmol) was reacted with lithium hydroxide (44.5 mg, 1.06 mmol) to afford the title compound (9.7 mg, 17%).
$^1$H-NMR (DMSO, 400 MHz): δ 13.42 (br, 1H), 8.03 (d, 1H), 7.82 (t, 1H), 7.65-7.61 (m, 2H), 7.58-7.54 (m, 1H), 7.13 (d, 1H), 6.87 (dd, 1H), 5.01 (s, 2H), 1.05-1.32 (m, 5H).

<Example 20>5-((2-chloro-4-((5-cyclopropyl-3-(2,6-dichlorophenyl)isoxazol-4-yl)methoxy)phenyl)ethynyl)nicotinic acid (I-20)

Step 1: Preparation of methyl 5-((2-chloro-4-((5-cyclopropyl-3-(2,6-dichlorophenyl)isoxazol-4-yl)methoxy)phenyl)ethynyl)nicotinate This compound was made using the procedure described in Example 1 (Step 5). Thus 4-((3-chloro-4-ethynylphenoxy)methyl)-5-cyclopropyl-3-(2,6-dichloro phenyl)isoxazole (Example 5)(100 mg, 0.239 mmol) was reacted with methyl 5-bromonicotinate (65.9 mg, 0.287 mmol), bis(triphenylphosphine) palladium(II)Dichloride (PdCl$_2$(PPh$_3$)$_2$, 21 mg, 0.03 mmol), copper(I)iodide (5.7 mg, 0.03 mmol) and triethylamine (0.2 ml, 1.44 mmol) to afford the intermediate compound methyl 5-((2-chloro-4-((5-cyclopropyl-3-(2,6-dichlorophenyl) isoxazol-4-yl)methoxy)phenyl)ethynyl)nicotinate (68.8 mg, 52%).
$^1$H-NMR (CDCl$_3$, 400 MHz): δ 9.13 (s, 1H), 8.90 (s, 1H), 8.41 (d, 1H), 7.46-7.40 (m, 3H), 7.36-7.32 (m, 1H), 6.90 (d, 1H), 6.72 (dd, 1H), 4.84 (s, 2H), 3.97 (s, 3H), 2.16 (m, 1H), 1.32-1.28 (m, 2H), 1.21-1.15 (m, 2H).

Step 2: Preparation of 5-((2-chloro-4-((5-cyclopropyl-3-(2,6-dichlorophenyl) isoxazol-4-yl)methoxy)phenyl)ethynyl)nicotinic acid This compound was made using the procedure described in Example 1 (Step 6). Thus the intermediate compound (Step 1)(68.8 mg, 0.124 mmol) was reacted with lithium hydroxide (52 mg, 1.24 mmol) to afford the title compound (44.8 mg, 67%).
$^1$H-NMR (CDCl$_3$, 400 MHz): δ 9.26 (s, 1H), 8.98 (s, 1H), 8.54 (d, 1H), 7.45-7.40 (m, 3H), 7.36-7.32 (m, 1H), 6.89 (d, 1H), 6.72 (dd, 1H), 4.84 (s, 2H), 2.16 (m, 1H), 1.32-1.28 (m, 2H), 1.19-1.17 (m, 2H).

<Example 21> 3-((2-chloro-4-((5-cyclopropyl-3-(2,6-dichlorophenyl)isoxazol-4-yl)methoxy)phenyl)ethynyl)-5-(dimethylamino)benzoic acid (I-21)

Step 1: Preparation of methyl 3-((2-chloro-4-((5-cyclopropyl-3-(2,6-dichlorophenyl)isoxazol-4-yl)methoxy)phenyl)ethynyl)-5-(dimethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 4-bromo-3-(dimethylamino)benzoate (67 mg, 0.26 mmol), bis(triphenylphosphine) palladium(II) dichloride ($PdCl_2(PPh_3)_2$, 21 mg, 0.03 mmol), Copper(I) iodide (5.7 mg, 0.03 mmol) and 1,8-Diazabicyclo[5.4.0]undec-7-ene (DBU, 0.2 ml, 1.3 mmol) to afford the intermediate compound methyl 3-((2-chloro-4-((5-cyclopropyl-3-(2,6-dichlorophenyl)isoxazol-4-yl)methoxy)phenyl)ethynyl)-5-(dimethylamino)benzoate (70 mg, 42%).

$^1$H-NMR ($CDCl_3$, 400 MHz): δ 7.55-7.54 (m, 1H), 7.42-7.31 (m, 5H), 7.02-7.01 (m, 1H), 6.87-6.86 (m, 1H), 6.70-6.67 (m, 1H), 4.82 (s, 2H), 3.91 (s, 3H), 3.01 (s, 6H), 2.18-2.14 (m, 1H), 1.32-1.28 (m, 2H), 1.19-1.16 (m, 2H).

Step 2: Preparation of 3-((2-chloro-4-((5-cyclopropyl-3-(2,6-dichlorophenyl) isoxazol-4-yl)methoxy)phenyl)ethynyl)-5-(dimethylamino)benzoic acid This compound was made using the procedure described in Example 1 (Step 6). Thus, this intermediate compound (Step 1)(70 mg, 0.118 mmol) was reacted with lithium hydroxide (4.9 mg, 0.118 mmol) to afford the title compound (54 mg, 78%).

$^1$H-NMR ($CDCl_3$, 400 MHz): δ 7.60 (s, 1H), 7.43-7.32 (m, 5H), 7.05-7.04 (m, 1H), 6.88-6.87 (m, 1H), 6.70-6.68 (m, 1H), 4.82 (s, 2H), 3.02 (s, 6H), 2.18-2.14 (m, 1H), 1.32-1.29 (m, 2H), 1.19-1.16 (m, 2H).

<Example 22> 4-((2-chloro-4-((5-cyclopropyl-3-(2,6-dichlorophenyl)isoxazol-4-yl)methoxy)phenyl)ethynyl)-3-(dimethylamino)benzoic acid (I-22)

Step 1: Preparation of methyl 4-((2-chloro-4-((5-cyclopropyl-3-(2,6-dichlorophenyl)isoxazol-4-yl)methoxy)phenyl)ethynyl)-3-(dimethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 4-bromo-3-(dimethylamino)benzoate (67 mg, 0.26 mmol), bis(triphenylphosphine) palladium(II) dichloride ($PdCl_2(PPh_3)_2$, 21 mg, 0.03 mmol), copper(I) iodide (5.7 mg, 0.03 mmol) and 1,8-Diazabicyclo[5.4.0]undec-7-ene (DBU, 0.2 ml, 1.3 mmol) to afford the intermediate compound methyl 4-((2-chloro-4-((5-cyclopropyl-3-(2,6-dichlorophenyl)isoxazol-4-yl)methoxy)phenyl)ethynyl)-3-(dimethylamino)benzoate (80 mg, 55%).

$^1$H-NMR ($CDCl_3$, 400 MHz): δ 7.58 (br, 1H), 7.53 (br, 1H), 7.43-7.41 (m, 3H), 7.35-7.31 (m, 2H), 6.87 (d, 1H), 6.716.68 (dd, 1H), 4.82 (s, 2H), 3.91 (s, 3H), 3.02 (s, 6H), 2.15 (m, 1H), 1.32-1.29 (m, 2H), 1.19-1.14 (m, 2H).

Step 2: Preparation of 4-((2-chloro-4-((5-cyclopropyl-3-(2,6-dichlorophenyl)isoxazol-4-yl)methoxy)phenyl)ethynyl)-3-(dimethylamino)benzoic acid This compound was made using the procedure described in Example 1 (Step 6). Thus, the intermediate compound (Step 1)(80 mg, 0.14 mmol) was reacted with lithium hydroxide (58.7 mg, 1.4 mmol) to afford the title compound (42 mg, 55%).

$^1$H-NMR (DMSO, 400 MHz): δ 7.92 (d, 1H), 7.79-7.76 (dd, 1H), 7.65-7.62 (m, 2H), 7.57-7.52 (m, 2H), 7.07 (d, 1H), 6.93 (d, 1H), 6.83-6.80 (dd, 1H), 4.98 (s, 2H), 3.08 (s, 6H), 2.49 (m, 1H), 1.21-1.13 (m, 4H).

<Example 23> 4-((2-chloro-4-((5-cyclopropyl-3-(2,6-dichlorophenyl)isoxazol-4-yl)methoxy)phenyl)ethynyl)-2-(dimethylamino)benzoic acid (I-23)

Step 1: Preparation of methyl 4-((2-chloro-4-((5-cyclopropyl-3-(2,6-dichlorophenyl)isoxazol-4-yl)methoxy)phenyl)ethynyl)-2-(dimethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 4-bromo-2-(dimethylamino)benzoate (134 mg, 0.52 mmol), bis(triphenyl phosphine)palladium(II) dichloride ($PdCl_2(PPh_3)_2$, 42 mg, 0.06 mmol), Copper(I) iodide (11.4 mg, 0.06 mmol) and 1,8-Diazabicyclo[5.4.0]undec-7-ene (DBU, 0.4 ml, 2.6 mmol) to afford the intermediate compound methyl 4-((2-chloro-4-((5-cyclopropyl-3-(2,6-dichlorophenyl)isoxazol-4-yl)methoxy)phenyl)ethynyl)-2-(dimethylamino)benzoate (132 mg, 43%).

$^1$H-NMR ($CDCl_3$, 400 MHz): δ 7.66-7.64 (m, 1H), 7.43-7.32 (m, 4H), 7.09-7.08 (m, 1H), 7.02-6.99 (m, 1H), 6.88-6.87 (m, 1H), 6.70-6.68 (m, 1H), 4.82 (s, 2H), 3.91 (s, 3H), 2.87 (s, 6H), 2.18-2.14 (m, 1H), 1.32-1.28 (m, 2H), 1.20-1.16 (m, 2H).

Step 2: Preparation of 4-((2-chloro-4-((5-cyclopropyl-3-(2,6-dichlorophenyl) isoxazol-4-yl)methoxy)phenyl)ethynyl)-2-(dimethylamino)benzoic acid This compound was made using the procedure described in Example 1 (Step 6). Thus, this intermediate compound (Step 1)(132 mg, 0.221 mmol) was reacted with lithium hydroxide (9.3 mg, 0.221 mmol) to afford the title compound (36 mg, 28%).

$^1$H-NMR ($CDCl_3$, 400 MHz): δ 8.26-8.24 (m, 1H), 7.57-7.52 (m, 2H), 7.43-7.33 (m, 4H), 6.89-6.88 (m, 1H), 6.72-6.69 (m, 1H), 4.83 (s, 2H), 2.84 (s, 6H), 2.16-2.12 (m, 1H), 1.31-1.28 (m, 2H), 1.19-1.15 (m, 2H).

<Example 24> 3-((2-chloro-4-((5-cyclopropyl-3-(2,6-dichlorophenyl)isoxazol-4-yl)methoxy)phenyl)ethynyl)-5-(diethylamino)benzoic acid (I-24)

Step 1: Preparation of Methyl 3-((2-chloro-4-((5-cyclopropyl-3-(2,6-dichlorophenyl)isoxazol-4-yl)methoxy)phenyl)ethynyl)-5-(diethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(20 mg, 0.052 mmol) was reacted with methyl 3-bromo-5-(diethylamino)benzoate (14.9 mg, 0.052 mmol), bis(triphenylphosphine)palladium(II) dichloride (PdCl$_2$(PPh$_3$)$_2$, 4.2 mg, 0.006 mmol), Copper(I) iodide (1.14 mg, 0.006 mmol) and 1,8-Diazabicyclo[5.4.0]undec-7-ene (DBU, 0.04 ml, 0.26 mmol) to afford the intermediate compound methyl 3-((2-chloro-4-((5-cyclopropyl-3-(2,6-dichlorophenyl)isoxazol-4-yl) methoxy)phenyl)ethynyl)-5-(diethylamino)benzoate (9 mg, 28%).

$^1$H-NMR (CDCl$_3$, 400 MHz): δ 7.55-7.54 (m, 1H), 7.42-7.31 (m, 5H), 7.02-7.01 (m, 1H), 6.87-6.86 (m, 1H), 6.70-6.67 (m, 1H), 4.82 (s, 2H), 3.91 (s, 3H), 3.49 (s, 3H), 3.42-3.37 (m, 3H), 2.18-2.14 (m, 1H), 1.32-1.28 (m, 2H), 1.20-1.16 (m, 6H).

Step 2: Preparation of 3-((2-chloro-4-((5-cyclopropyl-3-(2,6-dichlorophenyl) isoxazol-4-yl)methoxy)phenyl)ethynyl)-5-(diethylamino)benzoic acid This compound was made using the procedure described in Example 1 (Step 6). Thus, this intermediate compound (Step 1)(9 mg, 0.0144 mmol) was reacted with lithium hydroxide (0.6 mg, 0.0144 mmol) to afford the title compound (5 mg, 57%).

$^1$H-NMR (CDCl$_3$, 400 MHz): δ 7.52-7.50 (m, 1H), 7.42-7.40 (m, 3H), 7.35-7.31 (m, 2H), 6.99-6.98 (m, 1H), 6.87-6.86 (m, 1H), 6.70-6.67 (m, 1H), 4.82 (s, 2H), 3.49 (s, 3H), 3.42-3.37 (m, 3H), 2.17-2.15 (m, 1H), 1.31-1.30 (m, 2H), 1.20-1.16 (m, 6H).

<Example 25>3-amino-5-((2-chloro-4-((5-cyclopropyl-3-(2,6-dichlorophenyl)isoxazol-4-yl)methoxy)phenyl)ethynyl)benzoic acid (I-25)

Step 1: Preparation of 3-amino-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, methyl 3-amino-5-((2-chloro-4-((5-cyclopropyl-3-(2,6-dichlorophenyl) isoxazol-4-yl)methoxy)phenyl)ethynyl)benzoate (Step 2 of Example 8)(71 mg, 0.13 mmol) was reacted with lithium hydroxide (54.6 mg, 1.30 mmol) to afford the title compound (54 mg, 78%).

$^1$H-NMR (CDCl$_3$, 400 MHz): δ 7.62 (s, 1H), 7.41-7.31 (m, 5H), 7.01-6.99 (m, 1H), 6.86-6.85 (m, 1H), 6.69-6.68 (m, 1H), 4.81 (s, 2H), 2.16-2.14 (m, 1H), 1.31-1.29 (m, 2H), 1.18-1.15 (m, 2H).

<Example 26>3-((2-chloro-4-((5-cyclopropyl-3-(2,6-dichlorophenyl)isoxazol-4-yl)methoxy)phenyl)ethynyl)-4-(dimethylamino)benzoic acid (I-26)

Step 1: Preparation of methyl 3-((2-chloro-4-((5-cyclopropyl-3-(2,6-dichlorophenyl)isoxazol-4-yl)methoxy)phenyl)ethynyl)-4-(dimethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-4-(dimethylamino)benzoate (67 mg, 0.26 mmol), bis(triphenylphosphine) palladium(II) dichloride (PdCl$_2$(PPh$_3$)$_2$, 21 mg, 0.03 mmol), copper(I) iodide (5.7 mg, 0.03 mmol) and 1,8-Diazabicyclo[5.4.0]undec-7-ene (DBU, 0.2 ml, 1.3 mmol) to afford the intermediate compound methyl 3-((2-chloro-4-((5-cyclopropyl-3-(2,6-dichlorophenyl)isoxazol-4-yl)methoxy)phenyl)ethynyl)-4-(dimethylamino)benzoate (70 mg, 48%).

$^1$H-NMR (CDCl$_3$, 400 MHz): δ 8.14 (d, 1H), 7.87-7.84 (dd, 1H), 7.42-7.38 (m, 3H), 7.35-7.31 (m, 1H), 6.86 (d, 1H), 6.82 (d, 1H), 6.70-6.68 (dd, 1H), 4.82 (s, 2H), 3.88 (s, 3H), 3.14 (s, 6H), 2.16 (m, 1H), 1.30-1.26 (m, 2H), 1.24-1.16 (m, 2H).

Step 2: Preparation of 3-((2-chloro-4-((5-cyclopropyl-3-(2,6-dichlorophenyl) isoxazol-4-yl)methoxy)phenyl)ethynyl)-4-(dimethylamino)benzoic acid This compound was made using the procedure described in Example 1 (Step 6). Thus, this intermediate compound (Step 1)(70 mg, 0.12 mmol) was reacted with lithium hydroxide (50.4 mg, 1.2 mmol) to afford the title compound (35 mg, 53%).

$^1$H-NMR (DMSO, 400 MHz): δ 7.95 (d, 1H), 7.79-7.76 (dd, 1H), 7.64-7.62 (m, 2H), 7.57-7.51 (m, 2H), 7.07 (d, 1H), 6.93 (d, 1H), 6.83-6.80 (dd, 1H), 4.97 (d, 1H), 3.08 (s, 6H), 2.47 (m, 1H), 1.23-1.13 (m, 4H).

<Example 27>3-chloro-5-((2-chloro-4-((5-cyclopropyl-3-(2,6-dichloro phenyl)isoxazol-4-yl)methoxy)phenyl)ethynyl)benzoic acid (I-27)

Step 1: Preparation of methyl 3-chloro-5-((2-chloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-5-chlorobenzoate (65 mg, 0.26 mmol), bis(triphenylphosphine) palladium(II) dichloride (PdCl$_2$(PPh$_3$)$_2$, 21 mg, 0.03 mmol), copper(I) iodide (5.7 mg, 0.03 mmol) and 1,8-Diazabicyclo[5.4.0]undec-7-ene (DBU, 0.2 ml, 1.3 mmol) to afford the intermediate compound methyl 3-chloro-5-((2-chloro-4-((5-cyclopropyl-3-(2,6-dichlorophenyl)isoxazol-4-yl)methoxy)phenyl)ethynyl)benzoate (87 mg, 61%).

$^1$H-NMR (CDCl$_3$, 400 MHz): δ 8.06 (m, 1H), 7.96 (m, 1H), 7.67 (m, 1H), 7.42-7.35 (m, 3H), 7.34-7.31 (m, 1H), 6.88 (d, 1H), 6.71-6.68 (dd, 1H), 4.83 (s, 2H), 3.94 (s, 3H), 2.15 (m, 1H), 1.31-1.24 (m, 2H), 1.18-1.16 (m, 2H).

Step 2: Preparation of 3-chloro-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(87 mg, 0.16 mmol) was reacted with lithium hydroxide (67.2 mg, 1.6 mmol) to afford the title compound (43 mg, 50%).

$^1$H-NMR (DMSO, 400 MHz): δ 7.93 (br, 1H), 7.88 (br, 1H), 7.64-7.62 (m, 3H), 7.56 (m, 2H), 7.10 (d, 1H), 6.85-6.83 (dd, 1H), 4.99 (s, 2H), 2.47 (m, 1H), 1.22-1.14 (m, 4H).

<Example 28>4-chloro-3-((2-chloro-4-((5-cyclopropyl-3-(2,6-dichloro phenyl)isoxazol-4-yl)methoxy)phenyl)ethynyl)benzoic acid (I-28)

Step 1: Preparation of methyl 4-chloro-3-((2-chloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-4-chlorobenzoate (65 mg, 0.26 mmol), bis(triphenylphosphine) palladium(II) dichloride (PdCl$_2$(PPh$_3$)$_2$, 21 mg, 0.03 mmol), copper(I) iodide (5.7 mg, 0.03 mmol) and 1,8-diazabicyclo[5.4.0]undec-7-ene (DBU, 0.2 ml, 1.3 mmol) to afford the intermediate compound methyl 4-chloro-3-((2-chloro-4-((5-cyclopropyl-3-(2,6-dichlorophenyl)isoxazol-4-yl)methoxy)phenyl)ethynyl)benzoate (87 mg, 61%).

$^1$H-NMR (CDCl$_3$, 400 MHz): δ 8.22 (d, 1H), 7.92-7.89 (dd, 1H), 7.51-7.40 (m, 4H), 7.35-7.33 (m, 1H), 6.88 (d, 1H), 6.71-6.69 (dd, 1H), 4.83 (s, 2H), 3.93 (s, 3H), 2.15 (m, 1H), 1.31-1.24 (m, 2H), 1.18-1.16 (m, 2H).

Step 2: Preparation of 4-chloro-3-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(87 mg, 0.16 mmol) was reacted with lithium hydroxide (67.2 mg, 1.6 mmol) to afford the title compound (43 mg, 50%).

$^1$H-NMR (DMSO, 400 MHz): δ 8.10 (d, 1H), 7.94-7.91 (dd, 1H), 7.72 (d, 1H), 7.65-7.53 (m, 4H), 7.11 (d, 1H), 6.87-6.84 (d, 1H), 5.00 (s, 2H), 2.47 (m, 1H), 1.21-1.13 (m, 4H).

<Example 29>2-chloro-5-((2-chloro-4-((5-cyclopropyl-3-(2,6-dichloro phenyl)isoxazol-4-yl)methoxy)phenyl)ethynyl)benzoic acid (I-29)

Step 1: Preparation of methyl 2-chloro-5-((2-chloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(155 mg, 0.37 mmol) was reacted with methyl 5-bromo-2-chlorobenzoate (100 mg, 0.34 mmol), bis(triphenylphosphine) palladium(II) dichloride (PdCl$_2$(PPh$_3$)$_2$, 48 mg, 0.06 mmol), copper(I) iodide (6.5 mg, 0.03 mmol) and triethylamine (0.23 ml, 1.7 mmol) to afford the intermediate compound methyl 2-chloro-5-((2-chloro-4-((5-cyclopropyl-3-(2,6-dichloro phenyl)isoxazol-4-yl)methoxy)phenyl)ethynyl)benzoate (155 mg, 78%).

$^1$H-NMR (CDCl$_3$, 400 MHz): δ 7.98 (s, 1H), 7.55 (dd, 1H), 7.44-7.31 (m, 5H), 6.87 (d, 1H), 6.69 (dd, 1H), 4.82 (s, 2H), 3.94 (s, 3H), 2.17-2.13 (m, 1H), 1.32-1.27 (m, 2H), 1.19-1.15 (m, 2H).

Step 2: Preparation of 2-chloro-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, the intermediate compound (Step 1)(155 mg, 0.264 mmol) was reacted with lithium hydroxide (58.7 mg, 2.64 mmol) to afford the title compound (75 mg, 50%).

$^1$H-NMR (DMSO, 400 MHz): δ 13.65 (s, 1H), 7.88 (d, 1H), 7.67-7.53 (m, 6H), 7.10 (d, 1H), 6.85 (dd, 1H), 4.99 (s, 2H), 2.46 (m, 1H), 1.22-1.12 (m, 4H).

<Example 30>3-((2-chloro-4-((5-cyclopropyl-3-(2,6-dichlorophenyl)isoxazol-4-yl)methoxy)phenyl)ethynyl)-5-fluorobenzoic acid (I-30)

Step 1: Preparation of methyl 3-((2-chloro-4-((5-cyclopropyl-3-(2,6-dichlorophenyl)isoxazol-4-yl)methoxy)phenyl)ethynyl)-5-fluorobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(50 mg, 0.119 mmol) was reacted with methyl 3-fluoro-5-iodobenzoate (40 mg, 0.143 mmol), bis(triphenylphosphine) palladium(II) dichloride (PdCl$_2$(PPh$_3$)$_2$, 8.4 mg, 0.012 mmol), Copper(I) iodide (2.3 mg, 0.012 mmol) and triethylamine (0.020 ml, 0.143 mmol) to afford the intermediate compound methyl 3-((2-chloro-4-((5-cyclopropyl-3-(2,6-dichlorophenyl)isoxazol-4-yl)methoxy)phenyl)ethynyl)-5-fluorobenzoate (23 mg, 34%).

$^1$H-NMR (CDCl$_3$, 400 MHz): δ 7.99-7.98 (m, 1H), 7.71-7.67 (m, 1H), 7.43-7.32 (m, 5H), 6.88-6.87 (m, 1H), 6.71-6.69 (m, 1H), 4.83 (s, 2H), 3.94 (s, 3H), 2.17-2.15 (m, 1H), 1.33-1.28 (m, 2H), 1.19-1.16 (m, 2H).

Step 2: Preparation of 3-((2-chloro-4-((5-cyclopropyl-3-(2,6-dichlorophenyl) isoxazol-4-yl)methoxy)phenyl)ethynyl)-5-fluorobenzoic acid This compound was made using the procedure described in Example 1 (Step 6). Thus, this intermediate compound (Step 1)(23 mg, 0.040 mmol) was reacted with lithium hydroxide (1.7 mg, 0.040 mmol) to afford the title compound (17 mg, 76%).

$^1$H-NMR (CDCl$_3$, 400 MHz): δ 8.05-8.04 (m, 1H), 7.76-7.73 (m, 1H), 7.47-7.43 (m, 4H), 7.36-7.32 (m, 1H), 6.89-6.88 (m, 1H), 6.72-6.69 (m, 1H), 4.83 (s, 2H), 2.18-2.14 (m, 1H), 1.33-1.30 (m, 2H), 1.17-1.15 (m, 2H).

<Example 31>3-((2-chloro-4-((5-cyclopropyl-3-(2,6-dichlorophenyl)isoxazol-4-yl)methoxy)phenyl)ethynyl)-5-(trifluoromethyl)benzoic acid (I-31)

Step 1: Preparation of methyl 3-((2-chloro-4-((5-cyclopropyl-3-(2,6-dichlorophenyl)isoxazol-4-yl)methoxy)phenyl)ethynyl)-5-(trifluoromethyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(50 mg, 0.119 mmol) was reacted with methyl 3-bromo-5-(trifluoromethyl)benzoate (41 mg, 0.143 mmol), bis(triphenyl phosphine)palladium(II) dichloride (PdCl$_2$(PPh$_3$)$_2$, 8.4 mg, 0.012 mmol), Copper(I) iodide (2.3 mg, 0.012 mmol) and triethylamine (0.020 ml, 0.143 mmol) to afford the intermediate compound methyl 3-((2-chloro-4-((5-cyclopropyl-3-(2,6-dichloro phenyl)isoxazol-4-yl)methoxy)phenyl)ethynyl)-5-(trifluoromethyl)benzoate (56 mg, 76%).

$^1$H-NMR (CDCl$_3$, 400 MHz): δ 8.35 (s, 1H), 8.23 (s, 1H), 7.94 (s, 1H), 7.43-7.31 (m, 4H), 6.89-6.88 (m, 1H), 6.73-6.70 (m, 1H), 4.83 (s, 2H), 3.98 (s, 3H), 2.18-2.14 (m, 1H), 1.33-1.28 (m, 2H), 1.20-1.17 (m, 2H).

Step 2: Preparation of 3-((2-chloro-4-((5-cyclopropyl-3-(2,6-dichlorophenyl) isoxazol-4-yl)methoxy)phenyl)ethynyl)-5-(trifluoromethyl)benzoic acid This compound was made using the procedure described in Example 1 (Step 6). Thus, this intermediate compound (Step 1)(55 mg, 0.089 mmol) was reacted with lithium hydroxide (3.7 mg, 0.089 mmol) to afford the title compound (50 mg, 93%).

$^1$H-NMR (CDCl$_3$, 400 MHz): δ 8.40 (s, 1H), 8.29 (s, 1H), 7.99 (s, 1H), 7.52-7.32 (m, 4H), 6.90-6.89 (m, 1H), 6.73-6.70 (m, 1H), 4.84 (s, 2H), 2.18-2.14 (m, 1H), 1.32-1.28 (m, 2H), 1.20-1.15 (m, 2H).

<Example 32>3-((2-chloro-4-((cyclopropyl-3-(2,6-dichlorophenyl)isoxazol-4-yl)methoxy)phenyl)ethynyl)-5-ethynylbenzoic acid (I-32)

Step 1: Preparation of methyl 3-((2-chloro-4-((cyclopropyl-3-(2,6-dichlorophenyl)isoxazol-4-yl)methoxy)phenyl)ethynyl)-5-ethynylbenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(11.2 mg, 0.027 mmol) was reacted with methyl 3-bromo-5-((trimethylsilyl)ethynyl)benzoate (7.6 mg, 0.032 mmol), bis(triphenyl phosphine)palladium(II)dichloride (PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate methyl 3-((2-chloro-4-((cyclopropyl-3-(2,6-dichlorophenyl) isoxazol-4-yl)methoxy)phenyl)ethynyl)-5-ethynylbenzoate (14.7 mg, 85%).

$^1$H-NMR (CDCl$_3$, 400 MHz): δ 8.10 (t, 1H), 8.08 (t, 1H), 7.78 (t, 1H), 7.51-7.32 (m, 4H), 6.87 (d, 1H), 6.69 (dd, 1H), 4.82 (s, 2H), 3.93 (s, 3H), 2.24-2.10 (m, 1H), 1.30-1.26 (m, 2H), 1.23-1.12 (m, 2H).

Step 2: Preparation of 3-((2-chloro-4-((cyclopropyl-3-(2,6-dichlorophenyl) isoxazol-4-yl)methoxy)phenyl)ethynyl)-5-ethynylbenzoic acid This compound was made using the procedure described in Example 1 (Step 6). Thus, the intermediate compound (Step 1)(14.7 mg, 0.023 mmol) was reacted with lithium hydroxide (9.5 mg, 0.23 mmol) to afford the title compound (4.0 mg, 31%).

$^1$H-NMR (CDCl$_3$, 400 MHz): δ 8.98 (br, 1H), 8.24-8.20 (m, 1H), 8.17-8.12 (m, 1H), 7.87-7.85 (m, 1H), 7.44-7.39 (m, 3H), 7.37-7.34 (m, 1H), 6.88 (d, 1H), 6.70 (dd, 1H), 4.83 (s, 2H), 3.16 (s, 1H), 2.12-2.19 (m, 1H), 1.35-1.28 (m, 2H), 1.22-1.14 (m, 2H).

<Example 33>3-((2-chloro-4-((5-cyclopropyl-3-(2,6-dichlorophenyl)isoxazol-4-yl)methoxy)phenyl)ethynyl)-5-cyanobenzoic acid (I-33)

Step 1: Preparation of methyl 3-((2-chloro-4-((5-cyclopropyl-3-(2,6-dichlorophenyl)isoxazol-4-yl)methoxy)phenyl)ethynyl)-5-cyanobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 3-bromo-5-cyanobenzoate (129 mg, 0.52 mmol), bis(triphenylphosphine) palladium(II) dichloride (PdCl$_2$(PPh$_3$)$_2$, 42 mg, 0.06 mmol), copper(I) iodide (11.4 mg, 0.06 mmol) and 1,8-diazabicyclo[5.4.0]undec-7-ene (DBU, 0.4 ml, 2.6 mmol) to afford the intermediate compound methyl 3-((2-chloro-4-((5-cyclopropyl-3-(2,6-dichlorophenyl) isoxazol-4-yl)methoxy)phenyl)ethynyl)-5-cyanobenzoate (165 mg, 55%).

$^1$H-NMR (CDCl$_3$, 400 MHz): δ 8.39 (s, 1H), 8.26 (s, 1H), 7.97 (s, 1H), 7.45-7.34 (m, 4H), 6.91 (d, 1H), 6.75-6.72 (dd, 1H), 4.86 (s, 2H), 4.00 (s, 3H), 2.19-2.15 (m, 1H), 1.35-1.31 (m, 2H), 1.22-1.17 (m, 2H).

Step 2: Preparation of 3-((2-chloro-4-((5-cyclopropyl-3-(2,6-dichlorophenyl) isoxazol-4-yl)methoxy)phenyl)ethynyl)-5-cyanobenzoic acid This compound was made using the procedure described in Example 1 (Step 6). Thus, this intermediate compound (Step 1)(165 mg, 0.28 mmol) was reacted with lithium hydroxide (117 mg, 2.8 mmol) to afford the title compound (97 mg, 62%).

$^1$H-NMR (DMSO, 400 MHz): δ 8.20 (s, 1H), 8.17 (s, 1H), 8.01 (s, 1H), 7.64-7.53 (m, 4H), 7.11 (dd, 1H), 6.86-6.83 (dd, 1H), 4.99 (s, 2H), 2.48 (m, 1H), 1.24-1.12 (m, 4H).

<Example 34>3-((2,6-dichloro-4-((5-cyclopropyl-3-(2,6-dichlorophenyl) isoxazol-4-yl)methoxy)phenyl) ethynyl)benzoic acid (I-34)

Step 1: Preparation of tert-butyl(3,5-dichloro-4-iodophenoxy)dimethylsillane

This compound was made using the procedure described in Example 1 (Step 1). Thus, 3,5-dichloro-4-iodophenol (2 g, 6.92 mmol) was reacted with tert-butyldimethylsilyl chloride (TBSCl, 1.56 g, 10.38 mmol) and imidazole (0.94 g, 13.84 mmol) to afford the intermediate compound tert-butyl (3,5-dichloro-4-iodophenoxy)dimethylsillane (2.45 g, 88%).

$^1$H-NMR (CDCl$_3$, 400 MHz): δ 7.82 (s, 2H), 0.96 (s, 9H), 0.16 (s, 6H).

Step 2: Preparation of tert-butyl(3,5-dichloro-4-((trimethylsilyl)ethynyl) phenoxy)dimethylsillane This compound was made using the procedure described in Example 1 (Step 2). Thus, this intermediate compound (Step 1)(2.45 g, 6.09 mmol) was reacted with Trimethylsilylacetylene (1.73 ml, 12.18 mmol), bis(triphenylphosphine) palladium(II) dichloride (PdCl$_2$(PPh$_3$)$_2$, 0.43 g, 0.61 mmol), Copper(I) iodide (0.12 g, 0.61 mmol) and triethylamine (1.7 ml, 12.18 mmol) to afford the intermediate compound tert-butyl(3,5-dichloro-4-((trimethylsilyl)ethynyl)phenoxy) dimethyl silane (1.12 g, 52%).

$^1$H-NMR (CDCl$_3$, 400 MHz): δ 7.82 (s, 2H), 0.96 (s, 9H), 0.25 (s, 9H), 0.16 (s, 6H).

Step 3: Preparation of 3,5-dichloro-4-((trimethylsilyl)ethynyl)phenol

This compound was made using the procedure described in Example 1 (Step 3). Thus, this intermediate compound (Step 2)(1.12 g, 3.17 mmol) was reacted with potassium fluoride (KF, 1.84 g, 31.7 mmol) to afford the intermediate compound 3,5-dichloro-4-((trimethylsilyl)ethynyl)phenol. The resulting residue was used for next step without any further purification.

Step 4: Preparation of 5-cyclopropyl-4-((3,5-dichloro-4-ethynylphenoxy)methyl)-3-(2,6-dichlorophenyl)isoxazole This compound was made using the procedure described in Example 1 (Step 4). Thus, this intermediate compound (Step 3)(3.17 mmol) was reacted with 4-(bromomethyl)-5-cyclopropyl-3-(2,6-dichlorophenyl)isoxlazole (Intermediate 1)(1.1 g, 3.17 mmol) and potassium carbonate (0.66 g, 4.76 mmol) to afford the intermediate compound 5-cyclopropyl-4-((3,5-dichloro-4-ethynylphenoxy)methyl)-3-(2,6-dichlorophenyl)isoxazole (1.16 g, 81%).

$^1$H-NMR (CDCl$_3$, 400 MHz): δ 7.41-7.30 (m, 3H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 5: Preparation of methyl 3-((2,6-dichloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, this intermediate compound (Step 4)(200 mg, 0.48 mmol) was reacted with methyl 3-bromobenzoate (103 mg, 0.48 mmol), bis(triphenylphosphine) palladium(II) dichloride (PdCl$_2$(PPh$_3$)$_2$, 35 mg, 0.05 mmol), Copper(I) iodide (10 mg, 0.05 mmol) and triethylamine (0.14 ml, 0.96 mmol) to afford the intermediate compound methyl 3-((2,6-dichloro-4-((5-cyclopropyl-3-(2,6-dichlorophenyl) isoxazol-4-yl)methoxy)phenyl)ethynyl) benzoate (158 mg, 56%).

$^1$H-NMR (CDCl$_3$, 400 MHz): δ 8.22-8.21 (m, 1H), 8.02-8.00 (m, 1H), 7.75-7.72 (m, 1H), 7.46-7.32 (m, 4H), 6.81 (d, 2H), 4.83 (s, 2H), 3.94 (s, 3H), 2.17-2.12 (m, 1H), 1.34-1.30 (m, 2H), 1.20-1.16 (m, 2H).

Step 6: Preparation of 3-((2,6-dichloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 5)(158 mg, 0.269 mmol) was reacted with lithium hydroxide (112 mg, 2.70 mmol) to afford the title compound (150 mg, 97%).

$^1$H-NMR (CDCl$_3$, 400 MHz): δ 8.08-8.07 (m, 1H), 7.89-7.88 (m, 1H), 7.45-7.28 (m, 5H), 6.68-6.67 (m, 2H), 4.75 (s, 2H), 2.11-2.08 (m, 1H), 1.27-1.26 (m, 2H), 1.15-1.13 (m, 2H).

<Example 35>2-chloro-3-((2-chloro-4-((5-cyclopropyl-3-(2,6-dichloro phenyl)isoxazol-4-yl)methoxy)phenyl)ethynyl)benzoic acid (I-35)

Step 1: Preparation of methyl 2-chloro-3-((2-chloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(268 mg, 0.64 mmol) was reacted with methyl 3-boromo-2-chlorobenzoate (173 mg, 0.58 mmol), bis(triphenylphosphine) palladium(II) dichloride (PdCl$_2$(PPh$_3$)$_2$, 81 mg, 0.12 mmol), copper(I) iodide (11 mg, 0.06 mmol) and triethylamine (0.4 ml, 2.9 mmol) to afford the intermediate compound methyl 2-chloro-3-((2-chloro-4-((5-cyclopropyl-3-(2,6-dichloro phenyl)isoxazol-4-yl)methoxy) phenyl)ethynyl)benzoate (152 mg, 44%).

$^1$H-NMR (CDCl$_3$, 400 MHz): δ 7.72-7.67 (m, 2H), 7.46-7.40 (m, 3H), 7.35-7.24 (m, 2H), 6.88 (d, 1H), 6.71 (dd, 1H), 4.82 (s, 2H), 3.94 (s, 3H), 2.17-2.13 (m, 1H), 1.32-1.28 (m, 2H), 1.19-1.14 (m, 2H).

Step 2: Preparation of 2-chloro-3-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, the intermediate compound (Step 1)(152 mg, 0.26 mmol) was reacted with lithium hydroxide (109 mg, 2.6 mmol) to afford the title compound (86 mg, 58%).

$^1$H-NMR (DMSO, 400 MHz): δ 13.61 (s, 1H), 7.78 (t, 2H), 7.64-7.53 (m, 4H), 7.48 (t, 1H), 7.11 (d, 1H), 6.86 (dd, 1H), 4.99 (s, 2H), 2.47 (m, 1H), 1.24-1.12 (m, 4H).

<Example 36>3-((2-chloro-4-((5-cyclopropyl-3-(2,6-dichlorophenyl)isoxazol-4-yl)methoxy)phenyl)ethynyl)-2-fluorobenzoic acid (I-36)

Step 1: Preparation of methyl 3-((2-chloro-4-((5-cyclopropyl-3-(2,6-dichlorophenyl)isoxazol-4-yl)methoxy)phenyl)ethynyl)-2-fluorobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(60 mg, 0.143 mmol) was reacted with methyl 2-fluoro-3-iodobenzoate (48 mg, 0.171 mmol), bis(triphenylphosphine) palladium(II) dichloride (PdCl$_2$(PPh$_3$)$_2$, 10.1 mg, 0.014 mmol), Copper(I) iodide (2.8 mg, 0.014 mmol) and triethylamine (0.024 ml, 0.172 mmol) to afford the intermediate compound methyl 3-((2-chloro-4-((5-cyclopropyl-3-(2,6-dichlorophenyl)isoxazol-4-yl)methoxy)phenyl)ethynyl)-2-fluorobenzoate (76 mg, 93%).

$^1$H-NMR (CDCl$_3$, 400 MHz): δ 7.99-7.98 (m, 1H), 7.71-7.30 (m, 4H), 6.98-6.97 (m, 1H), 6.78-6.77 (m, 1H), 6.61-6.59 (m, 1H), 4.80 (s, 2H), 3.93 (s, 3H), 2.17-2.15 (m, 1H), 1.23-1.19 (m, 2H), 1.15-1.10 (m, 2H).

Step 2: Preparation of 3-((2-chloro-4-((5-cyclopropyl-3-(2,6-dichlorophenyl) isoxazol-4-yl)methoxy) phenyl)ethynyl)-2-fluorobenzoic acid This compound was made using the procedure described in Example 1 (Step 6). Thus, this intermediate compound (Step 1)(76 mg, 0.133 mmol) was reacted with lithium hydroxide (11.2 mg, 0.266 mmol) to afford the title compound (62 mg, 83%).

$^1$H-NMR (CDCl$_3$, 400 MHz): δ 7.82-7.80 (m, 1H), 7.43-7.28 (m, 4H), 6.94-6.93 (m, 1H), 6.77-6.76 (m, 1H), 6.59-6.57 (m, 1H), 4.76 (s, 2H), 2.14-2.07 (m, 1H), 1.23-1.19 (m, 2H), 1.15-1.10 (m, 2H).

<Example 37>5-((2-chloro-4-((5-cyclopropyl-3-(2,6-dichlorophenyl)isoxazol-4-yl)methoxy)phenyl)ethynyl)-2-fluorobenzoic acid (I-37)

Step 1: Preparation of methyl 5-((2-chloro-4-((5-cyclopropyl-3-(2,6-dichlorophenyl)isoxazol-4-yl)methoxy)phenyl)ethynyl)-2-fluorobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(60 mg, 0.143 mmol) was reacted with methyl 2-fluoro-5-iodobenzoate (48 mg, 0.171 mmol), bis (triphenylphosphine) palladium(II) dichloride (PdCl$_2$(PPh$_3$)$_2$, 10.1 mg, 0.014 mmol), Copper(I) iodide (2.8 mg, 0.014 mmol) and triethylamine (0.024 ml, 0.172 mmol) to afford the intermediate compound methyl 5((2-chloro-4-((5-cyclopropyl-3-(2,6-dichloro phenyl)isoxazol-4-yl)methoxy)phenyl)ethynyl)-2-fluorobenzoate (42 mg, 51%).

$^1$H-NMR (CDCl$_3$, 400 MHz): δ 8.21-8.20 (m, 1H), 7.78-7.75 (m, 1H), 7.50-7.40 (m, 4H), 7.20-7.15 (m, 1H), 7.00-6.98 (m, 1H), 6.84-6.81 (m, 1H), 5.14 (s, 2H), 4.15 (s, 3H), 2.23-2.21 (m, 1H), 1.45-1.41 (m, 2H), 1.21-1.18 (m, 2H).

Step 2: Preparation of 5-((2-chloro-4-((5-cyclopropyl-3-(2,6-dichlorophenyl) isoxazol-4-yl)methoxy) phenyl)ethynyl)-2-fluorobenzoic acid This compound was made using the procedure described in Example 1 (Step 6). Thus, this intermediate compound (Step 1)(42 mg, 0.0735 mmol) was reacted with lithium hydroxide (9.3 mg, 0.221 mmol) to afford the title compound (32 mg, 79%).

$^1$H-NMR (CDCl$_3$, 400 MHz): δ 8.14-8.13 (m, 1H), 7.64-7.61 (m, 1H), 7.41-7.31 (m, 4H), 7.12-7.07 (m, 1H), 6.85-6.84 (m, 1H), 6.68-6.66 (m, 1H), 4.81 (s, 2H), 2.17-2.10 (m, 1H), 1.31-1.27 (m, 2H), 1.19-1.14 (m, 2H).

<Example 38>3-((2-chloro-4-((5-cyclopropyl-3-(2, 6-dichlorophenyl)isoxazol-4-yl)methoxy)phenyl) ethynyl)-4-fluorobenzoic acid (I-38)

Step 1: Preparation of methyl 3-((2-chloro-4-((5-cyclopropyl-3-(2,6-dichlorophenyl)isoxazol-4-yl) methoxy)phenyl)ethynyl)-4-fluorobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(50 mg, 0.119 mmol) was reacted with methyl 4-fluoro-3-iodobenzoate (40 mg, 0.143 mmol), bis(triphenylphosphine) palladium(II) dichloride (PdCl$_2$(PPh$_3$)$_2$, 8.4 mg, 0.012 mmol), Copper(I) iodide (2.3 mg, 0.012 mmol) and triethylamine (0.020 ml, 0.143 mmol) to afford the intermediate compound methyl 3-((2-chloro-4-((5-cyclopropyl-3-(2,6-dichloro phenyl)isoxazol-4-yl)methoxy)phenyl)ethynyl)-4-fluorobenzoate (54 mg, 66%).

$^1$H-NMR (CDCl$_3$, 400 MHz): δ 8.20-8.19 (m, 1H), 7.79-7.76 (m, 1H), 7.52-7.41 (m, 4H), 7.22-7.17 (m, 1H), 7.01-6.99 (m, 1H), 6.84-6.81 (m, 1H), 5.14 (s, 2H), 4.16 (s, 3H), 2.23-2.21 (m, 1H), 1.46-1.42 (m, 2H), 1.22-1.19 (m, 2H).

Step 2: Preparation of 3-((2-chloro-4-((5-cyclopropyl-3-(2,6-dichlorophenyl) isoxazol-4-yl)methoxy) phenyl)ethynyl)-4-fluorobenzoic acid This compound was made using the procedure described in Example 1 (Step 6). Thus, this intermediate compound (Step 1)(54 mg, 0.0946 mmol) was reacted with lithium hydroxide (7.9 mg, 0.189 mmol) to afford the title compound (40 mg, 76%).

$^1$H-NMR (CDCl$_3$, 400 MHz): δ 8.20-8.19 (m, 1H), 7.97-7.96 (m, 1H), 7.46-7.29 (m, 4H), 7.04-7.02 (m, 1H), 6.84-6.83 (m, 1H), 6.66-6.64 (m, 1H), 4.80 (s, 2H), 2.17-2.10 (m, 1H), 1.30-1.28 (m, 2H), 1.18-1.13 (m, 2H).

<Example 39>3-((2-chloro-4-((5-cyclopropyl-3-(2, 6-dichlorophenyl)isoxazol-4-yl)methoxy)phenyl) ethynyl)-5-(trifluoromethoxy)benzoic acid (I-39)

Step 1: Preparation of methyl 3-((2-chloro-4-((5-cyclopropyl-3-(2,6-dichlorophenyl)isoxazol-4-yl) methoxy)phenyl)ethynyl)-5-(trifluoromethoxy)benzoate This compound was made using the procedure described in Example 1 (Step 5). Thus 4-((3-chloro-4-ethynylphenoxy)methyl)-5-cyclopropyl-3-(2,6-dichloro phenyl)isoxazole (Example 5)(100 mg, 0.23 mmol) was reacted with methyl 3-bromo-5-(trifluoromethoxy)benzoate (68.8 mg, 0.23 mmol), bis(triphenyl phosphine)palladium(II)dichloride (PdCl$_2$(PPh$_3$)$_2$, 16 mg, 0.023 mmol), Copper(I) iodide (4.4. mg, 0.023 mmol) and triethylamine (0.1 ml, 0.71 mmol) to afford the intermediate compound methyl 3-((2-chloro-4-((5-cyclopropyl-3-(2,6-dichlorophenyl)isoxazol-4-yl)methoxy)phenyl)ethynyl)-5-(trifluoromethoxy)benzoate (67.0 mg, 50%).

$^1$H-NMR (CDCl$_3$, 400 MHz): δ 8.12 (s, 1H), 8.11 (s, 1H), 7.73 (s, 1H), 7.54-7.31 (m, 4H), 6.88 (d, 1H), 6.71 (dd, 1H), 4.83 (s, 2H), 3.95 (s, 3H), 2.19-2.12 (m, 1H), 1.37-1.29 (m, 2H), 1.26-1.18 (m, 2H).

Step 2: Preparation of 3-((2-chloro-4-((5-cyclopropyl-3-(2,6-dichlorophenyl) isoxazol-4-yl)methoxy) phenyl)ethynyl)-5-(trifluoromethoxy)benzoic acid This compound was made using the procedure described in Example 1 (Step 6). Thus, this intermediate compound (Step 1)(67.0 mg, 0.10 mmol) was reacted with LiOH (44.0 mg, 1.05 mmol) to afford the title compound (58 mg, 93%).

$^1$H-NMR (CDCl$_3$, 400 MHz): δ 8.17 (s, 1H), 7.89 (s, 1H), 7.59 (s, 1H), 7.43-7.32 (m, 4H), 6.88 (d, 1H), 6.72 (dd, 1H), 4.83 (s, 2H), 2.19-2.12 (m, 1H), 1.32-1.27 (m, 2H), 1.24-1.14 (m, 2H).

<Example 40>3-((2-chloro-4-((5-cyclopropyl-3-(2, 6-dichlorophenyl)isoxazol-4-yl)methoxy)phenyl) ethynyl)-5-methoxybenzoic acid (I-40)

Step 1: Preparation of methyl 3-((2-chloro-4-((5-cyclopropyl-3-(2,6-dichlorophenyl)isoxazol-4-yl) methoxy)phenyl)ethynyl)-5-methoxybenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 6)(150 mg, 0.35 mmol) was reacted with methyl 3-bromo-5-methoxybenzoate (88 mg, 0.35 mmol), bis(triphenylphosphine) palladium(II)dichloride (PdCl$_2$(PPh$_3$)$_2$, 12.5 mg, 0.018 mmol), Copper(I) iodide (3.4. mg, 0.018 mmol) and triethylamine (0.1 ml, 1.07 mmol) to afford the intermediate compound methyl 3-((2-chloro-4-((5-cyclopropyl-3-(2,6-dichlorophenyl)isoxazol-4-yl)methoxy)phenyl)ethyl)-5-methoxybenzoate (24.0 mg, 12%).

$^1$H-NMR (CDCl$_3$, 400 MHz): δ 7.80 (s, 1H), 7.79 (s, 1H), 7.54-7.52 (m, 2H), 7.42-7.33 (m, 2H), 7.23 (t, 1H), 6.87 (d, 1H), 6.70 (dd, 1H), 4.82 (s, 2H), 4.0 (s, 3H), 3.86 (s, 3H), 2.17-2.13 (m, 1H), 1.32-1.28 (m, 2H), 1.19-1.14 (m, 2H).

Step 2: Preparation of 3-((2-chloro-4-((5-cyclopropyl-3-(2,6-dichlorophenyl) isoxazol-4-yl)methoxy) phenyl)ethynyl)-5-methoxybenzoic acid This compound was made using the procedure described in Example 1 (Step 6). Thus, this intermediate compound (Step 1)(24.0 mg, 0.04 mmol) was reacted with LiOH (16.7 mg, 0.40 mmol) to afford the title compound (9 mg, 40%).

$^1$H-NMR (CDCl$_3$, 400 MHz): δ 7.76 (s, 1H), 7.50 (s, 1H), 7.49-7.30 (m, 4H), 7.27 (s, 1H), 7.17 (s, 1H), 6.81 (dd, 1H), 4.77 (s, 2H), 3.81 (s, 3H), 2.13-2.10 (m, 1H), 1.26-1.20 (m, 2H), 1.14-1.10 (m, 2H).

<Example 41> 3-((2-chloro-4-((5-cyclopropyl-3-(2,6-dichlorophenyl)isoxazol-4-yl)methoxy)phenyl)ethynyl)-5-formylbenzoic acid (I-41)

Step 1: Preparation of methyl 3-((2-chloro-4-((5-cyclopropyl-3-(2,6-dichlorophenyl)isoxazol-4-yl)methoxy)phenyl)ethynyl)-5-formylbenzoate This compound was made using the procedure described in Example 1 (Step 5). Thus 4-((3-chloro-4-ethynylphenoxy)methyl)-5-cyclopropyl-3-(2,6-dichloro phenyl)isoxazole (Example 5)(3.2 g, 13 mmol) was reacted with methyl 3-bromo-5-formylbenzoate (3.71 g, 16 mmol), bis(triphenylphosphine) palladium(II) dichloride (PdCl$_2$(PPh$_3$)$_2$ (420 mg, 0.65 mol), copper(I)iodide (114 mg, 0.65 mol) and triethylamine (2.2 ml, 16 mmol) to afford the intermediate compound methyl 3-((2-chloro-4-((5-cyclopropyl-3-(2,6-dichlorophenyl)isoxazol-4-yl) methoxy)phenyl)ethynyl)-5-formylbenzoate (4.1 g, 58%).

$^1$H-NMR (CDCl$_3$, 400 MHz): δ 10.06 (s, 1H), 8.46-8.40 (m, 2H), 8.20-8.19 (m, 1H), 7.43-7.31 (m, 4H), 6.89 (d, 1H), 6.71 (dd, 1H), 4.83 (s, 2H), 3.98 (s, 3H), 2.17-2.13 (m, 1H), 1.32-1.25 (m, 2H), 1.19-1.16 (m, 2H).

Step 2: Preparation of 3-((2-chloro-4-((5-cyclopropyl-3-(2,6-dichlorophenyl) isoxazol-4-yl)methoxy)phenyl)ethynyl)-5-formylbenzoic acid This compound was made using the procedure described in Example 1 (Step 6). Thus the intermediate compound (Step 1)(100 mg, 0.172 mmol) was reacted with lithium hydroxide (72.2 mg, 1.72 mmol) to afford the title compound (35 mg, 33%).

$^1$H-NMR (DMSO, 400 MHz): δ 13.70 (s, 1H), 10.10 (s, 1H), 8.41 (s, 1H), 8.26-8.23 (m, 2H), 7.64-7.53 (m, 4H), 7.11 (d, 1H), 6.86 (dd, 1H), 4.99 (s, 2H), 2.66-2.32 (m, 1H), 1.20-1.14 (m, 4H).

<Example 42> 3-((2-Chloro-4-((5-cyclopropyl-3-(2,6-dichlorophenyl) isoxazole-4-yl)methoxy)phenyl)ethynyl)-5-((cyclopropylamino)methyl)benzoic acid (I-42)

Step 1: Preparation of methyl 3-((2-chloro-4-((5-cyclopropyl-3-(2,6-dichlorophenyl)isoxazole-4-yl)methoxy)phenyl)ethynyl)-5-((cyclopropylamino)methyl)benzoate Cyclopropylamine (0.042 ml, 0.60 mmol) and acetic acid (16 mg, 0.258 mmol) was added to a solution of intermediate compound (Step 1 of Example 41)(150 mg, 0.258 mmol) in 1,2-dichloroethane (2 ml) and stirred for 12 hours at room temperature. Sodium cyanoborohydride (49 mg, 0.775 mmol) was added to a solution of reaction mixture and stirred for 2 hours at room temperature. The reaction mixture was concentrated in vacuum, added dichloromethane and washed brine. The combined organic layers were dried over MgSO$_4$, filtered, evaporated in vacuum and purified using silica chromatography to give the intermediate compound 3-((2-Chloro-4-((5-cyclopropyl-3-(2,6-dichloro phenyl)isoxazole-4-yl)methoxy)phenyl)ethynyl)-5-((cyclopropylamino)methyl)benzoate (100 mg, 64%).

$^1$H-NMR (CDCl$_3$, 400 MHz): δ 8.10 (s, 1H), 7.93 (s, 1H), 7.68 (s, 1H), 7.42-7.35 (m, 4H), 6.87 (d, 1H), 6.69 (dd, 1H), 4.82 (s, 2H), 3.92 (s, 3H), 3.45-3.41 (m, 4H), 2.25-2.12 (m, 4H), 1.32-1.14 (m, 4H).

Step 2: Preparation of 3-((2-Chloro-4-((5-cyclopropyl-3-(2,6-dichlorophenyl) isoxazole-4-yl)methoxy)phenyl)ethynyl)-5-((cyclopropylamino)methyl)benzoic acid This compound was made using the procedure described in Example 1 (Step 6). Thus, this intermediate compound (Step 1)(58 mg, 0.12 mmol) was reacted with lithium hydroxide (40 mg, 0.96 mmol) to afford the title compound (62 mg, 82%).

$^1$H-NMR (DMSO, 400 MHz): δ 12.50 (brs, 1H), 7.93 (s, 1H), 7.88 (s, 1H), 7.70 (s, 1H), 7.63-7.53 (m, 4H), 7.09 (d, 1H), 6.83 (dd, 1H), 4.98 (s, 2H), 3.82 (s, 2H), 2.10-2.04 (m, 1H), 1.20-1.13 (m, 5H), 0.38-0.30 (m, 4H).

<Example 43> 3-(Azetidine-1-ylmethyl)-5-((2-chloro-4-((5-cyclopropyl-3-(2,6-dichlorophenyl)isoxazole-4-yl)methoxy)phenyl)ethynyl)benzoic acid (I-43)

Step 1: Preparation of Methyl 3-(azetidine-1-ylmethyl)-5-((2-chloro-4-((5-cyclopropyl-3-(2,6-dichlorophenyl)isoxazole-4-yl)methoxy)phenyl)ethynyl)benzoate This compound was made using the procedure described in Example 42 (Step 1). Thus, methyl-3-((chloro-4((cyclopropyl-3-(2,6-dichlorophenyl)isoxazole-4-yl)methoxy)phenyl)ethynyl)-5-formylbenzoate (Step 1 of Example 41)(150 mg, 0.258 mmol) was reacted with azetidinecyclopropylamine (40 ul, 0.60 mmol) and acetic acid (16 mg, 0.258 mmol), Sodium cyanoborohydride (49 mg, 0.775 mmol) to afford the intermediate compound methyl 3-(azetidine-1-ylmethyl)-5-((2-chloro-4-((5-cyclopropyl-3-(2,6-dichlorophenyl)isoxazole-4-yl)methoxy)phenyl)ethynyl)benzoate (100 mg, 64%).

$^1$H-NMR (CDCl$_3$, 400 MHz): δ 8.07 (s, 1H), 7.94 (s, 1H), 7.66 (s, 1H), 7.41-7.30 (m, 4H), 6.87 (d, 1H), 6.69 (dd, 1H), 4.81 (s, 2H), 3.92 (s, 3H), 3.88 (s, 2H), 2.17-2.11 (m, 2H), 1.31-1.13 (m, 5H), 0.47-0.39 (m, 4H).

Step 2: Preparation of 3-(Azetidine-1-ylmethyl)-5-((2-chloro-4-((5-cyclopropyl-3-(2,6-dichlorophenyl) isoxazole-4-yl)methoxy)phenyl)ethynyl)benzoic acid This compound was made using the procedure described in Example 1 (Step 6). Thus, this intermediate compound (Step 1)(23 mg, 0.04 mmol) was reacted with lithium hydroxide (15 mg, 0.36 mmol) to afford the title compound (11 mg, 49%).

$^1$H-NMR (CDCl$_3$, 400 MHz): δ 8.64 (s, 1H), 8.25 (s, 1H), 7.47 (s, 1H), 7.41-7.31 (m, 4H), 6.86 (d, 1H), 6.68 (dd, 1H), 4.81 (s, 2H), 4.05 (s, 2H), 3.95-3.90 (m, 2H), 2.18-2.11 (m, 1H), 1.31-1.14 (m, 6H).

<Example 44> 3-((2-Chloro-4-((5-cyclopropyl-3-(2,6-dichlorophenyl) isoxazole-4-yl)methoxy)phenyl)ethynyl)-5-((methylamino)methyl)benzoic acid (I-44)

Step 1: Preparation of Methyl 3-((2-chloro-4-((5-cyclopropyl-3-(2,6-dichloro phenyl)isoxazole-4-yl)methoxy)phenyl)ethynyl)-5-((methylamino)methyl)benzoate This compound was made using the procedure described in Example 42 (Step 1). Thus, methyl-3-((chloro-4((cyclopropyl-3-(2,6-dichlorophenyl)isoxazole-4-yl)methoxy)phenyl)ethynyl)-5-formylbenzoate (Step 1 of Example 41) (150 mg, 0.258 mmol) was reacted with methylamine (0.1 ml, 0.60 mmol) and acetic acid (16 mg, 0.258 mmol), Sodium cyanoborohydride (49 mg, 0.775 mmol) to afford the intermediate compound methy 3-((2-chloro-4-((5-cyclopropyl-3-(2,6-dichlorophenyl)isoxazole-4-yl)methoxy)phenyl)ethynyl)-5-((methylamino)methyl)benzoate (100 mg, 64%).

$^1$H-NMR (CDCl$_3$, 400 MHz): δ 8.19 (s, 1H), 7.99 (s, 1H), 7.69 (s, 1H), 7.41-7.31 (m, 4H), 6.87 (d, 1H), 6.70 (dd, 1H), 4.82 (s, 2H), 3.93 (s, 3H), 3.66 (s, NH, 1H), 2.50 (s, 2H), 2.17-2.13 (m, 1H), 2.04 (s, 3H), 1.31-1.27 (m, 2H), 1.23-1.13 (m, 2H).

Step 2: Preparation of 3-((2-Chloro-4-((5-cyclopropyl-3-(2,6-dichlorophenyl)isoxazole-4-yl)methoxy)phenyl)ethynyl)-5-((methylamino)methyl)benzoic acid This compound was made using the procedure described in Example 1 (Step 6). Thus, this intermediate compound (Step 1)(26 mg, 0.04 mmol) was reacted with lithium hydroxide (18 mg, 0.43 mmol) to afford the title compound (8.5 mg, 32%).

$^1$H-NMR (DMSO, 400 MHz): δ 8.18 (s, 1H), 7.93 (s, 1H), 7.67-7.52 (m, 5H), 7.09 (d, 1H), 6.83 (dd, 1H), 4.98 (s, 2H), 4.01 (s, 2H), 1.25-1.11 (m, 5H).

<Example 45>3-((2-chloro-4-((5-cyclopropyl-3-(2,6-dichlorophenyl)isoxazol-4-yl)methoxy)phenyl)ethynyl)-5-((ethylamino)methyl)benzoic acid (I-45)

Step 1: Preparation of methyl 3-((2-chloro-4-((5-cyclopropyl-3-(2,6-dichloro phenyl)isoxazol-4-yl)methoxy)phenyl)ethynyl)-5-((ethylamino)methyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of Example 41) (150 mg, 0.258 mmol) was reacted with acetic acid (16 mg, 0.258 mmol), 6.0M ethylamine (0.1 ml, 0.60 mmol) and sodium cyanoborohydride (49 mg, 0.775 mmol) to afford the intermediate compound 3-((2-chloro-4-((5-cyclopropyl-3-(2,6-dichlorophenyl)isoxazol-4-yl)methoxy)phenyl)ethynyl)-5-((ethylamino)methyl)benzoate (100 mg, 64%).

$^1$H-NMR (CDCl$_3$, 400 MHz): δ 8.08 (s, 1H), 7.95 (s, 1H), 7.69 (s, 1H), 7.42-7.38 (m, 3H), 7.35-7.31 (m, 1H), 6.87 (d, 1H), 6.69 (dd, 1H), 4.81 (s, 2H), 3.92 (s, 3H), 3.84 (s, 2H), 2.70 (q, 2H), 2.18-2.13 (m, 1H), 1.31-1.27 (m, 2H), 1.20-1.12 (m, 5H).

Step 2: Preparation of 3-((2-chloro-4-((5-cyclopropyl-3-(2,6-dichlorophenyl) isoxazol-4-yl)methoxy)phenyl)ethynyl)-5-((ethylamino)methyl)benzoic acid This compound was made using the procedure described in Example 1 (Step 6). Thus the intermediate compound (Step 1)(100 mg, 0.164 mmol) was reacted with lithium hydroxide (69 mg, 1.64 mmol) to afford the title compound (88 mg, 91%).

$^1$H-NMR (DMSO, 400 MHz): δ 8.14 (s, 1H), 8.01 (s, 1H), 7.88 (s, 1H), 7.64-7.61 (m, 2H), 7.57-7.53 (m, 2H), 7.10 (d, 1H), 6.85 (dd, 1H), 4.98 (s, 2H), 4.18 (s, 2H), 2.97 (q, 2H), 2.52-2.47 (m, 1H), 1.23-1.17 (m, 5H), 1.59-1.32 (m, 2H).

<Example 46>3-((2-chloro-4-((5-cyclopropyl-3-(2,6-dichlorophenyl)isoxazol-4-yl)methoxy)phenyl)ethynyl)-5-(((2,2,2-trifluoroethyl)amino)methyl)benzoic acid (I-46)

Step 1: Preparation of methyl 3-((2-chloro-4-((5-cyclopropyl-3-(2,6-dichlorophenyl)isoxazol-4-yl)methoxy)phenyl)ethynyl)-5-(((2,2,2-trifluoroethyl)amino)methyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of Example 41) (200 mg, 0.344 mmol) was reacted with acetic acid (21 mg, 0.344 mmol), trifluoroethylamine (51 mg, 0.516 mmol) and sodium cyanoborohydride (65 mg, 1.03 mmol) to afford the intermediate compound 3-((2-chloro-4-((5-cyclopropyl-3-(2,6-dichlorophenyl)isoxazol-4-yl)methoxy)phenyl)ethynyl)-5-(((2,2,2-trifluoroethyl)amino)methyl)benzoate (176 mg, 77%).

$^1$H-NMR (CDCl$_3$, 400 MHz): δ 8.08 (s, 1H), 7.94 (s, 1H), 7.68 (s, 1H), 7.43-7.38 (m, 3H), 7.33-7.29 (m, 1H), 6.86 (d, 1H), 6.69 (dd, 1H), 4.81 (s, 3H), 3.96-3.93 (m, 5H), 3.22 (q, 2H), 2.18-2.12 (m, 1H), 1.29-1.22 (m, 2H), 1.19-1.16 (m, 2H).

Step 2: Preparation of 3-((2-chloro-4-((5-cyclopropyl-3-(2,6-dichlorophenyl) isoxazol-4-yl)methoxy)phenyl)ethynyl)-5-(((2,2,2-trifluoroethyl)amino)methyl)benzoic acid This compound was made using the procedure described in Example 1 (Step 6). Thus the intermediate compound (Step 1)(176 mg, 0.254 mmol) was reacted with lithium hydroxide (54 mg, 1.28 mmol) to afford the title compound (130 mg, 78%).

$^1$H-NMR (CDCl$_3$, 400 MHz): δ 7.83-7.74 (m, 2H), 7.37-7.33 (m, 3H), 7.27-7.23 (m, 2H), 7.15-7.13 (m, 1H), 6.74 (d, 1H), 6.55 (dd, 1H), 4.72 (s, 2H), 4.14 (q, 2H), 3.59 (s, 2H), 2.11-2.02 (m, 1H), 1.20-1.11 (m, 2H), 0.90-0.85 (m, 2H).

<Example 47>3-((2-chloro-4-((5-cyclopropyl-3-(2,6-dichlorophenyl)isoxazol-4-yl)methoxy)phenyl)ethynyl)-5-((isopropylamino)methyl)benzoic acid (I-47)

Step 1: Preparation of methyl 3-((2-chloro-4-((5-cyclopropyl-3-(2,6-dichlorophenyl)isoxazol-4-yl)methoxy)phenyl)ethynyl)-5-((isopropylamino)methyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of Example 41) (200 mg, 0.344 mmol) was reacted with acetic acid (21 mg, 0.344 mmol), isopropylamine (31 mg, 0.516 mmol) and sodium cyanoborohydride (65 mg, 1.03 mmol) to afford the intermediate compound 3-((2-chloro-4-((5-cyclopropyl-3-(2,6-dichlorophenyl)isoxazol-4-yl)methoxy)phenyl)ethynyl)-5-((isopropylamino)methyl)benzoate (95 mg, 44%).

$^1$H-NMR (CDCl$_3$, 400 MHz): δ 8.07 (s, 1H), 7.95 (s, 1H), 7.69 (s, 1H), 7.42-7.39 (m, 3H), 7.35-7.31 (m, 1H), 6.87 (d, 1H), 6.69 (dd, 1H), 4.82 (s, 2H), 3.92 (s, 3H), 3.82 (s, 2H), 2.88-2.82 (m, 1H), 2.17-2.12 (m, 1H), 1.32-1.27 (m, 2H), 1.25-1.24 (m, 2H), 1.16 (d, 6H).

Step 2: Preparation of 3-((2-chloro-4-((5-cyclopropyl-3-(2,6-dichlorophenyl) isoxazol-4-yl)methoxy)phenyl)ethynyl)-5-((isopropylamino)methyl)benzoic acid This compound was made using the procedure described in Example 1 (Step 6). Thus the intermediate compound (Step 1)(95 mg, 0.144 mmol) was reacted with lithium hydroxide (61 mg, 1.44 mmol) to afford the title compound (71 mg, 81%).

$^1$H-NMR (DMSO, 400 MHz): δ 9.04 (s, 1H), 8.17 (s, 1H), 8.03 (s, 1H), 7.99 (s, 1H), 7.64-7.62 (m, 2H), 7.57-7.53 (m, 2H), 7.11 (d, 1H), 6.86 (dd, 1H), 4.99 (s, 2H), 4.24 (s, 2H), 3.30-3.25 (m, 1H), 2.50-2.47 (m, 1H), 1.31 (d, 6H), 1.20-1.12 (m, 4H).

<Example 48>3-((tert-butylamino)methyl)-5-((2-chloro-4-((5-cyclopropyl-3-(2,6-dichlorophenyl) isoxazol-4-yl)methoxy)phenyl)ethynyl)benzoic acid (I-48)

Step 1: Preparation of methyl 3-((tert-butylamino)methyl)-5-((2-chloro-4-((5-cyclopropyl-3-(2,6-dichlorophenyl)isoxazol-4-yl)methoxy)phenyl)ethynyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of Example 41) (200 mg, 0.344 mmol) was reacted with acetic acid (21 mg, 0.344 mmol), tert-butylamine (38 mg, 0.516 mmol) and sodium cyanoborohydride (65 mg, 1.03 mmol) to afford the intermediate compound methyl 3-((tert-butyl amino)methyl)-5-((2-chloro-4-((5-cyclopropyl-3-(2,6-dichlorophenyl) isoxazol-4-yl)methoxy)phenyl)ethynyl)benzoate (45 mg, 21%).

$^1$H-NMR (CDCl$_3$, 400 MHz): δ 8.05 (s, 1H), 7.96 (s, 1H), 7.71 (s, 1H), 7.41-7.38 (m, 3H), 7.35-7.31 (m, 1H), 6.87 (d, 1H), 6.69 (dd, 1H), 4.81 (s, 2H), 4.32 (s, 1H), 3.94 (s, 3H), 3.76 (s, 2H), 2.18-2.12 (m, 1H), 1.38-1.31 (m, 2H), 1.27-1.14 (m, 2H).

Step 2: Preparation of 3-((tert-butylamino)methyl)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus the intermediate compound (Step 1)(45 mg, 0.070 mmol) was reacted with lithium hydroxide (30 mg, 0.70 mmol) to afford the title compound (45 mg, 83%).

$^1$H-NMR (DMSO, 400 MHz): δ 13.45 (s, 1H), 9.03 (s, 1H), 8.19 (s, 1H), 8.04 (s, 1H), 8.01 (s, 1H), 7.64-7.62 (m, 2H), 7.58-7.53 (m, 2H), 7.11 (d, 1H), 6.86 (dd, 1H), 4.99 (s, 2H), 4.22 (s, 2H), 3.30-3.25 (m, 1H), 2.50-2.46 (m, 1H), 1.38 (s, 9H), 1.20-1.12 (m, 4H).

<Example 49>3-((2-chloro-4-((5-cyclopropyl-3-(2,6-dichlorophenyl)isoxazol-4-yl)methoxy)phenyl)ethynyl)-5-((dimethylamino)methyl)benzoic acid (I-49)

Step 1: Preparation of methyl 3-((2-chloro-4-((5-cyclopropyl-3-(2,6-dichloro phenyl)isoxazol-4-yl)methoxy)phenyl)ethynyl)-5-((dimethylamino)methyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of Example 41) (200 mg, 0.344 mmol) was reacted with acetic acid (21 mg, 0.344 mmol), dimethylamine (34 ul, 0.516 mmol) and sodium cyanoborohydride (65 mg, 1.03 mmol) to afford the intermediate compound methyl 3-((2-chloro-4-((5-cyclopropyl-3-(2,6-dichlorophenyl)isoxazol-4-yl)methoxy)phenyl)ethynyl)-5-((dimethylamino)methyl)benzoate (65 mg, 34%).

$^1$H-NMR (CDCl$_3$, 400 MHz): δ 8.13 (s, 1H), 7.95 (s, 1H), 7.72 (s, 1H), 7.41-7.31 (m, 4H), 6.86 (d, 1H), 6.68 (dd, 1H), 4.81 (s, 2H), 3.92 (s, 3H), 3.63 (s, 2H), 2.38 (s, 6H), 2.18-2.12 (m, 1H), 1.31-1.25 (m, 2H), 1.17-1.12 (m, 2H).

Step 2: Preparation of 3-((2-chloro-4-((5-cyclopropyl-3-(2,6-dichlorophenyl) isoxazol-4-yl)methoxy)phenyl)ethynyl)-5-((dimethylamino)methyl)benzoic acid This compound was made using the procedure described in Example 1 (Step 6). Thus the intermediate compound (Step 1)(65 mg, 0.04 mmol) was reacted with lithium hydroxide (40 mg, 0.40 mmol) to afford the title compound (9.7 mg, 40%).

$^1$H-NMR (CDCl$_3$, 400 MHz): δ 8.71 (s, 1H), 8.23 (s, 1H), 7.48 (s, 1H), 7.41-7.31 (m, 4H), 6.86 (d, 1H), 6.68 (dd, 1H), 4.81 (s, 2H), 3.69 (s, 2H), 2.69 (s, 6H), 2.18-2.11 (m, 1H), 1.31-1.27 (m, 2H), 1.19-1.14 (m, 2H).

<Example 50>3-((2-chloro-4-((5-cyclopropyl-3-(2,6-dichlorophenyl)isoxazol-4-yl)methoxy)phenyl)ethynyl)-5-(morpholinomethyl)benzoic acid (I-50)

Step 1: Preparation of methyl 3-((2-chloro-4-((5-cyclopropyl-3-(2,6-dichlorophenyl)isoxazol-4-yl)methoxy)phenyl)ethynyl)-5-(morpholinomethyl)benzoate This compound was made using the procedure described in Example 41 (Step 1). Thus methyl 3-((2-chloro-4-((5-cyclopropyl-3-(2,6-dichlorophenyl) isoxazol-4-yl)methoxy)phenyl)ethynyl)-5-formylbenzoate (Step 1 of example 41) (200 mg, 0.344 mmol) was reacted with acetic acid (21 mg, 0.344 mmol), morpholine (45 mg, 0.516 mmol) and sodium cyanoborohydride (65 mg, 1.03 mmol) to afford the intermediate compound methyl 3-((2-chloro-4-((5-cyclopropyl-3-(2,6-dichlorophenyl)isoxazol-4-yl)methoxy)phenyl)ethynyl)-5-(morpholinomethyl)benzoate (99 mg, 44%).

$^1$H-NMR (CDCl$_3$, 400 MHz): δ 8.09 (s, 1H), 7.95 (s, 1H), 7.69 (s, 1H), 7.42-7.39 (m, 3H), 7.35-7.31 (m, 1H), 6.88 (d, 1H), 6.70 (dd, 1H), 4.82 (s, 2H), 3.93 (s, 3H), 3.72-3.70 (m, 4H), 3.52 (s, 2H), 2.45-2.44 (m, 4H), 2.17-2.13 (m, 1H), 1.32-1.24 (m, 2H), 1.19-1.14 (m, 2H).

Step 2: Preparation of 3-((2-chloro-4-((5-cyclopropyl-3-(2,6-dichlorophenyl) isoxazol-4-yl)methoxy) phenyl)ethynyl)-5-(morpholinomethyl)benzoic acid This compound was made using the procedure described in Example 1 (Step 6). Thus the intermediate compound (Step 1)(99 mg, 0.151 mmol) was reacted with lithium hydroxide (63 mg, 1.51 mmol) to afford the title compound (85 mg, 96%).
$^1$H-NMR (DMSO, 400 MHz): δ 7.96-7.76 (m, 3H), 7.64-7.62 (m, 2H), 7.57-7.53 (m, 2H), 7.10 (d, 1H), 6.85 (dd, 1H), 4.99 (s, 2H), 3.78 (s, 2H), 3.30-3.25 (m, 4H), 2.50-2.46 (m, 5H), 1.27-1.11 (m, 4H).

<Example 51> 3-((2-chloro-4-((5-cyclopropyl-3-(2, 6-dichlorophenyl)isoxazol-4-yl)methoxy)phenyl) ethynyl)-5-((oxetan-3-ylamino)methyl)benzoic acid (I-51)

Step 1: Preparation of methyl 3-((2-chloro-4-((5-cyclopropyl-3-(2,6-dichlorophenyl)isoxazol-4-yl) methoxy)phenyl)ethynyl)-5-((oxetan-3-ylamino) methyl)benzoate This compound was made using the procedure described in Example 42 (Step 1). Thus methyl 3-((2-chloro-4-((5-cyclopropyl-3-(2,6-dichlorophenyl) isoxazol-4-yl)methoxy) phenyl)ethynyl)-5-formylbenzoate (Step 1 of Example 41) (200 mg, 0.344 mmol) was reacted with acetic acid (21 mg, 0.344 mmol), oxetan-3-yl amine (38 mg, 0.516 mmol) and sodium cyanoborohydride (65 mg, 1.03 mmol) to afford the intermediate compound methyl 3-((2-chloro-4-((5-cyclopropyl-3-(2,6-dichlorophenyl)isoxazol-4-yl)methoxy)phenyl) ethynyl)-5-((oxetan-3-ylamino)methyl)benzoate (98 mg, 45%).
$^1$H-NMR (CDCl$_3$, 400 MHz): δ 8.08 (s, 1H), 7.92 (s, 1H), 7.66 (s, 1H), 7.41-7.29 (m, 4H), 6.88 (d, 1H), 6.70 (dd, 1H), 4.82 (s, 2H), 4.78 (t, 2H), 4.42 (t, 2H), 4.03-3.99 (m, 1H), 3.92 (s, 3H), 3.77 (s, 2H), 2.19-2.11 (m, 1H), 1.29-1.23 (m, 2H), 1.17-1.13 (m, 2H).

Step 2: Preparation of 3-((2-chloro-4-((5-cyclopropyl-3-(2,6-dichlorophenyl) isoxazol-4-yl)methoxy) phenyl)ethynyl)-5-((oxetan-3-ylamino)methyl)benzoic acid This compound was made using the procedure described in Example 1 (Step 6). Thus the intermediate compound (Step 1)(98 mg, 0.154 mmol) was reacted with lithium hydroxide (64 mg, 1.54 mmol) to afford the title compound (40 mg, 46%).
$^1$H-NMR (DMSO, 400 MHz): δ 7.91-7.89 (m, 2H), 7.66 (s, 1H), 7.59-7.56 (m, 2H), 7.53-7.49 (m, 2H), 6.98 (d, 1H), 6.80 (dd, 1H), 4.94 (s, 2H), 4.60 (t, 2H), 4.37 (t, 2H), 4.01-3.97 (m, 1H), 3.77 (s, 2H), 2.42-2.38 (m, 1H), 1.21-1.17 (m, 2H), 1.10-1.07 (m, 2H).

<Example 52> 3-((2-chloro-4-((5-cyclopropyl-3-(2, 6-dichlorophenyl)isoxazol-4-yl)methoxy)phenyl) ethynyl)-5-(methylamino)benzoic acid (I-52)

Step 1: Preparation of methyl 3-((2-chloro-4-((5-cyclopropyl-3-(2,6-dichlorophenyl)isoxazol-4-yl) methoxy)phenyl)ethynyl)-5-(methylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-5-(methylamino)benzoate (63 mg, 0.26 mmol), bis(triphenylphosphine) palladium(II) dichloride (PdCl$_2$(PPh$_3$)$_2$, 21 mg, 0.03 mmol), copper(I) iodide (5.7 mg, 0.03 mmol) and 1,8-diazabicyclo[5.4.0]undec-7-ene (DBU, 0.2 ml, 1.3 mmol) to afford the intermediate compound methyl 3-((2-chloro-4-((5-cyclopropyl-3-(2,6-dichlorophenyl)isoxazol-4-yl)methoxy)phenyl)ethynyl)-5-(methylamino)benzoate (70 mg, 48%).
$^1$H-NMR (DMSO, 400 MHz): δ 7.52-7.39 (m, 4H), 7.34 (t, 1H), 7.21-7.20 (dd, 1H), 6.91-6.88 (m, 2H), 6.76-6.73 (dd, 1H), 4.39 (s, 2H), 3.88 (s, 3H), 2.79 (s, 3H), 2.34 (m, 1H), 1.28-1.20 (m, 4H).

Step 2: Preparation of 3-((2-chloro-4-((5-cyclopropyl-3-(2,6-dichlorophenyl) isoxazol-4-yl)methoxy) phenyl)ethynyl)-5-(methylamino)benzoic acid This compound was made using the procedure described in Example 1 (Step 6). Thus, this intermediate compound (Step 1)(70 mg, 0.13 mmol) was reacted with lithium hydroxide (54.5 mg, 1.3 mmol) to afford the title compound (36.8 mg, 53%).
$^1$H-NMR (DMSO, 400 MHz): δ 7.64 (d, 1H), 7.62 (d, 1H), 7.57-7.52 (m, 2H), 7.21 (m, 1H), 7.14 (t, 1H), 7.08 (d, 1H), 6.83 (d, 1H), 6.80 (m, 1H), 6.13 (br, 1H), 4.98 (s, 2H), 2.71 (d, 3H), 2.47 (m, 1H), 1.23-1.12 (m, 4H).

<Example 53> 3-((2-chloro-4-((5-cyclopropyl-3-(2, 6-dichlorophenyl)isoxazol-4-yl)methoxy)phenyl) ethynyl)-5-(ethylamino)benzoic acid (I-53)

Step 1: Preparation of methyl 3-((2-chloro-4-((5-cyclopropyl-3-(2,6-dichlorophenyl)isoxazol-4-yl) methoxy)phenyl)ethynyl)-5-(ethylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-5-(ethylamino)benzoate (67 mg, 0.26 mmol), bis(triphenyl phosphine)palladium(II) dichloride (PdCl$_2$(PPh$_3$)$_2$, 21 mg, 0.03 mmol), copper(I) iodide (5.7 mg, 0.03 mmol) and 1,8-diazabicyclo[5.4.0]undec-7-ene (DBU, 0.2 ml, 1.3 mmol) to afford the intermediate compound methyl 3-((2-chloro-4-((5-cyclopropyl-3-(2,6-dichlorophenyl)isoxazol-4-yl)methoxy)phenyl)ethynyl)-5-(ethylamino)benzoate (70 mg, 48%).
$^1$H-NMR (DMSO, 400 MHz): δ 7.52-7.39 (m, 4H), 7.34 (t, 1H), 7.21-7.20 (dd, 1H), 6.91-6.88 (m, 2H), 6.76-6.73 (dd, 1H), 4.39 (s, 2H), 3.88 (s, 3H), 3.03 (m, 2H), 2.79 (s, 3H), 2.34 (m, 1H), 1.28-1.20 (m, 4H).

Step 2: Preparation of 3-((2-chloro-4-((5-cyclopropyl-3-(2,6-dichlorophenyl) isoxazol-4-yl)methoxy) phenyl)ethynyl)-5-(ethylamino)benzoic acid This compound was made using the procedure described in Example 1 (Step 6). Thus, this intermediate compound (Step 1)(70 mg, 0.13 mmol) was reacted with lithium hydroxide (54.5 mg, 1.3 mmol) to afford the title compound (37.7 mg, 53%).
$^1$H-NMR (DMSO, 400 MHz): δ 7.64 (d, 1H), 7.62 (d, 1H), 7.57-7.52 (m, 2H), 7.21 (1H), 7.14 (t, 1H), 7.08 (d, 1H), 6.83 (d, 1H), 6.80 (m, 1H), 6.13 (br, 1H), 4.98 (s, 2H), 2.71 (d, 3H), 2.52 (m, 2H), 2.47 (m, 1H), 1.23-1.12 (m, 4H).

<Example 54>3-((2-chloro-4-((5-cyclopropyl-3-(2, 6-dichlorophenyl) isoxazol-4-yl)methoxy)phenyl) ethynyl)-5-(isopropylamino)benzoic acid (I-54)

Step 1: Preparation of methyl 3-((2-chloro-4-((5-cyclopropyl-3-(2,6-dichlorophenyl)isoxazol-4-yl) methoxy)phenyl)ethynyl)-5-(isopropylamino)benzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(50 mg, 0.119 mmol) was reacted with methyl 3-iodo-5-(isopropylamino)benzoate (46 mg, 0.143 mmol), bis(triphenylphosphine) palladium(II) dichloride (PdCl$_2$(PPh$_3$)$_2$, 8.4 mg, 0.012 mmol), Copper(I) iodide (2.3 mg, 0.012 mmol) and triethylamine (0.020 ml, 0.143 mmol) to afford the intermediate compound methyl 3-((2-chloro-4-((5-cyclopropyl-3-(2,6-dichlorophenyl)isoxazol-4-yl) methoxy)phenyl)ethynyl)-5-(isopropylamino)benzoate (23 mg, 34%).

$^1$H-NMR (CDCl$_3$, 400 MHz): δ 7.99-7.98 (m, 1H), 7.71-7.67 (m, 1H), 7.43-7.32 (m, 5H), 6.88-6.87 (m, 1H), 6.71-6.69 (m, 1H), 4.83 (s, 2H), 3.94 (s, 3H), 2.17-2.15 (m, 1H), 1.33-1.28 (m, 2H), 1.19-1.16 (m, 2H).

Step 2: Preparation of 3-((2-chloro-4-((5-cyclopropyl-3-(2,6-dichlorophenyl) isoxazol-4-yl)methoxy) phenyl)ethynyl)-5-(isopropylamino)benzoic acid This compound was made using the procedure described in Example 1 (Step 6). Thus, this intermediate compound (Step 1)(23 mg, 0.040 mmol) was reacted with lithium hydroxide (17 mg, 0.40 mmol) to afford the title compound (13 mg, 56%).

$^1$H-NMR (CDCl$_3$, 400 MHz): δ 8.05-8.04 (m, 1H), 7.76-7.73 (m, 1H), 7.47-7.43 (m, 4H), 7.36-7.32 (m, 1H), 6.89-6.88 (m, 1H), 6.72-6.69 (m, 1H), 4.83 (s, 2H), 2.18-2.14 (m, 1H), 1.33-1.30 (m, 2H), 1.17-1.15 (m, 2H).

<Example 55>3-(azetidin-1-yl)-5-((2-chloro-4-((5-cyclopropyl-3-(2,6-dichlorophenyl)isoxazol-4-yl) methoxy)phenyl)ethynyl)benzoic acid (I-55)

Step 1: Preparation of methyl 3-((2-chloro-4-((5-cyclopropyl-3-(2,6-dichlorophenyl)isoxazol-4-yl) methoxy)phenyl)ethynyl)-5-iodobenzoate tert-butyl nitrite (0.126 ml, 1.05 mmol) and iodine (536 mg, 2.11 mmol) were added to a solution of methyl 3-amino-5-((2-chloro-4-((5-cyclopropyl-3-(2,6-dichlorophenyl) isoxazol-4-yl)methoxy)phenyl)ethynyl)benzoate (Step 2 of example 8)(300 mg, 0.528 mmol) in toluene (5 ml) and stirred for 1 hour at 55° C. The reaction mixture was diluted with ethyl acetate and washed with water. The combined organic layers were dried over MgSO$_4$, filtered, evaporated in vacuum and purified using silica chromatography to give the intermediate compound methyl 3-((2-chloro-4-((5-cyclopropyl-3-(2,6-dichlorophenyl)isoxazol-4-yl) methoxy) phenyl)ethynyl)-5-iodobenzoate (108 mg, 44%).

$^1$H-NMR (CDCl$_3$, 400 MHz): δ 8.20 (t, 1H), 7.99 (dt, 1H), 7.70 (dt, 1H), 7.46-7.22 (m, 4H), 6.88 (d, 1H), 6.69 (dd, 1H), 4.82 (s, 2H), 3.94 (s, 3H), 2.19-2.12 (m, 1H), 1.33-1.24 (m, 2H), 1.23-1.14 (m, 2H).

Step 2: Preparation of methyl 3-(azetidin-1-yl)-5-((2-chloro-4-((5-cyclopropyl-3-(2,6-dichlorophenyl) isoxazol-4-yl)methoxy)phenyl)ethynyl)benzoate Azetidine (12 mg, 0.13 mmol), L-proline (2.2 mg, 0.019 mmol), cesium carbonate (36 mg, 0.11 mmol) and copper(I) iodide (1.6 mg, 0.01 mmol) were added to a solution of the intermediate compound (Step 1)(44 mg, 0.065 mmol) in dimethyl sulfoxide (1 ml) and stirred for 1 day at 80° C. The reaction mixture was diluted with ethyl acetate and washed with water. The combined organic layers were dried over MgSO$_4$, filtered, evaporated in vacuum and purified using silica chromatography to give the intermediate compound methyl 3-(azetidin-1-yl)-5-((2-chloro-4-((5-cyclopropyl-3-(2,6-dichlorophenyl)isoxazol-4-yl)methoxy)phenyl)ethynyl)benzoate (14 mg, 36%).

$^1$H-NMR (CDCl$_3$, 400 MHz): δ 7.55 (d, 1H), 7.42-7.31 (m, 4H), 7.05-7.04 (m, 1H), 6.87-6.86 (m, 1H), 6.72-6.67 (m, 2H), 4.82 (s, 2H), 3.97-3.90 (m, 7H), 2.43-2.38 (m, 2H), 2.18-2.13 (m, 1H), 1.32-1.29 (m, 2H), 1.19-1.16 (m, 2H).

Step 3: Preparation of 3-(azetidin-1-yl)-5-((2-chloro-4-((5-cyclopropyl-3-(2,6-dichlorophenyl) isoxazol-4-yl)methoxy)phenyl)ethynyl)benzoic acid This compound was made using the procedure described in Example 1 (Step 6). Thus, this intermediate compound (Step 2)(14 mg, 0.023 mmol) was reacted with lithium hydroxide (10 mg, 0.23 mmol) to afford the title compound (14 mg, 99%).

$^1$H-NMR (CDCl$_3$, 400 MHz): δ 7.60 (m, 1H), 7.41-7.31 (m, 4H), 7.07 (m, 1H), 6.87-6.86 (m, 1H), 6.68-6.66 (m, 2H), 4.81 (s, 2H), 3.94-3.90 (m, 4H), 2.40-2.37 (m, 2H), 2.16-2.14 (m, 1H), 1.30-1.27 (m, 2H), 1.18-1.14 (m, 2H).

<Example 56>3-((2-chloro-4-((5-cyclopropyl-3-(2, 6-dichlorophenyl)isoxazol-4-yl)methoxy)phenyl) ethynyl)-5-(pyrrolidin-1-yl)benzoic acid (I-56)

Step 1: Preparation of methyl 4-((2-chloro-4-((5-cyclopropyl-3-(2,6-dichlorophenyl)isoxazol-4-yl) methoxy)phenyl)ethynyl)-2-(pyrrolidin-1-yl)benzoate This compound was made using the procedure described in Example 55 (Step 2). Thus, methyl 3-((2-chloro-4-((5-cyclopropyl-3-(2,6-dichlorophenyl) isoxazol-4-yl)methoxy) phenyl)ethynyl)-5-iodobenzoate (Step 1 of example 55)(44 mg, 0.065 mmol) was reacted with pyrrolidine (15 mg, 0.13 mmol), L-proline (2.2 mg, 0.019 mmol), cesium carbonate (36 mg, 0.11 mmol) and copper(I) iodide (1.6 mg, 0.01 mmol) to afford the intermediate compound methyl 4-((2-chloro-4-((5-cyclopropyl-3-(2,6-dichlorophenyl)isoxazol-4-yl)methoxy)phenyl)ethynyl)-2-(pyrrolidin-1-yl)benzoate (14 mg, 36%).

$^1$H-NMR (CDCl$_3$, 400 MHz): δ 7.48 (d, 1H), 7.43-7.40 (m, 3H), 7.36-7.32 (m, 1H), 7.19-7.18 (m, 1H), 6.88-6.84 (m, 2H), 6.70-6.67 (m, 1H), 4.82 (s, 2H), 3.91 (s, 3H), 3.33 (t, 4H), 2.17-2.15 (m, 1H), 2.03-2.01 (m, 4H), 1.32-1.28 (m, 2H), 1.20-1.16 (m, 2H).

Step 2: Preparation of 3-((2-chloro-4-((5-cyclopropyl-3-(2,6-dichlorophenyl) isoxazol-4-yl)methoxy) phenyl)ethynyl)-5-(pyrrolidin-1-yl)benzoic acid This compound was made using the procedure described in Example 1 (Step 6). Thus, this intermediate compound

89

(Step 1)(14 mg, 0.031 mmol) was reacted with lithium hydroxide (13 mg, 0.31 mmol) to afford the title compound (11 mg, 62%).

$^1$H-NMR (CDCl$_3$, 400 MHz): δ 7.55-7.32 (m, 5H), 7.24-7.23 (m, 1H), 6.90-6.87 (m, 2H), 6.70-6.67 (m, 1H), 4.82 (s, 2H), 3.35 (t, 4H), 2.18-2.13 (m, 1H), 2.14-2.02 (m, 4H), 1.31-1.28 (m, 2H), 1.19-1.15 (m, 2H).

<Example 57>3-(azetidin-3-ylamino)-5-((2-chloro-4-((5-cyclopropyl-3-(2,6-dichlorophenyl)isoxazol-4-yl)methoxy)phenyl)ethynyl)benzoic acid hydrochloride (I-57)

Step 1: Preparation of tert-butyl 3-((3-((2-chloro-4-((5-cyclopropyl-3-(2,6-dichlorophenyl)isoxazol-4-yl)methoxy)phenyl)ethynyl)-5-(methoxycarbonyl)phenyl)amino)azetidine-1-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(300 mg, 0.72 mmol) was reacted with tert-butyl 3-((3-bromo-5-(methoxycarbonyl)phenyl)amino)azetidine-1-carboxylate (277.38 mg, 0.72 mmol), bis(triphenylphosphine) palladium(II) dichloride (PdCl$_2$(PPh$_3$)$_2$, 49 mg, 0.07 mmol), copper(I) iodide (13 mg, 0.07 mmol) and triethylamine (0.12 ml, 0.86 mmol) to afford the intermediate compound tert-butyl 3-((3-((2-chloro-4-((5-cyclopropyl-3-(2,6-dichlorophenyl)isoxazol-4-yl) methoxy)phenyl)ethynyl)-5-(methoxycarbonyl)phenyl)amino)azetidine-1-carboxylate (370 mg, 71%).

$^1$H-NMR (CDCl$_3$, 400 MHz): δ 7.60 (s, 1H), 7.41-7.32 (m, 4H), 7.21 (s, 1H), 6.90 (s, 1H), 6.81 (d, 1H), 6.69 (dd, 1H), 4.82 (s, 2H), 4.36-4.32 (m, 2H), 4.19-4.11 (m, 2H), 3.90 (s, 3H), 3.73 (dd, 1H), 2.16-2.05 (m, 1H), 1.48 (s, 9H), 1.42-1.24 (m, 2H), 1.19-1.15 (m, 2H).

Step 2: Preparation of 3-((1-(tert-butoxycarbonyl)azetidin-3-yl)amino)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(35 mg, 0.048 mmol) was reacted with lithium hydroxide (17 mg, 0.48 mmol) to afford the intermediate compound 3-((1-(tert-butoxycarbonyl)azetidin-3-yl)amino)-5-((2-chloro-4-((5-cyclopropyl-3-(2,6-dichlorophenyl)isoxazol-4-yl)methoxy)phenyl)ethynyl)benzoic acid (29 mg, 85%).

$^1$H-NMR (CDCl$_3$, 400 MHz): δ 7.66 (s, 1H), 7.43-7.39 (m, 3H), 7.35-7.33 (m, 1H), 7.19 (s, 1H), 6.87 (d, 2H), 6.70 (dd, 1H), 4.82 (s, 2H), 4.37-4.33 (m, 2H), 4.28-4.26 (m, 1H), 3.78-3.74 (m, 2H), 2.19-2.17 (m, 1H), 1.49 (s, 9H), 1.30-1.28 (m, 2H), 1.26-1.20 (m, 2H).

Step 3: Preparation of 3-(azetidine-3-ylamino)-5-((2-chloro-4-((5-cyclopropyl-3-(2,6-dichlorophenyl)isoxazol-4-yl)methoxy)phenyl)ethynyl)benzoic acid This intermediate compound (Step 2)(29 mg, 0.041 mmol) was dissolved in dichloromethane. 5-6N HCl solution (41 ul, 0.20 mmol) was added at 0° C., after stirring at room temperature for 3 h. The reaction mixture added ethyl acetate and washed with water. The combined organic layers were dried over MgSO$_4$, filtered, and recrystalized to afford the title compound (10 mg, 38%).

90

$^1$H-NMR (DMSO, 400 MHz): δ 8.93 (br s, 2H), 7.64 (d, 2H), 7.62-7.52 (m, 2H), 7.31 (s, 1H), 7.15 (d, 1H), 7.09 (d, 1H), 6.85-6.81 (m, 2H), 4.98 (s, 2H), 4.48-4.44 (m, 1H), 4.29-4.27 (m, 2H), 3.87-3.78 (m, 2H), 1.23-1.19 (m, 2H), 1.17-1.14 (m, 2H).

<Example 58>3-((2-chloro-4-((5-cyclopropyl-3-(2,6-dichlorophenyl)isoxazol-4-yl)methoxy)phenyl)ethynyl)-5-(piperidin-4-ylamino)benzoic acid hydrochloride (I-58)

Step 1: Preparation of tert-butyl 4-((3-((2-chloro-4-((5-cyclopropyl-3-(2,6-dichlorophenyl)isoxazol-4-yl)methoxy)phenyl)ethynyl)-5-(methoxycarbonyl)phenyl)amino)piperidine-1-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(300 mg, 0.72 mmol) was reacted with tert-butyl 4-((3-bromo-5-(methoxycarbonyl)phenyl)amino)piperidine-1-carboxylate (298 mg, 0.72 mmol), bis(triphenylphosphine)palladium(II) dichloride (PdCl$_2$(PPh$_3$)$_2$, 49 mg, 0.07 mmol), copper(I) iodide (13 mg, 0.07 mmol) and triethylamine (0.12 ml, 0.86 mmol) to afford the intermediate compound tert-butyl 4-((3-((2-chloro-4-((5-cyclopropyl-3-(2,6-dichlorophenyl)isoxazol-4-yl)methoxy)phenyl)ethynyl)-5-(methoxycarbonyl)phenyl)amino)piperidine-1-carboxylate (340 mg, 63%).

$^1$H-NMR (CDCl$_3$, 400 MHz): δ 7.52 (s, 1H), 7.41-7.31 (m, 3H), 7.26 (s, 1H), 7.21 (s, 1H), 6.89-6.86 (m, 2H), 6.67 (dd, 1H), 4.81 (s, 2H), 4.14-4.09 (m, 2H), 3.90 (s, 3H), 3.79-3.68 (m, 2H), 2.98-2.88 (m, 2H), 2.46-2.44 (m, 1H), 2.21-2.10 (m, 1H), 2.18-2.00 (m, 2H), 1.48 (s, 9H), 1.38-1.33 (m, 2H), 1.29-1.18 (m, 2H).

Step 2: Preparation of 3-((1-(tert-butoxycarbonyl)piperidine-4-yl)amino)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(49.4 mg, 0.07 mmol) was reacted with lithium hydroxide (27.6 mg, 0.7 mmol) to afford 3-((1-(tert-butoxycarbonyl) piperidine-4-yl)amino)-5-((2-chloro-4-((5-cyclopropyl-3-(2,6-dichlorophenyl)isoxazol-4-yl)methoxy)phenyl)ethynyl)benzoic acid (18 mg, 35%).

$^1$H-NMR (CDCl$_3$, 400 MHz): δ 7.72 (s, 2H), 7.58-7.29 (m, 4H), 6.93 (s, 1H), 6.87 (s, 1H), 6.68 (dd, 1H), 4.82 (s, 2H), 4.20-4.00 (m, 2H), 3.58-3.46 (m, 1H), 3.09-2.98 (m, 2H), 2.28-2.17 (m, 2H), 1.47 (s, 9H), 1.35-1.30 (m, 2H), 1.29-1.26 (m, 2H).

Step 3: Preparation of 3-((2-chloro-4-((5-cyclopropyl-3-(2,6-dichlorophenyl) isoxazol-4-yl)methoxy)phenyl)ethynyl)-5-(piperdine-4-ylamino)benzoic acid This intermediate compound (Step 2)(18 mg, 0.024 mmol) was dissolved in dichloromethane. 5-6N HCl solution (12 ul, 0.048 mmol) was added at 0° C., after stirring at room temperature for 3 h. The reaction mixture added ethyl acetate and washed with water. The combined organic layers were dried over MgSO$_4$, filtered, and recrystalized to afford the title compound (7 mg, 44%).

¹H-NMR (MeOD, 400 MHz): δ 7.66-7.50 (m, 3H), 7.48-7.43 (m, 3H), 7.14 (s, 1H), 6.94 (s, 1H), 6.78 (dd, 1H), 4.98 (s, 2H), 3.82-3.70 (m, 2H), 3.53-3.41 (m, 2H), 3.33-3.12 (m, 2H), 2.38-2.22 (m, 2H), 1.90-1.80 (m, 2H), 1.25-1.22 (m, 2H).

<Example 59>3-((2-chloro-4-((5-cyclopropyl-3-(2,6-dichlorophenyl)isoxazol-4-yl)methoxy)phenyl)ethynyl)-5-(piperazin-1-yl)benzoic acid hydrochloride (I-59)

Step 1: Preparation of tert-butyl 4-(3-((2-chloro-4-((5-cyclopropyl-3-(2,6-dichlorophenyl)isoxazol-4-yl)methoxy)phenyl)ethynyl)-5-(methoxycarbonyl)phenyl)piperazin-1-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with tert-butyl 4-(3-bromo-5-(methoxycarbonyl)phenyl)piperazin-1-carboxylate (70 mg, 0.287 mmol), bis(triphenylphosphine)palladium(II) dichloride (PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate compound tert-butyl 4-(3-((2-chloro-4-((5-cyclopropyl-3-(2,6-dichlorophenyl)isoxazol-4-yl)methoxy)phenyl)ethynyl)-5-(methoxycarbonyl)phenyl)piperazin-1-carboxylate (114 mg, 65%).

¹H-NMR (CDCl$_3$, 400 MHz): δ 7.71 (s, 1H), 7.57 (s, 1H), 7.44-7.41 (m, 3H), 7.38-7.34 (m, 1H), 7.24 (d, 1H), 6.90-6.89 (d, 1H), 6.72-6.70 (dd, 1H), 4.84 (s, 2H), 6.94 (s, 3H), 3.62-3.60 (t, 4H), 3.23 (s, 4H), 2.20-2.15 (m, 1H), 1.51 (s, 9H), 1.34-1.26 (m, 2H), 1.21-1.18 (m, 2H).

Step 2: Preparation of 3-(4-(tert-buthoxycarbonyl)piperazin-1-yl)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, the intermediate compound (Step 1)(114 mg, 0.15 mmol) lithium hydroxide (63 mg, 1.5 mmol) to afford the intermediate compound 3-(4-(tert-buthoxycarbonyl)piperazin-1-yl)-5-((2-chloro-4-((5-cyclopropyl-3-(2,6-dichlorophenyl)isoxazol-4-yl)methoxy)phenyl)ethynyl)benzoic acid (108 mg, 98%).

¹H-NMR (CDCl$_3$, 400 MHz): δ 7.68 (s, 1H), 7.53-7.52 (m, 1H), 7.35-7.32 (m, 3H), 7.28-7.24 (m, 1H), 6.81-6.80 (d, 1H), 6.64-6.61 (dd, 1H), 4.75 (s, 2H), 3.54-3.52 (t, 4H), 3.15 (s, 4H), 2.10-2.05 (m, 1H), 1.42 (s, 9H), 1.25-1.21 (m, 2H), 1.11-1.09 (m, 2H).

Step 3: Preparation of 3-((2-chloro-4-((5-cyclopropyl-3-(2,6-dichlorophenyl) isoxazol-4-yl)methoxy)phenyl)ethynyl)-5-(piperazin-1-yl)benzoic acid hydrochloride This compound was made using the procedure described in Example 57 (Step 3). Thus, the intermediate compound (Step 2)(108 mg, 0.14 mmol) was reacted with 6M solution of hydrochloric acid to afford the title compound (59 mg, 64%).

¹H-NMR (MeOD, 400 MHz): 7.70-7.67 (m, 2H), 7.55-7.44 (m, 4H), 7.39-7.38 (m, 1H), 6.95-6.94 (d, 1H), 6.80-6.77 (dd, 1H), 4.91 (s, 3H), 3.53-3.50 (m, 4H), 3.42-3.40 (m, 4H), 2.40-2.35 (m, 1H), 1.25-1.21 (m, 4H).

<Example 60>3-amino-5-((2-chloro-4-((5-cyclopropyl-3-(2,6-dichloro phenyl)isoxazol-4-yl)methoxy)phenyl)ethynyl)-4-methylbenzoic acid (I-60)

Step 1: Preparation of methyl 3-((2-chloro-4-((5-cyclopropyl-3-(2,6-dichlorophenyl)isoxazol-4-yl)methoxy)phenyl)ethynyl)-4-methy-5-nitrobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 3-bromo-4-methyl-5-nitrobenzoate (78.6 mg, 0.287 mmol), bis(triphenyl phosphine) palladium(II) dichloride (PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate compound methyl 3-((2-chloro-4-((5-cyclopropyl-3-(2,6-dichloro phenyl)isoxazol-4-yl)methoxy)phenyl)ethynyl)-4-methy-5-nitrobenzoate (88 mg, 60%).

¹H-NMR (CDCl$_3$, 400 MHz): δ 7.65 (d, 1H), 7.42-7.40 (m, 3H), 7.35-7.31 (m, 2H), 6.88 (d, 1H), 6.69 (dd, 1H), 4.82 (s, 2H), 3.89 (s, 3H), 2.42 (s, 3H), 2.18-2.13 (m, 1H), 1.32-1.28 (m, 2H), 1.19-1.15 (m, 2H).

Step 2: Preparation of methyl 3-amino-5-((2-chloro-4-((5-cyclopropyl-3-(2,6-dichlorophenyl)isoxazol-4-yl)methoxy)phenyl)ethynyl)-4-methylbenzoate This compound was made using the procedure described in Example 8 (Step 2). Thus, the intermediate compound (Step 1)(88 mg, 0.14 mmol) was reacted with tin(II) chloride dihydrate (315 mg, 1.4 mmol) to afford the intermediate compound methyl 3-amino-5-((2-chloro-4-((5-cyclopropyl-3-(2,6-dichlorophenyl) isoxazol-4-yl)methoxy)phenyl)ethynyl)-4-methybenzoate (50 mg, 61%).

¹H-NMR (CDCl$_3$, 400 MHz): δ 7.65 (d, 1H), 7.42-7.40 (m, 3H), 7.35-7.31 (m, 2H), 6.88 (d, 1H), 6.69 (dd, 1H), 4.82 (s, 2H), 3.89 (s, 3H), 3.78 (s, 2H), 2.42 (s, 3H), 2.18-2.13 (m, 1H), 1.32-1.28 (m, 2H), 1.19-1.15 (m, 2H).

Step 3: Preparation of 3-amino-5-((2-chloro-4-((5-cyclopropyl-3-(2,6-dichlorophenyl)isoxazol-4-yl)methoxy)phenyl)ethynyl)-4-methylbenzoic acid This compound was made using the procedure described in Example 1 (Step 6). Thus, the intermediate compound (Step 2)(50 mg, 0.08 mmol) was reacted with lithium hydroxide (36 mg, 0.8 mmol) to afford the title compound (53 mg, 108%).

¹H-NMR (DMSO, 400 MHz): δ 12.65 (s, 1H), 7.64 (d, 1H), 7.62 (s, 1H), 7.57-7.53 (m, 2H), 7.27 (s, 2H), 7.08 (d, 1H), 6.82 (dd, 1H), 5.34 (s, 2H), 4.98 (s, 2H), 2.47 (m, 1H), 2.29 (s, 3H), 1.23-1.19 (m, 2H), 1.17-1.13 (m, 2H).

<Example 61>3-amino-5-((2-chloro-4-((5-cyclopropyl-3-(2,6-dichloro phenyl)isoxazol-4-yl)methoxy)phenyl)ethynyl)-4-methoxybenzoic acid (I-61)

Step 1: Preparation of methyl 3-((2-chloro-4-((5-cyclopropyl-3-(2,6-dichlorophenyl)isoxazol-4-yl)methoxy)phenyl)ethynyl)-4-methoxy-5-nitrobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.26 mmol) was reacted with methyl 3-bromo-4-methoxy-5-nitrobenzoate (72 mg, 0.26 mmol), tetrakis(triphenyl phosphine) palladium(0) (Pd (PPh$_3$)$_4$, 21 mg, 0.03 mmol), copper(I) iodide (5.7 mg, 0.03 mmol) and N,N-diisopropylethylamine (0.52 ml, 2.98 mmol) to afford the intermediate compound methyl 3-((2-chloro-4-((5-cyclopropyl-3-(2,6-dichloro phenyl)isoxazol-4-yl)methoxy)phenyl)ethynyl)-4-methoxy-5-nitrobenzoate (102.8 mg, 63%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.50-7.44 (m, 1H), 7.40 (d, 1H), 7.21 (t, 1H), 4.37 (s, 2H), 3.79-3.67 (m, 1H), 3.59-3.33 (m, 3H), 3.29-3.06 (m, 3H).

Step 2: Preparation of methyl 3-amino-5-((2-chloro-4-((5-cyclopropyl-3-(2,6-dichlorophenyl)isoxazol-4-yl)methoxy)phenyl)ethynyl)-4-methoxybenzoate This compound was made using the procedure described in Example 8 (Step 2). Thus, this intermediate compound (Step 1)(102.8 mg, 0.164 mmol) was reacted with tin(II) chloride dihydrate (369 mg, 1.64 mmol) to afford the intermediate compound methyl 3-amino-5-((2-chloro-4-((5-cyclopropyl-3-(2,6-dichloro phenyl)isoxazol-4-yl)methoxy)phenyl)ethynyl)-4-methoxybenzoate (80 mg, 51%).

$^1$H-NMR (DMSO, 400 MHz): δ 12.60 (s, 1H), 8.26 (d, 1H), 7.97 (d, 1H), 7.89 (t, 1H), 7.83 (t, 1H), 7.50-7.44 (m, 1H), 7.40 (d, 1H), 7.21 (t, 1H), 4.37 (s, 2H), 3.79-3.67 (m, 1H), 3.59-3.33 (m, 3H), 3.29-3.06 (m, 3H).

Step 3: Preparation of 3-amino-5-((2-chloro-4-((5-cyclopropyl-3-(2,6-dichlorophenyl)isoxazol-4-yl)methoxy)phenyl)ethynyl)-4-methoxybenzoic acid This compound was made using the procedure described in Example 1 (Step 6). Thus, this intermediate compound (Step 2)(80 mg, 0.14 mmol) was reacted with lithium hydroxide (58.7 mg, 1.4 mmol) to afford the title compound (42 mg, 55%).

$^1$H-NMR (MeOD, 400 MHz): δ 7.54 (s, 1H), 7.43-7.51 (m, 4H), 6.94 (d, 1H), 6.79 (dd, 1H), 4.97 (s, 2H), 4.05 (s, 3H), 2.32-2.42 (m, 1H), 1.27-1.37 (m, 2H), 0.88-0.96 (m, 2H).

<Example 62> 3-amino-5-((2-chloro-4-((5-cyclopropyl-3-(2,6-dichloro phenyl)isoxazol-4-yl)methoxy)phenyl)ethynyl)-2-methoxybenzoic acid (I-62)

Step 1: Preparation of methyl 5-((2-chloro-4-((5-cyclopropyl-3-(2,6-dichlorophenyl)isoxazol-4-yl)methoxy)phenyl)ethynyl)-2-methoxy-3-nitrobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(140 mg, 0.33 mmol) was reacted with methyl 5-bromo-2-methoxy-3-nitrobenzoate (96.9 mg, 0.33 mmol), tetrakis(triphenyl phosphine)palladium(0)(Pd (PPh$_3$)$_4$, 34.7 mg, 0.03 mmol), copper(I) iodide (5.7 mg, 0.03 mmol) and N,N-diisopropylethylamine (69 ul, 0.4 mmol) to afford the intermediate compound methyl 5-((2-chloro-4-((5-cyclopropyl-3-(2,6-dichloro phenyl)isoxazol-4-yl)methoxy)phenyl)ethynyl)-2-methoxy-3-nitrobenzoate (126.5 mg, 61.1%).

$^1$H-NMR (CDCl$_3$, 400 MHz): δ 8.13 (s, 1H), 8.02 (s, 1H), 7.43-7.33 (m, 4H), 6.88 (d, 1H), 6.67-6.65 (m, 1H), 4.83 (s, 2H), 4.01 (s, 3H), 3.97 (s, 3H), 2.18-2.13 (m, 1H), 1.33-1.26 (m, 2H), 1.20-1.15 (m, 2H).

Step 2: Preparation of methyl 3-amino-5-((2-chloro-4-((5-cyclopropyl-3-(2,6-dichlorophenyl)isoxazol-4-yl)methoxy)phenyl)ethynyl)-2-methoxy benzoate This compound was made using the procedure described in Example 8 (Step 2). Thus, this intermediate compound (Step 1)(126.5 mg, 0.2 mmol) was reacted with tin(II) chloride dihydrate (225.63 mg, 1.0 mmol) to afford the intermediate compound methyl 3-amino-5-((2-chloro-4-((5-cyclopropyl-3-(2,6-dichloro phenyl)isoxazol-4-yl)methoxy)phenyl)ethynyl)-2-methoxybenzoate (51 mg, 43%).

$^1$H-NMR (CDCl$_3$, 400 MHz): δ 7.39-7.33 (m, 5H), 7.05 (s, 1H), 6.86 (s, 1H), 6.68 (dd, 1H), 4.80 (s, 2H), 3.86 (s, 3H), 3.84 (s, 3H), 2.15-2.05 (m, 1H), 1.29-1.24 (m, 2H), 1.16-1.11 (m, 2H).

Step 3: Preparation of 3-amino-5-((2-chloro-4-((5-cyclopropyl-3-(2,6-dichlorophenyl)isoxazol-4-yl)methoxy)phenyl)ethynyl)-2-methoxybenzoic acid This compound was made using the procedure described in Example 1 (Step 6). Thus, this intermediate compound (Step 2)(51 mg, 0.09 mmol) was reacted with lithium hydroxide (36 mg, 0.9 mmol) to afford the title compound (37.3 mg, 71%).

$^1$H-NMR (MeOD, 400 MHz): δ 7.55-7.50 (m, 2H), 7.48-7.46 (m, 1H), 7.41 (d, 1H), 7.21 (d, 1H), 7.08 (d, 1H), 6.92 (d, 1H), 6.76 (dd, 1H), 4.95 (s, 2H), 4.13 (s, 3H), 2.38-2.34 (m, 1H), 1.30-1.22 (m, 4H).

<Example 63> 3-((2-chloro-4-((5-cyclopropyl-3-(2,6-dichlorophenyl)isoxazol-4-yl)methoxy)phenyl)ethynyl)-5-methylbenzoic acid (I-63)

Step 1: Preparation of methyl 3-((2-chloro-4-((5-cyclopropyl-3-(2,6-dichlorophenyl)isoxazol-4-yl)methoxy)phenyl)ethynyl)-5-methylbenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 3-bromo-5-methylbenzoate (65.5 mg, 0.287 mmol), bis(triphenylphosphine) palladium(II)dichloride (PdCl$_2$(PPh$_3$)$_2$, 21 mg, 0.03 mmol), copper(I)iodide (5.7 mg, 0.03 mmol) and triethylamine (0.2 ml, 1.44 mmol) to afford the intermediate compound methyl 3-((2-chloro-4-((cyclopropyl-3-(2,6-dichlorophenyl) isoxazol-4-yl)methoxy)phenyl)ethynyl)-5-methylbenzoate (87 mg, 31%).

$^1$H-NMR (CDCl$_3$, 400 MHz): δ 8.00 (s, 1H), 7.82 (s, 1H), 7.53 (s, 1H), 7.42-7.35 (m, 3H), 7.33-7.26 (m, 1H), 6.87 (d, 1H), 6.69 (dd, 1H), 4.82 (s, 2H), 3.92 (s, 3H), 2.40 (s, 3H), 2.22-2.11 (m, 1H), 1.32-1.29 (m, 2H), 1.21-1.15 (m, 2H).

Step 2: Preparation of methyl 3-((2-chloro-4-((5-cyclopropyl-3-(2,6-dichlorophenyl)isoxazol-4-yl)methoxy)phenyl)ethynyl)-5-methylbenzoic acid This compound was made using the procedure described in Example 1 (Step 6). Thus, the intermediate compound (Step 1)(87 mg, 0.153 mmol) was reacted with lithium hydroxide (64.3 mg, 1.53 mmol) to afford the title compound (28.8 mg, 34%).

$^{1}$H-NMR (DMSO, 400 MHz): δ 13.43 (br, 1H), 7.81 (d, 1H), 7.65-7.63 (m, 1H), 7.59 (br, 1H), 7.58-7.54 (m, 1H), 7.10 (d, 1H), 6.84 (dd, 1H), 4.99 (s, 2H), 2.39 (s, 3H), 1.21-1.11 (m, 5H).

<Example 64> 3-((2-chloro-4-((5-cyclopropyl-3-(2,6-dichlorophenyl)isoxazol-4-yl)methoxy)phenyl)ethynyl)-5-cyclopropylbenzoic acid (I-64)

Step 1: Preparation of methyl 3-((2-chloro-4-((5-cyclopropyl-3-(2,6-dichlorophenyl)isoxazol-4-yl)methoxy)phenyl)ethynyl)-5-cyclopropylbenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(77.3 mg, 0.18 mmol) was reacted with methyl 3-cyclopropyl-5-iodobenzoate (55.8 mg, 0.18 mmol), tetrakis(triphenyl phosphine)palladium(0)(Pd(PPh$_3$)$_4$, 23 mg, 0.02 mmol), copper(I) iodide (4 mg, 0.02 mmol) and N,N-diisopropylethylamine (38 ul, 0.22 mmol) to afford the intermediate compound methyl 3-((2-chloro-4-((5-cyclopropyl-3-(2,6-dichloro phenyl)isoxazol-4-yl)methoxy)phenyl)ethynyl)-5-cyclopropylbenzoate (45.9 mg, 43%).

$^{1}$H-NMR (CDCl$_3$, 400 MHz): δ 7.97 (t, 1H), 7.69 (t, 1H), 7.43-7.38 (m, 4H), 7.36-7.31 (m, 1H), 6.87 (d, 1H), 6.69 (dd, 1H), 4.80 (s, 2H), 3.92 (s, 3H), 2.24-2.12 (m, 1H), 1.98-1.90 (m, 1H), 1.33-1.28 (m, 2H), 1.20-1.14 (m, 2H), 1.05-0.99 (m, 2H), 0.79-0.73 (m, 2H).

Step 2: Preparation of 3-amino-5-((2-chloro-4-((5-cyclopropyl-3-(2,6-dichlorophenyl)isoxazol-4-yl)methoxy)phenyl)ethynyl)-2-methoxybenzoic acid This compound was made using the procedure described in Example 1 (Step 6). Thus, this intermediate compound (Step 1)(45.9 mg, 0.077 mmol) was reacted with lithium hydroxide (32.5 mg, 0.77 mmol) to afford the title compound (22.8 mg, 51%).

$^{1}$H-NMR (DMSO, 400 MHz): δ 7.77 (d, 1H), 7.66-7.60 (m, 3H), 7.59-7.52 (m, 2H), 7.44 (s, 1H), 7.08 (d, 1H), 6.83 (dd, 1H), 4.98 (s, 2H), 2.57-2.53 (m, 1H), 2.10-2.01 (m, 1H), 1.24-1.18 (m, 2H), 1.16-1.09 (m, 2H).

<Example 65> 3-((2-chloro-4-((5-cyclopropyl-3-(2,6-dichlorophenyl)isoxazol-4-yl)methoxy)phenyl)ethynyl)-5-ethylbenzoic acid (I-65)

Step 1: Preparation of methyl 3-((2-chloro-4-((5-cyclopropyl-3-(2,6-dichlorophenyl)isoxazol-4-yl)methoxy)phenyl)ethynyl)-5-ethylbenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(84.7 mg, 0.2 mmol) was reacted with methyl 3-ethyl-5-iodobenzoate (58.7 mg, 0.2 mmol), tetrakis(triphenylphosphine) palladium(0)(Pd(PPh$_3$)$_4$, 23.1 mg, 0.02 mmol), copper(I) iodide (3.8 mg, 0.02 mmol) and N,N-diisopropylethylamine (41.8 ul, 0.24 mmol) to afford the intermediate compound methyl 3-((2-chloro-4-((5-cyclopropyl-3-(2,6-dichlorophenyl) isoxazol-4-yl)methoxy)phenyl)ethynyl)-5-ethylbenzoate (78.2 mg, 67%).

$^{1}$H-NMR (CDCl$_3$, 400 MHz): δ 8.01 (t, 1H), 7.84 (t, 1H), 7.54 (t, 1H), 7.43-7.41 (m, 1H), 7.39 (d, 2H), 7.36-7.32 (m, 1H), 6.87 (d, 1H), 6.69 (dd, 1H), 4.81 (s, 2H), 3.92 (s, 3H), 2.69 (q, 2H), 2.19-2.11 (m, 1H), 1.32-1.22 (m, 5H), 1.20-1.14 (m, 2H).

Step 2: Preparation of 3-((2-chloro-4-((5-cyclopropyl-3-(2,6-dichlorophenyl) isoxazol-4-yl)methoxy)phenyl)ethynyl)-5-ethylbenzoic acid This compound was made using the procedure described in Example 1 (Step 6). Thus, this intermediate compound (Step 1)(78.2 mg, 0.13 mmol) was reacted with lithium hydroxide (56.5 mg, 1.3 mmol) to afford the title compound (27 mg, 37%).

$^{1}$H-NMR (MeOD, 400 MHz): δ 7.93 (d, 2H), 7.62-7.53 (m, 3H), 7.52-7.46 (m, 2H), 6.96 (d, 1H), 6.80 (dd, 1H), 4.99 (s, 2H), 2.75 (q, 2H), 2.44-2.34 (m, 1H), 1.30 (t, 3H), 1.27-1.21 (m, 4H).

<Example 66> 3-((2-chloro-4-((5-cyclopropyl-3-(2,6-dichlorophenyl) isoxazol-4-yl)methoxy)phenyl)ethynyl)-5-isopropylbenzoic acid (I-66)

Step 1: Preparation of methyl 3-((2-chloro-4-((5-cyclopropyl-3-(2,6-dichlorophenyl)isoxazol-4-yl)methoxy)phenyl)ethynyl)-5-isopropylbenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(64.2 mg, 0.15 mmol) was reacted with methyl 3-iodo-5-isopropylbenzoate (46.6 mg, 0.15 mmol), tetrakis(triphenylphosphine) palladium(0)(Pd(PPh$_3$)$_4$, 17.3 mg, 0.02 mmol), copper(I) iodide (2.9 mg, 0.02 mmol) and N,N-diisopropylethylamine (31.3 ul, 0.18 mmol) to afford the intermediate compound methyl 3-((2-chloro-4-((5-cyclopropyl-3-(2,6-dichlorophenyl)isoxazol-4-yl)methoxy)phenyl)ethynyl)-5-isopropylbenzoate (76.3 mg, 86%).

$^{1}$H-NMR (CDCl$_3$, 400 MHz): δ 8.02 (t, 1H), 7.87 (t, 1H), 7.56 (t, 1H), 7.44-7.39 (m, 3H), 7.36-7.31 (m, 1H), 6.87 (d, 1H), 6.69 (dd, 1H), 4.82 (s, 2H), 3.92 (s, 3H), 3.00-2.91 (m, 1H), 2.20-2.12 (m, 1H), 1.32-1.29 (m, 2H), 1.28 (d, 6H), 1.21-1.14 (m, 2H).

Step 2: Preparation of 3-((2-chloro-4-((5-cyclopropyl-3-(2,6-dichlorophenyl) isoxazol-4-yl)methoxy)phenyl)ethynyl)-5-isopropylbenzoic acid This compound was made using the procedure described in Example 1 (Step 6). Thus, this intermediate compound (Step 1)(76.3 mg, 0.13 mmol) was reacted with lithium hydroxide (53.8 mg, 1.3 mmol) to afford the title compound (37 mg, 50%).

$^{1}$H-NMR (DMSO, 400 MHz): δ 7.84 (d, 2H), 7.65-7.61 (m, 2H), 7.53-7.59 (m, 2H), 7.09 (d, 1H), 6.84 (dd, 1H), 4.89 (s, 2H), 3.06-2.96 (m, 1H), 1.23 (d, 6H), 1.21-1.17 (m, 2H), 1.17-1.15 (m, 2H).

<Example 67> 3-((2-chloro-4-((5-cyclopropyl-3-(2,6-dichlorophenyl)isoxazol-4-yl)methoxy)phenyl)ethynyl)-5-iodobenzoic acid (I-67)

Step 1: Preparation of 3-((2-chloro-4-((5-cyclopropyl-3-(2,6-dichlorophenyl) isoxazol-4-yl)methoxy)phenyl)ethynyl)-5-iodobenzoic acid This compound was made using the procedure described in Example 1 (Step 6). Thus, the intermediate compound methyl 3-((2-chloro-4-((5-cyclopropyl-3-(2,6-dichlorophenyl)isoxazol-4-yl)methoxy)phenyl)ethynyl)-5-iodobenzoate (Step 2 of example 56)(108 mg, 0.159 mmol) was reacted with lithium hydroxide (66.7 mg, 1.59 mmol) to afford the title compound (41 mg, 39%).

$^1$H-NMR (DMSO, 400 MHz): δ 13.50 (br, 1H), 8.22 (t, 1H), 8.11 (t, 1H), 7.98 (t, 1H), 7.65-7.61 (m, 3H), 7.59-7.53 (m, 1H), 7.10 (d, 1H), 6.85 (dd, 1H), 4.99 (s, 2H), 2.39 (s, 3H), 1.27-1.12 (m, 5H).

<Example 68>3-((2,5-dichloro-4-((5-cyclopropyl-3-(2,6-dichlorophenyl) isoxazol-4-yl)methoxy)phenyl) ethynyl)benzoic acid (I-68)

Step 1: Preparation of tert-butyl(2,5-dichloro-4-iodophenoxy)dimethylsilane

This compound was made using the procedure described in Example 1 (Step 1). Thus, 2,5-dichloro-4-iodophenol (0.5 g, 1.73 mmol) was reacted with tert-butyldimethylsilylchloride (TBSCl, 0.39 g, 2.60 mmol), imidazole (0.23 g, 3.46 mmol) to afford the intermediate compound tert-butyl(2,5-dichloro-4-iodophenoxy)dimethylsilane (0.61 g, 88%).

$^1$H-NMR (CDCl$_3$, 400 MHz): δ 7.24 (s, 1H), 6.97 (s, 1H), 0.96 (s, 9H), 0.16 (s, 6H).

Step 2: Preparation of tert-butyl(2,5-dichloro-4-((trimethylsilyl)ethynyl) phanoxy)dimethylsilane This compound was made using the procedure described in Example 1 (Step 2). Thus, this intermediate compound (Step 1)(0.61 g, 1.52 mmol) was reacted with bis(triphenylphosphine)palladium(II) dichloride ((PdCl$_2$(PPh$_3$)$_2$, 106.68 mg, 0.15 mmol), Copper(I) iodide (29 mg, 1.22 mmol), triethylamine (0.42 ml, 3.04 mmol) to afford the intermediate compound tert-butyl(2,5-dichloro-4-((trimethylsilyl) ethynyl)phanoxy)dimethylsilane (368.97 mg, 65%).

$^1$H-NMR (CDCl$_3$, 400 MHz): δ 7.24 (s, 1H), 6.97 (s, 1H), 0.96 (s, 9H), 0.25 (s, 9H), 0.16 (s, 6H).

Step 3: Preparation of 2,5-dichloro-4-((trimethylsilyl)ethynylphenol

This compound was made using the procedure described in Example 1 (Step 3). Thus, this intermediate compound (Step 2)(368.97 mg, 0.99 mmol) was reacted with Potassium fluoride (KF, 574 mg, 9.9 mmol) to afford the intermediate compound 2,5-dichloro-4-((trimethylsilyl)ethynylphenol (185 mg, 45%) and used directly for the next step without further purification.

Step 4: Preparation of 5-cyclopropyl-4-((2,5-dichloro-4-ethynylphenoxy)methyl)-3-(2,6-duchlorophenyl)isoxazole This compound was made using the procedure described in Example 1 (Step 4). Thus, this intermediate compound (Step 3)(256.6 mg, 0.99 mmol) was reacted with 4-(bromomethyl)-5-cyclopropyl-3-(2,6-dichlorophenyl)isoxazole (Intermediate 1)(343.6 mg, 0.99 mmol), potassium carbonate (205.2 mg, 1.49 mmol) to afford the intermediate compound 5-cyclopropyl-4-((2,5-dichloro-4-ethynylphenoxy)methyl)-3-(2,6-duchlorophenyl)isoxazole (345.4 mg, 77%).

$^1$H-NMR (CDCl$_3$, 400 MHz): δ 7.41-7.30 (m, 3H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 5: Preparation of methyl 3-((2,5-dichloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, this intermediate compound (Step 4)(345.4 mg, 0.762 mmol) was reacted with methyl 3-bromobenzoate (163.9 mg, 0.762 mmol), bis(triphenylphosphine)palladium(II) dichloride ((PdCl$_2$(PPh$_3$)$_2$, 49 mg, 0.07 mmol), Copper(I) iodide (7 mg, 0.035 mmol) and 1,8-Diazabicyclo[5.4.0]undec-7-ene (DBU, 0.16 ml, 1.05 mmol) to afford the intermediate compound methyl 3-((2, 5-dichloro-4-((5-cyclopropyl-3-(2,6-dichlorophenyl)isoxazole-4-yl)methoxy)phenyl)ethynyl)benzoate (232.7 mg, 52%).

$^1$H-NMR (DMSO, 400 MHz): δ 11.33 (s, 1H), 8.06 (t, 1H), 8.02-7.98 (m, 1H), 7.83-7.79 (m, 1H), 7.77 (s, 1H), 7.61 (t, 1H), 7.12 (s, 1H), 3.89 (s, 3H).

Step 6: Preparation of 3-((2,5-dichloro-4-((5-cyclopropyl-3-(2,6-dichlorophenyl)isoxazol-4-yl) methoxy)phenyl)ethynyl)benzoic acid This compound was made using the procedure described in Example 2 (Step 6). Thus, this intermediate compound (Step 5)(232.7 mg, 0.40 mmol) was reacted with lithium hydroxide (167.8 mg, 4 mmol) to afford the title compound (133 mg, 58%).

$^1$H-NMR (CDCl$_3$, 400 MHz): δ 8.04 (t, 1H), 7.97 (d, 1H), 7.79-7.71 (m, 2H), 7.65-7.52 (m, 4H), 7.45 (s, 1H), 5.14 (s, 2H), 1.28-1.12 (m, 5H).

<Example 69>3-((2,3-dichloro-4-((5-cyclopropyl-3-(2,6-dichlorophenyl) isoxazol-4-yl)methoxy)phenyl) ethynyl)benzoic acid (I-69)

Step 1: Preparation of tert-butyl(2,3-dichloro-4-iodophenoxy)dimethylsilane

This compound was made using the procedure described in Example 1 (Step 1). Thus, 2,3-dichloro-4-iodophenol (0.5 g, 1.73 mmol) was reacted with tert-butyldimethylsilylchloride (TBSCl, 0.39 g, 2.60 mmol), imidazole (0.23 g, 3.46 mmol) to afford the intermediate compound tert-butyl(2,3-dichloro-4-iodophenoxy)dimethylsilane (0.61 g, 88%).

$^1$H-NMR (CDCl$_3$, 400 MHz): δ 7.42 (m, 1H), 6.42 (m, 1H), 0.96 (s, 9H), 0.16 (s, 6H).

Step 2: Preparation of tert-butyl(2,3-dichloro-4-((trimethylsilyl)ethynyl) phanoxy)dimethylsilane This compound was made using the procedure described in Example 1 (Step 2). Thus, this intermediate compound (Step 1)(0.61 g, 1.52 mmol) was reacted with bis(triphenylphosphine)palladium(II) dichloride ((PdCl$_2$(PPh$_3$)$_2$, 106.68 mg, 0.15 mmol), Copper(I) iodide (29 mg, 1.22 mmol), triethylamine (0.42 ml, 3.04 mmol), and trimethylsilylacetylene (0.42 ml, 3.04 mmol), to afford the intermediate compound tert-butyl(2,3-dichloro-4-((trimethylsilyl) ethynyl)phanoxy)dimethylsilane (368.97 mg, 65%).

$^1$H-NMR (CDCl$_3$, 400 MHz): δ 7.42 (m, 1H), 6.42 (m, 1H), 0.96 (s, 9H), 0.25 (s, 9H), 0.16 (s, 6H).

Step 3: Preparation of 2,3-dichloro-4-((trimethylsilyl)ethynylphenol

This compound was made using the procedure described in Example 1 (Step 3). Thus, this intermediate compound (Step 2)(368.97 mg, 0.99 mmol) was reacted with Potassium fluoride (KF, 574 mg, 9.9 mmol) to afford the intermediate compound 2,3-dichloro-4-((trimethylsilyl)ethynylphenol (185 mg, 45%) and used directly for the next step without further purification.

Step 4: Preparation of 5-cyclopropyl-4-((2,3-dichloro-4-ethynylphenoxy)methyl)-3-(2,6-duchlorophenyl)isoxazole This compound was made using the procedure described in Example 1 (Step 4). Thus, this intermediate compound (Step 3)(256.6 mg, 0.99 mmol) was reacted with 4-(bromomethyl)-5-cyclopropyl-3-(2,6-dichlorophenyl)isoxazole (Intermediate 1)(343.6 mg, 0.99 mmol) and potassium carbonate (205.2 mg, 1.49 mmol) to afford the intermediate compound 5-cyclopropyl-4-((2,3-dichloro-4-ethynylphenoxy)methyl)-3-(2,6-duchlorophenyl)isoxazole (345.4 mg, 77%).

$^1$H-NMR (CDCl$_3$, 400 MHz): δ 7.41-7.30 (m, 3H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 5: Preparation of methyl 3-((2,3-dichloro-4-((5-cyclopropyl-3-(2,6-dichlorophenyl)isoxazol-4-yl)methoxy)phenyl)ethynyl)benzoate This compound was made using the procedure described in Example 1 (Step 5). Thus, this intermediate compound (Step 4)(345.4 mg, 0.762 mmol) was reacted with methyl 3-bromobenzoate (163.9 mg, 0.762 mmol), bis(triphenylphosphine)palladium(II) dichloride ((PdCl$_2$(PPh$_3$)$_2$, 49 mg, 0.07 mmol), Copper(I) iodide (7 mg, 0.035 mmol) and 1,8-Diazabicyclo[5.4.0]undec-7-ene (DBU, 0.16 ml, 1.05 mmol) to afford the intermediate compound methyl 3-((2,3-dichloro-4-((5-cyclopropyl-3-(2,6-dichlorophenyl)isoxazol-4-yl) methoxy)phenyl)ethynyl)benzoate (232.7 mg, 52%).

$^1$H-NMR (DMSO, 400 MHz): δ 8.06 (t, 1H), 8.03-7.78 (m, 2H), 7.96-7.53 (m, 5H), 7.27 (d, 1H), 5.15 (s, 2H), 3.89 (s, 3H), 1.28-1.13 (m, 5H).

Step 6: Preparation of 3-((2,3-dichloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 5)(232.7 mg, 0.40 mmol) was reacted with lithium hydroxide (167.8 mg, 4 mmol) to afford the title compound (133 mg, 58%).

$^1$H-NMR (DMSO, 400 MHz): δ 8.05 (t, 1H), 7.99 (d, 1H), 7.79 (d, 1H), 7.67-7.53 (m, 5H), 7.26 (d, 1H), 5.14 (s, 2H), 1.12-1.26 (m, 5H).

<Example 70>3-((2-chloro-4-((5-cyclopropyl-3-(2,6-dichlorophenyl) isoxazole-4-yl)methoxy)-6-fluorophenyl)ethynyl)benzoic acid (I-70)

Step 1: Preparation of tert-butyl(3-chloro-5-fluoro-4-iodophenoxy)dimethyl silane This compound was made using the procedure described in Example 1 (Step 1). Thus, 3-chloro-5-fluoro-4-iodophenol (0.5 g, 1.84 mmol) was reacted with tert-butyldimethylsilyl chloride (TBSCl, 0.39 g, 2.60 mmol), imidazole (0.23 g, 3.46 mmol) to afford the intermediate compound tert-butyl(3-chloro-5-fluoro-4-iodophenoxy)dimethylsilane (0.54 g, 76%).

$^1$H-NMR (CDCl$_3$, 400 MHz): δ 7.69 (d, 1H), 6.97 (d, 1H), 0.96 (s, 9H), 0.16 (s, 6H).

Step 2: Preparation of tert-butyl(3-chloro-5-fluoro-4-((trimethylsilyl)ethynyl)phenoxy))dimethylsilane This compound was made using the procedure described in Example 1 (Step 2). Thus, this intermediate compound (Step 1)(0.54 g, 1.40 mmol) was reacted with bis(triphenylphosphine)palladium(II)dichloride ((PdCl$_2$(PPh$_3$)$_2$, 106.68 mg, 0.14 mmol), copper(I) iodide (29 mg, 0.14 mmol) triethylamine (0.42 ml, 3.04 mmol), and trimethylsilylacetylene (0.42 ml, 3.04 mmol), to afford the intermediate compound tert-butyl(3-chloro-5-fluoro-4-((trimethylsilyl)ethylnyl)phenoxy)dimethylsilane (239.91 mg, 48%).

$^1$H-NMR (CDCl$_3$, 400 MHz): δ 7.69 (d, 1H), 6.97 (d, 1H), 0.96 (s, 9H), 0.25 (s, 9H), 0.16 (s, 6H).

Step 3: Preparation of 3-chloro-5-fluoro-4-((trimethylsilyl)ethylnyl)phenol

This compound was made using the procedure described in Example 1 (Step 3). Thus, this intermediate compound (Step 2)(239.91 mg, 0.67 mmol) was reacted with Potassium fluoride (390 mg, 6.7 mmol) to afford the intermediate compound 3-chloro-5-fluoro-4-((trimethylsilyl)ethylnyl) phenol without further purification.

Step 4: Preparation of 4-((3-chloro-4-ethynyl-5-fluorophenoxy)methyl)-5-cyclopropyl-3-(2,6-dichlorophenyl)isoxazole This compound was made using the procedure described in Example 1 (Step 4). Thus, this intermediate compound (Step 3)(162.6 mg, 0.67 mmol) was reacted with 4-(bromomethyl)-5-cyclopropyl-3-(2,6-dichlorophenyl)isoxazole (Intermediate 1)(232.5 mg, 0.67 mmol), potassium carbonate (138.90 mg, 1.01 mmol) to afford the intermediate compound 4-((3-chloro-4-ethynyl-5-fluorophenoxy)methyl)-5-cyclopropyl-3-(2,6-dichlorophenyl)isoxazole (210.7 mg, 72%).

$^1$H-NMR (CDCl$_3$, 400 MHz): δ 7.41-7.30 (m, 3H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 5: Preparation of methyl 3-((2-chloro-4-((5-cyclopropyl-3-(2,6-dichlorophenyl)isoxazole-4-yl)methoxy)-6-fluorophenyl)ethynyl)benzoate This compound was made using the procedure described in Example 1 (Step 5). Thus, this intermediate compound (Step 4)(210.7 mg, 0.48 mmol) was reacted with methyl 3-bromobenzoate (103.2 mg, 0.48 mmol), bis(triphenylphosphine)palladium(II) dichloride ((PdCl$_2$(PPh$_3$)$_2$, 35 mg, 0.05 mmol), copper(I) iodide (9.5 mg, 0.05 mmol), 1,8-Diazabicyclo(5.4.0)undec-7-ene (DBU, 0.36 ml, 2.4 mmol) to afford the intermediate compound methyl 3-((2-chloro-4-((5-cyclopropyl-3-(2,6-dichlorophenyl)isoxazole-4-yl)methoxy)-6-fluorophenyl)ethynyl)benzoate (131.5 mg, 48%).

$^1$H-NMR (CDCl$_3$, 400 MHz): δ 8.21 (t, 1H), 8.02-7.99 (m, 1H), 7.73-7.71 (m, 1H), 7.45-7.32 (m, 4H), 6.71 (d, 1H), 6.50 (dd, 1H), 4.81 (s, 2H), 3.93 (s, 3H), 2.16-2.12 (m, 1H), 1.32-1.27 (m, 2H), 1.21-1.16 (m, 2H).

Step 6: Preparation of 3-((2-chloro-4-((5-cyclopropyl-3-(2,6-dichlorophenyl)isoxazole-4-yl)methoxy)-6-fluorophenyl)ethynyl)benzoic acid This compound was made using the procedure described in Example 1 (Step 6). Thus, this intermediate compound (Step 5)(131.5 mg, 0.23 mmol) was reacted with lithium hydroxide (96.5 mg, 2.3 mmol) to afford the title compound (79.4 mg, 62%). $^1$H-NMR (CDCl$_3$, 400 MHz): δ 8.29 (s, 1H), 8.09 (d, 1H), 7.79 (d, 1H), 7.50-7.33 (m, 4H), 6.71 (d, 1H), 6.51 (dd, 1H), 4.82 (s, 2H), 2.17-2.11 (m, 1H), 1.33-1.28 (m, 2H), 1.21-1.16 (m, 2H).

<Example 71>3-amino-5-((2-chloro-4-((5-cyclopropyl-3-(2,6-dichloro phenyl)isoxazol-4-yl)methoxy)phenyl)ethynyl)-2-methylbenzoic acid (I-71)

Step 1: Preparation of methyl 5-((2-chloro-4-((5-cyclopropyl-3-(2,6-dichloro phenyl)isoxazol-4-yl)methoxy)phenyl)ethynyl)-2-methyl-3-nitrobenzoate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 5-bromo-2-methyl-3-nitrobenzoate (70.1 mg, 0.287 mmol), bis(triphenyl phosphine)palladium(II) dichloride ((PdCl$_2$(PPh$_3$)$_2$, 21 mg, 0.03 mmol), copper(I) iodide (5.7 mg, 0.03 mmol) and triethylamine (0.2 ml, 1.44 mmol) to afford the intermediate compound methyl 5-((2-chloro-4-((5-cyclopropyl-3-(2,6-dichloro phenyl)isoxazol-4-yl)methoxy)phenyl)ethynyl)-2-methyl-3-nitrobenzoate (105.2 mg, 72%).
$^1$H-NMR (CDCl$_3$, 400 MHz): δ 8.11-8.10 (d, 1H), 7.96 (d, 1H), 7.42-7.39 (m, 3H), 7.35-7.31 (m, 1H), 6.88-6.87 (d, 1H), 6.71-6.69 (dd, 1H), 4.83 (s, 2H), 3.95 (s, 3H), 2.63 (s, 3H), 2.17-2.13 (m, 1H), 1.32-1.28 (m, 2H), 1.26-1.15 (m, 2H).

Step 2: Preparation of methyl 3-amino-5-((2-chloro-4-((5-cyclopropyl-3-(2,6-dichlorophenyl)isoxazol-4-yl)methoxy)phenyl)ethynyl)-2-methylbenzoate This compound was made using the procedure described in Example 8 (Step 2). Thus, the intermediate compound (Step 1)(105.2 mg, 0.172 mmol) was reacted with tin(II) chloride dihydrate (388 mg, 1.72 mmol) to afford the intermediate compound methyl 3-amino-5-((2-chloro-4-((5-cyclopropyl-3-(2,6-dichloro phenyl)isoxazol-4-yl)methoxy)phenyl)ethynyl)-2-methylbenzoate (62 mg, 62%).
$^1$H-NMR (CDCl$_3$, 400 MHz): δ 7.42-7.31 (m, 5H), 6.97 (d, 1H), 6.86 (d, 1H), 6.68 (dd, 1H), 4.81 (s, 2H), 3.89 (s, 3H), 3.76 (s, 2H), 2.35 (s, 3H), 2.17-2.13 (m, 1H), 1.32-1.28 (m, 2H), 1.19-1.15 (m, 2H).

Step 3: Preparation of 3-amino-5-((2-chloro-4-((5-cyclopropyl-3-(2,6-dichlorophenyl)isoxazol-4-yl)methoxy)phenyl)ethynyl)-2-methylbenzoic acid This compound was made using the procedure described in Example 1 (Step 6). Thus, the intermediate compound (Step 2)(62 mg, 0.106 mmol) was reacted with lithium hydroxide (44 mg, 1.06 mmol) to afford the title compound (53 mg, 88%).
$^1$H-NMR (DMSO, 400 MHz): δ 7.64-7.62 (m, 2H), 7.57-7.48 (m, 2H), 7.06 (dd, 2H), 6.92 (d, 1H), 6.82 (dd, 1H), 5.28 (s, 2H), 4.97 (s, 2H), 2.47 (m, 1H), 2.21 (s, 3H), 1.21-1.19 (m, 2H), 1.14-1.13 (m, 2H).

<Example 72>3-((2-chloro-4-((5-cyclopropyl-3-(2,6-dichlorophenyl)isoxazol-4-yl)methoxy)phenyl)ethynyl)-5-(3-ethylureido)benzoic acid (I-72)

Step 1: Preparation of methyl 3-((2-chloro-4-((5-cyclopropyl-3-(2,6-dichlorophenyl)isoxazol-4-yl)methoxy)phenyl)ethynyl)-5-(3-ethylureido)benzoate The intermediate compound methyl 3-amino-5-((2-chloro-4-((5-cyclopropyl-3-(2,6-dichlorophenyl)isoxazol-4-yl)methoxy)phenyl)ethynyl)benzoate (Step 2 of example 8)(150 mg, 0.264 mmol) was dissolved in dichlromethane (3 ml) and ethylisocyanite (31 ul, 0.396 mmol) was added. The reaction was stirred at room temperature for 1 day. The reaction mixture was extracted with ethyl acetate and washed with water. The combined organic phase was dried over MgSO$_4$, filtered, concentrated and purified by column chromatography on silica to afford the intermediate compound methyl 3-((2-chloro-4-((5-cyclopropyl-3-(2,6-dichlorophenyl)isoxazol-4-yl)methoxy)phenyl)ethynyl)-5-(3-ethylureido)benzoate (117 mg, 69%).
$^1$H-NMR (CDCl$_3$, 400 MHz): δ 7.95 (t, 1H), 7.86 (t, 1H), 7.79 (t, 1H), 7.44-7.38 (m, 2H), 7.36-7.30 (m, 2H), 6.85 (d, 1H), 6.67 (dd, 1H), 5.41 (s, 2H), 4.82 (s, 2H), 3.89 (s, 3H), 3.74 (q, 1H), 2.19-2.10 (m, 1H), 1.24-1.20 (m, 3H), 1.15-1.11 (m, 4H).

Step 2: Preparation of 3-((2-chloro-4-((5-cyclopropyl-3-(2,6-dichloro phenyl)isoxazol-4-yl)methoxy)phenyl)ethynyl)-5-(3-ethylureido)benzoic acid This compound was made using the procedure described in Example 1 (Step 6). Thus, the intermediate compound (Step 1)(105 mg, 0.165 mmol) was reacted with lithium hydroxide (58 mg, 1.65 mmol) to afford the title compound (20.6 mg, 20%).
$^1$H-NMR (DMSO, 400 MHz): δ 13.12 (br, 1H), 8.82 (s, 1H), 7.93 (s, 1H), 7.88 (s, 1H), 7.64-7.62 (m, 2H), 7.57-7.55 (m, 2H), 7.09 (d, 1H), 6.84 (dd, 1H), 4.99 (s, 2H), 3.11 (s, 2H), 1.24-1.15 (m, 5H), 1.07-1.04 (q, 3H).

<Example 73>3-acetamido-5-((2-chloro-4-((5-cyclopropyl-3-(2,6-dichloro phenyl)isoxazol-4-yl)methoxy)phenyl)ethynyl)benzoic acid (I-73)

Step 1: Preparation of methyl 3-acetamido-5-((2-chloro-4-((5-cyclopropyl-3-(2,6-dichlorophenyl)isoxazol-4-yl)methoxy)phenyl)ethynyl)benzoate The intermediate compound methyl 3-amino-5-((2-chloro-4-((5-cyclopropyl-3-(2,6-dichlorophenyl)isoxazol-4-yl)methoxy)phenyl)ethynyl)benzoate (Step 2 of example 8)(100 mg, 0.176 mmol) was dissolved in N,N-dimethylformamide (1.7 ml) and acetylchloride (26 ul, 0.264 mmol) and triethylamine (55 ul, 0.264 mmol) were added. The reaction was stirred at room temperature for 1 day. The reaction mixture was extracted with ethyl acetate and washed with water. The combined organic phase was dried over MgSO$_4$, filtered, concentrated and purified by column chromatography on silica to afford the intermediate compound methyl 3-acetamido-5-((2-chloro-4-((5-cyclopropyl-3-(2,6-dichloro phenyl)isoxazol-4-yl)methoxy)phenyl)ethynyl)benzoate (44 mg, 41%).

¹H-NMR (CDCl₃, 400 MHz): δ 8.23 (t, 1H), 7.91 (dd, 1H), 7.50-7.40 (m, 2H), 7.38-7.32 (m, 2H), 6.88 (d, 1H), 6.69 (dd, 1H), 4.82 (s, 2H), 4.27 (q, 1H), 4.26 (q, 2H), 3.94 (s, 3H), 2.31 (s, 3H), 2.19-2.12 (m, 1H), 1.33-1.24 (m, 2H), 1.23-1.14 (m, 2H).

Step 2: Preparation of 3-acetamido-5-((2-chloro-4-((5-cyclopropyl-3-(2,6-dichlorophenyl)isoxazol-4-yl)methoxy)phenyl)ethynyl)benzoic acid The intermediate compound (Step 1) was dissolved in 1,4-dioxane (1.0 ml)/water (0.14 ml) and lithium hydroxide (58 mg, 0.716 mmol) was added. The reaction was stirred at room temperature for 18 hours. The pH of reaction mixture was adjusted 4 to 5 with 1N solution of hydrochloric acid and the reaction mixture was extracted with ethyl acetate and washed with water. The combined organic phase was dried over MgSO₄, filtered, concentrated to afford the title compound (18.0 mg, 42%).

¹H-NMR (DMSO, 400 MHz): δ 13.45 (br, 1H), 10.25 (br, 1H), 8.15 (s, 1H), 8.04 (s, 1H), 7.68 (s, 1H), 7.64-7.20 (m, 2H), 7.58-7.54 (m, 2H), 7.09 (d, 1H), 6.84 (dd, 1H), 4.99 (s, 2H), 2.07 (s, 3H), 1.21-1.14 (m, 5H).

<Example 74>3-((2-chloro-4-((5-cyclopropyl-3-(2,6-dichlorophenyl)isoxazol-4-yl)methoxy)phenyl)ethynyl)-5-((ethoxycarbonyl)amino)benzoic acid (I-74)

Step 1: Preparation of 3-((2-chloro-4-((5-cyclopropyl-3-(2,6-dichloropheny) isoxazol-4-yl)methoxy)phenyl)ethynyl)-5-((ethoxycarbonyl)amino)benzoic acid This compound was made using the procedure described in Example 1 (Step 6). Thus, methyl 3-((2-chloro-4-((5-cyclopropyl-3-(2,6-dichlorophenyl)isoxazol-4-yl)methoxy)phenyl)ethynyl)-5-((ethoxycarbonyl)amino)benzoate (Example 8)(55.1 mg, 0.086 mmol) was reacted with lithium hydroxide (36.1 mg, 0.86 mmol) to afford the title compound (45.2 mg, 84%).

¹H-NMR (DMSO, 400 MHz): δ 13.55 (br, 1H), 9.98 (s, 1H), 8.09 (s, 1H), 7.87 (s, 1H), 7.64-7.62 (m, 3H), 7.58-7.54 (m, 1H), 7.09 (d, 1H), 6.69 (dd, 1H), 4.82 (s, 2H), 4.16 (q, 2H), 1.25 (t, 3H), 1.21-1.14 (m, 5H).

<Example 75>3-((2-chloro-4-((5-cyclopropyl-3-(2,6-dichlorophenyl)isoxazol-4-yl)methoxy)phenyl)ethynyl)-5-((ethoxycarbonyl)(methyl)amino)benzoic acid (I-75)

Step 1: Preparation of methyl 3-((2-chloro-4-((5-cyclopropyl-3-(2,6-dichlorophenyl)isoxazol-4-yl)methoxy)phenyl)ethynyl)-5-((ethoxycarbonyl)amino)benzoate This compound was made using the procedure described in Example 10 (Step 1). Thus, methyl 3-((2-chloro-4-((5-cyclopropyl-3-(2,6-dichlorophenyl)isoxazol-4-yl)methoxy)phenyl)ethynyl)-5-((ethoxycarbonyl)amino)benzoate (Example 8) (50 mg, 0.078 mmol) was reacted with sodium hydride (5.6 mg, 0.234 mmol) and iodomethane (6 ul, 0.093 mmol) to afford the intermediate compound methyl 3-((2-chloro-4-((5-cyclopropyl-3-(2,6-dichlorophenyl)isoxazol-4-yl)methoxy)phenyl)ethynyl)-5-((ethoxycarbonyl)(methyl)amino)benzoate (35 mg, 69%).

¹H-NMR (CDCl₃, 400 MHz): δ 8.02 (t, 1H), 7.88 (s, 1H), 7.62 (s, 1H), 7.42-7.38 (m, 1H), 7.35-7.31 (m, 1H), 6.87 (d, 1H), 6.70 (dd, 1H), 4.82 (s, 2H), 4.22 (q, 2H), 3.93 (s, 3H), 3.32 (s, 3H), 2.17-2.13 (m, 1H), 1.34 (t, 3H), 1.32-1.24 (m, 2H), 1.23-1.14 (m, 2H).

Step 2: Preparation of 3-((2-chloro-4-((5-cyclopropyl-3-(2,6-dichloro phenyl)isoxazol-4-yl)methoxy)phenyl)ethynyl)-5-((ethoxycarbonyl)amino)benzoic acid This compound was made using the procedure described in Example 1 (Step 6). Thus, the intermediate (Step 1)(20 mg, 0.031 mmol) was reacted with lithium hydroxide (12.8 mg, 0.31 mmol) to afford the title compound (18 mg, 94%).

¹H-NMR (DMSO, 400 MHz): δ 13.38 (br, 1H), 7.88 (t, 1H), 7.83 (t, 1H), 7.72 (t, 1H), 7.64-7.62 (m, 2H), 7.57-7.53 (m, 2H), 7.10 (d, 1H), 6.85 (dd, 1H), 4.98 (s, 2H), 4.13 (q, 2H), 3.27 (s, 3H), 1.23-1.11 (m, 8H).

<Example 76>3-((2-chloro-4-((5-cyclopropyl-3-(2,6-dichlorophenyl)isoxazol-4-yl)methoxy)phenyl)ethynyl)-5-((cyclopropoxycarbonyl)amino)benzoic acid (I-76)

Step 1: Preparation of methyl 3-((2-chloro-4-((5-cyclopropyl-3-(2,6-dichloro phenyl)isoxazol-4-yl)methoxy)phenyl)ethynyl)-5-((cyclopropoxycarbonyl)amino)benzoate Diisopropylamine (0.3 ml, 1.8 mmol) was added to a solution of cyclopropanol (0.1 ml, 1.8 mmol) and triphosgene (267 mg, 0.9 mmol) in dichloromethane which was cooled to 0° C. and stirred for 1 hour at room temperature. 3-Amino-5-((2-chloro-4-((5-cyclopropyl-3-(2,6-dichlorophenyl)isoxazol-4-yl)methoxy)phenyl)ethynyl)benzoate (Step 2 of example 8)(100 mg, 0.18 mmol) and diisopropylethylamine (0.12 ml, 0.54 mmol) was added to the reaction mixture and stirred for 3 hours at room temperature. Water was added to the reaction mixture and the product was extracted into dichloromethane. The combined organic layers were dried over MgSO₄, filtered, evaporated in vacuum and purified using silica chromatography to afford the intermediate compound methyl 3-((2-chloro-4-((5-cyclopropyl-3-(2,6-dichlorophenyl)isoxazol-4-yl)methoxy)phenyl)ethynyl)-5-((cyclopropoxycarbonyl)amino)benzoate (35 mg, 30%).

¹H-NMR (CDCl₃, 400 MHz): δ 7.96 (m, 1H), 7.84 (m, 2H), 6.86 (d, 1H), 6.69 (dd, 1H), 7.42-7.31 (m, 4H), 6.86 (d, 1H), 6.72 (dd, 1H), 5.64 (s, 2H), 4.82 (s, 2H), 3.92 (s, 3H), 2.16 (m, 1H), 1.31-1.14 (m, 4H).

Step 2: Preparation of 3-((2-chloro-4-((5-cyclopropyl-3-(2,6-dichlorophenyl) isoxazol-4-yl)methoxy)phenyl)ethynyl)-5-((cyclopropoxycarbonyl)amino)benzoic acid This compound was made using the procedure described in Example 1 (Step 6). Thus, this intermediate compound (Step 1)(30 mg, 0.046 mmol) was reacted with lithium hydroxide (19 mg, 0.46 mmol) to afford the title compound (9 mg, 31%).

¹H-NMR (DMSO, 400 MHz): δ 9.92 (s, 1H), 8.02 (s, 1H), 7.79 (s, 1H), 7.65-7.63 (m, 3H), 7.59-7.54 (m, 2H), 7.10 (m,

1H), 6.85-6.82 (m, 1H), 5.02 (s, 2H), 4.09 (m, 1H), 1.23-1.14 (m, 6H), 0.72-0.70 (m, 4H).

<Example 77> 3-((tert-butoxycarbonyl)amino)-5-((2-chloro-4-((5-cyclopropyl-3-(2,6-dichlorophenyl)isoxazol-4-yl)methoxy)phenyl)ethynyl)benzoic acid (I-77)

Step 1: Preparation of 3-((tert-butoxycarbonyl)amino)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, methyl 3-((tert-butoxycarbonyl)amino)-5-((2-chloro-4-((5-cyclopropyl-3-(2,6-dichlorophenyl)isoxazol-4-yl)methoxy)phenyl)ethynyl)benzoate (Example 9)(300 mg, 0.449 mmol) was reacted with lithium hydroxide (188 mg, 4.49 mmol) to afford the title compound (227 mg, 77%).
$^1$H-NMR (DMSO, 400 MHz): δ 13.27 (br, 1H), 8.10 (t, 1H), 7.84 (t, 1H), 7.64-7.60 (m, 3H), 7.57-7.56 (m, 2H), 7.09 (d, 1H), 6.84 (dd, 1H), 4.99 (s, 2H), 1.49 (s, 9H), 1.19-1.14 (m, 5H).

<Example 78> 3-((tert-butoxycarbonyl)(methyl)amino)-5-((2-chloro-4-((5-cyclo propyl-3-(2,6-dichlorophenyl)isoxazol-4-yl)methoxy)phenyl)ethynyl)benzoic acid (I-78)

Step 1: Preparation of methyl 3-((tert-butoxycarbonyl)(methyl)amino)-5-((2-chloro-4-((5-cyclopropyl-3-(2,6-dichlorophenyl)isoxazol-4-yl)methoxy)phenyl)ethynyl)benzoate This compound was made using the procedure described in Example 10 (Step 1). Thus, methyl 3-((tert-butoxycarbonyl)amino)-5-((2-chloro-4-((5-cyclopropyl-3-(2,6-dichlorophenyl)isoxazol-4-yl)methoxy)phenyl)ethynyl)benzoate (Example 9)(220 mg, 0.329 mmol) was reacted with sodium hydride (24 mg, 0.988 mmol) and iodomethane (87 ul, 1.31 mmol) to afford the intermediate compound methyl 3-((tert-butoxycarbonyl)(methyl)amino)-5-((2-chloro-4-((5-cyclopropyl-3-(2,6-dichlorophenyl)isoxazol-4-yl)methoxy)phenyl)ethynyl)benzoate (102 mg, 45%).
$^1$H-NMR (CDCl$_3$, 400 MHz): δ 7.98 (t, 1H), 7.88 (t, 1H), 7.60 (s, 1H), 7.42-7.39 (m, 3H), 7.35-7.31 (m, 1H), 6.87 (d, 1H), 6.70 (dd, 1H), 4.82 (s, 2H), 3.93 (s, 3H), 3.29 (s, 3H), 2.17 (m, 1H), 1.46 (s, 9H), 1.32-1.24 (m, 2H), 1.19-1.15 (m, 2H).

Step 2: Preparation of 3-((tert-butoxycarbonyl)(methyl)amino)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, the intermediate compound (Step 1)(100 mg, 0.146 mmol) was reacted with lithium hydroxide (61.5 mg, 1.46 mmol) to afford the title compound (28.3 mg, 29%).
$^1$H-NMR (DMSO, 400 MHz): δ 13.37 (br, 1H), 7.88 (t, 1H), 7.79 (t, 1H), 7.67 (s, 1H), 7.64-7.62 (m, 2H), 7.57-7.53 (m, 2H), 7.10 (d, 1H), 6.85 (dd, 1H), 4.98 (s, 2H), 3.27 (s, 3H), 1.40 (s, 9H), 1.21-1.11 (m, 5H).

<Example 79> 3-((2-chloro-4-((5-cyclopropyl-3-(2,6-dichlorophenyl)isoxazol-4-yl)methoxy)phenyl)ethynyl)-5-(((cyclopropylmethoxy)carbonyl)amino)benzoic acid (I-79)

Step 1: Preparation of methyl 3-((2-chloro-4-((5-cyclopropyl-3-(2,6-dichlorophenyl)isoxazol-4-yl)methoxy)phenyl)ethynyl)-5-(((cyclopropylmethoxy)carbonyl)amino)benzoate This compound was made using the procedure described in Example 76 (Step 1). Thus, 3-amino-5-((2-chloro-4-((5-cyclopropyl-3-(2,6-dichlorophenyl) isoxazol-4-yl)methoxy)phenyl)ethynyl)benzoate (Step 2 of Example 8)(100 mg, 0.18 mmol), diisopropylamine (0.3 ml, 1.6 mmol), triphosgene (53 mg, 0.18 mmol), cyclopropanemethanol (0.03 ml, 0.35 mmol) and N, N-diisopropylethyl amine (0.12 ml, 0.54 mmol) to afford the intermediate compound methyl 3-((2-chloro-4-((5-cyclopropyl-3-(2,6-dichlorophenyl)isoxazol-4-yl)methoxy)phenyl)ethynyl)-5-((cyclopropylmethoxy)amino)benzoate (38 mg, 32%).
$^1$H-NMR (CDCl$_3$, 400 MHz): δ 7.93 (m, 1H), 7.89 (m, 2H), 7.43-7.32 (m, 4H), 6.87 (d, 1H), 6.72 (dd, 1H), 4.82 (s, 2H), 4.03 (s, 1H), 4.01 (m, 1H), 3.93 (s, 3H), 2.16 (m, 1H), 1.56-1.16 (m, 4H), 0.62 (m, 2H), 0.34 (m, 2H).

Step 2: Preparation of 3-((2-chloro-4-((5-cyclopropyl-3-(2,6-dichloro phenyl)isoxazol-4-yl)methoxy)phenyl)ethynyl)-5-(((cyclopropylmethoxy)carbonyl)amino)benzoic acid This compound was made using the procedure described in Example 1 (Step 6). Thus, this intermediate compound (Step 1)(30 mg, 0.045 mmol) was reacted with lithium hydroxide (19 mg, 0.46 mmol) to afford the title compound (15 mg, 52%).
$^1$H-NMR (DMSO, 400 MHz): δ 9.92 (s, 1H), 7.97 (s, 1H), 7.74 (s, 1H), 7.54 (m, 3H), 7.46 (m, 2H), 6.99 (m, 1H), 6.72 (dd, 1H), 4.88 (s, 2H), 3.84 (d, 2H), 1.84 (d, 2H), 1.13-1.04 (m, 4H), 0.46 (m, 2H), 0.22 (m, 2H).

<Example 80> 3-((2-chloro-4-((5-cyclopropyl-3-(2,6-dichlorophenyl)isoxazol-4-yl)methoxy)phenyl)ethynyl)-5-(((2-cyclopropylethoxy)carbonyl)amino)benzoic acid (I-80)

Step 1: Preparation of methyl 3-((2-chloro-4-((5-cyclopropyl-3-(2,6-dichloro phenyl)isoxazol-4-yl)methoxy)phenyl)ethynyl)-5-(((2-cyclopropylethoxy)carbonyl)amino)benzoate This compound was made using the procedure described in Example 76 (Step 1). Thus, 3-amino-5-((2-chloro-4-((5-cyclopropyl-3-(2,6-dichlorophenyl) isoxazol-4-yl)methoxy)phenyl)ethynyl)benzoate (Step 2 of example 8)(150 mg, 0.264 mmol), 1,1'-carbonyldiimidazole (47 mg, 0.29 mmol) and cyclopropylethyl alcohol (43 mg, 0.5 mmol) to afford the intermediate compound methyl 3-((2-chloro-4-((5-cyclopropyl-3-(2,6-dichlorophenyl)isoxazol-4-yl)methoxy)phenyl)ethynyl)-5-(((2-cyclopropylethoxy)carbonyl)amino)benzoate (30 mg, 17%)).
$^1$H-NMR (CDCl$_3$, 400 MHz): δ 7.92 (s, 1H), 7.89 (s, 2H), 7.44-7.32 (m, 4H), 6.87 (m, 1H), 6.70 (m, 1H), 4.82 (s, 2H), 4.27 (m, 2H), 3.92 (s, 3H), 2.17 (m, 1H), 1.60 (m, 2H), 1.33-1.16 (m, 4H), 0.76 (m, 1H), 0.49 (m, 2H), 0.11 (m, 2H).

Step 2: Preparation of 3-((2-chloro-4-((5-cyclopropyl-3-(2,6-dichlorophenyl) isoxazol-4-yl)methoxy) phenyl)ethynyl)-5-(((2-cyclopropylethoxy)carbonyl) amino)benzoic acid This compound was made using the procedure described in Example 1 (Step 6). Thus, this intermediate compound (Step 1)(30 mg, 0.044 mmol) was reacted with lithium hydroxide (50 mg, 1.2 mmol) to afford the title compound (13 g, 44%).
$^1$H-NMR (DMSO, 400 MHz): δ 9.84 (s, 1H), 7.96 (s, 1H), 7.75 (s, 1H), 7.52 (m, 3H), 7.45 (d, 2H), 6.98 (d, 1H), 6.72 (dd, 1H), 5.64 (s, 2H), 4.87 (s, 2H), 4.06 (m, 2H), 1.43 (m, 2H), 0.74-0.65 (m, 4H), 0.30 (m, 2H), 0.01 (m, 2H).

<Example 81>3-((2-chloro-4-((5-cyclopropyl-3-(2, 6-dichlorophenyl) isoxazol-4-yl)methoxy)phenyl) ethynyl)-5-(((2-hydroxyethoxy)carbonyl)amino) benzoic acid (I-81)

Step 1: Preparation of methyl 3-((2-chloro-4-((5-cyclopropyl-3-(2,6-dichlorophenyl) isoxazol-4-yl) methoxy)phenyl)ethynyl)-5-(((2-hydroxyethoxy) carbonyl)amino)benzoate This compound was made using the procedure described in Example 78 (Step 1). Thus, methyl 3-amino-5-((2-chloro-4-((5-cyclopropyl-3-(2,6-dichlorophenyl) isoxazol-4-yl) methoxy)phenyl)ethynyl)benzoate (Step 2 of example 8)(70 mg, 0.123 mmol), 1,1'-carbonyldiimidazole (22 mg, 0.136 mmol) and ethylene glycol (13.6 ul, 0.24 mmol) to afford the intermediate compound methyl 3-((2-chloro-4-((5-cyclopropyl-3-(2,6-dichlorophenyl)isoxazol-4-yl)methoxy)phenyl) ethynyl)-5-(((2-hydroxyethoxy)carbonyl)amino)benzoate (20 mg, 25%)).
$^1$H-NMR (CDCl$_3$, 400 MHz): δ 7.94 (m, 1H), 7.90 (m, 1H), 7.42-7.32 (m, 4H), 7.00 (s, 1H), 6.87 (d, 1H), 6.69 (dd, 1H), 4.82 (s, 2H), 4.53 (m, 3H), 4.35 (m, 1H), 3.92 (s, 3H), 2.17 (m, 1H), 1.32-1.16 (m, 4H).

Step 2: Preparation of 3-((2-chloro-4-((5-cyclopropyl-3-(2,6-dichlorophenyl) isoxazol-4-yl)methoxy) phenyl)ethynyl)-5-(((2-hydroxyethoxy)carbonyl) amino)benzoic acid This compound was made using the procedure described in Example 1 (Step 6). Thus, this intermediate compound (Step 1)(20 mg, 0.03 mmol) was reacted with lithium hydroxide (50 mg, 1.2 mmol) to afford the title compound (11 mg, 57%).
$^1$H-NMR (DMSO, 400 MHz): δ 9.93 (s, 1H), 8.03 (s, 1H), 7.78 (s, 1H), 7.64 (m, 3H), 7.54 (m, 2H), 7.09 (d, 1H), 6.83 (dd, 1H), 4.98 (s, 2H), 4.12 (t, 2H), 3.63 (m, 2H), 1.23-1.14 (m, 5H).

<Example 82>3-(((azetidin-3-yloxy)carbonyl) amino)-5-((2-chloro-4-((5-cyclopropyl-3-(2,6-dichlorophenyl)isoxazol-4-yl)methoxy)phenyl)ethynyl)benzoic acid (I-82)

Step 1: Preparation of tert-butyl-3-(((3-((2-chloro-4-((5-cyclopropyl-3-(2,6-dichlorophenyl)isoxazol-4-yl)methoxy)phenyl-ethynyl)-5-(methoxycarbonyl) phenyl)carbamoyl)oxy)azetidine-1-carboxylate This compound was made using the procedure described in Example 78 (Step 1). Thus, methyl 3-amino-5-((2-chloro-4-((5-cyclopropyl-3-(2,6-dichlorophenyl) isoxazol-4-yl) methoxy)phenyl)ethynyl)benzoate (Step 2 of Example 8)(170 mg, 0.30 mmol), tert-butyl 3-hydroxyazetidine-1-carboxylate (120 mg, 0.69 mmol), N,N-diisopropylethylamine (0.19 ml, 1.04 mmol) and triphosgene (72 mg, 0.24 mmol) to afford the intermediate compound tert-butyl-3-(((3-((2-chloro-4-((5-cyclopropyl-3-(2,6-dichlorophenyl) isoxazol-4-yl)methoxy)phenyl-ethynyl)-5-(methoxycarbonyl)phenyl)carbamoyl)oxy)azetidine-1-carboxylate (80 mg, 35%).
$^1$H-NMR (CDCl$_3$, 400 MHz): δ 7.94 (m, 2H), 7.86 (s, 1H), 7.43-7.32 (m, 3H), 6.94 (s, 1H), 6.87 (m, 1H), 6.69 (dd, 1H), 5.23 (m, 1H), 4.82 (s, 2H), 4.29 (m, 2H), 3.98 (m, 2H), 3.93 (s, 3H), 2.16 (m, 1H), 1.56 (m, 9H), 1.45-1.15 (m, 4H).

Step 2: Preparation of 3-(((azetidin-3-yloxy)carbonyl)amino)-5-((2-chloro-4-((5-cyclopropyl-3-(2,6-dichlorophenyl)isoxazol-4-yl)methoxy)phenyl)ethynyl)benzoic acid This compound was made using the procedure described in Example 1 (Step 6). Thus, this intermediate compound (Step 1)(30 mg, 0.04 mmol) was reacted with lithium hydroxide (19 mg, 0.46 mmol) to afford the title compound (12 mg, 61%).
$^1$H-NMR (DMSO, 400 MHz): δ 13.28 (s, 1H), 10.08 (s, 1H), 8.10 (s, 1H), 7.87 (s, 1H), 7.64 (m, 3H), 7.55 (m, 2H), 7.10 (m, 1H), 6.84 (dd, 1H), 4.99 (s, 2H), 3.95 (d, 2H), 1.24-1.19 (m, 7H), 0.57 (m, 2H), 0.35 (m, 2H).

<Example 83>3-((2-chloro-4-((5-cyclopropyl-3-(2, 6-dichlorophenyl)isoxazol-4-yl)methoxy)phenyl) ethynyl)-5-(2-oxooxazolidin-3-yl)benzoic acid (I-83)

Step 1: Preparation of methyl 3-((2-chloro-4-((5-cyclopropyl-3-(2,6-dichloro phenyl)isoxazol-4-yl) methoxy)phenyl)ethynyl)-5-(2-oxooxazolidin-3-yl) benzoate The intermediate compound methyl 3-amino-5-((2-chloro-4-((5-cyclopropyl-3-(2,6-dichlorophenyl)isoxazol-4-yl)methoxy)phenyl)ethynyl)benzoate (Step 2 of example 8)(100 mg, 0.176 mmol) was dissolved in acetonitrile (2 ml) and 2-chloroethylchloroformate (27.3 ul, 0.264 mmol) and potassium carbonate (36.5 mg, 0.264 mmol) was added. The reaction was heated at 80° C. for 4 hours. The reaction mixture was extracted with ethyl acetate and washed with water. The combined organic phase was dried over MgSO$_4$, filtered, concentrated and purified by column chromatography on silica to afford the intermediate compound methyl 3-((2-chloro-4-((5-cyclopropyl-3-(2,6-dichlorophenyl) isoxazol-4-yl)methoxy)phenyl)ethynyl)-5-(2-oxooxazolidin-3-yl)benzoate (73 mg, 65%).
$^1$H-NMR (CDCl$_3$, 400 MHz): δ 8.01 (t, 1H), 7.97 (t, 1H), 7.95 (t, 1H), 7.42-7.40 (m, 3H), 7.35-7.31 (m, 1H), 6.87 (d, 1H), 6.70 (dd, 1H), 4.82 (s, 2H), 4.54 (q, 2H), 4.14 (q, 2H), 3.91 (s, 3H), 2.19 (m, 1H) 1.31-1.27 (m, 2H), 1.20-1.16 (m, 2H).

Step 2: Preparation of 3-((2-chloro-4-((5-cyclopropyl-3-(2,6-dichlorophenyl) isoxazol-4-yl)methoxy) phenyl)ethynyl)-5-(2-oxooxazolidin-3-yl)benzoic acid This compound was made using the procedure described in Example 1 (Step 6). Thus, the intermediate compound (Step 1)(65 mg, 0.101 mmol) was reacted with lithium hydroxide (43 mg, 1.019 mmol) to afford the title compound (21 mg, 33%).

$^{1}$H-NMR (DMSO, 400 MHz): δ 13.45 (br, 1H), 8.16 (s, 1H), 7.89 (s, 1H), 7.76 (s, 1H), 7.64-7.62 (m, 2H), 7.59-7.53 (m, 2H), 7.10 (d, 1H), 6.85 (dd, 1H), 4.99 (s, 2H), 4.48 (q, 2H), 4.16 (q, 2H), 1.24-1.13 (m, 5H).

<Example 84>5-((2-chloro-4-((5-cyclopropyl-3-(2,6-dichlorophenyl)isoxazol-4-yl)methoxy)phenyl) ethynyl)isophthalic acid (I-84)

Step 1: Preparation of dimethyl 5-((2-chloro-4-((5-cyclopropyl-3-(2,6-dichlorophenyl)isoxazol-4-yl) methoxy)phenyl)ethynyl)isophthalate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(196.2 mg, 0.47 mmol) was reacted with dimethyl 5-iodoisophthalate (150 mg, 0.47 mmol), tetrakis(triphenylphosphine) palladium(0) (Pd(PPh$_3$)$_4$, 54.3 mg, 0.05 mmol), copper(I) iodide (10 mg, 0.05 mmol) and N,N-diisopropylethylamine (0.1 ml, 0.56 mmol) to afford the intermediate compound dimethyl 5-((2-chloro-4-((5-cyclopropyl-3-(2,6-dichlorophenyl)isoxazol-4-yl) methoxy) phenyl)ethynyl)isophthalate (278 mg, 97%).

$^{1}$H-NMR (CDCl$_3$, 400 MHz): δ 8.64 (t, 1H), 8.37 (d, 1H), 7.41-7.50 (m, 2H), 7.32-7.40 (m, 3H), 6.90 (d, 1H), 6.73 (d, 1H), 4.85 (s, 2H), 3.98 (s, 6H), 2.13-2.23 (m, 1H), 1.30-1.37 (m, 2H), 1.16-1.24 (m, 2H).

Step 2: Preparation of 5-((2-chloro-4-((5-cyclopropyl-3-(2,6-dichlorophenyl) isoxazol-4-yl)metoxy) phenyl)ethynyl)isophthalic acid This compound was made using the procedure described in Example 1 (Step 6). Thus, this intermediate compound (Step 1)(278 mg, 0.46 mmol) was reacted with lithium hydroxide (193 mg, 4.6 mmol) to afford the title compound (66.6 mg, 71.5%).

$^{1}$H-NMR (MeOD, 400 MHz): δ 8.61 (t, 1H), 8.30 (d, 2H), 7.55 (d, 1H), 7.53 (d, 1H), 7.50 (d, 1H), 7.48 (d, 1H), 6.96 (d, 1H), 6.80 (d, 1H), 4.97 (s, 2H), 2.33-2.42 (m, 1H), 1.21-1.27 (m, 4H).

<Example 85>3-((2-chloro-4-((5-cyclopropyl-3-(2,6-dichlorophenyl) isoxazol-4-yl)methoxy)phenyl) ethynyl)-5-(piperazine-1-carbonyl)benzoic acid hydrochloride (I-85)

Step 1: Preparation of tert-butyl 4-(3-((2-chloro-4-((5-cyclopropyl-3-(2,6-dichlorophenyl)isoxazol-4-yl)methoxy)phenyl)ethynyl)-5-(methoxycarbonyl) benzoyl)piperazine-1-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(115 mg, 0.27 mmol) was reacted with tert-butyl 4-(3-(methoxycarbonyl)benzoyl)piperazine-1-carboxylate (130 mg, 0.27 mmol), tetrakis(triphenylphosphine) palladium(0)(Pd(PPh$_3$)$_4$, 34.7 mg, 0.03 mmol), copper(I) iodide (5.7 mg, 0.03 mmol), N,N-diisopropylethyl amine (56.4 ul, 0.32 mmol) to afford the intermediate compound tert-butyl 4-(3-((2-chloro-4-((5-cyclopropyl-3-(2,6-dichlorophenyl)isoxazol-4-yl)methoxy)phenyl)ethynyl)-5-(methoxycarbonyl)benzoyl)piperazine-1-carboxylate (88 mg, 43%).

$^{1}$H-NMR (CDCl$_3$, 400 MHz): δ 8.24 (s, 1H), 8.00 (s, 1H), 7.74 (s, 1H), 7.50-7.38 (m, 3H), 7.35-7.31 (m, 1H), 6.88 (d, 1H), 6.70 (dd, 1H), 4.83 (s, 3H), 3.99 (s, 3H), 3.85-3.80 (m, 2H), 3.66-3.40 (m, 6H), 2.21-2.12 (m, 1H), 1.48 (s, 9H), 1.38-1.32 (m, 2H), 1.20-1.12 (m, 2H).

Step 2: Preparation of 3-(4-(tert-butoxycarbonyl) piperazine-1-carbonyl)-5-((2-chloro-4-((5-cyclopropyl-3-(2,6-dichlorophenyl)isoxazol-4-yl)methoxy) phenyl)ethynyl)benzoic acid This compound was made using the procedure described in Example 1 (Step 6). Thus, this intermediate compound (Step 1)(88 mg, 0.12 mmol) was reacted with lithium hydroxide (48.3 mg, 1.2 mmol) to afford the 3-(4-(tert-butoxycarbonyl) piperazine-1-carbonyl)-5-((2-chloro-4-((5-cyclopropyl-3-(2,6-dichlorophenyl)isoxazol-4-yl)methoxy) phenyl)ethynyl)benzoic acid (61 mg, 67.7%).

$^{1}$H-NMR (CDCl$_3$, 400 MHz): δ 8.28 (s, 1H), 8.05 (s, 1H), 7.79 (s, 1H), 7.45-7.33 (m, 3H), 7.31-7.28 (m, 1H), 6.88 (s, 1H), 6.70 (dd, 1H), 4.83 (s, 2H), 3.90-3.82 (m, 1H), 3.62-3.30 (m, 6H), 2.30-2.12 (m, 2H), 1.48 (s, 9H), 1.38-1.33 (m, 2H), 1.29-1.16 (m, 2H).

Step 3: Preparation of 3-((2-chloro-4-((5-cyclopropyl-3-(2,6-dichlorophenyl) isoxazol-4-yl)methoxy) phenyl)ethynyl)-5-(piperazine-1-carbonyl)benzoic acid hydrochloride This compound was made using the procedure described in Example 57 (step 3).

Thus, this intermediate compound (Step 2)(61 mg, 0.08 mmol) was reacted with 5-6N HCl solution (48 ul, 0.24 mmol) to afford the title compound (35 mg, 64%).

$^{1}$H-NMR (DMSO, 400 MHz): δ 13.56 (br, 1H), 8.07 (s, 1H), 7.99 (s, 1H), 7.84 (s, 1H), 7.66-7.60 (m, 2H), 7.58-7.52 (m, 2H), 7.19 (s, 1H), 6.85 (dd, 1H), 4.99 (s, 2H), 3.82-3.74 (m, 3H), 3.42-3.34 (m, 2H), 3.21-3.10 (m, 4H), 1.31-1.19 (m, 4H).

<Example 86>3-((2-chloro-4-((5-cyclopropyl-3-(2,6-dichlorophenyl)isoxazol-4-yl)methoxy)phenyl) ethynyl)-5-(methylsulfonamido)benzoic acid (I-86)

Step 1: Preparation of methyl 3-((2-chloro-4-((5-cyclopropyl-3-(2,6-dichlorophenyl)isoxazol-4-yl) methoxy)phenyl)ethynyl)-5-(methylsulfonamido) benzoate The intermediate compound methyl 3-amino-5-((2-chloro-4-((5-cyclopropyl-3-(2,6-dichlorophenyl)isoxazol-4-yl)methoxy)phenyl)ethynyl)benzoate (Step 2 of Example 8)(150 mg, 0.264 mmol) was dissolved in dichloromethane (2 ml)/N,N-dimethylformamide (1 ml) and methylsulfonyl chloride (22.5 ul, 0.290 mmol) and 1,8-diazobicyclo[5.4.0] undec-7-ene (DBU, 40 ul, 0.264 mmol) were added. The reaction was stirred at room temperature for 1 day. The reaction mixture was extracted with ethyl acetate and washed with water. The combined organic phase was dried over MgSO$_4$, filtered, concentrated and purified by column chromatography on silica to afford the intermediate compound methyl 3-((2-chloro-4-((5-cyclopropyl-3-(2,6-dichlorophenyl)isoxazol-4-yl)methoxy)phenyl)ethynyl)-5-(methylsulfonamido)benzoate (74 mg, 44%).

¹H-NMR (CDCl₃, 400 MHz): δ 8.01 (t, 1H), 7.79 (t, 1H), 7.61 (t, 1H), 7.42-7.40 (m, 2H), 7.35-7.31 (m, 1H), 6.88 (d, 1H), 6.71 (dd, 1H), 6.56 (s, 1H), 4.82 (s, 2H), 3.94 (s, 3H), 2.19 (m, 1H) 1.05-1.32 (m, 4H).

Step 2: Preparation of 3-((2-chloro-4-((5-cyclopropyl-3-(2,6-dichlorophenyl) isoxazol-4-yl)methoxy)phenyl)ethynyl)-5-(methylsulfonamido)benzoic acid This compound was made using the procedure described in Example 1 (Step 6). Thus, the intermediate compound (Step 1)(20 mg, 0.031 mmol) was reacted with lithium hydroxide (13 mg, 0.31 mmol) to afford the title compound (16 mg, 85%).

¹H-NMR (DMSO, 400 MHz): δ 13.33 (br, 1H), 10.14 (s, 1H), 7.81 (s, 1H), 7.73 (s, 1H), 7.64-7.61 (m, 2H), 7.59-7.57 (m, 1H), 7.53 (s, 1H), 7.10 (d, 1H), 6.85 (dd, 1H), 4.98 (s, 2H), 3.06 (s, 3H), 1.05-1.32 (m, 5H).

<Example 87>3-((2-chloro-4-((5-cyclopropyl-3-(2-(trifluoromethyl)phenyl) isoxazol-4-yl)methoxy)phenyl)ethynyl)benzoic acid (I-87)

Step 1: Preparation of 2-(trifluoromethyl)benzoaldehyde oxime

This compound was made using the procedure described for Intermediate 1 (Step 1). Thus, 2-(trifluoromethyl)benzoaldehyde (11 g, 160 mmol) was reacted with sodium hydroxide (6.3 g, 160 mmol), 2,6-dichlorobenzoaldehyde (25 g, 140 mmol) to afford the intermediate compound 2-(trifluoromethyl)benzo aldehyde oxime (25.9 g, 96%).

¹H-NMR (CDCl₃, 400 MHz): δ 8.53-8.52 (t, 1H), 8.04-8.02 (d, 1H), 7.85 (s, 1H), 7.72-7.70 (d, 1H), 7.60-7.56 (t, 1H), 7.53-7.51 (d, 1H).

Step 2: Preparation of N-hydroxy-2-(trifluoromethyl)bezamidoyl chloride

This compound was made using the procedure described for Intermediate 1 (Step 2). Thus, the intermediate compound (Step 1)(25.9 g, 140 mmol) was reacted with N-chloro succinimide (NCS, 18.4 g, 140 mmol) to afford N-hydroxy-2-(trifluoro methyl)bezamidoyl chloride (29 g) and used without further purification.

¹H-NMR (CDCl₃, 400 MHz): δ 8.57 (s, 1H), 7.77-7.75 (d, 1H), 7.67-7.58 (m, 3H).

Step 3: Preparation of ethyl 5-cyclopropyl-3-(2-(trifluoromethyl)phenyl)ioxazol-4-carboxylate This compound was made using the procedure described for Intermediate 1 (Step 3). Thus, the intermediate compound (Step 2)(29 g, 129 mmol) was reacted with ethyl 3-cyclopropyl-3-oxopropanoate (25 ml, 194 mmol) and triethylamine (150 ml) to afford the intermediate compound ethyl 5-cyclopropyl-3-(2-(trifluoromethyl)phenyl)ioxazol-4-carboxylate (22.37 g, 56%).

¹H-NMR (CDCl₃, 400 MHz): δ 7.80-7.78 (m, 1H), 7.66-7.62 (m, 2H), 7.42-7.40 (m, 1H), 3.64 (s, 3H), 2.07-2.03 (m, 1H), 1.16-1.12 (m, 2H), 1.01-0.97 (m, 2H).

Step 4: Preparation of (5-cyclopropyl-3-(2-(trifluoromethyl)phenyl)isoxazol-4-yl)methanol This compound was made using the procedure described for Intermediate 1 (Step 4). Thus, the intermediate compound (Step 3)(22.37 g, 71.7 mmol) was reacted with 1M diisobutylaluminium hydride in THF (DIBAL-H, 144 ml, 144 mmol) to afford the intermediate compound (5-cyclopropyl-3-(2-(trifluoromethyl)phenyl)isoxazol-4-yl)methanol (12.2 g, 60%).

¹H-NMR (CDCl₃, 400 MHz): δ 7.81-7.79 (m, 1H), 7.65-7.57 (m, 2H), 7.47-7.45 (m, 1H), 4.40 (s, 2H), 2.19-2.12 (m, 1H), 1.27-1.23 (m, 2H), 1.15-1.10 (m, 2H).

Step 5: Preparation of 4-(bromomethyl)-5-cyclopropyl-3-(2-(trifluoromethyl)phenyl)ioxazole This compound was made using the procedure described for Intermediate 1 (Step 5). Thus, the intermediate compound (Step 4)(12.2 g, 43.02 mmol) was reacted with triphenyl phosphite (TPP, 16.9 g, 64.53 mmol), tetrabromomethane (21.4 g, 64.53 mmol) to afford the intermediate compound 4-(bromomethyl)-5-cyclopropyl-3-(2-(trifluoromethyl)phenyl)ioxazole (13.44 g, 90%).

¹H-NMR (CDCl₃, 400 MHz): δ7.83-7.81 (m, 1H), 7.68-7.62 (m, 2H), 7.55-7.53 (m, 1H), 4.20 (s, 2H), 2.12-2.08 (m, 1H), 1.30-1.25 (m, 2H), 1.24-1.18 (m, 2H).

Step 6: Preparation of 4-((3-chloro-4-ethynylphenoxy)methyl)-5-cyclopropyl-3-(2-(trifluoromethyl)phenyl)ioxazole This compound was made using the procedure described in Example 1 (Step 4). Thus, the intermediate compound (Step 5)(7.59 g, 21.9 mmol) was reacted with 3-chloro-4-((trimethylsilyl)ethynyl)phenol (Step 3 of Example 5)(4.92 g, 21.9 mmol), potassium carbonate (4.54 g, 32.9 mmol) to afford the intermediate compound 4-((3-chloro-4-ethynylphenoxy)methyl)-5-cyclopropyl-3-(2-(trifluoro methyl)phenyl)ioxazole (7.15 g, 78%).

¹H-NMR (CDCl₃, 400 MHz): δ 7.41-7.30 (m, 4H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 7: Preparation of methyl 3-((2-chloro-4-((5-cyclopropyl-3-(2-(trifluoro methyl)phenyl)ioxazol-4-yl)methoxy)phenyl)ethynyl)benzoate This compound was made using the procedure described in Example 1 (Step 5). Thus, the intermediate compound (Step 6)(128 mg, 0.31 mmol) was reacted with methyl 3-iodobenzoate (80 mg, 0.31 mmol), bis(triphenylphosphine)palladium(II) dichloride (PdCl₂(PPh₃)₂, 22 mg, 0.03 mmol), copper(I) iodide (5.8 mg, 0.03 mmol), triethylamine (0.052 ml, 0.37 mmol) to afford the intermediate compound methyl 3-((2-chloro-4-((5-cyclopropyl-3-(2-(trifluoromethyl)phenyl)ioxazol-4-yl)methoxy)phenyl)ethynyl)benzoate (107 mg, 63%).

¹H-NMR (CDCl₃, 400 MHz): δ 8.20 (s, 1H), 8.00-7.98 (m, 1H), 7.81-7.79 (m, 1H), 7.72-7.69 (m, 1H), 7.62-7.59 (m, 2H), 7.45-7.41 (m, 3H), 6.88-6.87 (d, 1H), 6.71-6.68 (dd, 1H), 4.75 (s, 2H), 3.93 (s, 3H), 2.14-2.10 (m, 1H), 1.28-1.26 (m, 2H), 1.18-1.14 (m, 2H).

Step 8: Preparation of 3-((2-chloro-4-((5-cyclopropyl-3-(2-(trifluoromethyl)phenyl)isoxazol-4-yl)methoxy)phenyl)ethynyl)benzoic acid This compound was made using the procedure described in Example 1 (Step 6). Thus, the intermediate compound (Step 7)(107 mg, 0.20 mmol) was reacted with lithium hydroxide (84 mg, 2.0 mmol) to afford the title compound (92.5 mg, 86%).

$^1$H-NMR (DMSO, 400 MHz): δ 13.27 (s, 1H), 8.02 (s, 1H), 7.97-7.65 (d, 1H), 7.92-7.90 (d, 1H), 7.80-7.71 (m, 3H), 7.59-7.55 (m, 3H), 7.14-7.13 (d, 1H), 6.89-6.86 (dd, 1H), 4.95 (s, 2H), 2.51-2.42 (m, 1H), 1.21-1.10 (m, 4H).

<Example 88>3-((2-chloro-4-((5-cyclopropyl-3-(2-(trifluoromethoxy)phenyl) isoxazol-4-yl)methoxy) phenyl)ethynyl)benzoic acid (I-88)

Step 1: Preparation of 2-(trifluoromethoxy)benzoaldehyde oxime

This compound was made using the procedure described for Intermediate 1 (Step 1). Thus, 2-(trifluoromethyl)benzoaldehyde (11 g, 160 mmol) was reacted with sodium hydroxide (6.3 g, 160 mmol), 2,6-dichlorobenzoaldehyde (25 g, 140 mmol) to afford the intermediate compound 2-(trifluoromethoxy)benzoaldehyde oxime (25.9 g, 96%).

$^1$H-NMR (CDCl$_3$, 400 MHz): δ8.41 (s, 1H), 7.89-7.87 (dd, 1H), 7.47-7.41 (m, 1H), 7.38-7.26 (m, 2H).

Step 2: Preparation of N-hydroxy-2-(trrifluoromethoxy)benzamidoyl chloride

This compound was made using the procedure described for Intermediate 1 (Step 2). Thus, the intermediate compound (Step 1)(25.9 g, 140 mmol) was reacted with N-chlorosuccinimide (NCS, 18.4 g, 140 mmol) to afford the intermediate compound N-hydroxy-2-(trifluoromethoxy)benzamidoyl chloride (29 g) and used without further purification.

$^1$H-NMR (CDCl$_3$, 400 MHz): δ 8.79 (s, 1H), 7.62-7.59 (m, 1H), 7.51-7.47 (m, 1H), 7.40-7.33 (m, 2H).

Step 3: Preparation of ethyl 5-cyclopropyl-3-(2-(trifluoromethoxy)phenyl) isoxazol-4-carboxylate This compound was made using the procedure described for Intermediate 1 (Step 3). Thus, the intermediate compound (Step 2)(29 g, 129 mmol) was reacted with ethyl 3-cyclopropyl-3-oxopropanoate (25 ml, 194 mmol) and triethylamine (150 ml) to afford the intermediate compound 5-cyclopropyl-3-(2-(trifluoromethoxy)phenyl)isoxazol-4-carboxylate (22.37 g, 56%).

$^1$H-NMR (CDCl$_3$, 400 MHz): δ 7.54-7.48 (m, 2H), 7.41-7.33 (m, 2H), 3.77 (s, 3H), 2.05-2.01 (m, 1H), 1.14-1.10 (m, 2H), 0.99-0.94 (m, 2H).

Step 4: Preparation of (5-cyclopropyl-3-(2-(trifluoromethoxy)phenyl)isoxazol-4-yl)methanol This compound was made using the procedure described for Intermediate 1 (Step 4). Thus, the intermediate compound (Step 3)(22.37 g, 71.7 mmol) was reacted with 1M diisobutylaluminium hydride in THF(DIBAL-H, 144 ml, 144 mmol) to afford the intermediate compound (5-cyclopropyl-3-(2-(trifluoromethoxy)phenyl)isoxazol-4-yl)methanol (12.2 g, 60%).

$^1$H-NMR (CDCl$_3$, 400 MHz): δ 7.58-7.50 (m, 2H), 7.42-7.38 (m, 2H), 4.50 (s, 2H), 2.21-2.16 (m, 1H), 1.27-1.22 (m, 2H), 1.15-1.11 (m, 2H).

Step 5: Preparation of 4-(bromomethyl)-5-cyclopropyl-3-(2-(trifluoromethoxy)phenyl)isoxazole This compound was made using the procedure described for Intermediate 1 (Step 5). Thus, the intermediate compound (Step 4)(12.2 g, 43.02 mmol) was reacted with triphenyl phosphite (TPP, 16.9 g, 64.53 mmol), tetrabromomethane (21.4 g, 64.53 mmol) to afford the intermediate compound 4-(bromomethyl)-5-cyclopropyl-3-(2-(trifluoromethoxy)phenyl)isoxazole (13.44 g, 90%).

$^1$H-NMR (CDCl$_3$, 400 MHz): δ 7.60-7.53 (m, 2H), 7.45-7.40 (m, 2H), 4.33 (s, 2H), 2.15 (m, 1H), 1.29-1.26 (m, 2H), 1.25-1.20 (m, 2H).

Step 6: Preparation of 4-((3-chloro-4-ethynylphenoxy)methyl)-5-cyclopropyl-3-(2-(trifluoromethoxy) phenyl)isoxazole This compound was made using the procedure described in Example 1 (Step 4). Thus, the intermediate compound (Step 5)(7.59 g, 21.9 mmol) was reacted with 3-chloro-4-((trimethylsilyl)ethynyl)phenol (Step 3 of Example 5)(4.92 g, 21.9 mmol) and potassium carbonate (4.54 g, 32.9 mmol) to afford the intermediate compound 4-((3-chloro-4-ethynylphenoxy)methyl)-5-cyclopropyl-3-(2-(trifluoromethoxy) phenyl)isoxazole (7.15 g, 78%).

$^1$H-NMR (CDCl$_3$, 400 MHz): δ 7.41-7.30 (m, 4H), 6.83 (d, 1H), 6.66 (dd, 1H), 4.80 (s, 2H), 3.26 (s, 1H), 2.17-2.10 (m, 1H), 1.31-1.27 (m, 2H), 1.23-1.17 (m, 2H).

Step 7: Preparation of methyl 3-((2-chloro-4-((5-cyclopropyl-3-(2-(trifluoromethoxy)phenyl)isoxazol-4-yl)methoxy)phenyl)ethynyl)benzoate This compound was made using the procedure described in Example 1 (Step 5). Thus, the intermediate compound (Step 6)(128 mg, 0.31 mmol) was reacted with methyl 3-iodobenzoate (80 mg, 0.31 mmol), bis(triphenylphosphine)palladium(II) dichloride (PdCl$_2$(PPh$_3$)$_2$, 22 mg, 0.03 mmol), copper(I) iodide (5.8 mg, 0.03 mmol) and triethylamine (0.052 ml, 0.37 mmol) to afford the intermediate compound methyl 3-((2-chloro-4-((5-cyclopropyl-3-(2-(trifluoromethoxy)phenyl)isoxazol-4-yl)methoxy)phenyl)ethynyl)benzoate (107 mg, 63%).

$^1$H-NMR (CDCl$_3$, 400 MHz): δ 8.20 (s, 1H), 8.00-7.98 (m, 1H), 7.72-7.69 (m, 1H), 7.45-7.37 (m, 4H), 4.88 (s, 2H), 3.93 (s, 3H), 2.16-2.11 (m, 1H), 1.28-1.24 (m, 2H), 1.14-1.13 (m, 2H).

Step 8: Preparation of 3-((2-chloro-4-((5-cyclopropyl-3-(2-(trifluoro methoxy)phenyl)isoxazol-4-yl) methoxy)phenyl)ethynyl)benzoic acid This compound was made using the procedure described in Example 1 (Step 6). Thus, the intermediate compound (Step 7)(107 mg, 0.20 mmol) was reacted with lithium hydroxide (84 mg, 2.0 mmol) to afford the title compound (92.5 mg, 86%).

$^1$H-NMR (DMSO, 400 MHz): δ 13.6 (s, 1H), 8.02 (s, 1H), 7.97-7.95 (d, 1H) 7.78-7.76 (d, 1H), 7.69-51 (m, 6H), 7.15 (d, 1H), 6.90-6.88 (dd, 1H), 5.02 (s, 2H), 2.47-2.42 (m, 1H), 1.20-1.15 (m, 2H), 1.14-1.11 (m, 2H).

\<Example 89\> 4-((2-chloro-4-((5-cyclopropyl-3-(2,6-dichlorophenyl)isoxazol-4-yl)methoxy)phenyl)ethynyl)-1H-indazole-6-carboxylic acid (I-89)

Step 1: Preparation of 1-(tert-butyl) 6-methyl 4-((2-chloro-4-((5-cyclopropyl-3-(2,6-dichlorophenyl)isoxazol-4-yl)methoxy)phenyl)ethynyl)-1H-indazole-1,6-dicarboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(176 mg, 0.422 mmol) was reacted with 1-(tert-butyl) 6-methyl 4-bromo-1H-indazole-1,6-dicarboxylate (100 mg, 0.281 mmol), copper(I) iodide (5.3 mg, 0.028 mmol) and bis(triphenylphosphine)palladium(II) dichloride ($PdCl_2(PPh_3)_2$, 39.5 g, 0.056 mmol) to afford the intermediate compound 1-(tert-butyl) 6-methyl-4-((2-chloro-4-((5-cyclopropyl-3-(2,6-dichlorophenyl)isoxazol-4-yl)methoxy)phenyl) ethynyl)-1H-indazole-1,6-dicarboxylate (107 mg, 55%).

$^1$H-NMR ($CDCl_3$, 400 MHz): δ 8.70 (s, 1H), 8.62 (s, 1H), 8.17-8.16 (d, 1H), 7.45-7.39 (m, 4H), 7.36-7.32 (m, 1H), 6.89 (d, 1H), 6.73-6.70 (dd, 1H), 4.83 (s, 2H), 4.04 (s, 3H), 2.19-2.13 (m, 1H), 1.74 (s, 9H), 1.33-1.29 (m, 2H), 1.20-1.18 (m, 2H).

Step 2: Preparation of methyl 4-((2-chloro-4-((5-cyclopropyl-3-(2,6-dichlorophenyl)isoxazol-4-yl)methoxy)phenyl)ethynyl)-1H-indazole-6-carboxylate Trifluoroacetic acid (0.15 ml) was added to a solution of intermediate compound (Step 1)(98 mg, 0.140 mmol) in dichloromethane (3 ml) and stirred for 3 days at room temperature. The reaction mixture was concentrated in vacuum, added ethyl acetate and washed with water. The combined organic layers were dried over $MgSO_4$, filtered, evaporated in vacuum and purified using silica chromatography to afford the intermediate compound methyl 4-((2-chloro-4-((5-cyclopropyl-3-(2,6-dichlorophenyl)isoxazol-4-yl)methoxy)phenyl)ethynyl)-1H-indazole-6-carboxylate (24 mg, 28%).

$^1$H-NMR ($CDCl_3$, 400 MHz): δ 10.47 (s, 1H), 8.59 (s, 1H), 8.08 (d, 1H), 7.87 (s, 1H), 7.45-7.40 (m, 3H), 7.35-7.31 (m, 1H), 6.89-6.88 (d, 1H), 6.72-6.69 (dd, 1H), 4.83 (s, 1H), 4.09 (s, 3H), 2.18-2.13 (m, 1H), 1.32-1.26 (m, 2H), 1.20-1.16 (m, 2H).

Step 3: Preparation of 4-((2-chloro-4-((5-cyclopropyl-3-(2,6-dichlorophenyl) isoxazol-4-yl)methoxy)phenyl)ethynyl)-1H-indazole-6-carboxylic acid This compound was made using the procedure described in Example 1 (Step 6). Thus, the intermediate compound (Step 2)(24 mg, 0.04 mmol) was reacted with lithium hydroxide (17 mg, 0.405 mmol) to afford the title compound (20 mg, 86%).

$^1$H-NMR ($CDCl_3$, 400 MHz): δ 8.62 (s, 1H), 8.11 (s, 1H), 7.90 (s, 1H), 7.45-7.41 (m, 3H), 7.36-7.32 (m, 1H), 6.89-6.88 (d, 1H), 6.72-6.69 (dd, 1H), 4.83 (s, 2H), 2.02-2.12 (m, 1H), 1.32-1.19 (m, 4H).

\<Example 90\> 4-((2-chloro-4-((5-cyclopropyl-3-(2,6-dichlorophenyl)isoxazol-4-yl)methoxy)phenyl)ethynyl)-1H-benzo[d]imidazole-6-carboxylic acid (I-90)

Step 1: Preparation of methyl 4-((2-chloro-4-((5-cyclopropyl-3-(2,6-dichlorophenyl)isoxazol-4-yl)methoxy)phenyl)ethynyl)-1H-benzo[d]imidazole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(101 mg, 0.24 mmol) was reacted with 1-(tert-butyl) 6-methyl-4-bromo-1H-benzo[d]imidazole-1,6-dicarboxylate (71 mg, 0.20 mmol), bis(triphenylphosphine)palladium(II) dichloride (($PdCl_2(PPh_3)_2$, 7 mg, 0.01 mmol), Copper(I) iodide (2 mg, 0.01 mmol) and triethylamine (0.03 ml, 0.24 mmol) to afford the intermediate compound methyl 4-((2-chloro-4-((5-cyclopropyl-3-(2,6-dichlorophenyl)isoxazol-4-yl)methoxy)phenyl)ethynyl)-1H-benzo[d]imidazole-6-carboxylate (57 mg, 48%).

$^1$H-NMR ($CDCl_3$, 400 MHz): δ 8.19 (s, 1H), 8.02 (s, 1H), 7.69-7.32 (m, 5H), 7.00 (m, 1H), 6.70 (m, 1H), 4.84 (s, 2H), 3.96 (s, 3H), 2.17 (m, 1H), 1.32-1.28 (m, 2H), 1.20-1.15 (m, 2H).

Step 2: Preparation of 4-((2-chloro-4-((5-cyclopropyl-3-(2,6-dichlorophenyl) isoxazol-4-yl)methoxy)phenyl)ethynyl)-1H-benzo[d]imidazole-6-carboxylic acid This compound was made using the procedure described in Example 1 (Step 6). Thus, this intermediate compound (Step 1)(30 mg, 0.05 mmol) was reacted with lithium hydroxide (50 mg, 1.2 mmol) to afford the title compound (15 mg, 52%).

$^1$H-NMR (DMSO, 400 MHz): δ 8.39 (s, 1H), 8.18 (s, 1H), 7.97 (s, 1H), 7.64 (m, 2H), 7.56 (m, 2H), 7.10 (d, 1H), 6.87 (dd, 1H), 5.00 (s, 2H), 3.16 (m, 2H), 1.23-1.13 (m, 4H).

\<Example 91\> 4-((2-chloro-4-((5-cyclopropyl-3-(2,6-dichlorophenyl)isoxazol-4-yl)methoxy)phenyl)ethynyl)-1H-indole-6-carboxylic acid (I-91)

Step 1: Preparation of 1-(tert-butyl) 6-methyl 4-((2-chloro-4-((5-cyclopropyl-3-(2,6-dichlorophenyl)isoxazol-4-yl)methoxy)phenyl)ethynyl)-1H-indole-1,6-dicarboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(236 mg, 0.56 mmol) was reacted with 1-(tert-butyl) 6-methyl 4-bromo-1H-indole-1,6-dicarboxylate (200 mg, 0.56 mmol), bis(triphenylphosphine)palladium(II) dichloride (($PdCl_2(PPh_3)_2$, 79 mg, 0.11 mmol), copper (I) iodide (11 mg, 0.06 mmol) and triethylamine (0.39 ml, 2.82 mmol) to afford the intermediate compound 1-(tert-butyl) 6-methyl 4-((2-chloro-4-((5-cyclopropyl-3-(2,6-dichlorophenyl)isoxazol-4-yl)methoxy)phenyl)ethynyl)-1H-indole-1,6-dicarboxylate (141 mg, 36%).

$^1$H-NMR ($CDCl_3$, 400 MHz): δ 8.83 (s, 1H), 8.12 (d, 1H), 7.97 (d, 1H), 7.48-7.32 (m, 5H), 6.92-6.90 (m, 2H), 6.73 (dd, 1H), 4.83 (s, 2H), 3.95 (s, 3H), 2.18-2.14 (m, 1H), 1.70 (s, 9H), 1.32-1.28 (m, 2H), 1.20-1.16 (m, 2H).

Step 2: Preparation of methyl 4-((2-chloro-4-((5-cyclopropyl-3-(2,6-dichlorophenyl)isoxazol-4-yl)methoxy)phenyl)ethynyl)-1H-indole-6-carboxylate This compound was made using the procedure described in Example 89 (Step 2). Thus, the intermediate compound (Step 1)(141 mg, 0.2 mmol) was reacted with trifluoroacetic acid (0.28 ml, 3.8 mmol) to afford the intermediate compound methyl 4-((2-chloro-4-((5-cyclopropyl-3-(2,6-dichlorophenyl)isoxazol-4-yl) methoxy)phenyl)ethynyl)-1H-indole-6-carboxylate (49 mg, 41%).

$^1$H-NMR (CDCl$_3$, 400 MHz): δ 8.52 (s, 1H), 8.14 (t, 1H), 8.03 (d, 1H), 7.52-7.32 (m, 5H), 6.91-6.89 (dd, 2H), 6.73 (dd, 1H), 4.83 (s, 2H), 3.95 (s, 3H), 2.19-2.14 (m, 1H), 1.33-1.29 (m, 2H), 1.20-1.16 (m, 2H).

Step 3: Preparation of 4-((2-chloro-4-((5-cyclopropyl-3-(2,6-dichlorophenyl) isoxazol-4-yl)methoxy) phenyl)ethynyl)-1H-indole-6-carboxylic acid This compound was made using the procedure described in Example 1 (Step 6). Thus, the intermediate compound (Step 2)(49 mg, 0.08 mmol) was reacted with lithium hydroxide (33 mg, 0.8 mmol) to afford the title compound (45 mg, 98%).

$^1$H-NMR (DMSO, 400 MHz): δ 11.77 (s, 1H), 8.09 (s, 1H), 7.77 (d, 1H), 7.72 (t, 1H), 7.65-7.61 (m, 3H), 7.58 (dd, 1H), 7.11 (d, 1H), 6.86 (dd, 1H), 6.70 (s, 1H), 4.99 (s, 2H), 2.48 (m, 1H), 1.24-1.21 (m, 2H), 1.17-1.12 (m, 2H).

<Example 92>4-((2-chloro-4-((5-cyclopropyl-3-(2,6-dichlorophenyl)isoxazol-4-yl)methoxy)phenyl)ethynyl)-1-(2-(dimethylamino)ethyl)-1H-indole-6-carboxylic acid (I-92)

Step 1: Preparation of methyl 4-((2-chloro-4-((5-cyclopropyl-3-(2,6-dichlorophenyl)isoxazol-4-yl)methoxy)phenyl)ethynyl)-1-(2-(dimethylamino)ethyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(41.87 mg, 0.10 mmol) was reacted with 1-(tert-butyl) 6-methyl 4-bromo-1H-indole-1,6-dicarboxylate (32.52 mg, 0.10 mmol), bis(triphenylphosphine)palladium(II) dichloride (PdCl$_2$(PPh$_3$)$_2$, 7.7 mg, 0.011 mmol), copper(I) iodide (2 mg, 0.011 mmol) and triethylamine (42 ul, 0.30 mmol) to afford the intermediate compound methyl 4-((2-chloro-4-((5-cyclopropyl-3-(2,6-dichlorophenyl) isoxazol-4-yl)methoxy)phenyl)ethynyl)-1H-indole-1,6-dicarboxylate (67 mg, 68%).

$^1$H-NMR (CDCl$_3$, 400 MHz): δ 8.12 (s, 1H), 8.03 (d, 1H), 7.50-7.34 (m, 5H), 6.92 (d, 1H), 6.84-6.83 (d, 1H), 6.74-6.71 (dd, 1H), 4.85 (s, 2H), 4.33-4.29 (t, 2H), 3.97 (s, 3H), 2.75-2.71 (t, 2H), 2.31 (s, 6H), 2.20-2.17 (m, 1H), 1.34-1.30 (m, 2H), 1.22-1.19 (m, 2H).

Step 2: Preparation of 4-((2-chloro-4-((5-cyclopropyl-3-(2,6-dichlorophenyl) isoxazol-4-yl)methoxy) phenyl)ethynyl)-1-(2-(dimethylamino)ethyl)-1H-indole-6-carboxylic acid This compound was made using the procedure described in Example 1 (Step 6). Thus, the intermediate compound (Step 1)(46 mg, 0.069 mmol) was reacted with lithium hydroxide (29 mg, 0.694 mmol) to afford the title compound (0.014 g, 31%).

$^1$H-NMR (DMSO, 400 MHz): δ 12.85 (s, 1H), 8.16 (s, 1H), 7.78 (d, 1H), 7.74-7.73 (d, 1H), 7.65-7.61 (m, 3H), 7.58-7.54 (m, 1H), 7.12-7.11 (d, 1H), 6.86-6.83 (m, 1H), 6.68 (d, 1H), 4.99 (s, 2H), 4.4-4.36 (t, 2H), 2.64-2.60 (t, 2H), 2.18 (s, 6H), 1.23-1.18 (m, 2H), 1.16-1.14 (m, 2H).

<Example 93>4-((2-chloro-4-((5-cyclopropyl-3-(2,6-dichlorophenyl)isoxazol-4-yl)methoxy)phenyl)ethynyl)-1-(3-(isopropylamino)propyl)-1H-indole-6-carboxylic acid (I-93)

Step 1: Preparation of methyl 1-(3-((tert-butoxycarbonyl)(isopropyl)amino) propyl)-4-((2-chloro-4-((5-cyclopropyl-3-(2,6-dichlorophenyl)isoxazol-4-yl)methoxy)phenyl)ethynyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 4-bromo-1-(3-((tert-butoxycarbonyl)(isopropyl)amino)propyl)-1H-indole-6-carboxylate (235 mg, 0.52 mmol), bis(triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-diazabicyclo[5.4.0]undec-7-ene (DBU, 0.4 ml, 2.6 mmol) to afford the intermediate compound methyl 1-(3-((tert-butoxycarbonyl)(isopropyl)amino)propyl)-4-((2-chloro-4-((5-cyclopropyl-3-(2,6-dichlorophenyl)isoxazol-4-yl)methoxy)phenyl)ethynyl)-1H-indole-6-carboxylate (165 mg, 38%).

$^1$H-NMR (CDCl$_3$, 400 MHz): δ 8.07 (s, 1H), 8.01 (s, 1H), 7.47 (d, 1H), 7.42-7.31 (m, 4H), 6.90 (d, 1H), 6.83 (d, 1H), 6.72-6.69 (dd, 1H), 4.82 (s, 2H), 4.21 (q, 2H), 3.95 (s, 3H), 3.12 (br, 2H), 2.16-2.04 (m, 3H), 1.52 (br, 1H), 1.45 (s, 9H), 1.31-1.27 (m, 2H), 1.86-1.15 (m, 2H), 1.05 (s, 3H), 1.03 (s, 3H).

Step 2: Preparation of methyl 4-((2-chloro-4-((5-cyclopropyl-3-(2,6-dichlorophenyl)isoxazol-4-yl)methoxy)phenyl)ethynyl)-1-(3-(isopropylamino)propyl)-1H-indole-6-carboxylate This compound was made using the procedure described in Example 89 (Step 2). Thus, this intermediate compound (Step 1)(165 mg, 0.20 mmol) was reacted with trifluoroacetic acid (0.2 ml, 2.0 mmol) to afford the intermediate compound methyl 4-((2-chloro-4-((5-cyclopropyl-3-(2,6-dichlorophenyl)isoxazol-4-yl) methoxy)phenyl)ethynyl)-1-(3-(isopropylamino)propyl)-1H-indole-6-carboxylate (85.7 mg, 62%).

$^1$H-NMR (CDCl$_3$, 400 MHz): δ 8.07 (s, 1H), 8.01 (s, 1H), 7.47 (d, 1H), 7.42-7.31 (m, 4H), 6.90 (d, 1H), 6.83 (d, 1H), 6.72-6.69 (dd, 1H), 4.82 (s, 2H), 4.21 (q, 2H), 3.95 (s, 3H), 3.12 (br, 2H), 2.16-2.04 (m, 3H), 1.52 (br, 1H), 1.31-1.27 (m, 2H), 1.86-1.15 (m, 2H), 1.05 (s, 3H), 1.03 (s, 3H).

Step 3: Preparation of 4-((2-chloro-4-((5-cyclopropyl-3-(2,6-dichlorophenyl) isoxazol-4-yl)methoxy) phenyl)ethynyl)-1-(3-(isopropylamino)propyl)-1H-indole-6-carboxylic acid This compound was made using the procedure described in Example 1 (Step 6). Thus, this intermediate compound (Step 2)(85.7 mg, 0.12 mmol) was reacted with lithium hydroxide (50 mg, 1.2 mmol) to afford the title compound (32 mg, 39%).

$^1$H-NMR (DMSO, 400 MHz): δ 8.14 (s, 1H), 7.08 (s, 1H), 7.71 (d, 1H), 7.65-7.53 (m, 5H), 7.11 (d, 1H), 6.86-6.83 (dd, 1H), 6.68 (d, 1H), 4.90 (s, 2H), 4.30 (q, 2H), 3.06 (br, 2H), 2.46 (m, 2H), 1.48 (m, 1H), 1.22-1.12 (m, 4H), 1.01 (s, 3H), 1.00 (s, 3H).

<Example 94> 4-((2-chloro-4-((5-cyclopropyl-3-(2,6-dichlorophenyl)isoxazol-4-yl)methoxy)phenyl)ethynyl)-1-(pyridin-4-ylmethyl)-1H-indole-6-carboxylic acid (I-94)

Step 1: Preparation of methyl 4-((2-chloro-4-((5-cyclopropyl-3-(2,6-dichlorophenyl)isoxazol-4-yl)methoxy)phenyl)ethynyl)-1-(pyridin-4-ylmethyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 4-bromo-1-(pyridin-4-ylmethyl)-1H-indole-6-carboxylate (82.5 mg, 0.287 mmol), bis(triphenylphosphine)palladium(II) dichloride (21 mg, 0.03 mmol), copper(I) iodide (5.7 mg, 0.03 mmol) and triethylamine (0.2 ml, 1.44 mmol) to afford the intermediate compound methyl 4-((2-chloro-4-((5-cyclopropyl-3-(2,6-dichlorophenyl)isoxazol-4-yl)methoxy)phenyl)ethynyl)-1-(pyridin-4-ylmethyl)-1H-indole-6-carboxylate (78 mg, 48%).

$^1$H-NMR (CDCl$_3$, 400 MHz): δ 8.54-8.53 (d, 2H), 8.04 (s, 1H), 7.95 (s, 1H), 7.49-7.47 (d, 1H), 7.43 (d, 2H), 7.41-7.34 (m, 2H), 6.95-6.91 (m, 4H), 6.74-6.71 (m, 1H), 5.42 (s, 2H), 4.83 (s, 2H), 3.91 (s, 3H), 2.19-2.14 (m, 1H), 1.33-1.30 (m, 2H), 1.20-1.15 (m, 2H).

Step 2: Preparation of 4-((2-chloro-4-((5-cyclopropyl-3-(2,6-dichlorophenyl) isoxazol-4-yl)methoxy)phenyl)ethynyl)-1-(pyridin-4-ylmethyl)-1H-indole-6-carboxylic acid This compound was made using the procedure described in Example 1 (Step 6). Thus, the intermediate compound (Step 1)(78 mg, 0.114 mmol) lithium hydroxide (47.8 mg, 1.14 mmol) to afford the title compound (72.4 mg, 95%).

$^1$H-NMR (DMSO, 400 MHz): δ 12.88 (s, 1H), 8.50 (s, 2H), 8.06 (s, 1H), 7.89-7.88 (d, 1H), 7.80 (s, 1H), 7.65-7.54 (m, 4H), 7.13-7.12 (d, 1H), 7.04-7.03 (d, 2H), 6.87-6.81 (m, 2H), 5.68 (s, 2H), 5.00 (s, 2H), 1.23-1.19 (m, 2H), 1.15 (m, 2H).

<Example 95> 4-((2-chloro-4-((5-cyclopropyl-3-(2,6-dichlorophenyl)isoxazol-4-yl)methoxy)phenyl)ethynyl)-1-(2-morpholinoethyl)-1H-indole-6-carboxylic acid hydrochloride (I-95)

Step 1: Preparation of methyl 4-((2-chloro-4-((5-cyclopropyl-3-(2,6-dichlorophenyl)isoxazol-4-yl)methoxy)phenyl)ethynyl)-1-(2-morpholine-ethyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 4-bromo-1-(2-morpholinoethyl)-1H-indole-6-carboxylate (105 mg, 0.287 mmol), bis(triphenylphosphine)palladium(II) dichloride (21 mg, 0.03 mmol), copper(I) iodide (5.7 mg, 0.03 mmol) and triethylamine (0.2 ml, 1.44 mmol) to afford the intermediate compound methyl 4-((2-chloro-4-((5-cyclopropyl-3-(2,6-dichloro phenyl)isoxazol-4-yl)methoxy)phenyl)ethynyl)-1-(2-morpholine-ethyl)-1H-indole-6-carboxylate (87.6 mg, 52%).

$^1$H-NMR (CDCl$_3$, 400 MHz): δ 8.12 (s, 1H), 8.01 (s, 1H), 7.48-7.31 (m, 5H), 6.90 (d, 1H), 6.82-6.81 (d, 1H), 6.72-6.69 (m, 1H), 4.83 (s, 2H), 4.32-4.28 (t, 2H), 3.95 (s, 3H), 3.69-3.37 (t, 3H), 2.77-2.74 (m, 2H), 2.48-2.46 (m, 4H), 2.18-2.12 (m, 1H), 1.32-1.29 (m, 2H), 1.19-1.15 (m, 2H).

Step 2: Preparation of 4-((2-chloro-4-((5-cyclopropyl-3-(2,6-dichlorophenyl) isoxazol-4-yl)methoxy)phenyl)ethynyl)-1-(2-morpholinoethyl)-1H-indole-6-carboxylic acid hydrochloride This compound was made using the procedure described in Example 1 (Step 6). Thus, the intermediate compound (Step 1)(87.6 mg, 0.124 mmol) was reacted with lithium hydroxide (52 mg, 1.24 mmol) to afford the title compound (72.8 mg, 85%).

$^1$H-NMR (DMSO, 400 MHz): δ 12.89 (s, 1H), 10.96 (s, 1H), 8.30 (s, 1H), 7.83-7.81 (m, 2H), 7.65-7.62 (m, 3H), 7.58-7.54 (m, 1H), 7.12 (d, 1H), 6.87-6.84 (dd, 1H), 6.78 (s, 1H), 5.00 (s, 2H), 4.79 (s, 2H), 4.00-3.90 (m, 2H), 3.75 (m, 2H), 3.57-3.56 (m, 2H), 3.47-3.44 (m, 2H), 3.15 (m, 2H), 1.23-1.17 (m, 2H), 1.15-1.12 (m, 2H).

<Example 96> 4-((2-chloro-4-((5-cyclopropyl-3-(2,6-dichlorophenyl)isoxazol-4-yl)methoxy)phenyl)ethynyl)-1-(2,2-dimethoxyethyl)-1H-indole-6-carboxylic acid (I-96)

Step 1: Preparation of methyl 4-((2-chloro-4-((5-cyclopropyl-3-(2,6-dichlorophenyl)isoxazol-4-yl)methoxy)phenyl)ethynyl)-1-(2,2-dimethoxyethyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 4-bromo-1-(2,2-dimethoxyethyl)-1H-indole-6-carboxylate (178 mg, 0.52 mmol), bis(triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-diazabicyclo[5.4.0]undec-7-ene (DBU, 0.4 ml, 2.6 mmol) to afford the intermediate compound methyl 4-((2-chloro-4-((5-cyclopropyl-3-(2,6-dichlorophenyl)isoxazol-4-yl)methoxy)phenyl)ethynyl)-1-(2,2-dimethoxyethyl)-1H-indole-6-carboxylate (205 mg, 58%).

$^1$H-NMR (CDCl$_3$, 400 MHz): δ 8.13 (s, 1H), 8.02 (d, 1H), 7.48-7.31 (m, 6H), 6.90 (d, 1H), 6.84 (d, 1H), 6.72-6.70 (dd, 1H), 4.83 (s, 2H), 4.55 (m, 1H), 4.28 (d, 2H), 6.96 (s, 3H), 3.35 (s, 6H), 2.16 (m, 1H), 1.32-1.27 (m, 2H), 1.20-1.16 (m, 2H).

Step 2: Preparation of 4-((2-chloro-4-((5-cyclopropyl-3-(2,6-dichlorophenyl) isoxazol-4-yl)methoxy)phenyl)ethynyl)-1-(2,2-dimethoxyethyl)-1H-indole-6-carboxylic acid This compound was made using the procedure described in Example 1 (Step 6). Thus, this intermediate compound (Step 1)(205 mg, 0.30 mmol) was reacted with lithium hydroxide (126 mg, 3.0 mmol) to afford the title compound (115 mg, 58%).

$^1$H-NMR (DMSO 400 MHz): δ 8.19 (s, 1H), 7.80 (s, 1H), 7.69 (d, 1H), 7.65-7.54 (m, 4H), 7.12 (d, 1H), 6.86-6.84 (dd, 1H), 6.71 (d, 1H), 6.99 (s, 2H), 4.62 (q, 1H), 4.01 (dd, 2H), 6.27 (s, 6H), 2.51 (m, 1H), 1.23-1.14 (m, 4H).

<Example 97>4-((2-chloro-4-((5-cyclopropyl-3-(2,6-dichlorophenyl)isoxazol-4-yl)methoxy)phenyl)ethynyl)-1-(2-hydroxyethyl)-1H-indole-6-carboxylic acid (I-97)

Step 1: Preparation of methyl 4-((2-chloro-4-((5-cyclopropyl-3-(2,6-dichlorophenyl)isoxazol-4-yl)methoxy)phenyl)ethynyl)-1-(2-hydroxyethyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 4-bromo-1-(2-((tert-butyldimethylsilyl)oxy)ethyl)-1H-indole-6-carboxylate (118 mg, 0.287 mmol), bis(triphenylphosphine)palladium(II) dichloride (21 mg, 0.03 mmol), copper(I) iodide (5.7 mg, 0.03 mmol) and triethylamine (0.2 ml, 1.44 mmol) to afford the intermediate compound methyl 4-((2-chloro-4-((5-cyclopropyl-3-(2,6-dichlorophenyl)isoxazol-4-yl)methoxy)phenyl)ethynyl)-1-(2-hydroxyethyl)-1H-indole-6-carboxylate (48.6 mg, 32%).

$^1$H-NMR (CDCl$_3$, 400 MHz): δ 8.10 (s, 1H), 8.01 (d, 1H), 7.48-7.40 (m, 4H), 7.35-7.31 (m, 1H), 6.90 (d, 1H), 6.85-6.84 (d, 1H), 6.72-6.69 (m, 1H), 4.83 (s, 2H), 4.37-4.35 (t, 2H), 4.00-3.99 (d, 2H), 3.94 (s, 2H), 2.18-2.13 (m, 1H), 1.61 (s, 1H), 1.32-1.28 (m, 2H), 1.25-1.16 (m, 2H).

Step 2: Preparation of 4-((2-chloro-4-((5-cyclopropyl-3-(2,6-dichlorophenyl) isoxazol-4-yl)methoxy)phenyl)ethynyl)-1-(2-hydroxyethyl)-1H-indole-6-carboxylic acid This compound was made using the procedure described in Example 1 (Step 6). Thus, the intermediate compound (Step 1)(48.6 mg, 0.076 mmol) was reacted with lithium hydroxide (32 mg, 0.76 mmol) to afford the title compound (41.5 mg, 88%).

$^1$H-NMR (CDCl$_3$, 400 MHz): δ 8.18 (s, 1H), 8.08 (d, 1H), 7.49-7.40 (m, 4H), 7.36-7.32 (m, 1H), 6.91-6.90 (d, 1H), 6.87 (d, 1H), 6.73-6.70 (m, 1H), 4.83 (s, 2H), 4.40-4.37 (t, 2H), 4.02-4.00 (t, 2H), 2.18-2.17 (m, 1H), 1.32-1.27 (m, 2H), 1.20-1.16 (m, 2H).

<Example 98>4-((2-chloro-4-((5-cyclopropyl-3-(2,6-dichlorophenyl)isoxazol-4-yl)methoxy)phenyl)ethynyl)-1-(2-hydroxy-2-methylpropyl)-1H-indole-6-carboxylic acid (I-98)

Step 1: Preparation of methyl 4-((2-chloro-4-((5-cyclopropyl-3-(2,6-dichlorophenyl)isoxazol-4-yl)methoxy)phenyl)ethynyl)-1-(2-hydroxy-2-methylpropyl)-1H-indole-6-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.239 mmol) was reacted with methyl 4-bromo-1-(2-((tert-butyldimethylsilyl)oxy)-2-methylpropyl)-1H-indole-6-carboxylate (126 mg, 0.287 mmol), bis(triphenylphosphine)palladium(II) dichloride (21 mg, 0.03 mmol), copper(I) iodide (5.7 mg, 0.03 mmol) and triethylamine (0.2 ml, 1.44 mmol) to afford the intermediate compound methyl 4-((2-chloro-4-((5-cyclopropyl-3-(2,6-dichlorophenyl)isoxazol-4-yl)methoxy)phenyl)ethynyl)-1-(2-hydroxyethyl)-1H-indole-6-carboxylate (44.4 mg, 28%).

$^1$H-NMR (DMSO, 400 MHz): δ 8.27 (s, 1H), 7.77 (d, 1H), 7.66-7.8 (m, 4H), 7.56-7.54 (t, 1H), 7.12-7.11 (d, 1H), 6.96 (s, 3H), 6.68-6.84 (m, 1H), 6.70-6.69 (d, 1H), 4.99 (s, 2H), 4.74 (s, 1H), 4.19 (s, 2H), 1.23-1.14 (m, 4H), 1.09 (s, 6H).

Step 2: Preparation of 4-((2-chloro-4-((5-cyclopropyl-3-(2,6-dichlorophenyl) isoxazol-4-yl)methoxy)phenyl)ethynyl)-1-(2-hydroxy-2-methylpropyl)-1H-indole-6-carboxylic acid This compound was made using the procedure described in Example 1 (Step 6). Thus, the intermediate compound (Step 1)(44.4 mg, 0.066 mmol) was reacted with lithium hydroxide (27 mg, 0.66 mmol) to afford the title compound (39 mg, 91%).

$^1$H-NMR (DMSO, 400 MHz): δ 8.27 (s, 1H), 7.77 (d, 1H), 7.66-7.8 (m, 4H), 7.56-7.54 (t, 1H), 7.12-7.11 (d, 1H), 6.68-6.84 (m, 1H), 6.70-6.69 (d, 1H), 4.99 (s, 2H), 4.74 (s, 1H), 4.19 (s, 2H), 1.23-1.14 (m, 4H), 1.09 (s, 6H).

<Example 99>6-((2-chloro-4-((5-cyclopropyl-3-(2,6-dichlorophenyl)isoxazol-4-yl)methoxy)phenyl)ethynyl)-1H-indazole-4-carboxylic acid (I-99)

Step 1: Preparation of 1-(tert-butyl) 4-methyl 6-((2-chloro-4-((5-cyclopropyl-3-(2,6-dichlorophenyl)isoxazol-4-yl)methoxy)phenyl)ethynyl)-1H-indazole-1,4-dicarboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(118 mg, 0.28 mmol) was reacted with 1-(tert-butyl) 4-methyl 6-bromo-1H-indazole-1,4-dicarboxylate (100 mg, 0.28 mmol), bis(triphenylphosphine)palladium(II) dichloride ((PdCl$_2$(PPh$_3$)$_2$, 20 mg, 0.028 mmol), copper(I) iodide (2.6 mg, 0.014 mmol) and triethylamine (0.08 ml, 0.56 mmol) to afford the intermediate compound 1-(tert-butyl) 4-methyl 6-((2-chloro-4-((5-cyclopropyl-3-(2,6-dichlorophenyl)isoxazol-4-yl)methoxy)phenyl)ethynyl)-1H-indazole-1,4-dicarboxylate (74 mg, 38%).

$^1$H-NMR (CDCl$_3$, 400 MHz): δ 8.63 (s, 1H), 8.55 (s, 1H), 8.09 (d, 1H), 7.37-7.33 (m, 3H), 7.29-7.25 (m, 1H), 6.82 (d, 1H), 6.65 (dd, 1H), 4.76 (s, 2H), 3.96 (s, 3H), 2.11-2.07 (m, 1H), 1.67 (s, 9H), 1.26-1.22 (m, 2H), 1.17-1.10 (m, 2H).

Step 2: Preparation of methyl 6-((2-chloro-4-((5-cyclopropyl-3-(2,6-dichlorophenyl)isoxazol-4-yl)methoxy)phenyl)ethynyl)-1H-indazole-4-carboxylate This compound was made using the procedure described in Example 89 (Step 2). Thus, the intermediate compound (Step 1)(74 mg, 0.11 mmol) was reacted with trifluoroacetic acid (0.2 ml, 2.7 mmol) to afford the intermediate compound methyl 6-((2-chloro-4-((5-cyclopropyl-3-(2,6-dichlorophenyl)isoxazol-4-yl) methoxy)phenyl)ethynyl)-1H-indazole-4-carboxylate (36 mg, 55%).

¹H-NMR (CDCl₃, 400 MHz): δ 8.62 (s, 1H), 8.11 (s, 1H), 7.90 (s, 1H), 7.50-7.34 (m, 4H), 6.91 (d, 1H), 6.74 (dd, 1H), 4.85 (s, 2H), 4.06 (s, 3H), 2.20-2.14 (m, 1H), 1.35-1.30 (m, 2H), 1.22-1.17 (m, 2H).

Step 3: Preparation of 6-((2-chloro-4-((5-cyclopropyl-3-(2,6-dichlorophenyl) isoxazol-4-yl)methoxy)phenyl)ethynyl)-1H-indazole-4-carboxylic acid This compound was made using the procedure described in Example 1 (Step 6). Thus, the intermediate compound (Step 1)(36 mg, 0.06 mmol) was reacted with lithium hydroxide (25 mg, 0.6 mmol) to afford the title compound (35 mg, 100%).

¹H-NMR (DMSO, 400 MHz): δ 13.57 (s, 1H), 8.42 (s, 1H), 7.97 (s, 1H), 7.83 (d, 1H), 7.65-7.54 (m, 4H), 7.11 (d, 1H), 6.86 (dd, 1H), 4.99 (s, 2H), 2.46 (m, 1H), 1.30-1.21 (m, 2H), 1.16-1.12 (m, 2H).

<Example 100>5-((2-chloro-4-((5-cyclopropyl-3-(2,6-dichlorophenyl) isoxazol-4-yl)methoxy)phenyl)ethynyl)-2,3-dihydrobenzofuran-7-carboxylic acid (I-100)

Step 1: Preparation of methyl 5-((2-chloro-4-((5-cyclopropyl-3-(2,6-dichlorophenyl)isoxazol-4-yl)methoxy)phenyl)ethynyl)-2,3-dihydrobenzofuran-7-carboxylate This compound was made using the procedure described in Example 1 (Step 5). Thus 4-((3-chloro-4-ethynylphenoxy)methyl)-5-cyclopropyl-3-(2,6-dichloro phenyl)isoxazole (Example 5)(100 mg, 0.23 mmol) was reacted with methyl 3-bromo-2,3-dihydrobenzofuran-7-carboxylate (61 mg, 0.23 mmol), bis(triphenyl phosphine)palladium(II)dichloride (PdCl₂(PPh₃)₂, 8 mg, 0.0 mmol), Copper(I) iodide (2.2. mg, 0.01 mmol) and triethylamine (0.1 ml, 0.71 mmol) to afford the intermediate compound methyl 5-((2-chloro-4-((5-cyclopropyl-3-(2,6-dichloro phenyl)isoxazol-4-yl)methoxy)phenyl)ethyl)-2,3-dihydrobenzofuran-7-carboxylate (50 mg, 37%).

¹H-NMR (CDCl₃, 400 MHz): δ 7.93 (s, 1H), 7.76-7.71 (m, 1H), 7.52-7.50 (m, 1H), 7.44-7.33 (m, 5H), 6.99 (s, 1H), 6.69 (dd, 1H), 4.81 (s, 2H), 4.78 (t, 2H), 3.91 (s, 3H), 3.26 (t, 2H), 2.17-2.13 (m, 1H), 1.32-1.28 (m, 2H), 1.19-1.14 (m, 2H).

Step 2: Preparation of 5-((2-chloro-4-((5-cyclopropyl-3(2,6-dichlorophenyl) isoxazol-4-yl)methoxy)phenyl)ethynyl)-2,3-dihydrobenzofuran-7-carboxylic acid This compound was made using the procedure described in Example 1 (Step 6). Thus, this intermediate compound (Step 1)(50 mg, 0.08 mmol) was reacted with lithium hydroxide (35 mg, 0.84 mmol) to afford the title compound (27 mg, 56%).

¹H-NMR (DMSO, 400 MHz): δ 7.95 (s, 1H), 7.70-7.48 (m, 5H), 7.09 (s, 1H), 6.82 (dd, 1H), 4.97 (s, 2H), 4.67 (t, 2H), 3.26-3.14 (t, 3H), 1.24-1.12 (m, 2H), 0.87-0.84 (m, 2H).

<Example 101>6-((2-chloro-4-((5-cyclopropyl-3-(2,6-dichlorophenyl) isoxazol-4-yl)methoxy)phenyl)ethynyl)-1H-indole-4-carboxylic acid (I-101)

Step 1: Preparation of 1-(tert-butyl) 4-methyl 6-((2-chloro-4-((5-cyclopropyl-3-(2,6-dichlorophenyl)isoxazol-4-yl)methoxy)phenyl)ethynyl)-1H-indole-1,4-dicarboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(354 mg, 0.846 mmol) was reacted with 1-(tert-butyl) 4-methyl 6-bromo-1H-indole-1,4-dicarboxylate (100 mg, 0.282 mmol) was reacted with copper(I) iodide (5.3 mg, 0.028 mmol), bis(triphenylphosphine)palladium(II) dichloride (PdCl₂(PPh₃)₂, 40 mg, 0.056 mmol) and triethylamine (0.2 ml, 1.411 mmol) to afford the intermediate compound 1-(tert-butyl) 4-methyl 6-((2-chloro-4-((5-cyclopropyl-3-(2,6-dichloro phenyl)isoxazol-4-yl)methoxy)phenyl)ethynyl)-1H-indole-1,4-dicarboxylate (74 mg, 38%).

¹H-NMR (CDCl₃, 400 MHz): δ 8.18 (d, 1H), 8.32 (s, 1H), 7.48-7.45 (m, 4H), 7.42-7.38 (m, 1H), 7.16 (s, 1H), 6.89 (d, 1H), 6.72-6.69 m, 1H), 4.83 (s, 2H), 3.94 (s, 3H), 2.20-2.15 (m, 1H), 1.62 (s, 9H), 1.33-1.31 (m, 2H), 1.20-1.17 (m, 2H).

Step 2: Preparation of methyl 6-((2-chloro-4-((5-cyclopropyl-3-(2,6-dichlorophenyl)isoxazol-4-yl)methoxy)phenyl)ethynyl)-1H-indole-4-carboxylate This compound was made using the procedure described in Example 89 (Step 2). Thus, the intermediate compound (Step 1)(74 mg, 0.108 mmol) was reacted with trifluoroacetic acid (0.2 ml) to afford the intermediate compound methyl 6-((2-chloro-4-((5-cyclopropyl-3-(2,6-dichlorophenyl)isoxazol-4-yl)methoxy)phenyl)ethynyl)-1H-indole-4-carboxylate (29 mg, 45%).

¹H-NMR (CDCl₃, 400 MHz): δ 9.56 (s, 1H), 8.07 (d, 1H), 7.78 (s, 1H), 7.43-7.41 (m, 4H), 7.37-7.33 (m, 1H), 7.15 (s, 1H), 6.88 (d, 1H), 6.71-6.68 (m, 1H), 4.83 (s, 2H), 3.99 (s, 3H), 2.19-2.15 (m, 1H), 1.32-1.28 (m, 2H), 1.20-1.15 (m, 2H).

Step 3: Preparation of 6-((2-chloro-4-((5-cyclopropyl-3-(2,6-dichlorophenyl) isoxazol-4-yl)methoxy)phenyl)ethynyl)-1H-indole-4-carboxylic acid This compound was made using the procedure described in Example 1 (Step 6). Thus, the intermediate compound (Step 2)(29 mg, 0.049 mmol) was reacted with lithium hydroxide (20 mg, 0.489 mmol) to afford the title compound (19 mg, 67%).

¹H-NMR (CDCl₃, 400 MHz): δ 8.45 (s, 1H), 8.19 (d, 1H), 7.82 (s, 1H), 7.46-7.42 (m, 4H), 7.36-7.32 (m, 1H), 6.88 (d, 1H), 6.71-6.68 (dd, 1H), 4.82 (s, 1H), 2.18-2.14 (m, 1H), 2.32-1.24 (m, 4H).

<Example 102>5-((2-chloro-4-((5-cyclopropyl-3-(2,6-dichlorophenyl) isoxazol-4-yl)methoxy)phenyl)ethynyl)benzo[d]oxazole-7-carboxylic acid (I-102)

Step 1: Preparation of methyl 5-((2-chloro-4-((5-cyclopropyl-3-(2,6-dichlorophenyl)isoxazol-4-yl)methoxy)phenyl)ethynyl)benzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(127.2 mg, 0.30 mmol) was reacted with methyl 5-bromobenzo[d]oxazole-7-carboxylate (77.8 mg, 0.30 mmol), tetrakis(triphenyl phosphine)palladium(0)(Pd (PPh$_3$)$_4$, 34.7 mg, 0.03 mmol), copper(I) iodide (5.7 mg, 0.03 mmol) and N,N-diisopropylethylamine (63 ul, 0.36 mmol) to afford the intermediate compound methyl 5-((2-chloro-4-((5-cyclopropyl-3-(2,6-dichlorophenyl)isoxazol-4-yl)methoxy)phenyl)ethynyl)benzo[d]oxazole-7-carboxylate (31 mg, 17%).

$^1$H-NMR (CDCl$_3$, 400 MHz): δ 8.24-8.22 (m, 2H), 8.14 (d, 1H), 7.74-7.40 (m, 2H), 7.36-7.31 (m, 2H), 6.89 (d, 1H), 6.70 (dd, 1H), 4.83 (s, 2H), 4.04 (s, 3H), 2.18-2.14 (m, 1H), 1.33-1.26 (m, 2H), 1.24-1.15 (m, 2H).

Step 2: Preparation of 5-((2-chloro-4-((5-cyclopropyl-3-(2,6-dichlorophenyl) isoxazol-4-yl)methoxy)phenyl)ethynyl)benzo[d]oxazole-7-carboxylic acid This compound was made using the procedure described in Example 1 (Step 6). Thus, this intermediate compound (Step 1)(31 mg, 0.05 mmol) was reacted with lithium hydroxide (22 mg, 0.52 mmol) to afford the title compound (20 mg, 69%).

$^1$H-NMR (MeOD$_4$, 400 MHz): δ 8.42 (s, 1H), 8.36 (s, 1H), 7.77 (s, 1H), 7.53-7.44 (m, 3H), 7.40-7.37 (m, 1H), 6.88 (d, 1H), 6.73 (dd, 1H), 4.93 (s, 2H), 2.36-2.33 (m, 1H), 1.34-1.20 (m, 4H).

<Example 103>5-((2-chloro-4-((5-cyclopropyl-3-(2,6-dichlorophenyl) isoxazol-4-yl)methoxy)phenyl)ethynyl)-2-methylbenzo[d]oxazole-7-carboxylic acid (I-103)

Step 1: Preparation of methyl 5-((2-chloro-4-((5-cyclopropyl-3-(2,6-dichloro phenyl)isoxazol-4-yl)methoxy)phenyl)ethynyl)-2-methylbenzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(100 mg, 0.24 mmol) was reacted with methyl 5-bromo-2-methylbenzo[d]oxazole-7-carboxylate (64 mg, 0.24 mmol), tetrakis (triphenylphosphine)palladium(0)(Pd(PPh$_3$)$_4$, 23 mg, 0.02 mmol), copper(I) iodide (3.8 mg, 0.02 mmol) and N,N-diisopropylethylamine (50 ul, 0.28 mmol) to afford the intermediate compound methyl 5-((2-chloro-4-((5-cyclopropyl-3-(2,6-dichlorophenyl)isoxazol-4-yl)methoxy)phenyl)ethynyl)-2-methylbenzo[d]oxazole-7-carboxylate (44.2 mg, 30%).

$^1$H-NMR (CDCl$_3$, 400 MHz): δ 8.24-8.22 (m, 2H), 8.14 (d, 1H), 7.74-7.40 (m, 2H), 7.36-7.31 (m, 2H), 6.89 (d, 1H), 6.70 (dd, 1H), 4.83 (s, 2H), 4.04 (s, 3H), 2.18-2.14 (m, 1H), 1.33-1.26 (m, 2H), 1.24-1.15 (m, 2H).

Step 2: Preparation of 5-((2-chloro-4-((5-cyclopropyl-3-(2,6-dichlorophenyl) isoxazol-4-yl)methoxy)phenyl)ethynyl)-2-methylbenzo[d]oxazole-7-carboxylic acid This compound was made using the procedure described in Example 1 (Step 6). Thus, this intermediate compound (Step 1)(44 mg, 0.073 mmol) was reacted with lithium hydroxide (30.4 mg, 0.73 mmol) to afford the title compound (30 mg, 69%).

$^1$H-NMR (MeOD$_4$, 400 MHz): δ 8.42 (s, 1H), 8.36 (s, 1H), 7.77 (s, 1H), 7.53-7.44 (m, 3H), 7.40-7.37 (m, 1H), 6.88 (d, 1H), 6.73 (dd, 1H), 4.93 (s, 2H), 2.36-2.33 (m, 1H), 1.34-1.20 (m, 4H).

<Example 104>5-((2-chloro-4-((5-cyclopropyl-3-(2,6-dichlorophenyl) isoxazol-4-yl)methoxy)phenyl)ethynyl)-2-ethylbenzo[d]oxazole-7-carboxylic acid (I-104)

Step 1: Preparation of methyl 5-((2-chloro-4-((5-cyclopropyl-3-(2,6-dichlorophenyl)isoxazol-4-yl)methoxy)phenyl)ethynyl)-2-ethylbenzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(143.7 mg, 0.34 mmol) was reacted with methyl 5-bromo-2-ethylbenzo[d]oxazole-7-carboxylate (97.5 mg, 0.34 mmol), tetrakis (triphenylphosphine)palladium(0)(Pd(PPh$_3$)$_4$, 34.7 mg, 0.03 mmol), copper (I) iodide (5.7 mg, 0.03 mmol) and N,N-diisopropylethylamine (71 ul, 0.41 mmol) to afford the intermediate compound methyl 5-((2-chloro-4-((5-cyclopropyl-3-(2,6-dichlorophenyl)isoxazol-4-yl)methoxy)phenyl)ethynyl)-2-ethylbenzo[d]oxazole-7-carboxylate (45.9 mg, 22%).

$^1$H-NMR (CDCl$_3$, 400 MHz): δ 8.12 (s, 1H), 7.99 (s, 1H), 7.44-7.40 (m, 3H), 7.36-7.33 (m, 1H), 6.86 (d, 1H), 6.68 (dd, 1H), 4.83 (s, 2H), 4.02 (s, 3H), 3.04 (q, 2H), 2.19-2.14 (m, 1H), 1.49 (t, 3H), 1.29-1.25 (m, 2H), 1.19-1.16 (m, 2H).

Step 2: Preparation of 5-((2-chloro-4-((5-cyclopropyl-3-(2,6-dichlorophenyl) isoxazol-4-yl)methoxy)phenyl)ethynyl)-2-ethylbenzo[d]oxazole-7-carboxylic acid This compound was made using the procedure described in Example 1 (Step 6). Thus, this intermediate compound (Step 1)(45 mg, 0.07 mmol) was reacted with lithium hydroxide (30.4 mg, 0.72 mmol) to afford the title compound (24 mg, 56.3%).

$^1$H-NMR (MeOD$_4$, 400 MHz): δ 8.05 (s, 1H), 7.96 (s, 1H), 7.56-7.53 (m, 2H), 7.50-7.46 (m, 2H), 6.95 (s, 1H), 6.79 (d, 1H), 3.07 (q, 2H), 2.40-2.36 (m, 1H), 1.48 (t, 3H), 1.26-1.23 (m, 4H).

<Example 105>5-((2-chloro-4-((5-cyclopropyl-3-(2,6-dichlorophenyl) isoxazol-4-yl)methoxy)phenyl)ethynyl)-2-propylbenzo[d]oxazole-7-carboxylic acid (I-105)

Step 1: Preparation of methyl 5-((2-chloro-4-((5-cyclopropyl-3-(2,6-dichlorophenyl)isoxazol-4-yl)methoxy)phenyl)ethynyl)-2-propylbenzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(130 mg, 0.31 mmol) was reacted with methyl 5-bromo-2-propylbenzo[d]oxazole-7-carboxylate (92.2 mg, 0.31 mmol), tetrakis (triphenylphosphine)palladium(0)(Pd(PPh$_3$)$_4$, 34.7 mg, 0.03 mmol), copper(I) iodide (5.7 mg, 0.03 mmol) and N,N-diisopropylethylamine (64.8 ul, 0.37 mmol) to afford the intermediate compound methyl 5-((2-chloro-4-((5-cyclopropyl-3-(2,6-dichlorophenyl)

isoxazol-4-yl)methoxy)phenyl)ethynyl)-2-propylbenzo[d] oxazole-7-carboxylate (88.4 mg, 45%).

¹H-NMR (CDCl₃, 400 MHz): δ 8.11 (dd, 1H), 7.99 (dd, 1H), 7.44-7.40 (m, 3H), 7.36-7.32 (m, 1H), 6.88 (d, 1H), 6.70 (dd, 1H), 4.83 (s, 2H), 4.02 (s, 3H), 3.01-2.96 (m, 2H), 2.20-2.14 (m, 1H), 2.13-1.91 (m, 2H), 1.33-1.29 (m, 2H), 1.20-1.19 (m, 2H), 1.17 (t, 3H).

Step 2: Preparation of 5-((2-chloro-4-((5-cyclopropyl-3-(2,6-dichlorophenyl) isoxazol-4-yl)methoxy) phenyl)ethynyl)-2-propylbenzo[d]oxazole-7-carboxylic acid This compound was made using the procedure described in Example 1 (Step 6). Thus, this intermediate compound (Step 1)(88 mg, 0.14 mmol) was reacted with lithium hydroxide (58 mg, 1.4 mmol) to afford the title compound (61 mg, 70%).

¹H-NMR (DMSO, 400 MHz): δ 13.68 (br s, 1H), 8.08 (d, 1H), 7.93 (d, 1H), 7.65-7.63 (m, 2H), 7.59-7.54 (m, 2H), 7.11 (d, 1H), 6.85 (dd, 1H), 4.99 (s, 2H), 2.99 (t, 2H), 1.91-1.80 (m, 2H), 1.26-1.12 (m, 4H), 1.02 (t, 3H).

<Example 106>5-((2-chloro-4-((5-cyclopropyl-3-(2, 6-dichlorophenyl) isoxazol-4-yl)methoxy)phenyl) ethynyl)-2-isopropylbenzo[d]oxazole-7-carboxylic acid (I-106)

Step 1: Preparation of methyl 5-((2-chloro-4-((5-cyclopropyl-3-(2,6-dichlorophenyl)isoxazol-4-yl) methoxy)phenyl)ethynyl)-2-isopropylbenzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(326 mg, 0.78 mmol) was reacted with methyl 5-bromo-2-isopropylbenzo[d]oxazole-7-carboxylate (232 mg, 0.78 mmol), tetrakis(triphenylphosphine)palladium(0)(Pd(PPh₃)₄, 92.4 mg, 0.08 mmol), copper(I) iodide (15.2 mg, 0.08 mmol) and N,N-diisopropylethylamine (0.16 ml, 0.94 mmol) to afford the intermediate compound methyl 5-((2-chloro-4-((5-cyclopropyl-3-(2,6-dichlorophenyl) isoxazol-4-yl)methoxy)phenyl) ethynyl)-2-isopropylbenzo [d]oxazole-7-carboxylate (210 mg, 64%).

¹H-NMR (CDCl₃, 400 MHz): δ 7.44-7.39 (m, 4H), 7.36-7.31 (m, 2H), 6.88 (s, 1H), 6.66-6.64 (m, 1H), 4.82 (s, 2H), 4.02 (s, 3H), 3.35-3.31 (m, 1H), 2.16-2.13 (m, 1H), 1.50 (d, 6H), 1.31-1.24 (m, 2H), 1.99-1.16 (m, 2H).

Step 2: Preparation of 5-((2-chloro-4-((5-cyclopropyl-3-(2,6-dichlorophenyl) isoxazol-4-yl)methoxy) phenyl)ethynyl)-2-isopropylbenzo[d]oxazole-7-carboxylic acid This compound was made using the procedure described in Example 1 (Step 6). Thus, this intermediate compound (Step 1)(86 mg, 0.14 mmol) was reacted with lithium hydroxide (56.7 mg, 1.4 mmol) to afford the title compound (74 mg, 85%).

¹H-NMR (MeOD₄, 400 MHz): δ 7.91 (s, 1H), 7.77 (s, 1H), 7.40-7.30 (m, 4H), 6.79 (s, 1H), 6.64 (d, 1H), 4.84 (s, 2H), 3.25-3.22 (m, 1H), 2.24-2.23 (m, 1H), 1.36 (d, 6H), 1.17-1.10 (m, 4H).

<Example 107>5-((2-chloro-4-((5-cyclopropyl-3-(2, 6-dichlorophenyl) isoxazol-4-yl)methoxy)phenyl) ethynyl)-2-(hydroxymethyl)benzo[d]oxazole-7-carboxylic acid (I-107)

Step 1: Preparation of methyl 5-((2-chloro-4-((5-cyclopropyl-3-(2,6-dichloro phenyl)isoxazol-4-yl) methoxy)phenyl)ethynyl)-2-(methoxymethyl)benzo [d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(224 mg, 0.53 mmol) was reacted with methyl 5-bromo-2-(methoxymethyl)benzo[d]oxazole-7-carboxylate (145.9 mg, 0.49 mmol), bis(triphenylphosphine) palladium(II)dichloride (PdCl₂(PPh₃)₂, 17.2 mg, 0.025 mmol), copper(I) iodide (4.8 mg, 0.025 mmol) and triethylamine (82.2 ul, 0.59 mmol) to afford the intermediate compound methyl 5-((2-chloro-4-((5-cyclopropyl-3-(2,6-dichlorophenyl)isoxazol-4-yl)methoxy)phenyl)ethynyl)-2-(methoxymethyl)benzo[d]oxazole-7-carboxylate (108 mg, 35%).

¹H-NMR (CDCl₃, 400 MHz): δ 7.75 (s, 1H), 7.48 (s, 1H), 7.47-7.31 (m, 4H), 6.86 (s, 1H), 6.67 (dd, 1H), 4.81 (s, 2H), 4.66 (s, 2H), 3.92 (s, 3H), 3.89 (s, 3H), 2.22-2.10 (m, 1H), 1.54-1.29 (m, 2H), 1.19-1.15 (m, 2H).

Step 2: Preparation of 5-((2-chloro-4-((5-cyclopropyl-3-(2,6-dichlorophenyl) isoxazol-4-yl)methoxy) phenyl)ethynyl)-2-(hydroxymethyl)benzo[d]oxazole-7-carboxylic acid This compound was made using the procedure described in Example 1 (Step 6). Thus, this intermediate compound (Step 1)(50 mg, 0.08 mmol) was reacted with lithium hydroxide (32.9 mg, 0.8 mmol) to afford the title compound (35 mg, 72%).

¹H-NMR (DMSO, 400 MHz): δ 13.17 (br, 1H), 7.65-7.62 (m, 2H), 7.57-7.53 (m, 2H), 7.43 (d, 1H), 7.13 (d, 1H), 7.09 (d, 1H), 6.82 (dd, 1H), 4.99 (s, 2H), 4.71 (s, 2H), 1.24-1.12 (m, 4H).

<Example 108>7-((2-chloro-4-((5-cyclopropyl-3-(2, 6-dichlorophenyl) isoxazol-4-yl)methoxy)phenyl) ethynyl)quinoxaline-5-carboxylic acid (I-108)

Step 1: Preparation of methyl 7-((2-chloro-4-((5-cyclopropyl-3-(2,6-dichlorophenyl)isoxazol-4-yl) methoxy)phenyl)ethynyl)quinoxaline-5-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 7-bromoquinoxaline-5-carboxylate (138 mg, 0.52 mmol), bis(triphenylphosphine) palladium(II) dichloride (PdCl₂(PPh₃)₂, 42 mg, 0.0.6 mmol), copper(I) iodide (11.4 mg, 0.06 mmol) and 1,8-Diazabicyclo[5.4.0]undec-7-ene (DBU, 0.4 ml, 2.6 mmol) to afford the intermediate compound methyl 7-((2-chloro-4-((5-cyclopropyl-3-(2,6-dichlorophenyl)isoxazol-4-yl)methoxy)phenyl)ethynyl)quinoxaline-5-carboxylate (223 mg, 71%).

¹H-NMR (CDCl₃, 400 MHz): δ 8.95 (s, 1H), 8.91 (s, 1H), 8.38 (s, 1H), 8.24 (s, 1H), 7.48-7.23 (m, 4H), 6.91 (d, 1H), 6.73 (d, 1H), 4.84 (s, 2H), 4.06 (s, 3H), 2.18 (m, 1H), 1.27-1.20 (m, 2H), 1.19-1.15 (m, 2H).

Step 2: Preparation of 7-((2-chloro-4-((5-cyclopropyl-3-(2,6-dichlorophenyl) isoxazol-4-yl)methoxy) phenyl)ethynyl)quinoxaline-5-carboxylic acid This compound was made using the procedure described in Example 1 (Step 6). Thus, this intermediate compound (Step 1)(223 mg, 0.37 mmol) was reacted with lithium hydroxide (155 mg, 3.7 mmol) to afford the title compound (46 mg, 21%).

$^1$H-NMR (DMSO, 400 MHz): δ 13.99 (s, 1H), 9.12 (s, 1H), 8.24 (s, 1H), 7.66-7.63 (m, 3H), 7.56-7.54 (m, 1H), 7.14 (d, 1H), 6.89 (d, 1H), 5.01 (s, 2H), 2.51 (m, 1H), 1.21-1.15 (m, 4H).

<Example 109>7-((2-chloro-4-((5-cyclopropyl-3-(2,6-dichlorophenyl) isoxazol-4-yl)methoxy)phenyl) ethynyl)-2,3-dimethylquinoxaline-5-carboxylic acid (I-109)

Step 1: Preparation of methyl 7-((2-chloro-4-((5-cyclopropyl-3-(2,6-dichloro phenyl)isoxazol-4-yl) methoxy)phenyl)ethynyl)-2,3-dimethylquinoxaline-5-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 7-bromo-2,3-dimethylquinoxaline-5-carboxylate (153 mg, 0.52 mmol), bis(triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-diazabicyclo[5.4.0] undec-7-ene (DBU, 0.4 ml, 2.6 mmol) to afford the intermediate compound methyl 7-((2-chloro-4-((5-cyclopropyl-3-(2,6-dichlorophenyl)isoxazol-4-yl)methoxy)phenyl) ethynyl)-2,3-dimethylquinoxaline-5-carboxylate (190 mg, 65%).

$^1$H-NMR (CDCl$_3$, 400 MHz): δ 8.24 (d, 1H), 8.11 (d, 1H), 7.45-7.32 (m, 4H), 6.89 (d, 1H), 6.72-6.70 (dd, 1H), 4.84 (s, 2H), 4.04 (s, 3H), 2.76 (s, 3H), 2.73 (s, 3H), 2.16 (m, 1H), 1.30-1.24 (m, 2H), 1.20-1.16 (m, 2H).

Step 2: Preparation of 7-((2-chloro-4-((5-cyclopropyl-3-(2,6-dichlorophenyl)isoxazol-4-yl)methoxy) phenyl)ethynyl)-2,3-dimethylquinoxaline-5-carboxylic acid This compound was made using the procedure described in Example 1 (Step 6). Thus, this intermediate compound (Step 1)(190 mg, 0.31 mmol) was reacted with lithium hydroxide (130 mg, 3.1 mmol) to afford the title compound (63 mg, 33%).

$^1$H-NMR (DMSO, 400 MHz): δ 14.52 (s, 1H), 8.31 (d, 1H), 8.25 (d, 1H), 7.64-7.62 (m, 3H), 7.58-7.54 (m, 1H), 7.13 (d, 1H), 6.88 (m, 1H), 5.01 (s, 2H), 2.77 (s, 3H), 2.67 (s, 3H), 2.51 (m, 1H), 1.21-1.14 (m, 2H).

<Example 110>5-((2-chloro-4-((5-cyclopropyl-3-(2, 6-dichlorophenyl) isoxazol-4-yl)methoxy)phenyl) ethynyl)-2-cyclopropylbenzo[d]oxazole-7-carboxylic acid (I-110)

Step 1: Preparation of methyl 5-((2-chloro-4-((5-cyclopropyl-3-(2,6-dichlorophenyl)isoxazol-4-yl) methoxy)phenyl)ethynyl)-2-cyclopropylbenzo[d] oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(182 mg, 0.43 mmol) was reacted with methyl 5-bromo-2-cyclopropylbenzo[d]oxazole-7-carboxylate (117 mg, 0.40 mmol), bis(triphenylphosphine)palladium (II)dichloride (PdCl$_2$(PPh$_3$)$_2$, 14 mg, 0.02 mmol), copper(I) iodide (3.8 mg, 0.02 mmol) and triethylamine (67 ul, 0.48 mmol) to afford the intermediate compound methyl 5-((2-chloro-4-((5-cyclopropyl-3-(2,6-dichlorophenyl)isoxazol-4-yl)methoxy)phenyl)ethynyl)-2-cyclopropylbenzo[d]oxazole-7-carboxylate (121 mg, 48%).

$^1$H-NMR (CDCl$_3$, 400 MHz): δ 8.06 (d, 1H), 7.90 (d, 1H), 7.43-7.40 (m, 3H), 7.36-7.31 (m, 1H), 6.88 (d, 1H), 6.69 (dd, 1H), 4.82 (s, 2H), 4.00 (s, 3H), 2.32-2.24 (m, 1H), 2.20-2.12 (m, 1H), 1.38-1.33 (m, 2H), 1.32-1.27 (m, 2H), 1.26-1.23 (m, 2H), 1.19-1.15 (m, 2H).

Step 2: Preparation of 5-((2-chloro-4-((5-cyclopropyl-3-(2,6-dichlorophenyl) isoxazol-4-yl)methoxy) phenyl)ethynyl)-2-cyclopropylbenzo[d]oxazole-7-carboxylic acid This compound was made using the procedure described in Example 1 (Step 6). Thus, this intermediate compound (Step 1)(120 mg, 0.19 mmol) was reacted with lithium hydroxide (79.4 mg, 1.9 mmol) to afford the title compound (102 mg, 87.4%).

$^1$H-NMR (DMSO, 400 MHz): δ 13.6 (br s, 1H), 7.99 (d, 1H), 7.97 (d, 1H), 7.87-7.62 (m, 2H), 7.57-7.55 (m, 2H), 7.09 (d, 1H), 6.83 (dd, 1H), 4.98 (s, 2H), 2.39-2.30 (m, 1H), 1.26-1.12 (m, 8H).

<Example 111>2-butyl-5-((2-chloro-4-((5-cyclopropyl-3-(2,6-dichloro phenyl)isoxazol-4-yl)methoxy) phenyl)ethynyl)benzo[d]oxazole-7-carboxylic acid (I-111)

Step 1: Preparation of methyl 2-butyl-5-((2-chloro-4-((5-cyclopropyl-3-(2,6-dichlorophenyl)isoxazol-4-yl)methoxy)phenyl)ethynyl)benzo[d]oxazole-7-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(339.3 mg, 0.81 mmol) was reacted with methyl 5-bromo-2-butylbenzo[d]oxazole-7-carboxylate (230 mg, 0.74 mmol), bis(triphenylphosphine)palladium(II) dichloride (PdCl$_2$(PPh$_3$)$_2$, 26 mg, 0.037 mmol), copper(I) iodide (7 mg, 0.037 mmol) and triethylamine (0.12 ml, 0.89 mmol) to afford the intermediate compound methyl 2-butyl-5-((2-chloro-4-((5-cyclopropyl-3-(2,6-dichlorophenyl) isoxazol-4-yl)methoxy)phenyl)ethynyl)benzo[d]oxazole-7-carboxylate (260 mg, 54%).

$^1$H-NMR (CDCl$_3$, 400 MHz): δ 8.11 (d, 1H), 7.98 (d, 1H), 7.44-7.40 (m, 3H), 7.36-7.32 (m, 1H), 6.88 (s, 1H), 6.69 (dd, 1H), 4.82 (s, 2H), 4.02 (s, 3H), 3.01 (t, 2H), 2.16-2.14 (m, 1H), 1.93-1.89 (m, 2H), 1.55-1.40 (m, 2H), 1.31-1.22 (m, 2H), 1.20-1.11 (m, 2H), 1.61 (t, 3H).

Step 2: Preparation of 2-butyl-5-((2-chloro-4-((5-cyclopropyl-3-(2,6-dichlorophenyl)isoxazol-4-yl) methoxy)phenyl)ethynyl)benzo[d]oxazole-7-carboxylic acid This compound was made using the procedure described in Example 1 (Step 6). Thus, this intermediate compound (Step 1)(260 mg, 0.40 mmol) was reacted with lithium hydroxide (167.9 mg, 4 mmol) to afford the title compound (203 mg, 80%).

$^1$H-NMR (DMSO, 400 MHz): δ 13.67 (br s, 1H), 8.06 (d, 1H), 7.91 (d, 1H), 7.68-7.61 (m, 2H), 7.59-7.54 (m, 2H), 7.09 (d, 1H), 6.85 (dd, 1H), 4.80 (s, 2H), 2.99 (t, 2H), 2.10-2.04 (m, 1H), 1.91-1.88 (m, 2H), 1.52-1.38 (m, 2H), 1.21-1.17 (m, 2H), 1.17-1.13 (m, 2H), 1.01 (t, 3H).

<Example 112>6-((2-chloro-4-((5-cyclopropyl-3-(2, 6-dichlorophenyl) isoxazol-4-yl)methoxy)phenyl) ethynyl)-2-methylbenzo[d]oxazole-4-carboxylic acid (I-112)

Step 1: Preparation of methyl 6-((2-chloro-4-((5-cyclopropyl-3-(2,6-dichlorophenyl)isoxazol-4-yl) methoxy)phenyl)ethynyl)-2-methylbenzo[d]oxazole-4-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 6-bromo-2-methylbenzo[d]oxazole-4-carboxylate (140 mg, 0.52 mmol), bis (triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-Diazabicyclo[5.4.0] undec-7-ene (DBU, 0.4 ml, 2.6 mmol) to afford the intermediate compound methyl 6-((2-chloro-4-((5-cyclopropyl-3-(2,6-dichlorophenyl)isoxazol-4-yl) methoxy)phenyl) ethynyl)-2-methylbenzo[d]oxazole-4-carboxylate (164 mg, 52%).

$^1$H-NMR (CDCl$_3$, 400 MHz): δ 8.15 (d, 1H), 7.81 (d, 1H), 7.81-7.26 (m, 4H), 6.89 (d, 1H), 6.72-6.69 (dd, 1H), 4.83 (s, 2H), 4.04 (s, 3H), 3.09-3.04 (m, 2H), 2.14-2.04 (m, 1H), 1.32-1.17 (m, 4H).

Step 2: Preparation of 6-((2-chloro-4-((5-cyclopropyl-3-(2,6-dichlorophenyl) isoxazol-4-yl)methoxy) phenyl)ethynyl)-2-methylbenzo[d]oxazole-4-carboxylic acid This compound was made using the procedure described in Example 1 (Step 6). Thus, this intermediate compound (Step 1)(164 mg, 0.27 mmol) was reacted with lithium hydroxide (113 mg, 2.7 mmol) to afford the title compound (34 mg, 21%).

$^1$H-NMR (DMSO, 400 MHz): δ 13.33 (s, 1H), 8.11 (d, 1H), 7.93 (d, 1H), 7.64-7.52 (m, 4H), 7.10 (d, 1H), 6.86-6.83 (dd, 1H), 5.02 (s, 2H), 3.06-3.00 (m, 3H), 1.23-1.08 (m, 4H).

<Example 113>6-((2-chloro-4-((5-cyclopropyl-3-(2, 6-dichlorophenyl) isoxazol-4-yl)methoxy)phenyl) ethynyl)-2-ethylbenzo[d]oxazole-4-carboxylic acid (I-113)

Step 1: Preparation of methyl 6-((2-chloro-4-((5-cyclopropyl-3-(2,6-dichlorophenyl)isoxazol-4-yl) methoxy)phenyl)ethynyl)-2-ethylbenzo[d]oxazole-4-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 6-bromo-2-ethylbenzo[d]oxazole-4-carboxylate (148 mg, 0.52 mmol), bis(triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-Diazabicyclo[5.4.0] undec-7-ene (DBU, 0.4 ml, 2.6 mmol) to afford the intermediate compound methyl 6-((2-chloro-4-((5-cyclopropyl-3-(2,6-dichlorophenyl)isoxazol-4-yl) methoxy)phenyl) ethynyl)-2-ethylbenzo[d]oxazole-4-carboxylate (200 mg, 62%).

$^1$H-NMR (CDCl$_3$, 400 MHz): δ 8.15 (d, 1H), 7.81 (d, 1H), 7.81-7.26 (m, 4H), 6.89 (d, 1H), 6.72-6.69 (dd, 1H), 4.83 (s, 2H), 4.04 (s, 3H), 3.09-3.04 (m, 2H), 2.14-2.04 (m, 1H), 1.47 (q, 3H), 1.32-1.17 (m, 4H).

Step 2: Preparation of 6-((2-chloro-4-((5-cyclopropyl-3-(2,6-dichlorophenyl) isoxazol-4-yl)methoxy) phenyl)ethynyl)-2-ethylbenzo[d]oxazole-4-carboxylic acid This compound was made using the procedure described in Example 1 (Step 6). Thus, this intermediate compound (Step 1)(200 mg, 0.32 mmol) was reacted with lithium hydroxide (134 mg, 3.2 mmol) to afford the title compound (35 mg, 18%).

$^1$H-NMR (DMSO, 400 MHz): δ 13.33 (s, 1H), 8.11 (d, 1H), 7.93 (d, 1H), 7.64-7.52 (m, 4H), 7.10 (d, 1H), 6.86-6.83 (dd, 1H), 5.02 (s, 2H), 3.06-3.00 (m, 2H), 1.38-1.14 (q, 3H), 1.23-1.08 (m, 4H).

<Example 114>6-((2-chloro-4-((5-cyclopropyl-3-(2, 6-dichlorophenyl) isoxazol-4-yl)methoxy)phenyl) ethynyl)-2-propylbenzo[d]oxazole-4-carboxylic acid (I-114)

Step 1: Preparation of methyl 6-((2-chloro-4-((5-cyclopropyl-3-(2,6-dichlorophenyl)isoxazol-4-yl) methoxy)phenyl)ethynyl)-2-propylbenzo[d]oxazole-4-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 6-bromo-2-propylbenzo[d]oxazole-4-carboxylate (155 mg, 0.52 mmol), bis(triphenylphosphine)palladium(II) dichloride (PdCl$_2$(PPh$_3$)$_2$, 42 mg, 0.0.6 mmol), copper(I) iodide (11.4 mg, 0.06 mmol) and 1,8-diazabicyclo[5.4.0] undec-7-ene (DBU, 0.4 ml, 2.6 mmol) to afford the intermediate compound methyl 6-((2-chloro-4-((5-cyclopropyl-3-(2,6-dichlorophenyl)isoxazol-4-yl)methoxy)phenyl) ethynyl)-2-propylbenzo[d]oxazole-4-carboxylate (191 mg, 58%).

$^1$H-NMR (CDCl$_3$, 400 MHz): δ 8.15 (d, 1H), 7.81 (d, 1H), 7.43-7.26 (m, 4H), 6.89 (d, 1H), 6.71-6.69 (dd, 1H), 4.83 (s, 2H), 4.03 (s, 3H), 3.01 (q, 2H), 2.18-2.14 (m, 1H), 1.97-1.91 (m, 2H), 1.32-1.19 (m, 4H), 1.20-1.17 (m, 3H).

Step 2: Preparation of 6-((2-chloro-4-((5-cyclopropyl-3-(2,6-dichlorophenyl) isoxazol-4-yl)methoxy) phenyl)ethynyl)-2-propylbenzo[d]oxazole-4-carboxylic acid This compound was made using the procedure described in Example 1 (Step 6). Thus, this intermediate compound (Step 1)(191 mg, 0.30 mmol) was reacted with lithium hydroxide (130 mg, 3.0 mmol) to afford the title compound (37 mg, 20%).

$^1$H-NMR (DMSO, 400 MHz): δ 13.34 (s, 1H), 8.11 (d, 1H), 7.94 (d, 1H), 7.64-7.53 (m, 4H), 7.11 (d, 1H), 6.86-6.83

(dd, 1H), 4.99 (s, 2H), 2.98 (q, 2H), 1.87-1.81 (m, 2H), 1.23-1.13 (m, 4H), 1.01 (q, 3H).

<Example 115> 6-((2-chloro-4-((5-cyclopropyl-3-(2, 6-dichlorophenyl) isoxazol-4-yl)methoxy)phenyl) ethynyl)-2-isopropylbenzo[d]oxazole-4-carboxylic acid (I-115)

Step 1: Preparation of methyl 6-((2-chloro-4-((5-cyclopropyl-3-(2,6-dichlorophenyl)isoxazol-4-yl) methoxy)phenyl)ethynyl)-2-isopropylbenzo[d]oxazole-4-carboxylate This compound was made using the procedure described in Example 1 (Step 5). Thus, 4-((3-chloro-4-ethynylphenoxy)methyl)-5-cyclopropyl-3-(2,6-dichloro phenyl)isoxazole (Example 5)(200 mg, 0.52 mmol) was reacted with methyl 6-bromo-2-isopropylbenzo[d]oxazole-4-carboxylate (148 mg, 0.52 mmol), bis(triphenylphosphine)palladium(II) dichloride ($PdCl_2(PPh_3)_2$, 42 mg, 0.0.6 mmol), copper(I) iodide (11.4 mg, 0.06 mmol) and 1,8-diazabicyclo[5.4.0] undec-7-ene (DBU, 0.4 ml, 2.6 mmol) to afford the intermediate compound methyl 6-((2-chloro-4-((5-cyclopropyl-3-(2,6-dichlorophenyl)isoxazol-4-yl)methoxy)phenyl) ethynyl)-2-isopropylbenzo[d]oxazole-4-carboxylate (158 mg, 48%). $^1$H-NMR ($CDCl_3$, 400 MHz): δ 8.15 (d, 1H), 7.81 (d, 1H), 7.43-7.26 (m, 4H), 6.89 (d, 1H), 6.71-6.69 (dd, 1H), 4.83 (s, 2H), 4.03 (s, 3H), 2.18-2.14 (m, 2H), 1.32-1.19 (m, 8H).

Step 2: Preparation of 6-((2-chloro-4-((5-cyclopropyl-3-(2,6-dichlorophenyl) isoxazol-4-yl)methoxy) phenyl)ethynyl)-2-isopropylbenzo[d]oxazole-4-carboxylic acid This compound was made using the procedure described in Example 1 (Step 6). Thus, this intermediate compound (Step 1)(158 mg, 0.25 mmol) was reacted with lithium hydroxide (105 mg, 2.5 mmol) to afford the title compound (37 mg, 24%).

$^1$H-NMR (DMSO, 400 MHz): δ 13.34 (s, 1H), 8.11 (d, 1H), 7.94 (d, 1H), 7.64-7.53 (m, 4H), 7.11 (d, 1H), 6.86-6.83 (dd, 1H), 4.99 (s, 2H), 2.49 (m, 2H), 1.23-1.13 (m, 8H).

<Experiment 1> In Vitro Test for FXR Activity

To evaluate the in vitro test, the invented compounds (from I-1 to I-115) were determined as follows and showed table 1.

1. Determination of Cellular FXR Activities

FXR reporter assay was performed to measure cellular FXR activities of the compounds in the present invention. FXR reporter cells with high expression level of human FXR were seeded into 96-well cell culture plates, and incubated for 1-2 hours at 37° C. under 5% $CO_2$ atmosphere. The invented compounds diluted in DMSO with various concentrations were added to the 96-well cell culture plates, and they were incubated for 24 hours at 37° C. under 5% $CO_2$ atmosphere. After incubation, we calculate $EC_{50}$ by using luciferase substrate. $E_{max}$ of the compounds in the present invention was calculated where the $E_{max}$ of GW-4064, a full FXR agonist, is 100%.

TABLE 1

| Compound | Experiment Reporter Cell $EC_{50}$ (nM) | $E_{max}$ (%) (GW4064 $E_{max}$ = 100%) | Compound | Experiment Reporter Cell $EC_{50}$ (nM) | $E_{max}$ (%) (GW4064 $E_{max}$ = 100%) |
|---|---|---|---|---|---|
| W02000037077 GW4064 | C | 100 | I-56 | A | 96 |
| W02011020615A1 Example 12 | D | 90 | I-58 | E | 75 |
| W02009012125A1 Example 32 | B | 89 | I-59 | D | 90 |
| I-1 | E | >100 | I-60 | B | 98 |
| I-2 | E | >100 | I-61 | C | 95 |
| I-3 | D | >100 | I-62 | C | >100 |
| I-4 | C | 91 | I-63 | C | 78 |
| I-5 | D | 84 | I-64 | B | >100 |
| I-7 | E | 85 | I-65 | C | 92 |
| I-8 | E | 98 | I-66 | C | 92 |
| I-11 | E | 90 | I-67 | B | >100 |
| I-12 | D | >100 | I-68 | E | 96 |
| I-13 | D | 90 | I-69 | D | >100 |
| I-14 | D | 96 | I-70 | C | >100 |
| I-15 | C | 82 | I-71 | D | >100 |
| I-16 | C | 91 | I-72 | D | >100 |
| I-17 | D | 89 | I-73 | D | >100 |
| I-18 | D | 87 | I-74 | A | >100 |
| I-19 | A | 99 | I-75 | B | 93 |
| I-20 | C | 94 | I-76 | A | >100 |
| I-21 | A | 92 | I-77 | A | 100 |
| I-22 | C | 93 | I-78 | B | 89 |
| I-23 | C | >100 | I-81 | D | >100 |
| I-24 | B | >100 | I-83 | B | 89 |
| I-25 | C | 97 | I-84 | D | 98 |
| I-26 | D | >100 | I-86 | C | 100 |
| I-27 | B | 91 | I-87 | D | >100 |
| I-28 | C | 91 | I-88 | D | 97 |
| I-29 | C | 93 | I-89 | B | 88 |
| I-30 | B | 92 | I-90 | D | 75 |
| I-31 | B | >100 | I-91 | A | >100 |
| I-32 | C | 94 | I-92 | B | 87 |

TABLE 1-continued

| Compound | Reporter Cell $EC_{50}$ (nM) | $E_{max}$ (%) (GW4064 $E_{max}$ = 100%) | Compound | Reporter Cell $EC_{50}$ (nM) | $E_{max}$ (%) (GW4064 $E_{max}$ = 100%) |
|---|---|---|---|---|---|
| I-33 | C | 99 | I-93 | D | 82 |
| I-34 | C | 100 | I-94 | C | >100 |
| I-35 | D | 86 | I-95 | B | >100 |
| I-36 | C | 93 | I-96 | A | 98 |
| I-37 | C | 94 | I-97 | A | 94 |
| I-38 | C | 92 | I-98 | B | >100 |
| I-39 | D | 85 | I-99 | C | 86 |
| I-40 | B | 83 | I-100 | C | >100 |
| I-41 | B | >100 | I-101 | A | 97 |
| I-42 | B | >100 | I-102 | D | >100 |
| I-43 | C | >100 | I-103 | A | >100 |
| I-44 | D | >100 | I-104 | A | 94 |
| I-45 | D | 88 | I-105 | A | >100 |
| I-46 | C | 99 | I-106 | B | 96 |
| I-48 | D | 81 | I-107 | E | >100 |
| I-49 | B | >100 | I-108 | B | 98 |
| I-50 | B | >100 | I-109 | B | 100 |
| I-51 | D | 75 | I-110 | A | 92 |
| I-52 | B | >100 | I-111 | B | 98 |
| I-53 | A | 93 | I-113 | B | 96 |
| I-54 | A | >100 | I-114 | B | >100 |
| I-55 | B | >100 | I-115 | B | 97 |

Range A: $EC_{50} \leq 20$
Range B: $20 < EC_{50} \leq 60$
Range C: $60 < EC_{50} \leq 200$
Range D: $200 < EC_{50} \leq 1,000$
Range E: $1,000 < EC_{50}$ According to the above table 1, we confirmed that the compounds in the present invention were FXR agonists by cell-based assay. The compounds with enhanced cellular FXR activities exhibited better activity than GW-4064, a full FXR agonist.

<Experiment 2> Mouse Pharmacokinetics

To evaluate the pharmacokinetics test, the invented 18 compounds of examples were determined as follows. Blood samples are collected at 15, 30, 60, 120, 240, 480, 1140 min. Quantification is by using a LC-MS/MS method specific to the selected compound. Pharmarcokinetics parameters are calculated using WinNonLinnon compartmental analysis software.

TABLE 2

| Compound | AUC[ng/mL*hr] | Compound | AUC[ng/mL*hr] | Compound | AUC[ng/mL*hr] |
|---|---|---|---|---|---|
| WO2000037077 GW4064 | 253.31 | I-20 | 438.46 | I-54 | 934.16 |
| WO2011020615A1 Example 12 | 352.09 | I-21 | 6139.28 | I-63 | 11876.91 |
| WO2009012125A1 Example 32 | 85.29 | I-25 | 722.38 | I-77 | 1006.29 |
| I-2 | 277.37 | I-28 | 1778.58 | I-89 | 270.97 |
| I-3 | 759.60 | I-30 | 680.21 | I-91 | 543.65 |
| I-15 | 521.09 | I-38 | 1000.33 | I-99 | 205.49 |
| I-16 | 2246.42 | I-52 | 3309.52 | I-106 | 2246.42 |

As can be seen from table 2, the selected compounds showed significant pharmacokinetics in Balb/c male mice.

The invention claimed is:
1. A method for treating or ameliorating metabolic diseases, cholestatic liver diseases, or organ fibrosis, the method comprising:
administering to a subject a therapeutically effective amount of a pharmaceutical composition comprising (i) a compound represented by Formula I, a racemate, an enantiomer, or a diastereoisomer thereof, or a pharmaceutically acceptable salt of the compound, the racemate, the enantiomer, or the diastereoisomer and (ii) a carrier,

[Formula I]

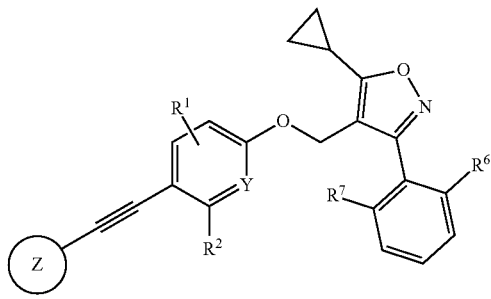

wherein:
$R^1$ and $R^2$ are each independently hydrogen, halo, or trifluoromethyl;
$R^6$ and $R^7$ are each independently hydrogen, halo, trifluoromethyl, or trifluoromethoxy;
Y is carbon or nitrogen; and
Z is

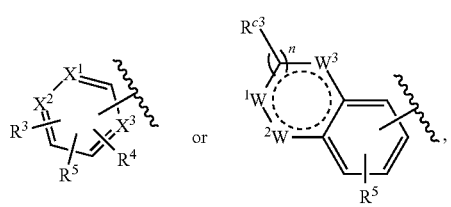

wherein:
n is 0, 1, or 2;
$X^1$, $X^2$, and $X^3$ are each independently carbon or nitrogen;
$R^{c3}$ is hydrogen, halo, $C_{1-6}$ alkyl, or $C_{3-6}$ cycloalkyl;
$W^1$, $W^2$, and $W^3$ are each independently oxygen, nitrogen, $CHR^{w1}$, $CR^{w1}$, $NR^{w1}$, or CO, wherein $R^{w1}$ is hydrogen, halo, $C_{1-6}$ alkyl, $C_{3-6}$ cycloalkyl, halo $C_{1-6}$ alkyl, $C_{1-6}$ alkylamine, $C_{1-6}$ alkyl alcohol,

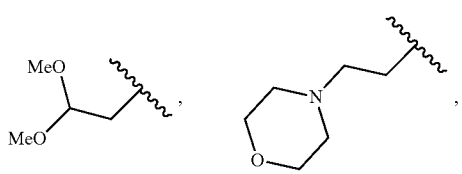 [SMILES: *CC(OC)OC ; *CCN1CCOCC1]

$(CH_2)_p$ heteroaryl, or $(CH_2)_p$ aryl, wherein, p is 1, 2, or 3;
$R^5$ is hydrogen

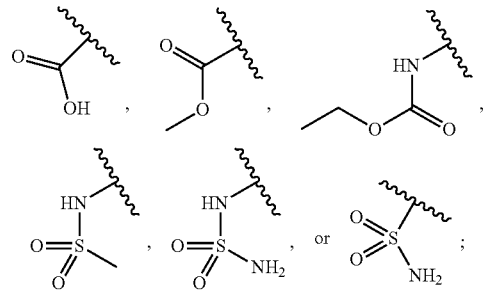

and
$R^3$ and $R^4$ are each independently hydrogen, halo, cyano, $C_{1-6}$ alkyl, $C_{3-6}$ cycloalkyl, halo $C_{1-6}$ alkyl,

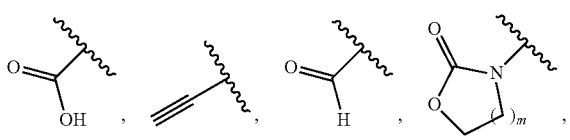

$CONR^{a1}R^{a2}$, $NR^{a1}R^{a2}$ $CH_2NR^{a1}R^{a2}$, $CH_2R^{c3}$, $COR^{a3}$, $OR^{a3}$, $NR^{a4}COR^{a3}$, $NR^{a4}CO_2R^{a3}$, $NHCONHR^{a3}$, $NHSO_2R^{a3}$, or 3- or 8-membered heterocycles containing one or two oxygen or nitrogen atom(s) therein,
wherein:
m is 1 or 2;
$R^{a1}$ and $R^{a2}$ are each independently hydrogen, $C_{1-6}$ alkyl, $C_{3-6}$ cycloalkyl, halo $C_{1-6}$ alkyl,

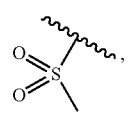 [SMILES: *S(C)(=O)=O]

or 3- or 8-membered heterocycles containing one or two oxygen or nitrogen atom(s) therein;
$R^{a3}$ is hydrogen, $C_{1-6}$ alkyl, $C_{3-6}$ cycloalkyl, halo $C_{1-6}$ alkyl,

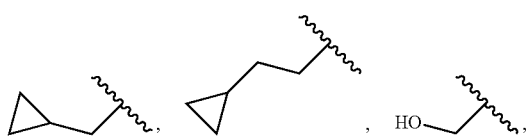

or 3- or 8-membered heterocycles containing one or two oxygen or nitrogen atom(s) therein; and
$R^{a4}$ is hydrogen or $C_{1-6}$ alkyl.

2. The method of claim 1, wherein $R^3$ and $R^4$ are each independently hydrogen, halo, cyano, $C_{1-6}$ alkyl, $C_{3-6}$ cycloalkyl, trifluoromethyl,

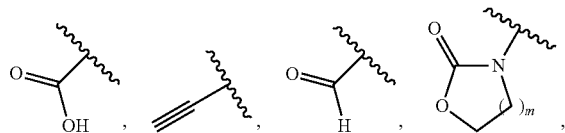

$NR^{a1}R^{a2}$, $CH_2NR^{a1}R^{a2}$, $OR^{a3}$,

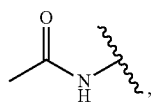

$NR^{a4}CO_2R^{a3}$,

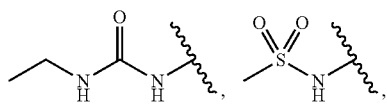

or 3- or 8-membered heterocycles containing one or two oxygen or nitrogen atom(s) therein, wherein: m is 1 or 2; Rai and $R^{a2}$ are each independently hydrogen, methyl, ethyl, isopropyl, tert-butyl, cyclopropyl, trifluoroethyl,

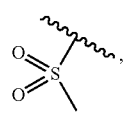

azetidine, or piperidine; $R^{a3}$ is hydrogen, methyl, ethyl, propyl, tert-butyl, cyclopropyl, trifluoromethyl,

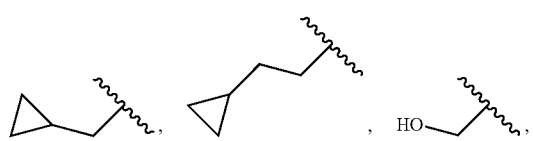

azetidine, piperidine, piperazine, or morpholine; $R^{a4}$ is hydrogen or methyl; $R^{c3}$ is hydrogen or methyl; and $R^{w1}$ is hydrogen, methyl, ethyl, propyl, cyclopropyl,

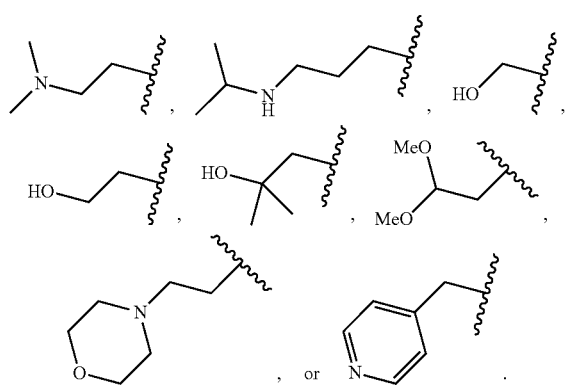

3. The method of claim 1, wherein $R^1$ and $R^2$ are each independently hydrogen, chloro, or trifluoromethyl, and wherein when Z is

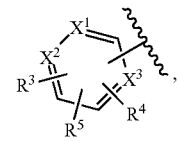

$R^3$ and $R^4$ are each independently hydrogen, chloro, fluoro, iodo, cyano, methyl, ethyl, isopropyl, cyclopropyl, trifluoromethyl,

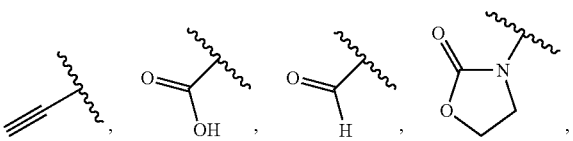

$NR^{a1}R^{a2}$ $CH_2NR^{a1}R^{a2}$, $NR^{a4}CO_2R^{a3}$ azetidine, piperazine, or pyrrolidine, wherein: $R^{a1}$ and $R^{a2}$ are each independently hydrogen, methyl, ethyl, isopropyl, tert-butyl, cyclopropyl, trifluoroethyl,

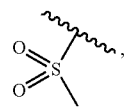

azetidine, piperidine, or oxetane; $R^{a3}$ is hydrogen, methyl, ethyl, tert-butyl, cyclopropyl, trifluoromethyl,

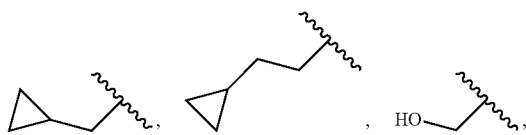

azetidine, piperidine, piperazine, or morpholine; and $R^{a4}$ is hydrogen, methyl, or ethyl.

4. The method of claim 1, wherein $R^1$ and $R^2$ are each independently hydrogen, chloro, or fluoro, and wherein when the Z is

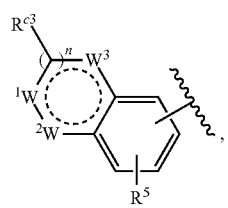

n is 0 or 1, R⁵ is

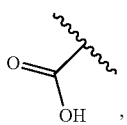 [SMILES: *C(=O)O]

and W¹, W², and W³ are each independently oxygen, nitrogen, CR^{w1}, or NR^{w1}, wherein, R^{w1} is hydrogen, methyl, ethyl, isopropyl, cyclopropyl,

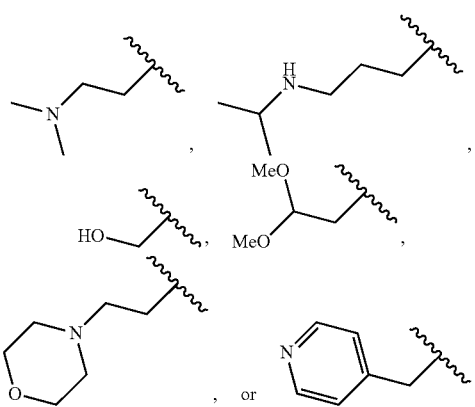

5. The method of claim 1, wherein, the compound, racemate, enantiomer, diastereoisomer, or pharmaceutically acceptable salt is selected from the group consisting of:
4-((4-((5-cyclopropyl-3-(2,6-dichlorophenyl)isoxazol-4-yl)methoxy)phenyl)ethynyl)benzoic acid;
3-((4-((5-cyclopropyl-3-(2,6-dichlorophenyl)isoxazol-4-yl)methoxy)phenyl)ethynyl)benzoic acid;
3-((4-((5-cyclopropyl-3-(2,6-dichlorophenyl)isoxazol-4-yl)methoxy)-2-(trifluoromethyl)phenyl)ethynyl)benzoic acid;
4-((4-((5-cyclopropyl-3-(2,6-dichlorophenyl)isoxazol-4-yl)methoxy)-2-(trifluoromethyl)phenyl)ethynyl)benzoic acid;
4-((3-chloro-4-(phenylethynyl)phenoxy)methyl)-5-cyclopropyl-3-(2,6-dichlorophenyl)isoxazole;
methyl 3-((2-chloro-4-((5-cyclopropyl-3-(2,6-dichlorophenyl)isoxazol-4-yl)methoxy)phenyl)ethynyl)benzoate;
methyl 3-((2-chloro-4-((5-cyclopropyl-3-(2,6-dichlorophenyl)isoxazol-4-yl)methoxy)phenyl)ethynyl)-5-((ethoxycarbonyl)amino)benzoate;
methyl 3-((tert-butoxycarbonyl)amino)-5-((2-chloro-4-((5-cyclopropyl-3-(2,6-dichlorophenyl)isoxazol-4-yl)methoxy)phenyl)ethynyl)benzoate;
methyl 3-((2-chloro-4-((5-cyclopropyl-3-(2,6-dichlorophenyl)isoxazol-4-yl)methoxy)phenyl)ethynyl)-5-((ethoxycarbonyl)(methyl)amino)benzoate;
ethyl(3-((2-chloro-4-((5-cyclopropyl-3-(2,6-dichlorophenyl)isoxazol-4-yl)methoxy)phenyl)ethynyl)phenyl)carbamate;
3-((2-chloro-4-((5-cyclopropyl-3-(2,6-dichlorophenyl)isoxazol-4-yl)methoxy)phenyl)ethynyl)benzenesulfonamide;
N-(3-((2-chloro-4-((5-cyclopropyl-3-(2,6-dichlorophenyl)isoxazol-4-yl)methoxy)phenyl)ethynyl)phenyl)methanesulfonamide;
N-(3-((2-chloro-4-((5-cyclopropyl-3-(2,6-dichlorophenyl)isoxazol-4-yl)methoxy)phenyl)ethynyl)phenyl)sulfamide;
3-((2-chloro-4-((5-cyclopropyl-3-(2,6-dichlorophenyl)isoxazol-4-yl)methoxy)phenyl)ethynyl)benzoic acid;
4-((2-chloro-4-((5-cyclopropyl-3-(2,6-dichlorophenyl)isoxazol-4-yl)methoxy)phenyl)ethynyl)benzoic acid;
6-((2-chloro-4-((5-cyclopropyl-3-(2,6-dichlorophenyl)isoxazol-4-yl)methoxy)phenyl)ethynyl)nicotinic acid;
2-((2-chloro-4-((5-cyclopropyl-3-(2,6-dichlorophenyl)isoxazol-4-yl)methoxy)phenyl)ethynyl)isonicotinic acid;
6-((2-chloro-4-((5-cyclopropyl-3-(2,6-dichlorophenyl)isoxazol-4-yl)methoxy)phenyl)ethynyl)picolinic acid;
5-((2-chloro-4-((5-cyclopropyl-3-(2,6-dichlorophenyl)isoxazol-4-yl)methoxy)phenyl)ethynyl)nicotinic acid;
3-((2-chloro-4-((5-cyclopropyl-3-(2,6-dichlorophenyl)isoxazol-4-yl)methoxy)phenyl)ethynyl)-5-(dimethylamino)benzoic acid;
4-((2-chloro-4-((5-cyclopropyl-3-(2,6-dichlorophenyl)isoxazol-4-yl)methoxy)phenyl)ethynyl)-3-(dimethylamino)benzoic acid;
4-((2-chloro-4-((5-cyclopropyl-3-(2,6-dichlorophenyl)isoxazol-4-yl)methoxy)phenyl)ethynyl)-2-(dimethylamino)benzoic acid;
3-((2-chloro-4-((5-cyclopropyl-3-(2,6-dichlorophenyl)isoxazol-4-yl)methoxy)phenyl)ethynyl)-5-(diethylamino)benzoic acid;
3-amino-5-((2-chloro-4-((5-cyclopropyl-3-(2,6-dichlorophenyl)isoxazol-4-yl)methoxy)phenyl)ethynyl)benzoic acid;
3-((2-chloro-4-((5-cyclopropyl-3-(2,6-dichlorophenyl)isoxazol-4-yl)methoxy)phenyl)ethynyl)-4-(dimethylamino)benzoic acid;
3-chloro-5-((2-chloro-4-((5-cyclopropyl-3-(2,6-dichlorophenyl)isoxazol-4-yl)methoxy)phenyl)ethynyl)benzoic acid;
4-chloro-3-((2-chloro-4-((5-cyclopropyl-3-(2,6-dichlorophenyl)isoxazol-4-yl)methoxy)phenyl)ethynyl)benzoic acid;
2-chloro-5-((2-chloro-4-((5-cyclopropyl-3-(2,6-dichlorophenyl)isoxazol-4-yl)methoxy)phenyl)ethynyl)benzoic acid;
3-((2-chloro-4-((5-cyclopropyl-3-(2,6-dichlorophenyl)isoxazol-4-yl)methoxy)phenyl)ethynyl)-5-fluorobenzoic acid;
3-((2-chloro-4-((5-cyclopropyl-3-(2,6-dichlorophenyl)isoxazol-4-yl)methoxy)phenyl)ethynyl)-5-(trifluoromethyl)benzoic acid;
3-((2-chloro-4-((5-cyclopropyl-3-(2,6-dichlorophenyl)isoxazol-4-yl)methoxy)phenyl)ethynyl)-5-ethynylbenzoic acid;
3-((2-chloro-4-((5-cyclopropyl-3-(2,6-dichlorophenyl)isoxazol-4-yl)methoxy)phenyl)ethynyl)-5-cyanobenzoic acid;
3-((2,6-dichloro-4-((5-cyclopropyl-3-(2,6-dichlorophenyl)isoxazol-4-yl)methoxy)phenyl)ethynyl)benzoic acid;
2-chloro-3-((2-chloro-4-((5-cyclopropyl-3-(2,6-dichlorophenyl)isoxazol-4-yl)methoxy)phenyl)ethynyl)benzoic acid;
3-((2-chloro-4-((5-cyclopropyl-3-(2,6-dichlorophenyl)isoxazol-4-yl)methoxy)phenyl)ethynyl)-2-fluorobenzoic acid;
5-((2-chloro-4-((5-cyclopropyl-3-(2,6-dichlorophenyl)isoxazol-4-yl)methoxy)phenyl)ethynyl)-2-fluorobenzoic acid;

3-((2-chloro-4-((5-cyclopropyl-3-(2,6-dichlorophenyl)
isoxazol-4-yl)methoxy)phenyl)ethynyl)-4-fluorobenzoic acid;
3-((2-chloro-4-((5-cyclopropyl-3-(2,6-dichlorophenyl)
isoxazol-4-yl)methoxy)phenyl)ethynyl)-5-(trifluoromethoxy)benzoic acid;
3-((2-chloro-4-((5-cyclopropyl-3-(2,6-dichlorophenyl)
isoxazol-4-yl)methoxy)phenyl)ethynyl)-5-methoxybenzoic acid;
3-((2-chloro-4-((5-cyclopropyl-3-(2,6-dichlorophenyl)
isoxazol-4-yl)methoxy)phenyl)ethynyl)-5-formylbenzoic acid;
3-((2-chloro-4-((5-cyclopropyl-3-(2,6-dichlorophenyl)
isoxazol-4-yl)methoxy)phenyl)ethynyl)-5-((cyclopropylamino)methyl)benzoic acid;
3-(azetidin-1-ylmethyl)-5-((2-chloro-4-((5-cyclopropyl-3-(2,6-dichlorophenyl)isoxazol-4-yl)methoxy)phenyl)
ethynyl)benzoic acid;
3-((2-chloro-4-((5-cyclopropyl-3-(2,6-dichlorophenyl)
isoxazol-4-yl)methoxy)phenyl)ethynyl)-5-((methylamino)methyl)benzoic acid;
3-((2-chloro-4-((5-cyclopropyl-3-(2,6-dichlorophenyl)
isoxazol-4-yl)methoxy)phenyl)ethynyl)-5-((ethylamino)methyl)benzoic acid;
3-((2-chloro-4-((5-cyclopropyl-3-(2,6-dichlorophenyl)
isoxazol-4-yl)methoxy)phenyl)ethynyl)-5-(((2,2,2-trifluoroethyl)amino)methyl)benzoic acid;
3-((2-chloro-4-((5-cyclopropyl-3-(2,6-dichlorophenyl)
isoxazol-4-yl)methoxy)phenyl)ethynyl)-5-((isopropylamino)methyl)benzoic acid;
3-((tert-butylamino)methyl)-5-((2-chloro-4-((5-cyclopropyl-3-(2,6-dichlorophenyl)isoxazol-4-yl)methoxy)phenyl)ethynyl)benzoic acid;
3-((2-chloro-4-((5-cyclopropyl-3-(2,6-dichlorophenyl)
isoxazol-4-yl)methoxy)phenyl)ethynyl)-5-((dimethylamino)methyl)benzoic acid;
3-((2-chloro-4-((5-cyclopropyl-3-(2,6-dichlorophenyl)
isoxazol-4-yl)methoxy)phenyl)ethynyl)-5-(morpholinomethyl)benzoic acid;
3-((2-chloro-4-((5-cyclopropyl-3-(2,6-dichlorophenyl)
isoxazol-4-yl)methoxy)phenyl)ethynyl)-5-((oxetan-3-ylamino)methyl)benzoic acid;
3-((2-chloro-4-((5-cyclopropyl-3-(2,6-dichlorophenyl)
isoxazol-4-yl)methoxy)phenyl)ethynyl)-5-(methylamino)benzoic acid;
3-((2-chloro-4-((5-cyclopropyl-3-(2,6-dichlorophenyl)
isoxazol-4-yl)methoxy)phenyl)ethynyl)-5-(ethylamino)benzoic acid;
3-((2-chloro-4-((5-cyclopropyl-3-(2,6-dichlorophenyl)
isoxazol-4-yl)methoxy)phenyl)ethynyl)-5-(isopropylamino)benzoic acid;
3-(azetidin-1-yl)-5-((2-chloro-4-((5-cyclopropyl-3-(2,6-dichlorophenyl)isoxazol-4-yl)methoxy)phenyl)ethynyl)benzoic acid;
3-((2-chloro-4-((5-cyclopropyl-3-(2,6-dichlorophenyl)
isoxazol-4-yl)methoxy)phenyl)ethynyl)-5-(pyrrolidin-1-yl)benzoic acid;
3-(azetidin-3-ylamino)-5-((2-chloro-4-((5-cyclopropyl-3-(2,6-dichlorophenyl)isoxazol-4-yl)methoxy)phenyl)
ethynyl)benzoic acid hydrochloride;
3-((2-chloro-4-((5-cyclopropyl-3-(2,6-dichlorophenyl)
isoxazol-4-yl)methoxy)phenyl)ethynyl)-5-(piperidin-4-ylamino)benzoic acid hydrochloride;
3-((2-chloro-4-((5-cyclopropyl-3-(2,6-dichlorophenyl)
isoxazol-4-yl)methoxy)phenyl)ethynyl)-5-(piperazin-1-yl)benzoic acid hydrochloride;

3-amino-5-((2-chloro-4-((5-cyclopropyl-3-(2,6-dichlorophenyl)isoxazol-4-yl)methoxy)phenyl)ethynyl)-4-methylbenzoic acid;
3-amino-5-((2-chloro-4-((5-cyclopropyl-3-(2,6-dichlorophenyl)isoxazol-4-yl)methoxy)phenyl)ethynyl)-4-methoxybenzoic acid;
3-amino-5-((2-chloro-4-((5-cyclopropyl-3-(2,6-dichlorophenyl)isoxazol-4-yl)methoxy)phenyl)ethynyl)-2-methoxybenzoic acid;
3-((2-chloro-4-((5-cyclopropyl-3-(2,6-dichlorophenyl)
isoxazol-4-yl)methoxy)phenyl)ethynyl)-5-methylbenzoic acid;
3-((2-chloro-4-((5-cyclopropyl-3-(2,6-dichlorophenyl)
isoxazol-4-yl)methoxy)phenyl)ethynyl)-5-cyclopropylbenzoic acid;
3-((2-chloro-4-((5-cyclopropyl-3-(2,6-dichlorophenyl)
isoxazol-4-yl)methoxy)phenyl)ethynyl)-5-ethylbenzoic acid;
3-((2-chloro-4-((5-cyclopropyl-3-(2,6-dichlorophenyl)
isoxazol-4-yl)methoxy)phenyl)ethynyl)-5-isopropylbenzoic acid;
3-((2-chloro-4-((5-cyclopropyl-3-(2,6-dichlorophenyl)
isoxazol-4-yl)methoxy)phenyl)ethynyl)-5-iodobenzoic
acid;
3-((2,5-dichloro-4-((5-cyclopropyl-3-(2,6-dichlorophenyl)isoxazol-4-yl)methoxy)phenyl)ethynyl)benzoic
acid;
3-((2,3-dichloro-4-((5-cyclopropyl-3-(2,6-dichlorophenyl)isoxazol-4-yl)methoxy)phenyl)ethynyl)benzoic
acid;
3-((2-chloro-4-((5-cyclopropyl-3-(2,6-dichlorophenyl)
isoxazol-4-yl)methoxy)-6-fluorophenyl)ethynyl)benzoic acid;
3-amino-5-((2-chloro-4-((5-cyclopropyl-3-(2,6-dichlorophenyl)isoxazol-4-yl)methoxy)phenyl)ethynyl)-2-methylbenzoic acid;
3-((2-chloro-4-((5-cyclopropyl-3-(2,6-dichlorophenyl)
isoxazol-4-yl)methoxy)phenyl)ethynyl)-5-(3-ethylureido)benzoic acid;
3-acetamido-5-((2-chloro-4-((5-cyclopropyl-3-(2,6-dichlorophenyl)isoxazol-4-yl)methoxy)phenyl)ethynyl)
benzoic acid;
3-((2-chloro-4-((5-cyclopropyl-3-(2,6-dichlorophenyl)
isoxazol-4-yl)methoxy)phenyl)ethynyl)-5-((ethoxycarbonyl)amino)benzoic acid;
3-((2-chloro-4-((5-cyclopropyl-3-(2,6-dichlorophenyl)
isoxazol-4-yl)methoxy)phenyl)ethynyl)-5-((ethoxycarbonyl)(methyl)amino)benzoic acid;
3-((2-chloro-4-((5-cyclopropyl-3-(2,6-dichlorophenyl)
isoxazol-4-yl)methoxy)phenyl)ethynyl)-5-((cyclopropoxycarbonyl)amino)benzoic acid;
3-((tert-butoxycarbonyl)amino)-5-((2-chloro-4-((5-cyclopropyl-3-(2,6-dichlorophenyl)isoxazol-4-yl)methoxy)
phenyl)ethynyl)benzoic acid;
3-((tert-butoxycarbonyl)(methyl)amino)-5-((2-chloro-4-((5-cyclopropyl-3-(2,6-dichlorophenyl)isoxazol-4-yl)
methoxy)phenyl)ethynyl)benzoic acid;
3-((2-chloro-4-((5-cyclopropyl-3-(2,6-dichlorophenyl)
isoxazol-4-yl)methoxy)phenyl)ethynyl)-5-(((cyclopropylmethoxy)carbonyl)amino)benzoic acid;
3-((2-chloro-4-((5-cyclopropyl-3-(2,6-dichlorophenyl)
isoxazol-4-yl)methoxy)phenyl)ethynyl)-5-(((2-cyclopropylethoxy)carbonyl)amino)benzoic acid;
3-((2-chloro-4-((5-cyclopropyl-3-(2,6-dichlorophenyl)
isoxazol-4-yl)methoxy)phenyl)ethynl)-5-(((2-cyclopropylethoxy)carbonyl)amino)benzoic acid;

3-((2-chloro-4-((5-cyclopropyl-3-(2,6-dichlorophenyl)
isoxazol-4-yl)methoxy)phenyl)ethynyl)-5-(2-oxooxa-
zolidin-3-yl)benzoic acid;
5-((2-chloro-4-((5-cyclopropyl-3-(2,6-dichlorophenyl)
isoxazol-4-yl)methoxy)phenyl)ethynyl)isophthalic
acid;
3-((2-chloro-4-((5-cyclopropyl-3-(2,6-dichlorophenyl)
isoxazol-4-yl)methoxy)phenyl)ethynyl)-5-(piperazine-
1-carbonyl)benzoic acid hydrochloride;
3-((2-chloro-4-((5-cyclopropyl-3-(2,6-dichlorophenyl)
isoxazol-4-yl)methoxy)phenyl)ethynyl)-5-(methyl-
sulfonamido)benzoic acid;
3-((2-chloro-4-((5-cyclopropyl-3-(2-(trifluoromethyl)
phenyl)isoxazol-4-yl)methoxy)phenyl)ethynyl)benzoic
acid;
3-((2-chloro-4-((5-cyclopropyl-3-(2-(trifluoromethoxy)
phenyl)isoxazol-4-yl)methoxy)phenyl)ethynyl)benzoic
acid;
4-((2-chloro-4-((5-cyclopropyl-3-(2,6-dichlorophenyl)
isoxazol-4-yl)methoxy)phenyl)ethynyl)-1H-indazole-
6-carboxylic acid;
4-((2-chloro-4-((5-cyclopropyl-3-(2,6-dichlorophenyl)
isoxazol-4-yl)methoxy)phenyl)ethynyl)-1H-benzo[d]
imidazole-6-carboxylic acid;
4-((2-chloro-4-((5-cyclopropyl-3-(2,6-dichlorophenyl)
isoxazol-4-yl)methoxy)phenyl)ethynyl)-1H-indole-6-
carboxylic acid;
4-((2-chloro-4-((5-cyclopropyl-3-(2,6-dichlorophenyl)
isoxazol-4-yl)methoxy)phenyl)ethynyl)-1-(2-(dimeth-
ylamino)ethyl)-1H-indole-6-carboxylic acid;
4-((2-chloro-4-((5-cyclopropyl-3-(2,6-dichlorophenyl)
isoxazol-4-yl)methoxy)phenyl)ethynyl)-1-(3-(isopro-
pylamino)propyl)-1H-indole-6-carboxylic acid;
4-((2-chloro-4-((5-cyclopropyl-3-(2,6-dichlorophenyl)
isoxazol-4-yl)methoxy)phenyl)ethynyl)-1-(pyridin-4-
ylmethyl)-1H-indole-6-carboxylic acid;
4-((2-chloro-4-((5-cyclopropyl-3-(2,6-dichlorophenyl)
isoxazol-4-yl)methoxy)phenyl)ethynyl)-1-(2-mor-
pholinoethyl)-1H-indole-6-carboxylic acid hydrochlo-
ride;
4-((2-chloro-4-((5-cyclopropyl-3-(2,6-dichlorophenyl)
isoxazol-4-yl)methoxy)phenyl)ethynyl)-1-(2,2-dime-
thoxyethyl)-1H-indole-6-carboxylic acid;
4-((2-chloro-4-((5-cyclopropyl-3-(2,6-dichlorophenyl)
isoxazol-4-yl)methoxy)phenyl)ethynyl)-1-(2-hydroxy-
ethyl)-1H-indole-6-carboxylic acid;
4-((2-chloro-4-((5-cyclopropyl-3-(2,6-dichlorophenyl)
isoxazol-4-yl)methoxy)phenyl)ethynyl)-1-(2-hydroxy-
2-methylpropyl)-1H-indole-6-carboxylic acid;
6-((2-chloro-4-((5-cyclopropyl-3-(2,6-dichlorophenyl)
isoxazol-4-yl)methoxy)phenyl)ethynyl)-1H-indazole-
4-carboxylic acid;
5-((2-chloro-4-((5-cyclopropyl-3-(2,6-dichlorophenyl)
isoxazol-4-yl)methoxy)phenyl)ethynyl)-2,3-dihyd-
robenzofuran-7-carboxylic acid;
6-((2-chloro-4-((5-cyclopropyl-3-(2,6-dichlorophenyl)
isoxazol-4-yl)methoxy)phenyl)ethynyl)-1H-indole-4-
carboxylic acid;
5-((2-chloro-4-((5-cyclopropyl-3-(2,6-dichlorophenyl)
isoxazol-4-yl)methoxy)phenyl)ethynyl)benzo[d]oxa-
zole-7-carboxylic acid;
5-((2-chloro-4-((5-cyclopropyl-3-(2,6-dichlorophenyl)
isoxazol-4-yl)methoxy)phenyl)ethynyl)-2-methyl-
benzo[d]oxazole-7-carboxylic acid;
5-((2-chloro-4-((5-cyclopropyl-3-(2,6-dichlorophenyl)
isoxazol-4-yl)methoxy)phenyl)ethynyl)-2-ethylbenzo
[d]oxazole-7-carboxylic acid;
5-((2-chloro-4-((5-cyclopropyl-3-(2,6-dichlorophenyl)
isoxazol-4-yl)methoxy)phenyl)ethynyl)-2-propylbenzo
[d]oxazole-7-carboxylic acid;
5-((2-chloro-4-((5-cyclopropyl-3-(2,6-dichlorophenyl)
isoxazol-4-yl)methoxy)phenyl)ethynyl)-2-isopropyl-
benzo[d]oxazole-7-carboxylic acid;
5-((2-chloro-4-((5-cyclopropyl-3-(2,6-dichlorophenyl)
isoxazol-4-yl)methoxy)phenyl)ethynyl)-2-(hydroxym-
ethyl)benzo[d]oxazole-7-carboxylic acid;
7-((2-chloro-4-((5-cyclopropyl-3-(2,6-dichlorophenyl)
isoxazol-4-yl)methoxy)phenyl)ethynyl)quinoxaline-5-
carboxylic acid;
7-((2-chloro-4-((5-cyclopropyl-3-(2,6-dichlorophenyl)
isoxazol-4-yl)methoxy)phenyl)ethynyl)-2,3-dimeth-
ylquinoxaline-5-carboxylic acid;
5-((2-chloro-4-((5-cyclopropyl-3-(2,6-dichlorophenyl)
isoxazol-4-yl)methoxy)phenyl)ethynyl)-2-cyclopropy-
lbenzo[d]oxazole-7-carboxylic acid;
2-butyl-5-((2-chloro-4-((5-cyclopropyl-3-(2,6-dichloro-
phenyl)isoxazol-4-yl)methoxy)phenyl)ethynyl)benzo
[d]oxazole-7-carboxylic acid;
6-((2-chloro-4-((5-cyclopropyl-3-(2,6-dichlorophenyl)
isoxazol-4-yl)methoxy)phenyl)ethynyl)-2-methyl-
benzo[d]oxazole-4-carboxylic acid;
6-((2-chloro-4-((5-cyclopropyl-3-(2,6-dichlorophenyl)
isoxazol-4-yl)methoxy)phenyl)ethynyl)-2-ethylbenzo
[d]oxazole-4-carboxylic acid;
6-((2-chloro-4-((5-cyclopropyl-3-(2,6-dichlorophenyl)
isoxazol-4-yl)methoxy)phenyl)ethynyl)-2-propylbenzo
[d]oxazole-4-carboxylic acid; and
6-((2-chloro-4-((5-cyclopropyl-3-(2,6-dichlorophenyl)
isoxazol-4-yl)methoxy)phenyl)ethynyl)-2-isopropyl-
benzo[d]oxazole-4-carboxylic acid.

6. The method of claim 1, wherein, the metabolic diseases, cholestatic liver diseases, and organ fibrosis are treated or ameliorated by activation of FXR receptors.

7. The method of claim 1, wherein, the metabolic diseases, cholestatic liver diseases, and organ fibrosis are selected from the group consisting of hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes, insulin resistance, metabolic inflexibility, nephropathy, liver diseases, atherosclerosis, cancer, inflammatory disorders, osteoporosis, and skin aging.

8. A method for treating or ameliorating metabolic diseases, cholestatic liver diseases, or organ fibrosis, the method comprising:
administering to a subject a therapeutically effective amount of a pharmaceutical composition comprising (i) 4-((3-chloro-4-ethynylphenoxy)methyl)-5-cyclopropyl-3-(2,6-dichlorophenyl)isoxazole, a racemate, an enantiomer, or a diastereoisomer thereof, or a pharmaceutically acceptable salt thereof, or a pharmaceutically acceptable salt of the racemate, the enantiomer, or the diastereoisomer and (ii) a carrier.

9. The method of claim 8, wherein, the metabolic diseases, cholestatic liver diseases, and organ fibrosis are treated or ameliorated by activation of FXR receptors.

10. The method of claim 8, wherein, the metabolic diseases, cholestatic liver diseases, and organ fibrosis are selected from the group consisting of hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes, insulin resistance, metabolic inflexibility, nephropathy, liver diseases, atherosclerosis, cancer, inflammatory disorders, osteoporosis, and skin aging.

11. A method for treating or ameliorating metabolic diseases, cholestatic liver diseases, or organ fibrosis, the method comprising:

administering to a subject a therapeutically effective amount of a pharmaceutical composition comprising (i) 3-((2-chloro-4-((5-cyclopropyl-3-(2,6-dichlorophenyl)isoxazol-4-yl)methoxy)phenyl)ethynyl)-5-(((2-hydroxyethoxy)carbonyl)amino)benzoic acid, a racemate, an enantiomer, or a diastereoisomer thereof, or a pharmaceutically acceptable salt thereof, or a pharmaceutically acceptable salt of the racemate, the enantiomer, or the diastereoisomer and (ii) a carrier.

12. The method of claim 11, wherein, the metabolic diseases, cholestatic liver diseases, and organ fibrosis are treated or ameliorated by activation of FXR receptors.

13. The method of claim 11, wherein, the metabolic diseases, cholestatic liver diseases, and organ fibrosis are selected from the group consisting of hypercholesterolemia, hyperlipoproteinemia, hypertriglyceridemia, dyslipidemia, lipodystrophy, cholestasis/fibrosis, cholesterol gallstone disease, gastrointestinal disease or condition, hyperglycemia, diabetes, insulin resistance, metabolic inflexibility, nephropathy, liver diseases, atherosclerosis, cancer, inflammatory disorders, osteoporosis, and skin aging.

* * * * *